US010308631B2

(12) United States Patent
Lee et al.

(10) Patent No.: US 10,308,631 B2
(45) Date of Patent: Jun. 4, 2019

(54) SELECTIVE ANTI-CANCER COMPOUNDS

(71) Applicant: NATIONAL UNIVERSITY OF SINGAPORE, Singapore (SG)

(72) Inventors: Sang Hyun Lee, Singapore (SG); Brian William Dymock, Singapore (SG); Mayumi Kitagawa, Singapore (SG); Cheng Shang See, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/580,978

(22) PCT Filed: Jun. 10, 2016

(86) PCT No.: PCT/SG2016/050269

§ 371 (c)(1),
(2) Date: Dec. 8, 2017

(87) PCT Pub. No.: WO2016/200339

PCT Pub. Date: Dec. 15, 2016

(65) Prior Publication Data

US 2018/0179178 A1 Jun. 28, 2018

(30) Foreign Application Priority Data

Jun. 12, 2015 (SG) .......................... 10201504656 U

(51) Int. Cl.

| | |
|---|---|
| ***A61P 35/00*** | (2006.01) |
| ***A61P 39/00*** | (2006.01) |
| ***C07D 401/06*** | (2006.01) |
| ***C07D 401/12*** | (2006.01) |
| ***C07D 401/14*** | (2006.01) |
| ***C07D 405/14*** | (2006.01) |
| ***C07D 471/04*** | (2006.01) |
| ***C07D 495/14*** | (2006.01) |
| ***C07D 519/00*** | (2006.01) |
| ***A61K 31/4709*** | (2006.01) |
| ***A61K 31/4725*** | (2006.01) |

(52) U.S. Cl.

CPC ........ *C07D 401/06* (2013.01); *A61K 31/4709* (2013.01); *A61K 31/4725* (2013.01); *A61P 35/00* (2018.01); *A61P 39/00* (2018.01); *C07D 401/12* (2013.01); *C07D 401/14* (2013.01); *C07D 405/14* (2013.01); *C07D 471/04* (2013.01); *C07D 495/14* (2013.01); *C07D 519/00* (2013.01)

(58) Field of Classification Search

CPC .. C07D 401/06; C07D 401/12; C07D 401/14; C07D 405/14; C07D 471/04; C07D 495/14; C07D 519/00; A61P 39/00; A61P 35/00; A61K 31/4709; A61K 31/4725

USPC .......................................................... 514/300

See application file for complete search history.

(56) References Cited

U.S. PATENT DOCUMENTS

| | | | | |
|---|---|---|---|---|
| 6,335,342 B1 * | 1/2002 | Longo .................. | C07D 471/04 514/234.5 |
| 2006/0004000 A1 | 1/2006 | D'Orchymont et al. | |
| 2013/0289083 A1 * | 10/2013 | Mautino .............. | A61K 31/138 514/367 |

FOREIGN PATENT DOCUMENTS

| | | |
|---|---|---|
| WO | 2004/031158 A1 | 4/2004 |
| WO | 2009/073620 A2 | 6/2009 |

OTHER PUBLICATIONS

Bahner; J. Med. Chem., 1965, 8, 397-398. (Year: 1965).*

Hayakawa; Bioorganic & Medicinal Chemistry Letters 2004, 14, 3411-3414. (Year: 2004).*

Nolan; Bioorganic & Medicinal Chemistry Letters 20 (2010) 7331-7336. (Year: 2010).*

Written Opinion and International Search Report corresponding to PCT/SG2016/050269 dated Jul. 27, 2016, 9 pages.

CAS Registry No. 1235327-94-2, STN Entry Date Aug. 5, 2010, 1H-Indazole-3-carboxamide, N-5-quinolinyl—(CA Index Name) the compound.

CAS Registry No. 1235117-62-0, STN Entry Date Aug. 5, 2010, 1H-Indole-3-carboxamide, N-(2-methyl-5-quinolinyl)—(CA Index Name) the compound.

CAS Registry No. 1234868-84-8, STN Entry Date Aug. 4, 2010, 1H-Indazole-3-carboxamide, N-(2-methyl-5-quinolinyl)—(CA Index Name) the compound.

(Continued)

*Primary Examiner* — Daniel R Carcanague

(74) *Attorney, Agent, or Firm* — Mintz, Levin, Cohn, Ferris, Glovsky and Popeo, P.C.

(57) ABSTRACT

A compound of formula I, wherein the compound of formula I has the structure: wherein $R^1$ to $R^5$, Y, L, Z and $X_1$ to $X_7$ have meanings given in the description, said compounds having utility in the treatment of hyperproliferative disease.

(I)

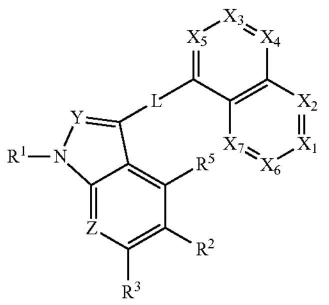

20 Claims, 24 Drawing Sheets

(56) References Cited

OTHER PUBLICATIONS

Figure 1:
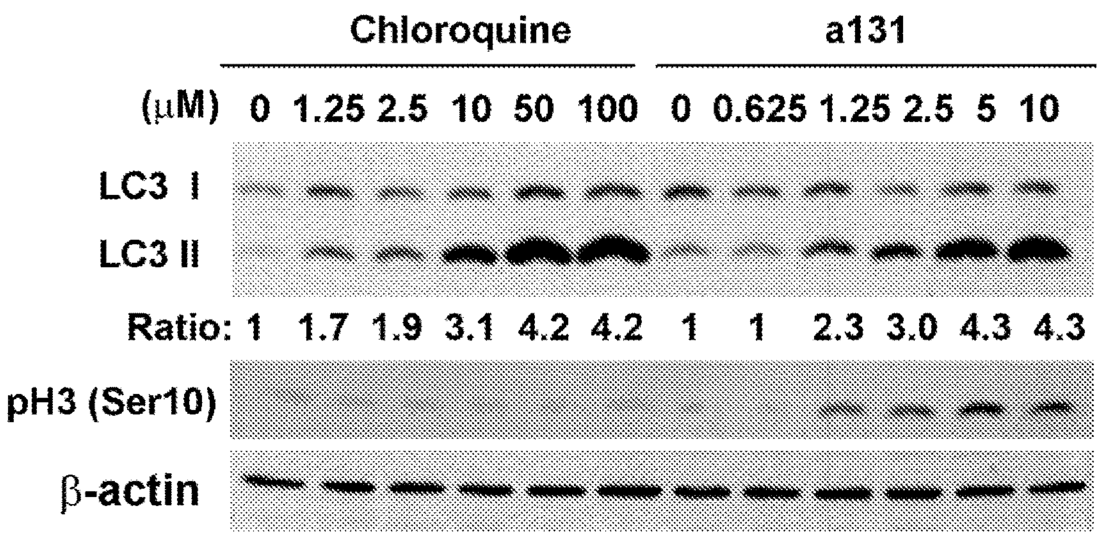

CAS Registry No. 1232776-29-2, STN Entry Date Jul. 19, 2010, 1H-Indole-3-carboxamide, N-5-quinolinyl—(CA Index Name) the compound.
Gordon, D.J. et al. (Jan. 24, 2012). "Causes and consequences of aneuploidy in cancer," *Nat Rev Genet* 13(3):189-203.
Jordan, M.A. et al. (Apr. 2004). "Microtubules as a target for anticancer drugs," *Nat Rev Cancer* 4(4):253-265.
MacIntosh, R.L. et al. (Oct. 2013, e-published Jun. 14, 2013). "Autophagy in tumour cell death," *Semin Cancer Biol* 23(5):344-351.
Siegel, J.J. et al. (2012, e-published Jul. 9, 2012). "New insights into the troubles of aneuploidy," *Annu Rev Cell Dev Biol* 28:189-214.
Tang, Y.C. et al. (Feb. 18, 2011). "Identification of aneuploidy-selective antiproliferation compounds," *Cell* 144(4):499-512.

* cited by examiner

| Number | Ex | Structure | mitosis | LC3 induction |
|---|---|---|---|---|
| a131 | Ex1 |  | +++ | +++ |
| a159 | Ex3 |  | +++ | >10uM |
| a166 | Ex25 |  | >10uM | +++ |

SELECTIVE ANTI-CANCER COMPOUNDS

FIELD OF INVENTION

The current invention relates to the use of compounds to treat hyperproliferative diseases, such as cancer, atherosclerosis, rheumatoid arthritis, psoriasis, idiopathic pulmonary fibrosis, scleroderma and cirrhosis of the liver.

BACKGROUND

The listing or discussion of an apparently prior-published document in this specification should not necessarily be taken as an acknowledgement that the document is part of the state of the art or is common general knowledge.

Errors in chromosomal segregation can lead to the loss or gain of chromosomes in daughter cells, a condition known as aneuploidy. In humans, aneuploidy is a key characteristic of cancer, with an estimated 70-90% of all human solid tumours harbouring aneuploidy genomes [Gordon D J, Resio B, Pellman D. (2012) *Nat Rev Genet.* 13(3):189-203]. Interrupting mitotic progress of tumour cells using anti-microtubule toxins (e.g. taxol, the best-selling cancer drug ever manufactured) is one of the most successful strategies to treat human cancers and has become the front-line anti-cancer therapy [Jordan, M. A., and Wilson, L. (2004) *Nat Rev Cancer* 4, 253-265].

More recently, advances in molecularly targeted drug discovery have facilitated the identification of a new generation of antimitotic therapies that target proteins with specific functions in mitosis. However, antimitotic agents often have a narrow therapeutic index, leading to toxic side effects as normal cells as well as cancer cells are targeted by the antimitotic agent. In addition to this undesirable toxicity, cancer cells can rapidly develop drug resistance to this class of drugs, which further limits their clinical efficacy. Thus, there is an urgent need to develop a new generation of antimitotic agents that preferentially eliminate cancer cells over normal cells, while overcoming the resistance to current anti-microtubule toxins in the clinic.

Autophagy (or autophagocytosis) is the basic catabolic mechanism that involves cell degradation of unnecessary or dysfunctional cellular components through the actions of lysosomes. Autophagy promotes the survival of cancer cells during proteotoxic and metabolic stress by maintaining cellular energy levels [Macintosh, R. L., and Ryan, K. M. (2013) *Seminars in Cancer Biology* 23, 344-351]. The best known autophagy inhibitor, chloroquine (CQ), has long been used in the treatment and prevention of malaria. Therefore, given its mechanism of action and long use in the treatment of humans, CQ and its derivatives are being investigated in a number of clinical trials to establish if they can also be effective in the treatment of solid tumours. It has also been shown that acquisition of aneuploidy by errors in chromosome segregation, or by treatment with antimitotic agents, causes proteotoxic stress and metabolic alteration in cancer cells that increase autophagosome formation and lysosome-mediated cell degradation of unnecessary or dysfunctional cellular components and proteins [Tang et al., (2011) *Cell* 144(4):499-512; Siegel J J, Amon A. (2012) *Annu Rev Cell Dev Biol.* 28:189-214]. Additionally or alternatively, there are very few, if any, therapeutic agents that can be provided to a subject that can act as a chemo-protective agent, that is, an agent that can protect normal cells while allowing cancer cells to be killed.

SUMMARY OF INVENTION

The invention is described below with regard to the following numbered aspects and embodiments.

1. A compound of formula I,

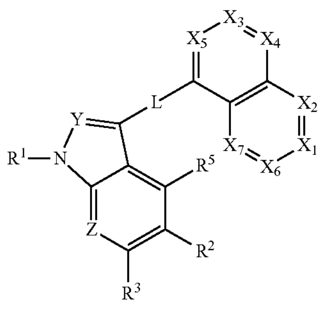

I wherein,

Z represents N or $CR^4$;

L represents a linking group selected from the group consisting of $-C(R^{6a})=C(R^{6b})-$, $-C(R^{6a})_2-C(R^{6b})_2-$, $-C(O)NR^{7a}-$ or $-NR^{7b}C(O)-$;

$X_1$ to $X_5$ are independently N or $CR^8$, provided that at least one of $X_1$ and $X_2$ is N;

$X_6$ and $X_7$ are independently N or $CR^9$;

Y represents N or $CR^{10}$;

$R^1$ represents H, $-C(O)R^{11a}$ or $-C(S)R^{11b}$;

$R^2$ to $R^4$, $R^8$ and $R^{10}$, at each occurrence, independently represents:

(a) H;

(b) halo;

(c) CN;

(d) $C_{1-6}$ alkyl, $C_{2-6}$ alkenyl, $C_{2-6}$ alkynyl (which latter three groups are unsubstituted or substituted by one or more substituents selected from halo, nitro, CN, $C_{1-6}$ alkyl, $C_{2-6}$ alkenyl, $C_{2-6}$ alkynyl (which latter three groups are unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{12a}$, $S(O)_qR^{12b}$, $S(O)_2NR^{12c}R^{12d}$, $NR^{12e}S(O)_2R^{12f}$, $NR^{12g}R^{12h}$, aryl and $Het^1$);

(e) $Cy^2$ (which $Cy^2$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$alkyl and $C_{1-4}$alkoxy), $OR^{13a}$, $S(O)_qR^{13b}$, $S(O)_2NR^{13c}R^{13d}$, $NR^{13e}S(O)_2R^{13f}$, $NR^{13g}R^{13h}$, aryl and $Het^2$), (f) $Het^a$ (which $Het^a$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$alkyl and $C_{1-4}$alkoxy), $OR^{14a}$, $S(O)_qR^{14b}$, $S(O)_2NR^{14c}R^{14d}$, $NR^{14e}S(O)_2R^{14f}$, $NR^{14g}R^{14h}$, aryl and $Het^3$);

(g) $OR^{15a}$;

(h) $S(O)_qR^{15b}$;

(i) $S(O)_2NR^{15c}R^{15d}$;

(j) $NR^{15e}S(O)_2R^{15f}$;

(k) $NR^{15g}R^{15h}$, where $R^3$, $R^4$ and each $R^8$, when present, may also, in addition, independently represent nitro;

$R^5$ and $R^9$, at each occurrence, independently represent H, halo, CN, nitro, $C_{1-4}$ alkyl (which latter group is unsubstituted or substituted by one or more substituents selected from halo, nitro, CN, $OR^{16a}$ and $NR^{16g}R^{16h}$), $OR^{17a}$, $S(O)_qR^{17b}$, $S(O)_2NR^{17c}R^{17d}$, $NR^{17e}S(O)_2R^{17f}$ or $NR^{17g}R^{17h}$;

$R^{6a}$ represents H, CN or —$C(O)NR^{18a}R^{18b}$;

$R^{6b}$, independently at each occurrence, represents H, CN or $C_{1-4}$ alkyl, which latter group is unsubstituted or substituted with halo or $OR^{19}$;

$R^{7a}$ and $R^{7b}$ represent H or $C_{1-4}$ alkyl, which latter group is unsubstituted or substituted with halo or $OR^{20}$;

$R^{11a}$ and $R^{11b}$, when present, represent, (a) H;

(b) $C_{1-6}$ alkyl, $C_{2-6}$ alkenyl, $C_{2-6}$ alkynyl (which latter three groups are unsubstituted or substituted by one or more substituents selected from halo, nitro, ═O, CN, $C_{1-6}$ alkyl, $C_{2-6}$ alkenyl, $C_{2-6}$ alkynyl (which latter three groups are unsubstituted or substituted by one or more substituents selected from OH, ═O, halo, $C_{1-4}$ alkyl and $C_{1-4}$ alkoxy), $OR^{21a}$, $S(O)_1R^{21b}$, $S(O)_2NR^{21c}R^{21d}$, $NR^{21e}S(O)_2R^{21f}$, $NR^{21g}R^{21h}$, aryl, $Cy^3$ (which $Cy^3$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$ alkyl and $C_{1-4}$ alkoxy), $OR^{22a}$, $S(O)_qR^{22b}$, $S(O)_2NR^{22c}R^{22d}$, $NR^{22e}S(O)_2R^{22f}$, $NR^{22g}R^{22h}$, aryl and $Het^4$) and $Het^5$);

(c) $C_{3-10}$ cycloalkyl, $C_{4-10}$ cycloalkenyl (which latter two groups are optionally substituted by one or more substituents selected from halo, OH, ═O, $C_{1-6}$ alkyl and $C_{1-6}$ alkoxy);

(d) $Het^b$ (which $Het^b$ group is unsubstituted or substituted by one or more substituents selected from halo, nitro, CN, $C(O)OC_{1-4}$ alkyl, $C_{1-6}$ alkyl, $C_{2-6}$ alkenyl, $C_{2-6}$ alkynyl (which latter three groups are optionally substituted by one or more substituents selected from $Het^8$, OH, ═O, halo, $C_{1-4}$ alkyl and $C_{1-4}$ alkoxy), $OR^{23a}$, $S(O)_qR^{23b}$, $S(O)_2NR^{23c}R^{23d}$, $NR^{23e}S(O)_2R^{23f}$, $NR^{23g}R^{23h}$, aryl and $Het^6$), (e) $OR^{24a}$;

(f) $NR^{24b}S(O)_2R^{24c}$;

(g) $NR^{24d}R^{24e}$;

$R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-6}$ alkyl, $C_{2-6}$ alkenyl, $C_{2-6}$ alkynyl (which latter three groups are optionally substituted by one or more substituents selected from halo, nitro, ═O, $C(O)OC_{1-4}$ alkyl, CN, $C_{1-6}$ alkyl, $C_{2-6}$ alkenyl, $C_{2-6}$ alkynyl, $C_{3-6}$ cycloalkyl (which latter three groups are optionally substituted by one or more substituents selected from OH, ═O, halo, $C_{1-4}$ alkyl and $C_{1-4}$ alkoxy), $OR^{25a}$, $S(O)_qR^{25b}$, $S(O)_2NR^{25c}R^{25d}$, $NR^{25e}S(O)_2R^{25f}$, $NR^{25g}R^{25h}$, aryl and $Het^7$), $C_{3-10}$ cycloalkyl, or $C_{4-10}$ cycloalkenyl (which latter two groups are optionally substituted by one or more substituents selected from halo, OH, ═O, $C_{1-6}$ alkyl and $C_{1-6}$ alkoxy) or $Het^c$, or $R^{12-17c}$ and $R^{12-17d}$, $R^{12-17g}$ and $R^{12-17b}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$ alkyl and $C_{1-4}$ alkoxy);

$Het^1$ to $Het^8$ (e.g. $Het^1$ to $Het^7$) and $Het^a$ to $Het^c$ independently represent a 4- to 14-membered heterocyclic groups containing one or more heteroatoms selected from O, S and N, which heterocyclic groups may comprise one, two or three rings and may be substituted by one or more substituents selected from ═O, or more particularly, halo, $C_{1-6}$ alkyl, which latter group is optionally substituted by one or more substituents selected from halo, —$OR^{26a}$, —$NR^{26b}R^{26c}$, —$C(O)OR^{26d}$ and —$C(O)NR^{26e}R^{26f}$;

$Cy^1$ to $Cy^3$, at each occurrence, independently represents a 3- to 10-membered aromatic, fully saturated or partially unsaturated carbocyclic ring;

$R^{25a}$ to $R^{25h}$ and $R^{26a}$ to $R^{26f}$ independently represent at each occurrence, H, $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, ═O, halo, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from halo, OH, ═O, $C_{1-4}$ alkyl and $C_{1-4}$ alkoxy), q represents 0, 1 or 2, or a pharmaceutically acceptable salt, solvate or a pharmaceutically functional derivative thereof.

2. The compound according to Clause 1, wherein L represents a linking group selected from the group consisting of —$C(O)NR^{7a}$— and, more particularly, —$C(R^{6a})$═$C(R^{6b})$—.

3. The compound according to Clause 1 or Clause 2, wherein $X_1$ to $X_3$ are independently N or $CR^8$;

$X_4$ and $X_5$ are independently $CR^8$; and $X_6$ and $X_7$ are independently $CR^9$.

4. The compound according to Clause 3, wherein:

$X_1$ represents N; and $X_2$ to $X_5$ are independently $CR^8$.

5. The compound according to any one of the preceding clauses, wherein Y represents $CR^{10}$ and/or Z represents $CR^4$.

6. The compound according to any one of the preceding clauses, wherein $R^1$ represents H, or —$C(O)R^{11a}$.

7. The compound according to any one of the preceding clauses, wherein $R^2$ represents:

(i) H;

(ii) Br, Cl, F;

(iii) $C_{1-4}$ alkyl which is unsubstituted or substituted by one or more substituents selected from halo, nitro, CN, $C_{1-3}$ alkyl (which latter group is unsubstituted or substituted by one or more substituents selected from OH, ═O, halo, $C_{1-4}$ alkyl and $C_{1-4}$ alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{12a}$, $NR^{12g}R^{12h}$, aryl and $Het^1$);

(iv) $Cy^2$ (which $Cy^2$ group is unsubstituted or is substituted by one or more substituents selected from halo, CN, $C_{1-3}$ alkyl (which latter group is optionally substituted by one or more substituents selected from OH, =O, halo, $C_{1-4}$ alkyl and $C_{1-4}$ alkoxy), $OR^{13a}$, $NR^{13g}R^{13h}$, aryl and $Het^2$);

(v) $Het^a$ (which $Het^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and $C_{1-4}$ alkoxy), $OR^{14a}$, $NR^{14g}R^{14h}$, aryl and $Het^3$);

(vi) $OR^{15a}$; or (vii) $NR^{15g}R^{15h}$.

8. The compound according to Clause 7, wherein $R^2$ represents:

(i) H;

(ii) Br, Cl, F;

(iii) $C_{1-4}$ alkyl which is unsubstituted or substituted by one or more substituents selected from F, $C_{1-3}$ alkyl (which latter group is unsubstituted or substituted by one or more substituents selected from OH, =O, F, $C_{1-4}$ alkyl and $C_{1-4}$ alkoxy), $OR^{12a}$ and $NR^{12g}R^{12h}$);

(iv) $OR^{15a}$; or (v) $NR^{15g}R^{15h}$.

9. The compound according to Clause 7 or Clause 8, wherein $R^2$ represents H, Br or Cl.

10. The compound according to any one of the preceding clauses, wherein $R^3$, $R^4$, $R^8$ and $R^{10}$, at each occurrence, independently represents:

(i) H;

(ii) Br, Cl, F;

(iii) CN;

(iv) $C_{1-4}$ alkyl, $C_{2-4}$ alkenyl, $C_{2-4}$ alkynyl (which latter three groups are unsubstituted or substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{12a}$, $NR^{12g}R^{12h}$; aryl and $Het^1$), (v) $Cy^2$ (which $Cy^2$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{13a}$, $NR^{13g}R^{13h}$, aryl and $Het^2$);

(vi) $Het^a$ (which $Het^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and $C_{1-4}$ alkoxy), $OR^{14a}$, $NR^{14g}R^{14h}$; aryl and $Het^3$);

(vii) $OR^{15a}$;

(viii) $NR^{15g}R^{15h}$; or (ix) nitro.

11. The compound according to Clause 10, wherein $R^3$, $R^4$, $R^8$ and $R^{10}$, at each occurrence, independently represents Br, Cl, F, CN, $C_{1-4}$ alkyl (which latter group is unsubstituted or substituted by one or more substituents selected from F, $C_{1-3}$ alkyl (which latter group is unsubstituted or substituted by one or more substituents selected from OH, =O, halo, $C_{1-4}$ alkyl and $C_{1-4}$ alkoxy), $OR^{12a}$ and $NR^{12g}R^{12h}$), $OR^{15a}$; $NR^{15g}R^{15h}$; nitro, or H.

12. The compound according to Clause 10 or Clause 11, wherein $R^3$, $R^4$, $R^8$ and $R^{10}$, at each occurrence, each independently represent H.

13. The compound according to any one of the preceding clauses, wherein $R^5$ and $R^9$, at each occurrence, independently represent H, Br, Cl, F, CN, nitro, $C_{1-4}$ alkyl (which latter group is unsubstituted or substituted by one or more substituents selected from Br, Cl, F, $OR^{16a}$ and $NR^{16g}R^{16h}$), $OR^{17a}$ or $NR^{17g}R^{17h}$.

14. The compound according to any one of the preceding clauses, wherein:

$R^{6a}$ represents H or CN; and $R^{6b}$, independently at each occurrence, represents H or $C_{1-4}$ alkyl, which latter group is unsubstituted or substituted with F or $OR^{19}$.

15. The compound according to Clause 14, wherein $R^{6a}$ represents CN and $R^{6b}$ represents H.

16. The compound according to any one of the preceding clauses, wherein $R^{11a}$ represents, (i) $C_{1-5}$ alkyl which group is unsubstituted or substituted by one or more substituents selected from halo, =O, CN, $C_{1-3}$ alkyl (which latter group is unsubstituted or substituted by one or more substituents selected from OH, =O, halo, $C_{1-4}$ alkyl and $C_{1-4}$ alkoxy), $OR^{21a}$, $NR^{21g}R^{21h}$, aryl, $Cy^3$ (which $Cy^3$ group is unsubstituted or is substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$alkoxy), $OR^{22a}$, $NR^{22g}R^{22h}$, aryl and $Het^4$) and $Het^5$;

(ii) $C_{3-6}$ cycloalkyl which latter group is unsubstituted or substituted by one or more substituents selected from halo, OH, =O, $C_{1-4}$ alkyl and $C_{1-4}$ alkoxy;

(iii) $Het^b$ (which $Het^b$ group is unsubstituted or substituted by one or more substituents selected from halo, nitro, CN, $C(O)OC_{1-4}$ alkyl, $C_{1-5}$ alkyl, (which latter group is unsubstituted or substituted by one or more substituents selected from $Het^8$, OH, =O, halo, $C_{1-4}$ alkyl and $C_{1-4}$ alkoxy), $OR^{23a}$, $NR^{23g}R^{23h}$, aryl and $Het^6$);

(iv) $OR^{24a}$; or (v) $NR^{24d}R^{24e}$.

17. The compound according to Clause 16, wherein $R^{11a}$ represents:

(i) $C_{1-5}$ alkyl which group is unsubstituted or substituted by one or more substituents selected from Cl, F, =O, CN, $C_{1-3}$ alkyl (which latter group is unsubstituted or substituted by one or more substituents selected from OH, =O, Cl, F, $C_{1-4}$ alkyl and $C_{1-4}$alkoxy), $OR^{21a}$, $NR^{21g}R^{21h}$;

(ii) $C_{3-6}$ cycloalkyl which latter group is unsubstituted or substituted by one or more substituents selected from Cl, F, OH, =O, $C_{1-4}$ alkyl and $C_{1-4}$ alkoxy;

(iii) $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, OH, =O, Cl, F, $C_{1-4}$ alkyl and $C_{1-4}$ alkoxy), $OR^{23a}$, $NR^{23g}R^{23h}$)

(e.g. $Het^b$ (which $Het^b$ group is unsubstituted or substituted by one or more substituents selected from halo, nitro, CN, $C(O)OC_{1-4}$ alkyl, $C_{1-4}$ alkyl, (which latter group is unsubstituted or substituted by one or more substituents selected from OH, =O, halo, $C_{1-4}$ alkyl and $C_{1-4}$ alkoxy), $OR^{23a}$, $NR^{23g}R^{23h}$, aryl and $Het^6$));
(iv) $OR^{24a}$; or
(v) $NR^{24d}R^{24e}$.

18. The compound according to Clause 16 or Clause 17, wherein $R^{11a}$ represents, $C_{1-5}$ alkyl which group is unsubstituted or substituted by one or more substituents selected from F, =O, $C_{1-3}$ alkyl (which latter group is unsubstituted or substituted by one or more substituents selected from OH, =O, F, $C_{1-4}$ alkyl and $C_{1-4}$ alkoxy), $OR^{21a}$, $NR^{21g}R^{21h}$, $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, or more particularly, OH, =O, Cl, F, $C_{1-4}$ alkyl and $C_{1-4}$ alkoxy), $OR^{23a}$, $NR^{23g}R^{23h}$) (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$alkoxy), $OR^{23a}$, $NR^{23g}R^{23h}$)), or $OR^{24a}$.

19. The compound according to any one of the preceding clauses, wherein $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl, $C_{2-4}$ alkenyl (which latter two groups are optionally substituted by one or more substituents selected from halo, nitro, =O, $C(O)OC_{1-4}$ alkyl, CN, $C_{1-3}$ alkyl, $C_{5-6}$ cycloalkyl (which latter two groups are optionally substituted by one or more substituents selected from OH, =O, halo, $C_{1-4}$ alkyl and $C_{1-4}$ alkoxy), $OR^{25a}$, $NR^{25g}R^{25h}$, aryl and $Het^7$), $C_{4-6}$ cycloalkyl, or $C_{5-6}$ cycloalkenyl (which latter two groups are optionally substituted by one or more substituents selected from halo, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 3- to 6-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy).

20. The compound according to Clause 19, wherein:

$R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl (which latter group is unsubstituted or substituted by one or more substituents selected from Cl, F, =O, $C(O)OC_{1-4}$ alkyl, $C_{1-3}$ alkyl, $C_{5-6}$ cycloalkyl (which latter two groups are optionally substituted by one or more substituents selected from OH, =O, Cl, F, $C_{1-4}$ alkyl and $C_{1-4}$ alkoxy), $OR^{25a}$, $NR^{25g}R^{25h}$, aryl and $Het^7$), $C_{4-6}$ cycloalkyl (which latter group is unsubstituted or substituted by one or more substituents selected from Cl, F, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 5- to 6-membered heterocyclic ring that may be aromatic, fully saturated or partially unsaturated and which may additionally contain one or more heteroatoms selected from O, S and N, which heterocyclic ring is unsubstituted or substituted by one or more substituents selected from halo, nitro, CN, $C_{1-3}$ alkyl (which latter group is unsubstituted or substituted by one or more substituents selected from OH, =O, Cl, F, $C_{1-4}$ alkyl and $C_{1-4}$ alkoxy.

21. The compound according to Clause 19 or Clause 20, wherein $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-3}$ alkyl (which latter group is unsubstituted or substituted by one or more substituents selected from F, =O, $C(O)OC_{1-4}$ alkyl, $C_{1-3}$ alkyl (which latter group is unsubstituted or substituted by one or more substituents selected from OH, =O, Cl, F, $C_{1-4}$ alkyl and $C_{1-4}$ alkoxy), $OR^{25a}$, $NR^{25g}R^{25h}$).

22. The compound according to any one of the preceding clauses, wherein $Het^1$ to $Het^8$ (e.g. $Het^1$ to $Het^7$) and $Het^a$ to $Het^c$ independently represent a 4- to 10-membered heterocyclic group containing one or more heteroatoms selected from O, S and N, which heterocyclic groups may comprise one, two or three rings and may be substituted by one or more substituents selected from =O, or more particularly, halo, $C_{1-3}$ alkyl, which latter group is optionally substituted by one or more substituents selected from halo, $—OR^{26a}$, $—NR^{26b}R^{26c}$, $—C(O)OR^{26d}$ and $—C(O)NR^{26e}R^{26f}$.

23. The compound according to Clause 22, wherein $Het^1$ to $Het^8$ (e.g. $Het^1$ to $Het^7$) and $Het^a$ to $Het^c$ independently represent a 5- to 8-membered heterocyclic group containing one or more heteroatoms selected from O, S and N, which heterocyclic groups may comprise one, two or three rings and may be substituted by one or more substituents selected from =O, or more particularly, Cl, Br, F, $C_{1-3}$ alkyl, which latter group is optionally substituted by one or more substituents selected from halo, $—OR^{26a}$, $—NR^{26b}R^{26c}$, $—C(O)OR^{26d}$ and $—C(O)NR^{26e}R^{26f}$.

24. The compound according to any one of the preceding clauses, wherein $Cy^1$ to $Cy^3$, at each occurrence, independently represent a 4- to 6-membered aromatic, fully saturated or partially unsaturated carbocyclic ring.

25. The compound according to any one of the preceding clauses, wherein $R^{25a}$ to $R^{25h}$ and $R^{26a}$ to $R^{26f}$ independently represent at each occurrence, H, $C_{1-4}$ alkyl, which latter group is optionally substituted by one or more substituents selected from halo, nitro, CN, $C_{1-4}$ alkyl, (which latter group is unsubstituted or substituted by one or more substituents selected from OH, =O, halo, $C_{1-4}$ alkyl and $C_{1-4}$ alkoxy), $C_{3-6}$ cycloalkyl (which latter group is unsubstituted or substituted by one or more substituents selected from halo, OH, =O, $C_{1-4}$ alkyl and $C_{1-4}$ alkoxy).

26. The compound according to any one of the preceding clauses, wherein L represents —C(CN)=C(H)—, Z represents $CR^4$, and the compound of formula I is represented as a compound of formula Ia, Ia

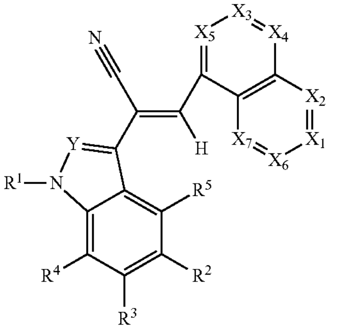

provided that no more than three of $X_1$ to $X_7$ represent N.

27. The compound according to any one of the preceding clauses, wherein L represents —C(CN)═C(H)—, Z represents $CR^4$, $X_1$ represents N, and the compound of formula I may be represented as a compound of formula Ib, Ib

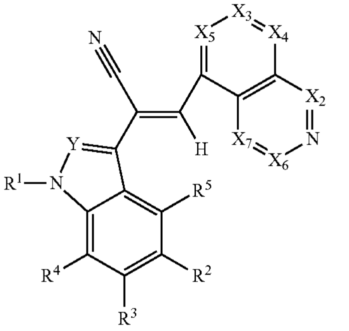

provided that no more than three of $X_2$ to $X_7$ represent N.

28. The compound according to any one of the preceding clauses, wherein L represents —C(CN)═C(H)—, $X_1$ represents N, Z represents $CR^4$, and $X_2$ to $X_5$ each represent $CR^8$, and the compound of formula I may be represented as a compound of formula Ic, Ic

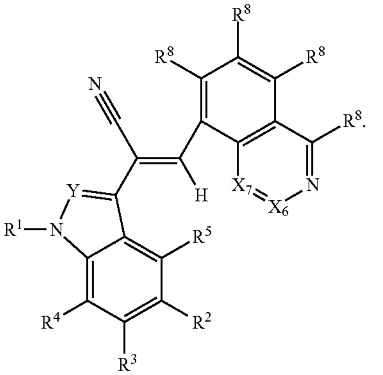

29. The compound according to any one of the preceding clauses, wherein L represents —C(CN)═C(H)—, $X_1$ represents N, $X_2$ to $X_5$ each represent $CR^8$, Z represents $CR^4$, and Y represents $CR^{10}$, and the compound of formula I may be represented as a compound of formula Id, Id

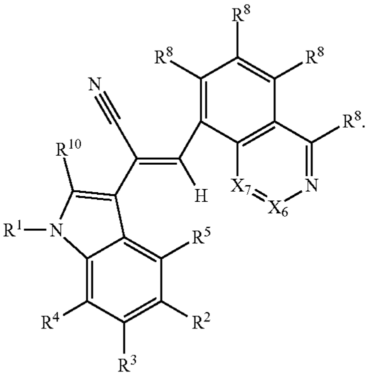

30. The compound according to any one of the preceding clauses, wherein L represents —C(CN)═C(H)—, $X_1$ represents N, $X_2$ to $X_5$ each represent $CR^8$, Z represents $CR^4$, Y represents $CR^{10}$ and $R^5$ represents H, and the compound of formula I may be represented as a compound of formula Ie, Ie

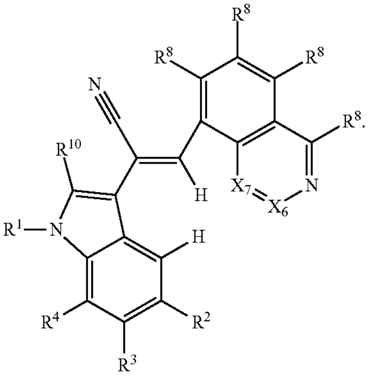

31. The compound according to any one of the preceding clauses, wherein when L represents —C($R^{6a}$)═C($R^{6b}$)—, the C═C double bond is in the E- or Z-configuration.

32. The compound according to any one of the preceding clauses, wherein:

(a) $R^2$ represents:

(i) H;

(ii) Br, Cl, F;

(iii) $C_{1-4}$ alkyl which is unsubstituted or substituted by one or more substituents selected from F, $C_{1-3}$ alkyl (which latter group is unsubstituted or substituted by one or more substituents selected from OH, ═O, F, $C_{1-4}$ alkyl and $C_{1-4}$ alkoxy), $OR^{12a}$ and $NR^{12g}R^{12h}$);

(iv) $OR^{15a}$; or (v) $NR^{15g}R^{15h}$); and/or (b) $R^3$, $R^4$, $R^8$ and $R^{10}$, at each occurrence, independently represents H, Br, Cl, F, CN, $C_{1-4}$ alkyl (which latter groups is unsubstituted or substituted by one or more substituents selected from F, $C_{1-3}$ alkyl (which latter group is unsubstituted or substituted by one or more substituents selected from OH, ═O, halo, $C_{1-4}$ alkyl and $C_{1-4}$alkoxy), $OR^{12a}$ and $NR^{12g}R^{12h}$), $OR^{15a}$, $NR^{15g}R^{15h}$, nitro); and/or (c) $R^{11a}$ represents, $C_{1-5}$ alkyl which group is unsubstituted or substituted by one or more substituents selected from F, =O, $C_{1-3}$ alkyl (which latter group is unsubstituted or substituted by one or more substituents selected from OH, =O, F, $C_{1-4}$ alkyl and $C_{1-4}$ alkoxy), $OR^{21a}$, $NR^{21g}R^{21h}$, $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, OH, =O, Cl, F, $C_{1-4}$ alkyl and $C_{1-4}$ alkoxy), $OR^{23a}$, $NR^{23g}R^{23h}$), or $OR^{24a}$ (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$)), or $OR^{24a}$); and/or (d) $R^{12a}$ to $R^{12h}$, $R^{13a}$ to $R^{13h}$, $R^{14a}$ to $R^{14h}$, $R^{15a}$ to $R^{15h}$, $R^{18a}$ to $R^{18h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl (which latter group is unsubstituted or substituted by one or more substituents selected from Cl, F, =O, $C(O)OC_{1-4}$ alkyl, $C_{1-3}$ alkyl, $C_{5-6}$ cycloalkyl (which latter two groups are optionally substituted by one or more substituents selected from OH, =O, Cl, F, $C_{1-4}$ alkyl and $C_{1-4}$ alkoxy), $OR^{25a}$, $NR^{25g}R^{25h}$, aryl and $Het^7$), $C_{4-6}$ cycloalkyl (which latter group is unsubstituted or substituted by one or more substituents selected from Cl, F, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 5- to 6-membered heterocyclic ring that may be aromatic, fully saturated or partially unsaturated and which may additionally contain one or more heteroatoms selected from O, S and N, which heterocyclic ring is unsubstituted or substituted by one or more substituents selected from halo, nitro, CN, $C_{1-3}$ alkyl (which latter group is unsubstituted or substituted by one or more substituents selected from OH, =O, Cl, F, $C_{1-4}$ alkyl and $C_{1-4}$ alkoxy); and/or (e) $Het^1$ to $Het^8$ (e.g. $Het^1$ to $Het^7$) and $Het^a$ to $Het^c$ independently represent a 5- to 8-membered heterocyclic group containing one or more heteroatoms selected from O, S and N, which heterocyclic groups may comprise one, two or three rings and may be substituted by one or more substituents selected from =O, or more particularly, Cl, Br, F, $C_{1-3}$ alkyl, which latter group is optionally substituted by one or more substituents selected from halo, $-OR^{26a}$, $-NR^{26b}R^{26c}$, $-C(O)OR^{26d}$ and $-C(O)NR^{28e}R^{28f}$).

33. The compound according to any one of the preceding clauses, wherein:

(a) $R^2$ represents Br, Cl or H;

(b) $R^3$, $R^4$, $R^8$ and $R^{10}$, at each occurrence, each represent H;

(c) represents, (i) $C_{1-5}$ alkyl which group is unsubstituted or substituted by one or more substituents selected from Cl, F, =O, CN, $C_{1-3}$ alkyl (which latter group is unsubstituted or substituted by one or more substituents selected from OH, =O, Cl, F, $C_{1-4}$ alkyl and $C_{1-4}$ alkoxy), $OR^{21a}$, $NR^{21g}R^{21h}$;

(ii) $C_{3-6}$ cycloalkyl which latter group is unsubstituted or substituted by one or more substituents selected from Cl, F, OH, =O, $C_{1-4}$ alkyl and $C_{1-4}$ alkoxy;

(iii) $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, OH, =O, Cl, F, $C_{1-4}$ alkyl and $C_{1-4}$ alkoxy), $OR^{23a}$, $NR^{23g}R^{23h}$) (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$));

(iv) $OR^{24a}$; or (v) $NR^{24d}R^{24e}$, (d) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22}$, $R^{23a}$ to $R^{23h}$ and $R^{24a}$ to $R^{24e}$ independently represent, at each occurrence, H, $C_{1-3}$ alkyl (which latter group is unsubstituted or substituted by one or more substituents selected from F, =O, $C(O)OC_{1-4}$ alkyl, $C_{1-3}$ alkyl (which latter group is unsubstituted or substituted by one or more substituents selected from OH, =O, Cl, F, $C_{1-4}$ alkyl and $C_{1-4}$ alkoxy), $OR^{25a}$, $NR^{25g}R^{25h}$).

34. The compound according to any one of the Clauses 1 to 25, wherein L represents —C(CN)=C(H)—, $X_1$ represents N, $X_2$ to $X_5$ each represent $CR^8$, $X_6$ and $X_7$ each represent $CR^9$, Z represents $CR^4$, Y represents $CR^{19}$ and $R^5$ represents H, and the compound of formula I may be represented as a compound of formula If, If

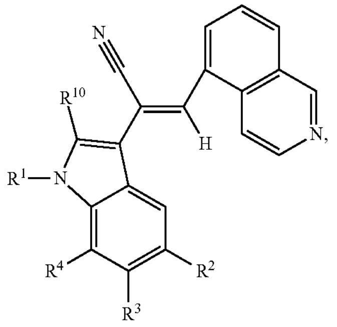

provided that $R^4$ is not Br or methylenepyrrolidine; and/or provided that $R^2$ is not Cl, F, or $OR^{15a}$ (where $R^{15a}$ comprises more than one carbon atom) or $NR^{15g}R^{15h}$.

35. The compound according to Clause 34, wherein:

$R^3$ represents H; and/or $R^{10}$ represents H or $CH_3$; and/or $R^2$ represents H, Br or $OCH_3$; and/or $R^4$ represents H or $OCH_3$.

36. The compound according to Clause 34 or Clause 35, wherein:

$R^1$ represents $C(O)R^{11a}$ and $R^{11a}$ represents:

(a) H;

(b) $C_{1-6}$ alkyl (which group is unsubstituted or substituted by one or more substituents selected from =O, $C_{1-6}$ alkyl (which latter group is unsubstituted or substituted by one or more substituents selected from OH, =O, $C_{1-4}$ alkyl and $C_{1-4}$ alkoxy), $OR^{21a}$, $NR^{21g}R^{21h}$, aryl, $Cy^3$, and $Het^5$);

(c) $C_{3-10}$ cycloalkyl (which group is optionally substituted by one or more substituents selected from halo, OH, =O, $C_{1-6}$ alkyl and $C_{1-6}$ alkoxy);

(d) $Het^b$ (which $Het^b$ group is unsubstituted or substituted by one or more substituents selected from halo, nitro, CN, $C(O)OC_{1-4}$ alkyl, $C_{1-6}$ alkyl (which latter group is optionally substituted by one or more substituents selected from $Het^8$, or more particularly, OH, =O, halo, $C_{1-4}$ alkyl and $C_{1-4}$ alkoxy), $OR^{23a}$, $NR^{23g}R^{23h}$, aryl and $Het^6$), (e) $OR^{24a}$;

(f) $NR^{24d}R^{24e}$.

37. The compound according to Clause 36, wherein:

$R^{11a}$ represents:

(a) H;

(b) $C_{1-6}$ alkyl (which group is unsubstituted or substituted by one or more substituents selected from =O, $OR^{21a}$, and $NR^{21g}R^{21h}$);

(c) piperidinyl or piperazinyl (which $Het^b$ group is unsubstituted or substituted by one or more substituents selected from $C(O)OC_{1-4}$ alkyl, $C_{1-6}$ alkyl (which group is optionally substituted by one or more substituents selected from $Het^8$, or more particularly, =O, $C_{1-4}$ alkyl and $C_{1-4}$ alkoxy), $OR^{23a}$, and $NR^{23g}R^{23h}$).

38. The compound according to any one of the Clauses 1 to 25, wherein L represents —C($R^{6a}$)=C(H)—, $X_1$ represents N, $X_2$, $X_4$ and $X_5$ each represent $CR^8$, $X_3$ represents N or $CR^8$, $X_6$ and $X_7$ each represent $CR^9$, and $R^5$ represents H, and the compound of formula I may be represented as a compound of formula Ig, Ig

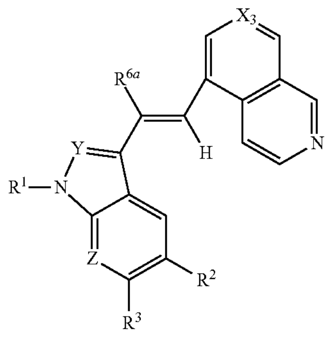

provided that when $R^{6a}$ represents CN:

$R^2$ is not F, Br or $OCH_3$; and/or when Z is $OR^4$, $OR^4$ is not $OCH_3$.

39. The compound according to Clause 38, wherein:

$R^3$ represents H or methylenepyrrolidinyl;

$R^2$ and $R^3$ independently represent H, $OR^{15a}$, Cl or $C_{1-6}$ alkyl (which latter group is unsubstituted or substituted by one or more substituents selected from $OR^{12a}$, $NR^{12g}R^{12h}$, aryl and $Het^1$); and/or $R^4$, when present, represents H or Br.

40. The compound according to any one of the preceding clauses, wherein the compound of formula I is selected from the list:

(i) (Z)-2-(1H-indol-3-yl)-3-(5-isoquinolyl)prop-2-enenitrile;

(ii) (Z)-3-(5-isoquinolyl)-2-(5-methoxy-1H-indol-3-yl)prop-2-enenitrile;

(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide;

(iv) (Z)-2-(5-chloro-1H-indol-3-yl)-3-(5-isoquinolyl)prop-2-enenitrile;

(v) (Z)-2-(5-bromo-1H-indol-3-yl)-3-(5-isoquinolyl)prop-2-enenitrile;

(vi) (Z)-3-(5-isoquinolyl)-2-[1-[2-(4-methylpiperazin-1-yl)acetyl]indol-3-yl]prop-2-enenitrile;

(vii) N-[3-[3-[(Z)-1-cyano-2-(5-isoquinolyl)vinyl]indol-1-yl]-3-oxo-propyl]acetamide;

(viii) (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl) prop-2-enenitrile and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile;

(ix) tert-butyl 4-[3-[(Z)-1-cyano-2-(5-isoquinolyl)vinyl]indole-1-carbonyl]piperidine-1-carboxylate;

(x) (Z)-3-(5-isoquinolyl)-2-[1-(piperidine-4-carbonyl)indol-3-yl]prop-2-enenitrile;

(xi) (Z)-3-(5-isoquinolyl)-2-[1-(1-methylpiperidine-4-carbonyl)indol-3-yl]prop-2-enenitrile;

(xii) (Z)-3-(5-isoquinolyl)-2-[1-(1-(3-fluorophenyl)-piperidine-4-carbonyl)indol-3-yl]prop-2-enenitrile;

(xiii) (Z)-3-(5-isoquinolyl)-2-[1-(1-oxazol-4-yl-piperidine-4-carbonyl)indol-3-yl]prop-2-enenitrile;

(xiv) (Z)-3-(5-isoquinolyl)-2-[1-(1-(2-methoxyacetyl)-piperidine-4-carbonyl)indol-3-yl]prop-2-enenitrile;

(xv) (Z)-2-(6-bromo-1H-indol-3-yl)-3-(5-isoquinolyl)prop-2-enenitrile;

(xvi) (Z)-2-(6-chloro-1H-indol-3-yl)-3-(5-isoquinolyl)prop-2-enenitrile;

(xvii) (Z)-3-(5-isoquinolyl)-2-(6-methoxy-1H-indol-3-yl)prop-2-enenitrile;

(xviii) (Z)-2-(5,6-dimethoxy-1H-indol-3-yl)-3-(5-isoquinolyl)prop-2-enenitrile;

(xix) (Z)-3-(5-isoquinolyl)-2-(7-methyl-1H-indol-3-yl)prop-2-enenitrile;

(xx) 3-[(Z)-1-cyano-2-(5-isoquinolyl)vinyl]-N-methyl-1H-indole-7-carboxamide;

(xxi) 5-chloro-3-[(Z)-1-cyano-2-(5-isoquinolyl)vinyl]-N-methyl-1H-indole-7-carboxamide;

(xxii) (Z)-2-(5,7-dimethoxy-1H-indol-3-yl)-3-(5-isoquinolyl)prop-2-enenitrile;

(xxiii) (Z)-3-(5-isoquinolyl)-2-(7-methoxy-1H-indol-3-yl)prop-2-enenitrile;

(xxiv) N-[3-[(Z)-1-cyano-2-(5-isoquinolyl)vinyl]-1H-indol-7-yl]acetamide;

(xxv) (Z)-2-(7-chloro-1H-indol-3-yl)-3-(5-isoquinolyl)prop-2-enenitrile;

(xxvi) (Z)-2-(7-fluoro-1H-indol-3-yl)-3-(5-isoquinolyl)prop-2-enenitrile;

(xxvii) (Z)-2-[7-(2-fluorophenyl)-1H-indol-3-yl]-3-(5-isoquinolyl)prop-2-enenitrile;

(xxviii) 2-(1H-indol-3-yl)-3-(5-isoquinolyl)propanenitrile;

(xxix) (Z)-2-(1H-indol-3-yl)-3-(5-isoquinolyl)but-2-enenitrile;

(xxx) (Z)-3-(1H-indol-3-yl)-2-(5-isoquinolyl)prop-2-enenitrile;

(xxxi) N-(1H-indol-3-yl)isoquinoline-5-carboxamide;

(xxxii) tert-butyl N-[3-[3-[(Z)-1-cyano-2-(5-isoquinolyl)vinyl]indol-1-yl]-3-oxopropyl]carbamate;

(xxxiii) (Z)-2-[1-(3-amino-1-oxo-propyl)indol-3-yl]-3-(5-isoquinolyl)prop-2-enenitrile;

(xxxiv) tert-butyl N-[5-[3-[(Z)-1-cyano-2-(5-isoquinolyl) vinyl]indol-1-yl]-5-oxo-pentyl]carbamate;

(xxxv) (Z)-2-[1-(5-amino-1-oxo-pentyl)indol-3-yl]-3-(5-isoquinolyl)prop-2-enenitrile;

(xxxvi) tert-butyl N-[6-[3-[(Z)-1-cyano-2-(5-isoquinolyl) vinyl]indol-1-yl]-6-oxo-hexyl]carbamate;

(xxxvii) (Z)-2-(1-(6-aminohexanoyl)-1H-indol-3-yl)-3-(isoquinolin-5-yl)acrylonitrile;

(xxxviii) (Z)-2-(1H-indazol-3-yl)-3-(5-isoquinolyl)prop-2-enenitrile;

(xxxlx) (Z)-3-(5-isoquinolyl)-2-(4-methyl-1H-indol-3-yl) prop-2-enenitrile;

(xl) (Z)-3-(5-isoquinolyl)-2-(4-methoxy-1H-indol-3-yl) prop-2-enenitrile;

(xli) (Z)-2-(4,5-dimethoxy-1H-indol-3-yl)-3-(5-isoquinolyl)prop-2-enenitrile;

(xlii) (Z)-2-(4-chloro-1H-indol-3-yl)-3-(5-isoquinolyl) prop-2-enenitrile;

(xliii) 4-chloro-3-[(Z)-1-cyano-2-(5-isoquinolyl)vinyl]-1H-indole-5-carboxamide;

(xliv) (Z)-2-(1H-indol-3-yl)-3-(5-quinolyl)prop-2-enenitrile;

(xlv) 5-((E)-2-(1H-indol-3-yl)vinyl)isoquinoline;

(xlvi) 4-((E)-2-(1H-indol-3-yl)vinyl)-2,7-naphthyridine;

(xlvii) 5-((E)-2-(1H-pyrrolo[2,3-b]pyridin-3-yl)vinyl)isoquinoline;

(xlviii) 4-((E)-2-(1H-pyrrolo[2,3-b]pyridin-3-yl)vinyl)-2,7-naphthyridine;

(xlix) [3-[(E)-2-(5-isoquinolyl)vinyl]-1H-indol-5-yl] azinic acid;

(l) N-(5-isoquinolyl)-1H-indole-3-carboxamide;

(li) (Z)-2-(1H-indol-3-yl)-3-(2,7-naphthyridin-4-yl)prop-2-enenitrile;

(lii) (Z)-3-(5-isoquinolyl)-2-[5-(3-pyrrolidin-1-yl-propoxy)-1H-indol-3-yl]prop-2-enenitrile;

(liii) (Z)-3-(5-isoquinolyl)-2-[5-(2-methoxyethoxy)-1H-indol-3-yl]prop-2-enenitrile;

(liv) (Z)-2-(6-chloro-1H-indol-3-yl)-3-(5-isoquinolyl) prop-2-enenitrile;

(lv) (Z)-2-(7-bromo-1H-indol-3-yl)-3-(5-isoquinolyl) prop-2-enenitrile;

(lvi) tert-butyl N-[3-[3-[(Z)-1-cyano-2-(5-isoquinolyl)vinyl]indol-1-yl]-3-oxo-propyl]carbamate;

(lvii) (Z)-2-[1-(3-aminopropanoyl)indol-3-yl]-3-(5-isoquinolyl) prop-2-enenitrile;

(lviii) 5-[(3aS,4S,6aR)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide and/or 5-[(3aR,4R,6aS)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide;

(lix) (Z)-2-(5-(2-(1,3-dioxolan-2-yl)ethoxy)-1H-indol-3-yl)-3-(isoquinolin-5-yl)acrylonitrile;

(lx) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile;

(lxi) (Z)-2-(1-(2-(2-methoxyethoxy)acetyl)-1H-indol-3-yl)-3-(isoquinolin-5-yl)acrylonitrile;

(lxii) (Z)-3-(isoquinolin-5-yl)-2-(6-((pyrrolidin-1-yl) methyl)-1H-indol-3-yl)acrylonitrile;

(lxiii) (Z)-3-(isoquinolin-5-yl)-2-(5-((pyrrolidin-1-yl) methyl)-1H-indol-3-yl)acrylonitrile;

(lxiv) (Z)-3-(isoquinolin-5-yl)-2-(7-((pyrrolidin-1-yl) methyl)-1H-indol-3-yl)acrylonitrile; and (lxv) (Z)-2-(1H-indazol-3-yl)-3-(isoquinolin-5-yl)acrylonitrile.

41. The compound according to Clause 40, wherein the compound of formula I is selected from the list:

(i) (Z)-2-(1H-indol-3-yl)-3-(5-isoquinolyl)prop-2-enenitrile;

(ii) (Z)-3-(5-isoquinolyl)-2-(5-methoxy-1H-indol-3-yl) prop-2-enenitrile;

(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide;

(iv) (Z)-2-(5-chloro-1H-indol-3-yl)-3-(5-isoquinolyl) prop-2-enenitrile;

(v) (Z)-2-(5-bromo-1H-indol-3-yl)-3-(5-isoquinolyl) prop-2-enenitrile;

(vi) (Z)-3-(5-isoquinolyl)-2-[1-[2-(4-methylpiperazin-1-yl)acetyl]indol-3-yl]prop-2-enenitrile;

(vii) N-[3-[3-[(Z)-1-cyano-2-(5-isoquinolyl)vinyl]indol-1-yl]-3-oxo-propyl]acetamide;

(viii) tert-butyl 4-[3-[(Z)-1-cyano-2-(5-isoquinolyl)vinyl] indole-1-carbonyl]piperidine-1-carboxylate;

(ix) (Z)-3-(5-isoquinolyl)-2-[1-(piperidine-4-carbonyl)indol-3-yl]prop-2-enenitrile;

(x) (Z)-3-(isoquinolin-5-yl)-2-(7-methoxy-1H-indol-3-yl) acrylonitrile;

(xi) (Z)-3-(isoquinolin-5-yl)-2-(6-methoxy-1H-indol-3-yl)acrylonitrile;

(xii) (Z)-tert-butyl (3-(3-(1-cyano-2-(isoquinolin-5-yl)vinyl)-1H-indol-1-yl)-3-oxopropyl)carbamate;

(xiii) N-(3-(3-(Z)-1-cyano-2-(isoquinolin-5-yl)vinyl)-1H-indol-1-yl)-3-oxopropyl)-5-((3aS,4S,6aR)-2-oxohexahydro-1H-thieno[3,4-d]imidazol-4-yl)pentanamide;

(xiv) N-(3-(Z)-1-cyano-2-(isoquinolin-5-yl)vinyl)-1H-indol-5-yl)acetamide (xv) (Z)-2-(6-bromo-1H-indol-3-yl)-3-(5-isoquinolyl) prop-2-enenitrile;

(xvi) (Z)-2-(7-bromo-1H-indol-3-yl)-3-(5-isoquinolyl) prop-2-enenitrile;

(xvii) (Z)-2-[1-(3-aminopropanoyl)indol-3-yl]-3-(5-isoquinolyl)prop-2-enenitrile;

(xviii) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile; and (xix) (Z)-2-(1-(2-(2-methoxyethoxy)acetyl)-1H-indol-3-yl)-3-(isoquinolin-5-yl)acrylonitrile.

42. The compound according to Clause 40, wherein the compound of formula I is (Z)-2-(1H-indol-3-yl)-3-(5-quinolyl)prop-2-enenitrile, (Z)-tert-butyl 4-(3-(1-cyano-2-(isoquinolin-5-yl)vinyl)-1H-indole-1-carbonyl)piperidine-1-carboxylate and (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl) prop-2-enenitrile.

43. The compound according to Clause 40, wherein the compound of formula I is selected from the list:

(a) 5-((E)-2-(1H-indol-3-yl)vinyl)isoquinoline;

(b) 4-((E)-2-(1H-indol-3-yl)vinyl)-2,7-naphthyridine;

(c) 5-((E)-2-(1H-pyrrolo[2,3-b]pyridin-3-yl)vinyl)isoquinoline;

(d) 4-((E)-2-(1H-pyrrolo[2,3-b]pyridin-3-yl)vinyl)-2,7-naphthyridine;

(e) N-(5-isoquinolyl)-1H-indole-3-carboxamide;

(f) (Z)-2-(1H-indol-3-yl)-3-(2,7-naphthyridin-4-yl)prop-2-enenitrile;

(g) (Z)-3-(5-isoquinolyl)-2-[5-(3-pyrrolidin-1-yl-propoxy)-1H-indol-3-yl]prop-2-enenitrile;

(h) (Z)-3-(5-isoquinolyl)-2-[5-(2-methoxyethoxy)-1H-indol-3-yl]prop-2-enenitrile;

(i) (Z)-2-(5-(2-(1,3-dioxolan-2-yl)ethoxy)-1H-indol-3-yl)-3-(isoquinolin-5-yl)acrylonitrile;

(j) (Z)-3-(isoquinolin-5-yl)-2-(6-((pyrrolidin-1-yl)methyl)-1H-indol-3-yl)acrylonitrile;

(k) (Z)-3-(isoquinolin-5-yl)-2-(5-((pyrrolidin-1-yl)methyl)-1H-indol-3-yl)acrylonitrile;

(l) (Z)-3-(isoquinolin-5-yl)-2-(7-((pyrrolidin-1-yl)methyl)-1H-indol-3-yl)acrylonitrile; and (m) (Z)-2-(1H-indazol-3-yl)-3-(isoquinolin-5-yl)acrylonitrile.

44. A pharmaceutical formulation including a compound of formula I, as defined in any one of Clauses 1 to 43, in admixture with a pharmaceutically-acceptable adjuvant, diluent or carrier.

45. A compound of formula I, as defined in any one of Clauses 1 to 43, for use in medicine.

46. A compound of formula I, as defined in any one of Clauses 1 to 43, for use in the treatment or prevention of a hyperproliferative disease or disorder.

47. Use of a compound of formula I, as defined in any one of Clauses 1 to 43, for the preparation of a medicament for the treatment of a hyperproliferative disease or disorder.

48. A method of treatment of a hyperproliferative disease or disorder, which method comprises the administration of an effective amount of a compound of formula I, as defined in any one of Clauses 1 to 43.

49. The compound for use of Clause 46, the use of Clause 47 or the method of Clause 48, wherein the therapy is an adjuvant therapy after surgical treatment or is a neoadjuvant therapy before main treatment of the proliferative disorder or disease.

50. A compound of formula I having only antimitotic activity, as defined in any one of Clauses 1 to 40 and 42, and an anti-autophagy and/or chemoprotective agent for use in the treatment of a hyperproliferative disease or disorder.

51. A compound of formula I having only antimitotic activity, as defined in any one of Clauses 1 to 40 and 42, for use in the treatment of a hyperproliferative disease or disorder, wherein the compound of formula I is administered sequentially, simultaneously or concomitantly with an anti-autophagy and/or chemoprotective agent.

52. Use of a compound of formula I having only antimitotic activity, as defined in any one of Clauses 1 to 40 and 42, and an anti-autophagy and/or chemoprotective agent for the preparation of a medicament for the treatment of a hyperproliferative disease or disorder, wherein the compound of formula I is administered sequentially, simultaneously or concomitantly with the other therapeutic agent.

53. Use of a compound of formula I having only antimitotic activity, as defined in any one of Clauses 1 to 40 and 42, for the preparation of a medicament for the treatment of a hyperproliferative disease or disorder, wherein the medicament is administered in combination with an anti-autophagy and/or chemoprotective agent.

54. A method of treatment of a hyperproliferative disease or disorder, which method comprises the administration of an effective amount of a compound of formula I having only antimitotic activity, as defined in any one of Clauses 1 to 40 and 42, and an anti-autophagy and/or chemoprotective agent to a patient in need of such treatment.

55. The compound for use of Clause 50 or Clause 51, the use of Clause 50 or Clause 51 or the method of Clause 54, wherein the therapy is an adjuvant therapy after surgical treatment or is a neoadjuvant therapy before main treatment of the proliferative disorder or disease.

56. A combination product comprising (A) an antimitotic compound of formula I, as defined in any one of Clauses 1 to 40 and 42, and (B) an anti-autophagy and/or chemoprotective agent, wherein each of components (A) and (B) is formulated in admixture with a pharmaceutically-acceptable adjuvant, diluent or carrier.

57. A combination product as defined in Clause 54 for use in the treatment of a hyperproliferative disease or disorder.

58. The use of a combination product as defined in Clause 54 for the manufacture of a medicament for the treatment of a hyperproliferative disease or disorder.

59. A method of treatment of a hyperproliferative disease or disorder, which method comprises the administration of an effective amount of a combination product as defined in Clause 54.

60. An anti-autophagy and/or chemoprotective compound of formula I, as defined in any one of Clauses 1 to 41 and 43, and an antimitotic agent for use in the treatment of a hyperproliferative disease or disorder.

61. An anti-autophagy and/or chemoprotective compound of formula I, as defined in any one of Clauses 1 to 41 and 43, for use in the treatment of a hyperproliferative disease or disorder, wherein the compound of formula I is administered sequentially, simultaneously or concomitantly with an antimitotic agent.

62. Use of a compound of formula I having only anti-autophagy and/or chemoprotective activity, as defined in any one of Clauses 1 to 40 and 43, and an antimitotic agent for the preparation of a medicament for the treatment of a hyperproliferative disease or disorder, wherein the compound of formula I is administered sequentially, simultaneously or concomitantly with the other therapeutic agent.

63. Use of a compound of formula I having only anti-autophagy and/or chemoprotective activity, as defined in any one of Clauses 1 to 40 and 43, for the preparation of a medicament for the treatment of a hyperproliferative disease or disorder, wherein the medicament is administered in combination with an antimitotic agent.

64. A method of treatment of a hyperproliferative disease or disorder, which method comprises the administration of an effective amount of a compound of formula I having only anti-autophagy and/or chemoprotective activity, as defined in any one of Clauses 1 to 40 and 43, and an antimitotic agent to a patient in need of such treatment.

65. The compound for use of any one of Clauses 57, 60 or 61, the use of any one of Clauses 58, 62 or 63 or the method of Clause 59 or Clause 64, wherein the therapy is an adjuvant therapy after surgical treatment or is a neoadjuvant therapy before main treatment of the proliferative disorder or disease.

66. A combination product comprising (A) a compound of formula I having only anti-autophagy and/or chemoprotective activity, as defined in any one of Clauses 1 to 40 and 43, and (B) an antimitotic agent, wherein each of components (A) and (B) is formulated in admixture with a pharmaceutically-acceptable adjuvant, diluent or carrier.

67. A combination product as defined in Clause 63 for use in the treatment of a hyperproliferative disease or disorder.

68. The use of a combination product as defined in Clause 63 for the manufacture of a medicament for the treatment of a hyperproliferative disease or disorder.

69. A method of treatment of a hyperproliferative disease or disorder, which method comprises the administration of an effective amount of a combination product as defined in Clause 63.

70. The compound for use of Clause 66, the use of Clause 67 or the method of Clause 68, wherein the therapy is an adjuvant therapy after surgical treatment or is a neoadjuvant therapy before main treatment of the proliferative disorder or disease.

FIGURES

FIG. 1 is a diagrammatic representation of an immunoblot analysis showing the dual inhibition of the autophagic process and mitotic progression by Compound 1 (a131). HeLa cells were treated with the indicated μM concentration of Compound 1 (a131) or chloroquine for 6 h. Cells were harvested and total lysates were analysed by detecting the mitotic marker phospho-histone H3 at serine 10 (pH3 (Ser10)) and the autophagosome marker LC3. The band intensity ratios of LC3-II/LC3-I as compared to DMSO control (lane 1, 0 μM chloroquine, and lane 7, 0 μM a131) are indicated (Ratio). Antibodies raised against β-actin were used as an internal loading control.

Figure 2:
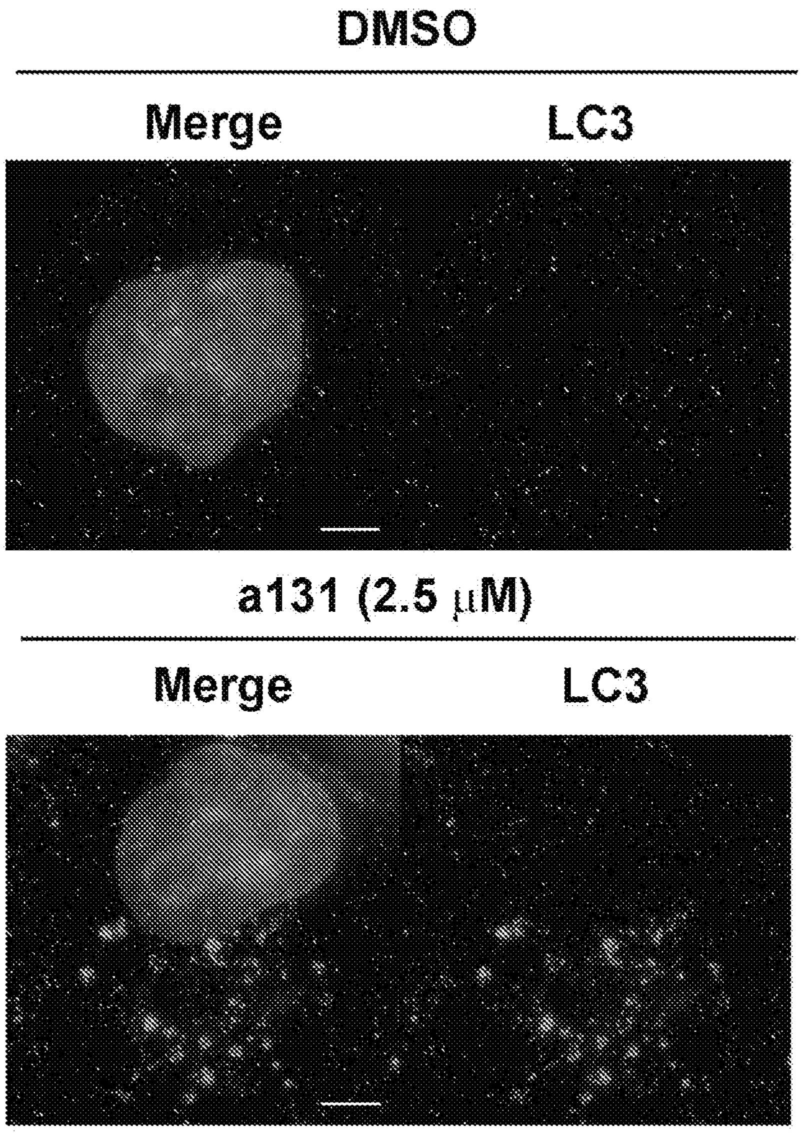

FIG. 2 is a representation of a photomicrograph that shows the inhibition of the autophagic process by Compound 1 (a131) by formation of LC3 fluorescent puncta in autophagosomes, indicating increase in lipidated LC3-II. HeLa cells, treated with either Compound 1 (a131) at 2.5 μM or DMSO for 6 h, were fixed in ice-cold methanol and subjected to immunofluorescence analysis using antibodies against LC3 and counterstained with diamidino-2-phenylindole (DAPI) to visualize the nucleus. The Merge boxes show both LC3 and DAPI staining. The bars represent 5 μm in length.

Figure 3:
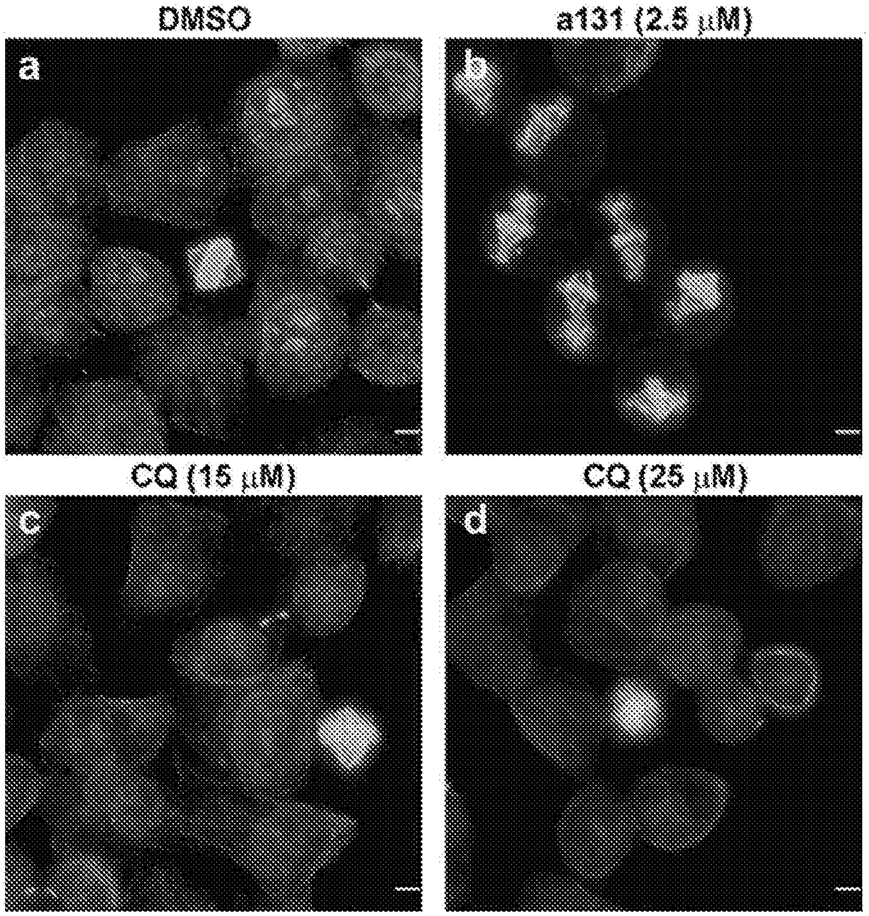

FIG. 3 shows representations of photomicrographs demonstrating that Compound 1 (a131), but not chloroquine (CQ), induces mitotic defects in spindle formation and chromosome alignment, which lead to mitotic arrest. HeLa cells, treated with Compound 1 (a131) at 2.5 μM (FIG. 3*b*), chloroquine (CQ) at 15 μM (FIG. 3*c*) or 25 μM (FIG. 3*d*), or DMSO (FIG. 3*a*) for 6 h, were fixed in methanol and subjected to immunofluorescence analysis using antibodies against β-tubulin to visualize proper formation of mitotic spindles. The condensed mitotic chromosomes were visualized by counterstaining with DAPI. Only Compound 1 (a131)-treated HeLa cells arrested in mitosis with misaligned chromosomes and disorganized spindles (FIG. 3*b*). The bars in FIGS. 3*a-d* represent 5 μm in length.

Figure 4:
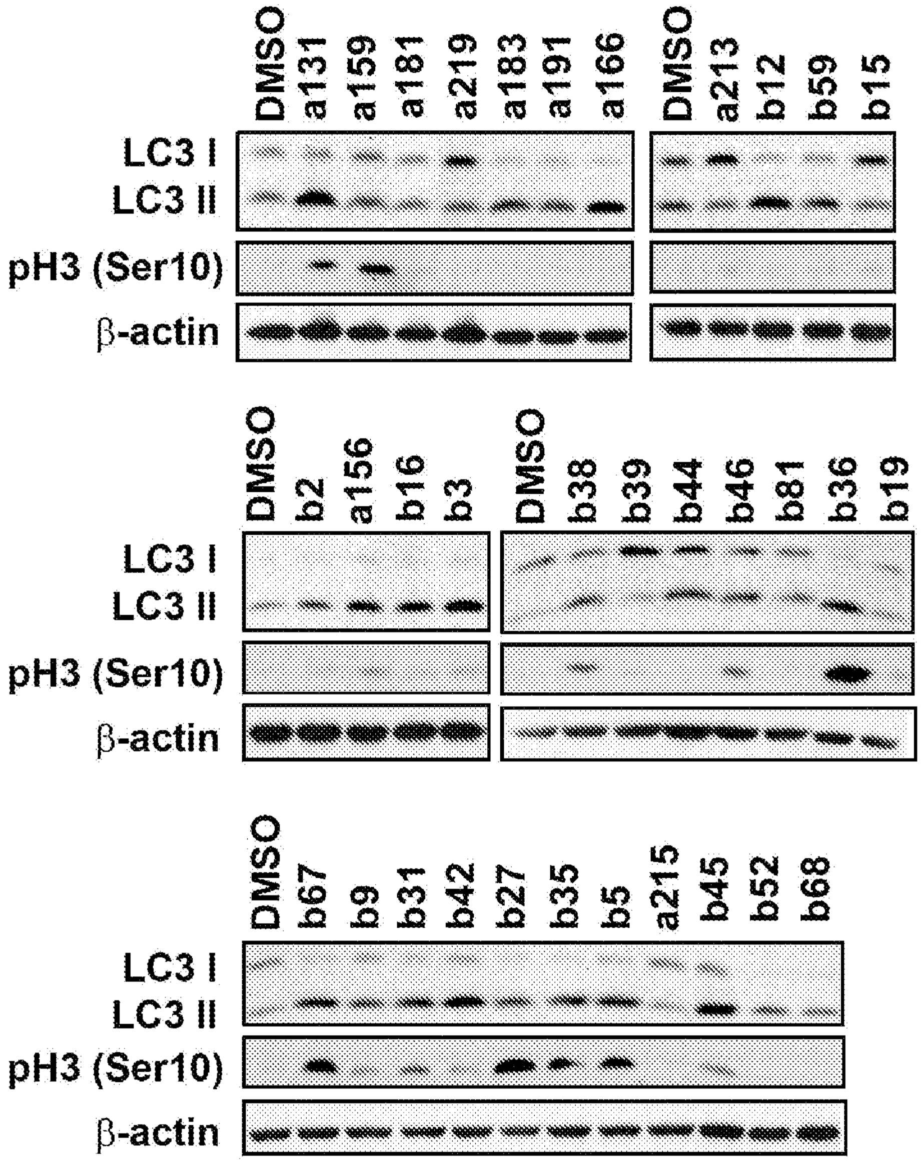

FIG. 4 compares the ability of Compound 1 (a131), and various derivatives thereof (referred to using their code numbers for brevity; the designated chemical compound for each code number is provided in the chemical examples section below), to inhibit autophagy and/or mitosis. BJ transformed cells were treated with 5 μM of various Compounds as shown, for 24 h. Cells were harvested and total lysates were analysed by detecting the mitotic marker phospho-histone H3 at serine 10 (pH3 (Ser10)) and the autophagosome marker LC3. Antibodies raised against β-actin were used as an internal loading control.

Figure 5:
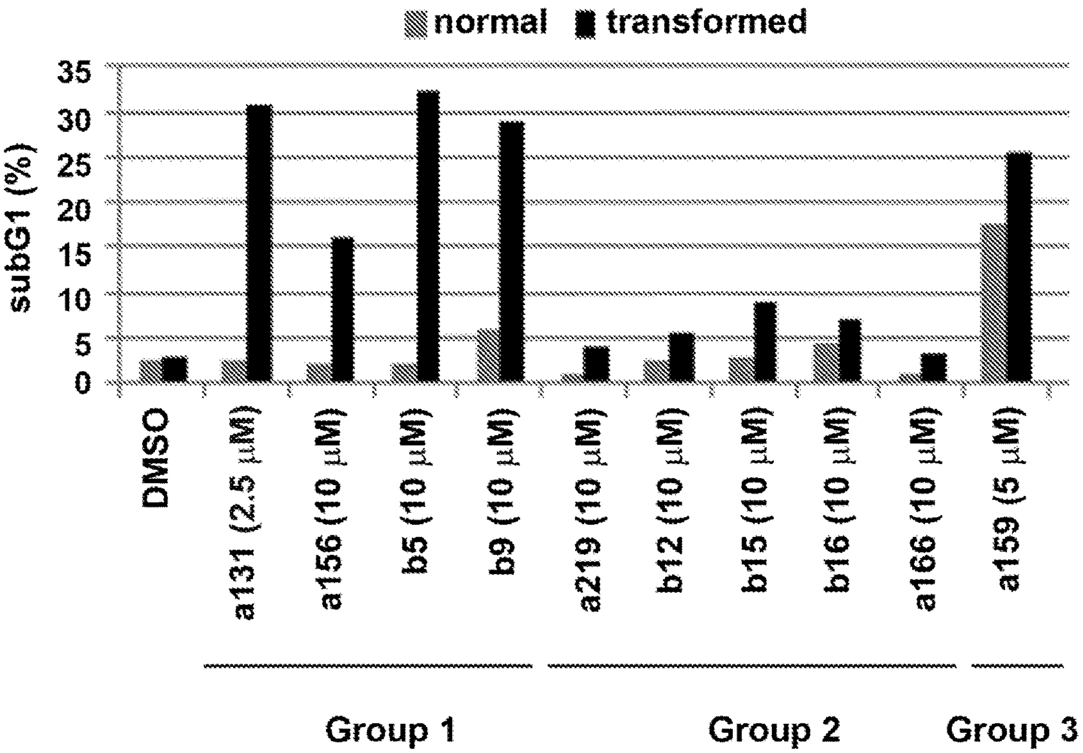
Figure 5:
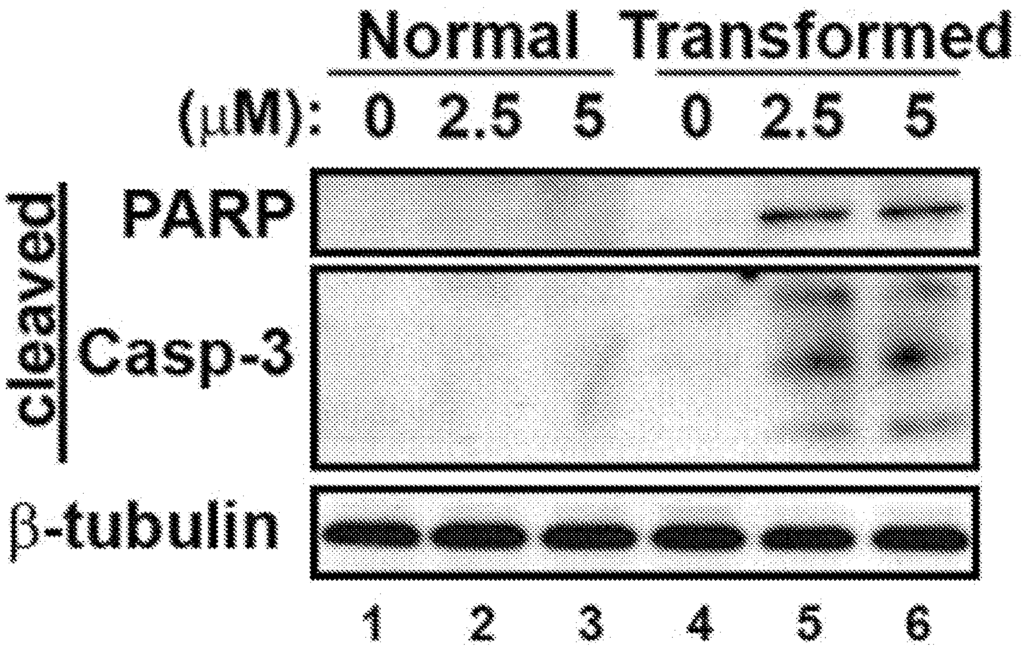
Figure 5:
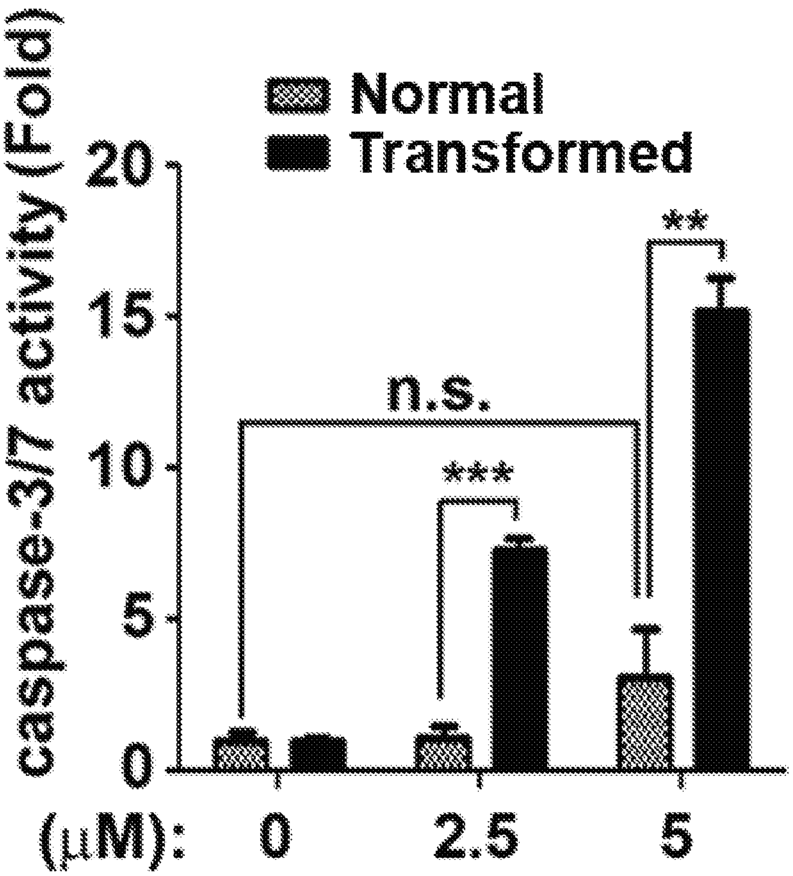

FIG. 5A is a histogram showing the ability of Compound 1 (a131) and its derivatives Compound 2 (a156), Compound 16 (b5), Compound 17 (b9), all in Group 1; Compound 29 (a219), Compound 13 (b12), Compound 11 (b15), Compound 12 (b16), Compound 25 (a166), all in Group 2; and Compound 3 (a159) from Group 3, to induce cancer selective cell death. Isogenic non-transformed (normal) and oncogene-transformed BJ cells were treated with each compound for 48 h and cells were stained with propidium iodide (PI) and subjected to FACS analysis. The percentage of cells in sub-G1 phase is indicative of the extent of cell death. Compounds in Group 1 with dual inhibitory properties markedly induced cell death (increased sub-G1 population) only in oncogene-transformed, but not in isogenic non-transformed BJ cells. In contrast, the ability of the compounds in Groups 2 and 3 to induce cancer selective cell death was markedly compromised (or reduced).

FIGS. 5B, C provide a representation of an immunoblot analysis to examine the PARP or caspase-3 cleavage (B) and a histogram showing Caspase-3/7 activities, plotted as fold induction compared to DMSO-treated cells (C). BJ normal and transformed cells were treated with Compound 1 (a131) for 48 h. Cells were harvested and total lysates were analysed by detecting cleaved PARP or caspase-3 or caspase-3/7 activities as markers for apoptotic induction. Together, these show that Compound 1 (a131) induces apoptosis in a dose-dependent manner only in transformed cells. Student's t-test was performed to determine the statistical significance (=$p<0.001$, *=$p<0.0001$, n.s.=no significance).

Figure 6:
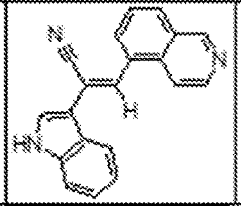
Figure 6:
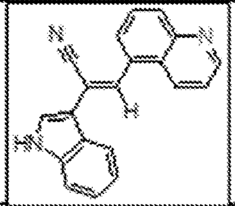
Figure 6:
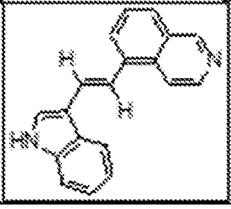
Figure 6:
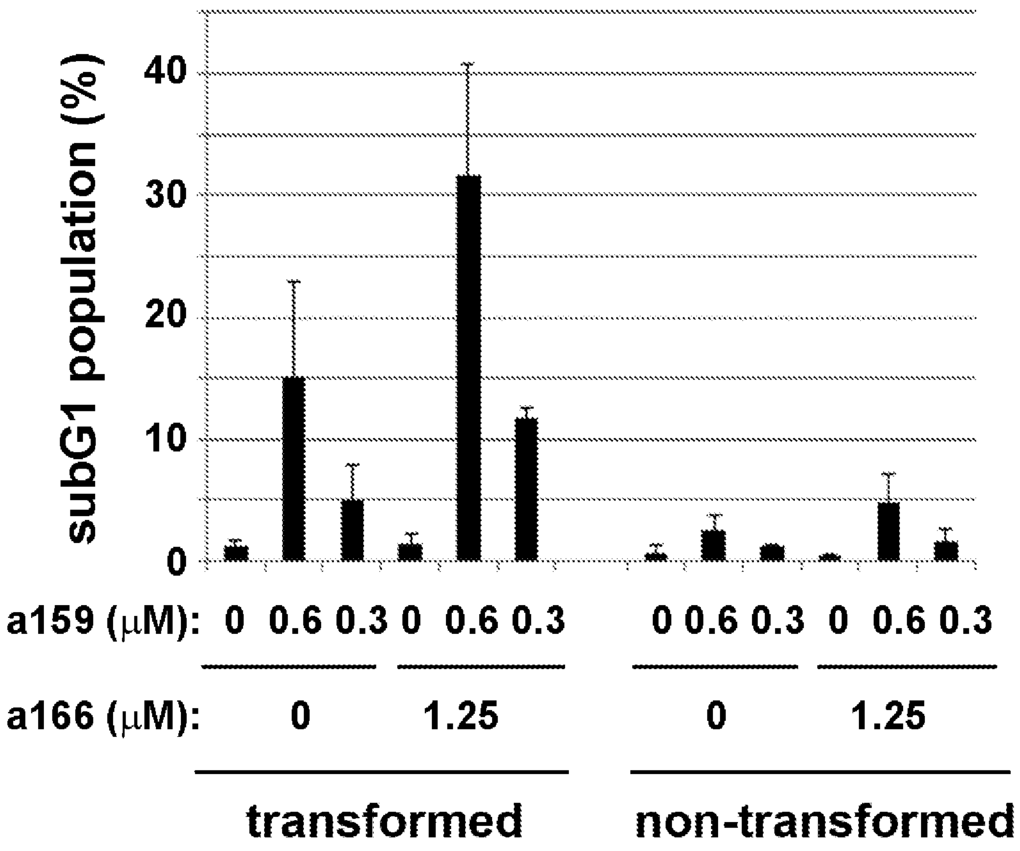

FIG. 6 shows that combined treatment of a Compound 1 (a131) derivative from Group 2 (a166) and a Compound 1 derivative from Group 3 (a159) reproduces the effects of Compound 1 (a131) and its Group 1 derivatives in inducing cancer selective cell death. The Compounds 25 (a166) and 3 (a159) were selected from Group 2 and Group 3, respectively. Isogenic non-transformed normal and oncogene-transformed BJ cells were treated with or without 0.3 μM or 0.6 μM Compound 3 (a159) alone or together with 1.25 μM Compound 25 (a166) for 48 h. Cells were stained with propidium iodide (PI) and subjected to FACS analysis. A: shows the compounds and their structures, as well as the extent of inhibition of mitosis and/or of autophagy (represented by LC3 induction) of each compound administered alone. B: is a histogram demonstrating the synergistically-enhanced cell death of oncogene-transformed BJ cells in comparison to either compound alone: the combination of Compound 3 (a159) at 0.3 μM and Compound 25 (a166) at 1.25 μM resulted in measureable cell death of approximately 12%, while the combination of Compound 3 (a159) at 0.6 μM and Compound 25 (a166) at 1.25 μM resulted in approximately 32% cell death. No such effects were seen in the isogenic non-transformed normal cells.

Figure 7:
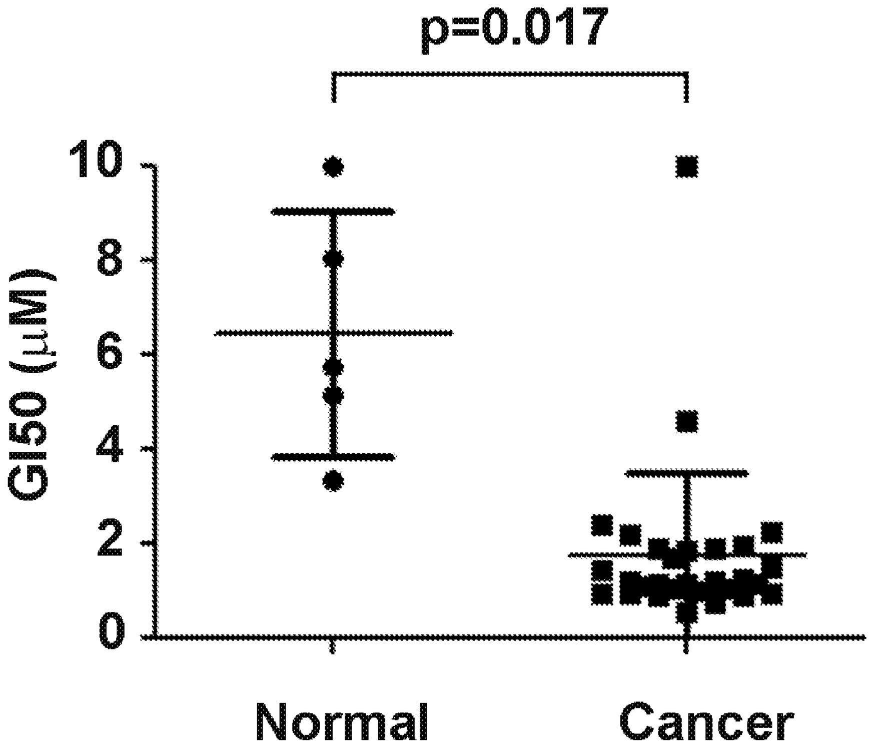

FIG. 7 is a graphical representation showing that Compound 1 (a131) induces selective cell growth inhibitory effects in a broad spectrum of human cancer cells. A panel of cancer and normal cell lines were treated with Compound 1 (a131) for 72 h and a mean G150 value (the concentration required to achieve 50% growth inhibition) was determined. A Student's t-test indicated a statistically significant difference at $p<0.05$ ($p=0.017$) between normal cells and cancer cells treated with Compound 1 (a131).

Figure 8:
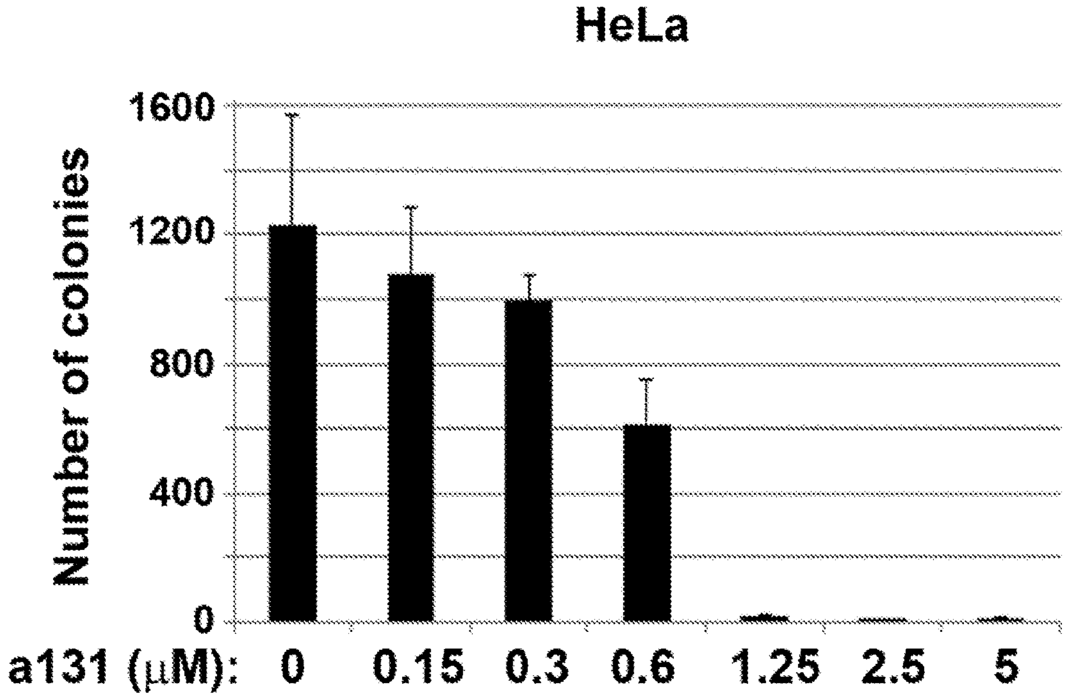

FIG. 8 is a histogram showing that Compound 1 (a131) potently suppresses anchorage-independent growth of cancer cells. HeLa cells were suspended in 2 mL of soft agar at the final concentration of 0.4%, and were then placed on the top of 2 mL layer of 1% agar in 6-well plates, in triplicate. Subsequently, Compound 1 (a131) was added to the plates at concentrations of 0, 0.15, 0.3, 0.6, 1.25. 2.5 and 5 μM. Seven (7) days after the addition of Compound 1 (a131) to soft agar cultures, the number of colonies per plate were counted in an unbiased manner using automated MATLAB software. The average number of colonies from triplicates was plotted with standard deviations.

FIGS. 9A-D show that Compound 1 (a131) and its derivatives induce cell cycle arrest only in non-transformed cells and in a p53-dependent manner. A: is output from a FACS analysis of isogenic-non-transformed, without (panels a-c) (WT) or with (panels d-f) shRNA-mediated knockdown of p53 (p53KD), and oncogene-transformed BJ cells (panels g-i), each treated with 0, 5 or 2.5 μM Compound 1 (a131) for 24 h. Cells were doubly stained with PI (horizontal axis) and BrdU (vertical axis). The BrdU-positive population in panels a-c are indicated as arrows. B: is a diagrammatic representation of an immunoblot analysis showing isogenic non-transformed (normal) and oncogene-transformed BJ cells (transformed) treated with Compound 1 (a131) at 0, 2.5 or 5 μM for 24 h or 48 h. Cells were harvested and total lysates were analysed by detecting p53 and p21. Antibodies raised against β-actin were used as an internal loading control. C and D are histograms showing the percentage of bromodeoxyuracil (BrdU)-positive non-transformed (normal) BJ cells. C: Cells were treated with Group 1 Compound 1 (a131) at 2.5 and 5 μM, Compound 23 (b36) at 2.5 and 5 μM, and Compound 21 (b35) at 5 μM, and Group 2 Compound 25 (a166) at 2.5 and 5 μM, for 24 h. Cells were doubly stained with propidium iodide (PI) and BrdU, and subjected to FACS analysis. The BrdU-positive population are plotted as bars. D: Cells were treated with Group 1 Compound 1 (a131), Compound 16 (b5), and Compound 17 (b9); Group 2 Compound 13 (b12), Compound 12 (b16) and Compound 25 (a166), and Group 3 Compound 3 (a159) at 5 μM for 48 h. The percentage of cells with BrdU positive population, in comparison with DMSO control vehicle, is shown with mean values±S.D. (n=3).

Figure 10:
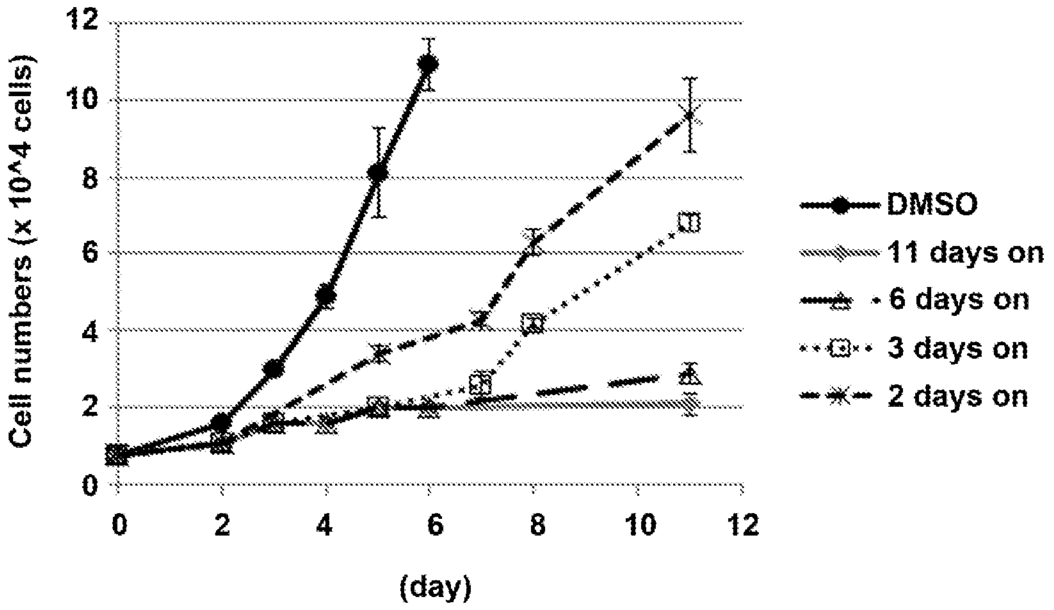

FIG. 10 shows a graphical representation indicating that Compound 1 (a131)-induced cell cycle arrest in non-transformed cells is transient and reversible. Non-transformed normal BJ cells were synchronized in G1 phase of the cell cycle by culturing in serum-starved conditions (0.1% FBS) for 2 days. Subsequently, cells were synchronously released in fresh media with 10% FBS and further treated with Compound 1 (a131) for 2, 3, 6 or 11 days. After treatment for the required amount of time, Compound 1 (a131) was removed by washing cells twice with fresh media, and culturing of the washed cells was continued in fresh media for up to 11 days. Cells were harvested and total numbers of cells, counted using automated Sceptor cell counter, were plotted with standard deviation (triplicates).

FIGS. 11A-D shows mitotic catastrophe and cell death in oncogene-transformed BJ cells. A: is a histogram showing isogenic non-transformed and oncogene-transformed BJ cells stably expressing GFP-tagged Histone H2B as a marker for chromosome segregation, treated with Compound 1 (a131) at 2.5 μM final concentration. Mitotic progression of these cells was monitored every 10 min. More than 100 cells per condition were quantified and classified into 3 groups: no, mild and severe mitotic defects with prolonged mitotic arrest, chromosome mis-segregation and failure in cytokinesis. B: is a representation of a photomicrograph that shows massive mis-alignment of chromosomes in oncogene-transformed BJ cells (transformed) treated with Compound 1 (a131) at 2.5 μM, but not in isogeneic non-transformed (normal) cells. The bars represent 5 μm in length. C: is a histogram showing quantification of defects in spindle formation and chromosome alignments (n>100 cells per condition). D: is a histogram demonstrating that Compound 2 (a156-Group 1) and Compound 3 (a159-Group 3) cause similar defects in chromosome alignment.

Figure 12:
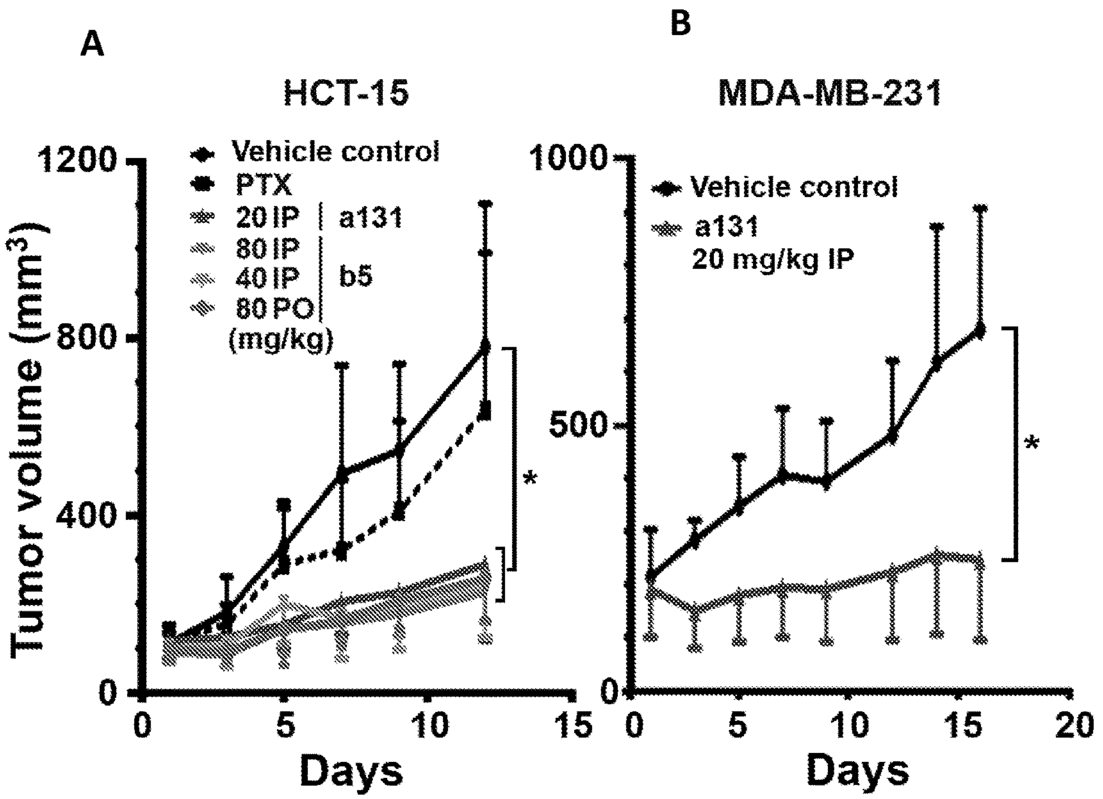

FIG. 12 shows the in vivo efficacies of Compound 1 (a131) and its derivative Compound 16 (b5) against HCT15 and MDA-MB-231 xenografts. A, B: is a graphical representation of tumour volumes estimated periodically as indicated. Mice bearing established tumour xenografts using HCT15 or MDA-MB-231 cells were treated orally (PO) or intraperitoneally (IP) twice a day with the indicated doses of Compound 1 or Compound 16 for 12 or 15 days. Paclitaxel (PTX) was given intravenously at dose of 40 mg/kg, 3 times every 4 days. Error bars show ±S.D. from mean tumour volumes obtained from 6 mice. Student's t-test was performed to determine the statistical significance (*=p<0.005). C: is a bar graph showing quantification of cells (n>100 per condition) with misaligned chromosomes and multipolar mitotic-spindles. HCT-115 tumour sections treated with Compound 16 (80 mg/kg) or control vehicle for 12 days were stained with anti-β-tubulin antibodies and DAPI. The percentage of cells with misaligned chromosomes and multipolar mitotic-spindles was quantified and plotted with mean values±S.D.

Figure 13:
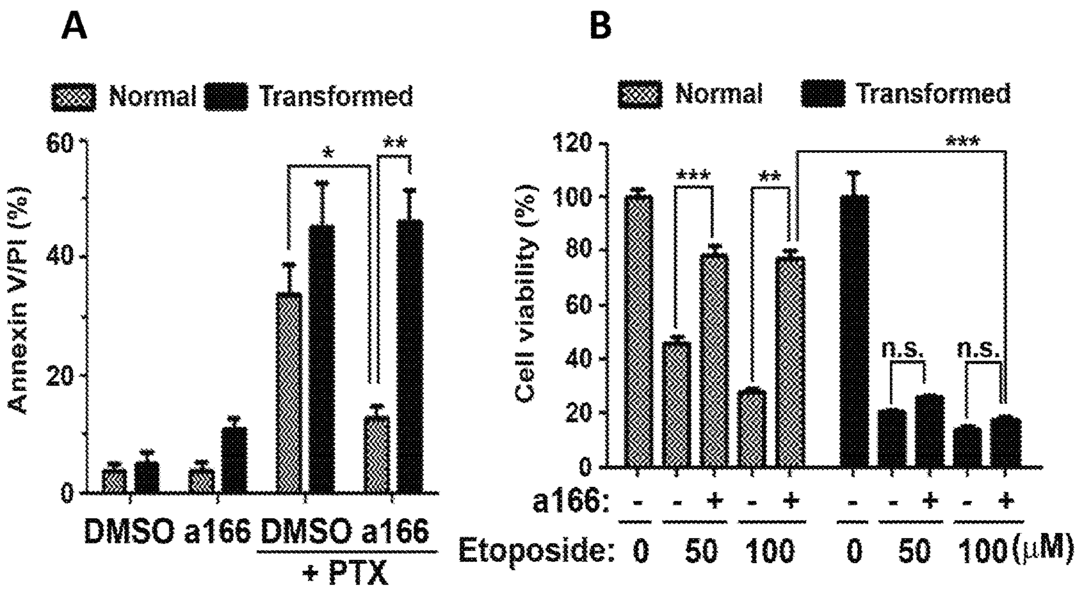

FIG. 13 shows the ability of Compound 25 (a166) to act as a chemoprotective agent. Normal and transformed BJ cells were treated with Compound 25 at 5 μM. 48 h after treatment, cells were further treated with (A) 50 nM paclitaxel (PTX) or (B) etoposide, at the concentrations shown, for additional 48 or 72 h, respectively. A: cells were collected, stained with Annexin V together with propidium iodide (PI) and subjected to FACS analysis. The histogram shows the percentage of doubly positive cells for Annexin V and PI with mean values±S.D. (n=3). B: is a histogram setting out the results of an MTT assay that shows cell viability plotted in comparison with DMSO control vehicle, with mean values±S.D. (n=4). Student's t-test was performed to determine the statistical significance (*=P<0.0001, =P<0.001, *=P<0.05, n.s.=no significance).

Figure 14:
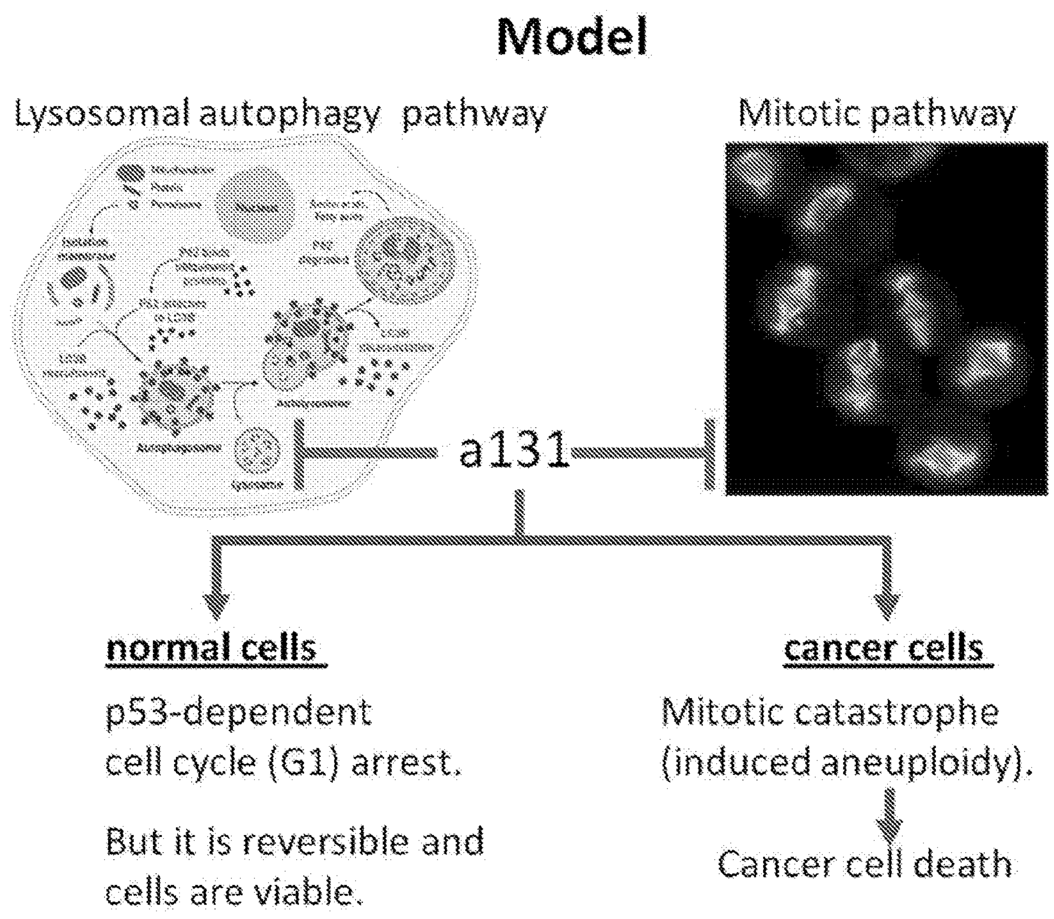

FIG. 14 shows a schematic model of the proposed mechanism of action of Compound 1 (a131) and its derivatives from Group 1. These compounds induce p53-dependent cell cycle arrest at the G1 phase without affecting normal cell viability. Notably, the cell cycle arrest caused by Compound 1 (a131) and its Group 1 derivatives in normal cells is only transient, as removing these compounds from growth media is sufficient to permit normal cells to resume their proliferation. In sharp contrast, Compound 1 (a131) and its derivatives do not induce a transient cell cycle arrest in cancer cells; instead, these compounds cause dramatic mitotic catastrophe and also possible metabolic alteration by disputing lysosome function. Consequently, Compound 1 (a131) and its Group 1 derivatives manifest selective killing of cancer cells, while sparing normal cells.

Figure 15:
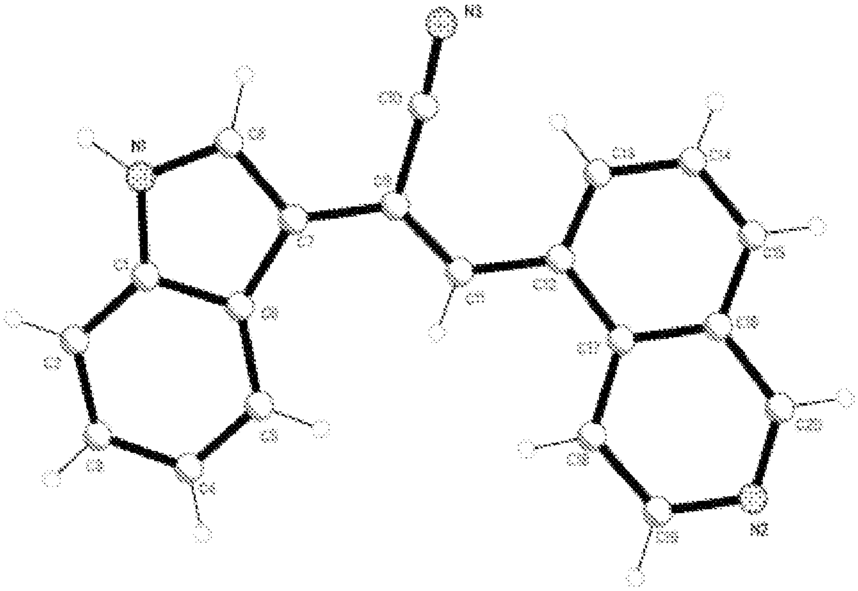

FIG. 15 is an ORTEP diagram showing X-ray crystal structure of Compound 1 (a131).

DESCRIPTION

It has been surprisingly found that compounds having a dual mechanism of action, inhibiting both autophagic processes as well as mitotic progression, synergistically compromise the proliferation and survival of cancer cells, while only causing transient and reversible growth arrest without affecting cell viability in non-cancer cells. Additionally or alternatively, it has been surprisingly found that compounds having a dual mechanism of action, where normal cells are inhibited from progressing through the cell cycle while cancer cells progress through the cell cycle and are subject to mitotic disruption, synergistically compromise the proliferation and survival of cancer cells, while only causing transient and reversible growth arrest without affecting cell viability in non-cancer cells. These compounds may also overcome the resistance of cancer cells to the current anti-microtubule toxins in the clinic (e.g. paclitaxel). In addition, it has been surprisingly found that the combination of a compound that inhibits autophagy with a compound that inhibits mitotic progression also produces some or all of the same effects. Additionally or alternatively, it has been surprisingly found that the combination of a compound that exhibits the inhibition (i.e. chemoprotective) effect in normal cells with a compound that inhibits mitotic progression also produces some or all of the same effects.

Thus, according to the first aspect of the invention, there is provided a compound of formula I:

I

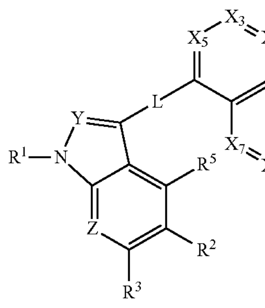

wherein,

Z represents N or $CR^4$;

L represents a linking group selected from the group consisting of $—C(R^{8a})═C(R^{8b})—$, $—C(R^{6a})_2—C(R^{6b})_2—$, $—C(O)NR^{7a}—$ or $—NR^{7b}C(O)—$;

$X_1$ to $X_5$ are independently N or $CR^8$, provided that at least one of $X_1$ and $X_2$ is N;

$X_6$ and $X_7$ are independently N or $CR^9$;

Y represents N or $CR^{10}$;

$R^1$ represents H, $—C(O)R^{11a}$ or $—C(S)R^{11b}$;

$R^2$ to $R^4$, $R^8$ and $R^{10}$, at each occurrence, independently represents:

(a) H;

(b) halo;

(c) CN;

(d) $C_{1-6}$ alkyl, $C_{2-6}$ alkenyl, $C_{2-6}$ alkynyl (which latter three groups are unsubstituted or substituted by one or more substituents selected from halo, nitro, CN, $C_{1-6}$ alkyl, $C_{2-6}$ alkenyl, $C_{2-6}$ alkynyl (which latter three groups are unsubstituted or substituted by one or more substituents selected from OH, ═O, halo, $C_{1-4}$ alkyl and $C_{1-4}$ alkoxy), $Cy^1$ (which $Cy^1$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$ alkyl and $C_{1-4}$ alkoxy), $OR^{12a}$, $S(O)_qR^{12b}$, $S(O)_2NR^{12c}R^{12d}$, $NR^{12e}S(O)_2R^{12f}$, $NR^{12g}R^{12h}$, aryl and $Het^1$);

(e) $Cy^2$ (which $Cy^2$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$alkyl and $C_{1-4}$alkoxy), $OR^{13a}$, $S(O)_qR^{13b}$, $S(O)_2NR^{13c}R^{13d}$, $NR^{13e}S(O)_2R^{13f}$, $NR^{13g}R^{13h}$, aryl and $Het^2$), (f) $Het^a$ (which $Het^a$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$alkyl and $C_{1-4}$alkoxy), $OR^{14a}$, $S(O)_qR^{14b}$, $S(O)_2NR^{14c}R^{14d}$, $NR^{14e}S(O)_2R^{14f}$, $NR^{14g}R^{14h}$, aryl and $Het^3$);

(g) $OR^{15a}$;

(h) $S(O)_qR^{15b}$;

(i) $S(O)_2NR^{15c}R^{15d}$;

(j) $NR^{18e}S(O)_2R^{18f}$;

(k) $NR^{15g}R^{15h}$, where $R^3$, $R^4$ and each $R^8$, when present, may also, in addition, independently represent nitro;

$R^5$ and $R^9$, at each occurrence, independently represent H, halo, CN, nitro, $C_{1-4}$ alkyl (which latter group is unsubstituted or substituted by one or more substituents selected from halo, nitro, CN, $OR^{16a}$ and $NR^{16g}R^{16h}$), $OR^{17a}$, $S(O)_qR^{17b}$, $S(O)_2NR^{17c}R^{17d}$, $NR^{17e}S(O)_2R^{17f}$ or $NR^{17g}R^{17h}$;

$R^{6a}$ represents H, CN or $—C(O)NR^{18a}R^{18b}$;

$R^{6b}$, independently at each occurrence, represents H, CN or $C_{1-4}$ alkyl, which latter group is unsubstituted or substituted with halo or $OR^{19}$;

$R^{7a}$ and $R^{7b}$ represent H or $C_{1-4}$ alkyl, which latter group is unsubstituted or substituted with halo or $OR^{20}$;

$R^{11a}$ and when present, represent, (a) H;

(b) $C_{1-6}$ alkyl, $C_{2-6}$ alkenyl, $C_{2-6}$ alkynyl (which latter three groups are unsubstituted or substituted by one or more substituents selected from halo, nitro, ═O, CN, $C_{1-6}$ alkyl, $C_{2-6}$ alkenyl, $C_{2-6}$ alkynyl (which latter three groups are unsubstituted or substituted by one or more substituents selected from OH, ═O, halo, $C_{1-4}$ alkyl and $C_{1-4}$ alkoxy), $OR^{21a}$, $S(O)_qR^{21b}$, $S(O)_2NR^{21c}R^{21d}$, $NR^{21e}S(O)_2R^{21f}$, $NR^{21g}R^{21h}$, aryl, $Cy^3$ (which $Cy^3$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, ═O, halo, $C_{1-4}$ alkyl and $C_{1-4}$ alkoxy), $OR^{22a}$, $S(O)_qR^{22b}$, $S(O)_2NR^{22c}R^{22d}$, $NR^{22e}S(O)_2R^{22f}$, $NR^{22g}R^{22h}$, aryl and $Het^4$) and $Het^5$);

(c) $C_{3-10}$ cycloalkyl, $C_{4-10}$ cycloalkenyl (which latter two groups are optionally substituted by one or more substituents selected from halo, OH, ═O, $C_{1-6}$ alkyl and $C_{1-6}$ alkoxy);

(d) $Het^b$ (which $Het^b$ group is unsubstituted or substituted by one or more substituents selected from halo, nitro, CN, $C(O)OC_{1-4}$ alkyl, $C_{1-6}$ alkyl, $C_{2-6}$ alkenyl, $C_{2-6}$ alkynyl (which latter three groups are optionally substituted by one or more substituents selected from $Het^8$, or more particularly, OH, ═O, halo, $C_{1-4}$ alkyl and $C_{1-4}$ alkoxy), $OR^{23a}$, $S(O)_qR^{23b}$, $S(O)_2NR^{23c}R^{23d}$, $NR^{23e}S(O)_2R^{23f}$, $NR^{23g}R^{23h}$, aryl and $Het^6$), (e) $OR^{24a}$;

(f) $NR^{24b}S(O)_2R^{24c}$;

(g) $NR^{24d}R^{24e}$;

$R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-6}$ alkyl, $C_{2-6}$ alkenyl, $C_{2-6}$ alkynyl (which latter three groups are optionally substituted by one or more substituents selected from halo, nitro, ═O, $C(O)OC_{1-4}$ alkyl, CN, $C_{1-6}$ alkyl, $C_{2-6}$ alkenyl, $C_{2-6}$ alkynyl, $C_{3-6}$ cycloalkyl (which latter three groups are optionally substituted by one or more substituents selected from OH, ═O, halo, $C_{1-4}$ alkyl and $C_{1-4}$ alkoxy), $OR^{25a}$, $S(O)_qR^{25b}$, $S(O)_2NR^{25c}R^{25d}$, $NR^{25e}S(O)_2R^{25f}$, $NR^{25g}R^{25h}$, aryl and $Het^7$), $C_{3-10}$ cycloalkyl, or $C_{4-10}$ cycloalkenyl (which latter two groups are optionally substituted by one or more substituents selected from halo, OH, =O, $C_{1-6}$ alkyl and $C_{1-6}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy);

$Het^1$ to $Het^8$ (e.g. $Het^1$ to $Het^7$) and $Het^a$ to $Het^c$ independently represent a 4- to 14-membered heterocyclic groups containing one or more heteroatoms selected from O, S and N, which heterocyclic groups may comprise one, two or three rings and may be substituted by one or more substituents selected from =O, or more particularly, halo, $C_{1-6}$ alkyl, which latter group is optionally substituted by one or more substituents selected from halo, $-OR^{26a}$, $-NR^{26b}R^{26c}$, $-C(O)OR^{26d}$ and $-C(O)NR^{26e}R^{26f}$;

$Cy^1$ to $Cy^3$, at each occurrence, independently represents a 3- to 10-membered aromatic, fully saturated or partially unsaturated carbocyclic ring;

$R^{25a}$ to $R^{25h}$ and $R^{26a}$ to $R^{26f}$ independently represent at each occurrence, H, $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, =O, halo, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from halo, OH, =O, $C_{1-4}$ alkyl and $C_{1-4}$ alkoxy), q represents 0, 1 or 2, or a pharmaceutically acceptable salt, solvate or a pharmaceutically functional derivative thereof.

When used herein, the terms "$R^{12-17c}$ and $R^{12-17d}$", "$R^{12-17g}$ and $R^{12-17h}$", "$R^{21-23c}$ and $R^{21-23d}$", and "$R^{21-23g}$ and $R^{21-23h}$" are used to represent specific pairings of R groups in a compressed format. For example, "$R^{12-17c}$ and $R^{12-17d}$" relates to the pairings: $R^{12c}$ and $R^{12d}$, $R^{13c}$ and $R^{13d}$, $R^{14c}$ and $R^{14d}$, $R^{15c}$ and $R^{15d}$, $R^{16c}$ and $R^{16d}$, and $R^{17c}$ and $R^{17d}$. The same expansion of the compressed form applies to each of "$R^{12-17g}$ and $R^{12-17h}$", "$R^{21-23c}$ and $R^{21-23d}$", and "$R^{21-23g}$ and $R^{21-23h}$" also.

References herein (in any aspect or embodiment of the invention) to compounds of formula I includes references to such compounds per se, to tautomers of such compounds, as well as to pharmaceutically acceptable salts or solvates, or pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (±)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

"Pharmaceutically functional derivatives" of compounds of formula I as defined herein includes ester derivatives and/or derivatives that have, or provide for, the same biological function and/or activity as any relevant compound of the invention. Thus, for the purposes of this invention, the term also includes prodrugs of compounds of formula I.

The term "prodrug" of a relevant compound of formula I includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. I-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The compound of formula I in the above-mentioned aspect of the invention may be utilised in a method of medical treatment. Thus, according to further aspects of the invention, there is provided:

(a) a compound of formula I for use in medicine;

(b) a compound of formula I for use in the treatment or prevention of a hyperproliferative disease or disorder;

(c) use of a compound of formula I for the preparation of a medicament for the treatment of a hyperproliferative disease or disorder; and (d) a method of treatment of a hyperproliferative disease or disorder, which method comprises the administration of an effective amount of a compound of formula I.

The term "hyperproliferative disease or disorder" will be understood by those skilled in the art to include a hyperproliferative vascular disease (such as intimal smooth muscle cell hyperplasia, restenosis, and vascular occlusion), a hyperproliferative skin disease (such as psoriasis) and cancer (such as adrenal cancer, anal cancer, bile duct cancer, bladder cancer, bone cancer, brain tumours, CNS tumours, breast cancer, Castleman disease, cervical cancer, colon cancer, rectum cancer, endometrial cancer, esophagus cancer, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal cancer, hypopharyngeal cancer, leukemia (e.g. acute lymphocytic, acute myeloid, chronic lymphocytic, chronic myeloid, chronic myelomonocytic), liver cancer, lung cancer (e.g. small cell or non-small cell), lung carcinoid tumour, lymphoma (e.g. of the skin), malignant mesothelioma, multiple myeloma, myelodysplastic syndrome, nasal cavity cancer, paranasal sinus cancer, nasopharyngeal cancer, neuroblastoma, non-Hodgkin lymphoma, oral cavity cancer, oropharyngeal cancer, osteosarcoma, ovarian cancer, pancreatic cancer, penile cancer, pituitary tumours, prostate cancer, retinoblastoma, rhabdomyosarcoma, salivary gland cancer, sarcoma, skin cancer (basal and squamous cell, melanoma, Merkel cell), small intestine cancer, stomach cancer, testicular cancer, thymus cancer, thyroid cancer, uterine sarcoma, vaginal cancer, vulvar cancer, Waldenstrom macroglobulinemia, Wilms tumour).

Particular hyperproliferative diseases or disorders that may be mentioned herein include a hyperproliferative vascular disease (such as intimal smooth muscle cell hyperplasia, restenosis, and vascular occlusion), a hyperproliferative skin disease (such as psoriasis) and solid tumours (such as adrenal cancer, anal cancer, bile duct cancer, bladder cancer, bone cancer, brain tumours, CNS tumours, breast cancer, Castleman disease, cervical cancer, colon cancer, rectum cancer, endometrial cancer, esophagus cancer, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal cancer, hypopharyngeal cancer, liver cancer, lung cancer (e.g. small cell or non-small cell), lung carcinoid tumour, malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumours, prostate cancer, retinoblastoma, rhabdomyosarcoma, salivary gland cancer, sarcoma, skin cancer (basal and squamous cell, melanoma, Merkel cell), small intestine cancer, stomach cancer, testicular cancer, thymus cancer, thyroid cancer, uterine sarcoma, vaginal cancer, vulvar cancer, Waldenstrom macroglobulinemia, Wilms tumour).

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

The term "halo", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Heterocyclic ($Het^1$ to $Het^8$ (e.g. $Het^1$ to $Het^7$) and $Het^a$ to $Het^c$) groups may be fully saturated, partly unsaturated, wholly aromatic or partly aromatic in character. Values of ($Het^1$ to $Het^8$ (e.g. $Het^1$ to $Het^7$) and $Het^a$ to $Het^c$ groups that may be mentioned include acridinyl, 1-azabicyclo[2.2.2]octanyl, azetidinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[6]furanyl, 1,3-dihydrobenzo[c]furanyl, 1,3-dihydro-2,1-benzisoxazolyl, 2,3-dihydropyrrolo[2,3-b]pyridinyl, dioxanyl, furanyl, furazanyl, hexahydropyrimidinyl, hydantoinyl, imidazolyl, imidazo[1,2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiaziolyl, isothiochromanyl, isoxazolidinyl, isoxazolyl, maleimido, morpholinyl, naphtho[1,2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, oxetanyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), tetrazolyl, thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like. Particular values of ($Het^1$ to $Het^8$ (e.g. $Het^1$ to $Het^7$) and $Het^a$ to $Het^c$ that may be mentioned include the 4- to 10-membered heterocyclic groups from the list above. Further, values of ($Het^1$ to $Het^8$ (e.g. $Het^1$ to $Het^7$) and $Het^a$ to $Het^c$ that may be mentioned include the 5- and 8-membered (e.g. 5- to 6-membered) heterocyclic groups from the list above.

Substituents on heterocyclic (($Het^1$ to $Het^8$ (e.g. $Het^1$ to $Het^7$) and $Het^a$ to $Het^c$) groups may, where appropriate, be located on any atom in the ring system including a heteroatom. The point of attachment of heterocyclic (($Het^1$ to $Het^8$ (e.g. $Het^1$ to $Het^7$) and $Het^a$ to $Het^c$) groups may be via any atom in the ring system including (where appropriate) a heteroatom (such as a nitrogen atom), or an atom on any fused carbocyclic ring that may be present as part of the ring system. Heterocyclic (($Het^1$ to $Het^8$ (e.g. $Het^1$ to $Het^7$) and $Het^a$ to $Het^c$) groups may also be in the N- or S-oxidised form.

For the avoidance of doubt, in cases in which the identity of two or more substituents in a compound of formula I may be the same, the actual identities of the respective substituents are not in any way interdependent.

Embodiments of the invention that may be mentioned include those that relate to compounds of formula I in which:

(a) L represents a linking group selected from the group consisting of $—C(O)NR^{7a}—$ and, more particularly, $—C(R^{6a})═C(R^{6b})$ (e.g. L represents $—C(R^{6a})═C(R^{6b})—$, for example the C═C double bond is in the Z configuration);

(b) $X_1$ to $X_3$ are independently N or $CR^8$, $X_4$ and $X_5$ are independently $CR^8$ and $X_6$ and $X_7$ are independently $CR^9$ (e.g. $X_1$ represents N and $X_2$ to $X_5$ are independently $CR^8$);

(c) Y represents $CR^{10}$;

(d) $R^1$ represents H, $—C(O)R^{11a}$;

(e) $R^2$ represents:

(i) H;

(ii) Br, Cl, F;

(iii) $C_{1-4}$ alkyl which is unsubstituted or substituted by one or more substituents selected from halo, nitro, CN, $C_{1-3}$ alkyl (which latter group is unsubstituted or substituted by one or more substituents selected from OH, ═O, halo, $C_{1-4}$ alkyl and $C_{1-4}$alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, ═O, halo, $C_{1-4}$ alkyl and $C_{1-4}$alkoxy), $OR^{12a}$, $NR^{12g}R^{12h}$, aryl and $Het^1$);

(iv) $Cy^2$ (which $Cy^2$ group is unsubstituted or is substituted by one or more substituents selected from halo, CN, $C_{1-3}$ alkyl (which latter group is optionally substituted by one or more substituents selected from OH, ═O, halo, $C_{1-4}$ alkyl and $C_{1-4}$alkoxy), $OR^{13a}$, $NR^{13g}R^{13h}$, aryl and $Het^2$);

(v) $Het^a$ (which $Het^a$ group is unsubstituted or substituted by one or more substituents selected from halo, nitro, CN, $C_{1-3}$ alkyl (which latter group is optionally substituted by one or more substituents selected from OH, ═O, halo, $C_{1-4}$ alkyl and alkoxy), $OR^{14a}$, $NR^{14g}R^{14h}$, aryl and $Het^3$);

(vi) $OR^{15a}$; or (vii) $NR^{15g}R^{15h}$, (e.g. wherein $R^2$ represents:

(i) H;

(ii) Br, Cl, F;

(iii) $C_{1-4}$ alkyl which is unsubstituted or substituted by one or more substituents selected from F, $C_{1-3}$ alkyl (which latter group is unsubstituted or substituted by one or more substituents selected from OH, =O, F, $C_{1-4}$ alkyl and $C_{1-4}$ alkoxy), $OR^{12a}$ and $NR^{12g}R^{12h}$);

(iv) $OR^{15a}$; or (v) $NR^{15g}R^{15h}$, such as $R^2$ represents Br, Cl or, more particularly, H);

(f) $R^3$, $R^4$, $R^8$ and $R^{10}$, at each occurrence, independently represents:

(i) H;

(ii) Br, Cl, F;

(iii) CN;

(iv) $C_{1-4}$ alkyl, $C_{2-4}$ alkenyl, $C_{2-4}$ alkynyl (which latter three groups are unsubstituted or substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{12a}$, $NR^{12g}R^{12h}$, aryl and $Het^1$), (v) $Cy^2$ (which $Cy^2$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and alkoxy), $OR^{13a}$, $NR^{13g}R^{13h}$, aryl and $Het^2$);

(vi) $Het^a$ (which $Het^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and alkoxy), $OR^{14a}$, $NR^{14g}R^{14h}$, aryl and $Het^3$);

(vii) $OR^{15a}$;

(viii) $NR^{15g}R^{15h}$; or (ix) nitro, (e.g. $R^3$, $R^4$, $R^8$ and $R^{10}$, at each occurrence, independently represents Br, Cl, F, CN, $C_{1-4}$ alkyl (which latter group is unsubstituted or substituted by one or more substituents selected from F, $C_{1-3}$ alkyl (which latter group is unsubstituted or substituted by one or more substituents selected from OH, =O, halo, $C_{1-4}$ alkyl and alkoxy), $OR^{12a}$ and $NR^{12g}R^{12h}$), $OR^{15a}$; $NR^{15g}R^{15h}$; nitro, or more particularly, H);

(g) $R^5$ and $R^9$, at each occurrence, independently represent H, Br, Cl, F, CN, nitro, $C_{1-4}$ alkyl (which latter group is unsubstituted or substituted by one or more substituents selected from Br, Cl, F, $OR^{16a}$ and $NR^{16g}R^{16h}$) $OR^{17a}$ or $NR^{17g}R^{17h}$;

(h) $R^{ha}$ represents H or CN and $R^{6b}$, independently at each occurrence, represents H or $C_{1-4}$ alkyl, which latter group is unsubstituted or substituted with F or $OR^{19}$ (e.g. $R^{6a}$ represents CN and $R^{6b}$ represents H);

(i) $R^{11a}$ represents, (i) $C_{1-5}$ alkyl which group is unsubstituted or substituted by one or more substituents selected from halo, =O, CN, $C_{1-3}$ alkyl (which latter group is unsubstituted or substituted by one or more substituents selected from OH, =O, halo, $C_{1-4}$ alkyl and $C_{1-4}$ alkoxy), $OR^{21a}$, $NR^{21g}R^{21h}$; aryl, $Cy^3$ (which $Cy^3$ group is unsubstituted or is substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $OR^{22a}$, $NR^{22g}R^{22h}$; aryl and $Het^4$) and $Het^5$;

(ii) $C_{3-6}$ cycloalkyl which latter group is unsubstituted or substituted by one or more substituents selected from halo, OH, =O, $C_{1-4}$ alkyl and $C_{1-4}$ alkoxy;

(iii) $Het^b$ (which $Het^b$ group is unsubstituted or substituted by one or more substituents selected from halo, nitro, CN, $C(O)OC_{1-4}$ alkyl, $C_{1-5}$ alkyl, (which latter group is unsubstituted or substituted by one or more substituents selected from $Het^8$, or more particularly, OH, =O, halo, $C_{1-4}$ alkyl and $C_{1-4}$ alkoxy), $OR^{23a}$, $NR^{23g}R^{23h}$ aryl and $Het^6$)

(e.g. $Het^b$ (which $Het^b$ group is unsubstituted or substituted by one or more substituents selected from halo, nitro, CN, $C(O)OC_{1-4}$ alkyl, $C_{1-4}$ alkyl, (which latter group is unsubstituted or substituted by one or more substituents selected from OH, =O, halo, $C_{1-4}$ alkyl and $C_{1-4}$ alkoxy), $OR^{23a}$, $NR^{23g}R^{23h}$, aryl and $Het^6$));

(iv) $OR^{24a}$; or (v) $NR^{24d}R^{24e}$, (e.g. $R^{11a}$ represents, (i) $C_{1-5}$ alkyl which group is unsubstituted or substituted by one or more substituents selected from Cl, F, =O, CN, $C_{1-3}$ alkyl (which latter group is unsubstituted or substituted by one or more substituents selected from OH, =O, Cl, F, $C_{1-4}$ alkyl and $C_{1-4}$ alkoxy), $OR^{21a}$, $NR^{21g}R^{21h}$;

(ii) $C_{3-6}$ cycloalkyl which latter group is unsubstituted or substituted by one or more substituents selected from Cl, F, OH, =O, $C_{1-4}$ alkyl and $C_{1-4}$ alkoxy;

(iii) $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, or more particularly, OH, =O, Cl, F, $C_{1-4}$ alkyl and $C_{1-4}$ alkoxy), $OR^{23a}$, $NR^{23g}R^{23h}$);

(e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$));

(iv) $OR^{24a}$; or (v) $NR^{24d}R^{24e}$;

or, more particularly, $R^{11a}$ represents, $C_{1-5}$ alkyl which group is unsubstituted or substituted by one or more substituents selected from F, =O, $C_{1-3}$ alkyl (which latter group is unsubstituted or substituted by one or more substituents selected from OH, =O, F, $C_{1-4}$ alkyl and $C_{1-4}$ alkoxy), $OR^{21a}$, $NR^{21g}R^{21h}$; $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, or more particularly, OH, =O, Cl, F, $C_{1-4}$ alkyl and $C_{1-4}$ alkoxy), $OR^{23a}$, $NR^{23g}R^{23h}$) (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$)), or $OR^{24a}$);

(j) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl, $C_{2-4}$ alkenyl (which latter two groups are optionally substituted by one or more substituents selected from halo, nitro, =O, $C(O)OC_{1-4}$ alkyl, CN, $C_{1-3}$ alkyl, $C_{5-6}$ cycloalkyl (which latter two groups are optionally substituted by one or more substituents selected from OH, =O, halo, $C_{1-4}$ alkyl and $C_{1-4}$ alkoxy), $OR^{25a}$, $NR^{25g}R^{25h}$, aryl and $Het^7$), $C_{4-6}$ cycloalkyl, or $C_{5-6}$ cycloalkenyl (which latter two groups are optionally substituted by one or more substituents selected from halo, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 3- to 6-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), (e.g. $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl (which latter group is unsubstituted or substituted by one or more substituents selected from Cl, F, =O, $C(O)OC_{1-4}$ alkyl, $C_{1-3}$ alkyl, $C_{5-6}$ cycloalkyl (which latter two groups are optionally substituted by one or more substituents selected from OH, =O, Cl, F, $C_{1-4}$ alkyl and $C_{1-4}$ alkoxy), $OR^{25a}$, $NR^{25g}R^{25h}$, aryl and $Het^7$), $C_{4-6}$ cycloalkyl (which latter group is unsubstituted or substituted by one or more substituents selected from Cl, F, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 5- to 6-membered heterocyclic ring that may be aromatic, fully saturated or partially unsaturated and which may additionally contain one or more heteroatoms selected from O, S and N, which heterocyclic ring is unsubstituted or substituted by one or more substituents selected from halo, nitro, CN, $C_{1-3}$ alkyl (which latter group is unsubstituted or substituted by one or more substituents selected from OH, =O, Cl, F, $C_{1-4}$ alkyl and $C_{1-4}$ alkoxy) or, more particularly, $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-3}$ alkyl (which latter group is unsubstituted or substituted by one or more substituents selected from F, =O, C(O)$OC_{1-4}$ alkyl, $C_{1-3}$ alkyl (which latter group is unsubstituted or substituted by one or more substituents selected from OH, =O, Cl, F, $C_{1-4}$ alkyl and $C_{1-4}$ alkoxy), $OR^{25a}$, $NR^{25g}R^{25h}$);

(k) $Het^1$ to $Het^8$ (e.g. $Het^1$ to $Het^7$) and $Het^a$ to $Het^c$ independently represent a 4- to 10-membered heterocyclic group containing one or more heteroatoms selected from O, S and N, which heterocyclic groups may comprise one, two or three rings and may be substituted by one or more substituents selected from =O, or more particularly, halo, $C_{1-3}$ alkyl, which latter group is optionally substituted by one or more substituents selected from halo, $-OR^{26a}$, $-NR^{26b}R^{26c}$, $-C(O)OR^{26d}$ and $-C(O)NR^{26e}R^{26f}$ (e.g. ($Het^1$ to $Het^8$ (e.g. $Het^1$ to $Het^7$) and $Het^a$ to $Het^c$ independently represent a 5- to 8-membered heterocyclic group containing one or more heteroatoms selected from O, S and N, which heterocyclic groups may comprise one, two or three rings and may be substituted by one or more substituents selected from =O, or more particularly, Cl, Br, F, $C_{1-3}$ alkyl, which latter group is optionally substituted by one or more substituents selected from halo, $-OR^{26a}$, $-NR^{26b}R^{26c}$, $-C(O)OR^{26d}$ and $-C(O)NR^{26e}R^{26f}$);

(l) $Cy^1$ to $Cy^3$, at each occurrence, independently represent a 4- to 6-membered aromatic, fully saturated or partially unsaturated carbocyclic ring;

(m) $R^{25a}$ to $R^{25h}$ and $R^{26a}$ to $R^{26f}$ independently represent at each occurrence, H, $C_{1-4}$ alkyl, which latter group is optionally substituted by one or more substituents selected from halo, nitro, CN, $C_{1-4}$ alkyl, (which latter group is unsubstituted or substituted by one or more substituents selected from OH, =O, halo, $C_{1-4}$ alkyl and $C_{1-4}$ alkoxy), $C_{3-6}$ cycloalkyl (which latter group is unsubstituted or substituted by one or more substituents selected from halo, OH, =O, $C_{1-4}$ alkyl and $C_{1-4}$ alkoxy);

(n) Z represents $CR^4$.

In certain embodiments of the invention, L represents —C(CN)=C(H)— and Z represents $CR^4$, and the compound of formula I may be represented as a compound of formula Ia, Ia

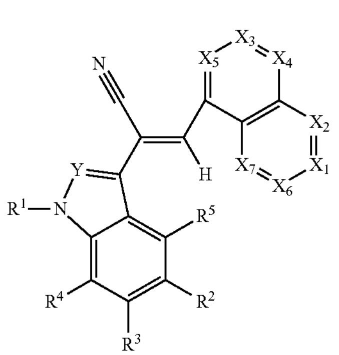

wherein $R^1$ to $R^5$, Y, and $X_1$ to $X_7$ are as defined above in relation to compounds of formula I provided that no more than three of $X_1$ to $X_7$ represent N.

In certain embodiments of the invention, L represents —C(CN)=C(H)—, Z represents $CR^4$, and $X_1$ represents N, and the compound of formula I may be represented as a compound of formula Ib, Ib

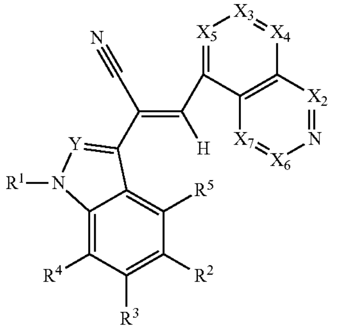

wherein $R^1$ to $R^5$, Y, and $X_2$ to $X_7$ are as defined above in relation to compounds of formula I provided that no more than three of $X_2$ to $X_7$ represent N.

In certain embodiments of the invention, L represents —C(CN)═C(H)—, $X_1$ represents N, Z represents $CR^4$, and $X_2$ to $X_5$ each represent $CR^8$, and the compound of formula I may be represented as a compound of formula Ic, Ic

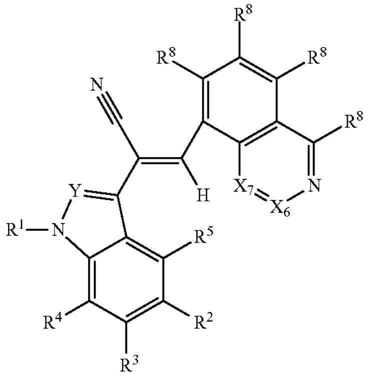

wherein $R^1$ to $R^5$, $R^8$, Y, $X_6$ and $X_7$ are as defined above in relation to compounds of formula I.

In certain embodiments of the invention, L represents —C(CN)═C(H)—, $X_1$ represents N, $X_2$ to $X_5$ each represent $CR^8$, Z represents $CR^4$, and Y represents $CR^{10}$, and the compound of formula I may be represented as a compound of formula Id, Id

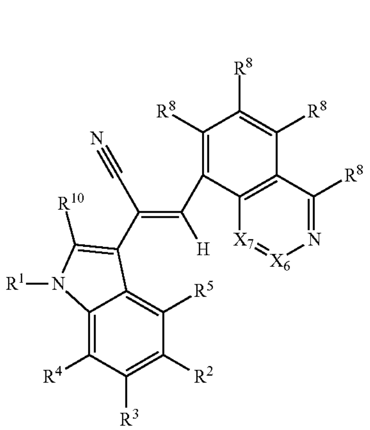

wherein $R^1$ to $R^5$, $R^8$, $R^{10}$, $X_6$ and $X_7$ are as defined above in relation to compounds of formula I.

In certain embodiments of the invention, L represents —C(CN)═C(H)—, $X_1$ represents N, $X_2$ to $X_5$ each represent $CR^8$, Z represents $CR^4$, Y represents $CR^{10}$ and $R^5$ represents H, and the compound of formula I may be represented as a compound of formula Ie, Ie

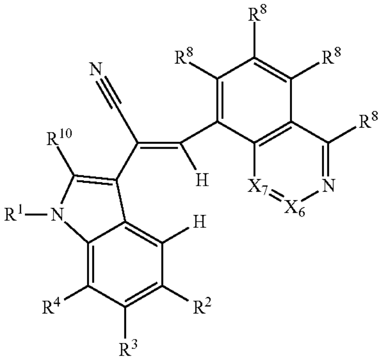

wherein $R^1$ to $R^4$, $R^8$, $R^{10}$, $X_6$ and $X_7$ are as defined above in relation to compounds of formula I.

In compounds of formula I (or Ia, Ib, Ic, Id, Ie, If or Ig (e.g. or Ia, Ib, Ic, Id or Ie)) that may be mentioned herein, when L represents —C($R^{6a}$)═C($R^{6b}$)—, the C═C double bond may be in the E- and/or Z-conformation. For example, for certain compounds of the current invention, the C═C double bond may be in the Z-configuration. Alternatively, for certain compounds of the current invention, the C═C double bond may be in the E-configuration.

Compounds of formula I (or Ia, Ib, Ic, Id or Ie) that may be mentioned include the following:

(a) $R^2$ represents:

(i) H;

(ii) Br, Cl, F;

(iii) $C_{1-4}$ alkyl which is unsubstituted or substituted by one or more substituents selected from F, $C_{1-3}$ alkyl (which latter group is unsubstituted or substituted by one or more substituents selected from OH, ═O, F, $C_{1-4}$ alkyl and $C_{1-4}$ alkoxy), $OR^{12a}$ and $NR^{12g}R^{12h}$);

(iv) $OR^{15a}$; or (v) $NR^{15g}R^{15h}$h);

(b) $R^3$, $R^4$, $R^8$ and $R^{10}$, at each occurrence, independently represents H, Br, Cl, F, CN, $C_{1-4}$ alkyl (which latter groups is unsubstituted or substituted by one or more substituents selected from F, $C_{1-3}$ alkyl (which latter group is unsubstituted or substituted by one or more substituents selected from OH, ═O, halo, $C_{1-4}$ alkyl and $C_{1-4}$ alkoxy), $OR^{12a}$ and $NR^{12g}R^{12h}$), $OR^{15a}$, $NR^{15g}R^{15h}$, nitro);

(c) $R^{11a}$ represents, $C_{1-5}$ alkyl which group is unsubstituted or substituted by one or more substituents selected from F, ═O, $C_{1-3}$ alkyl (which latter group is unsubstituted or substituted by one or more substituents selected from OH, ═O, F, $C_{1-4}$ alkyl and $C_{1-4}$ alkoxy), $OR^{21a}$, $NR^{21g}R^{21h}$, $Het^b$ (which $Het^b$ group is unsubstituted or substituted by one or more substituents selected from Cl, Br, F, C(O)O$C_{1-4}$ alkyl, $C_{1-5}$ alkyl, (which latter group is unsubstituted or substituted by one or more substituents selected from $Het^8$, or more particularly, OH, ═O, Cl, F, $C_{1-4}$ alkyl and $C_{1-4}$ alkoxy), $OR^{23a}$, $NR^{23g}R^{23h}$) (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$)) or $OR^{24a}$);

(d) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl (which latter group is unsubstituted or substituted by one or more substituents selected from Cl, F, =O, $C(O)OC_{1-4}$ alkyl, $C_{1-3}$ alkyl, $C_{5-6}$ cycloalkyl (which latter two groups are optionally substituted by one or more substituents selected from OH, =O, Cl, F, $C_{1-4}$ alkyl and $C_{1-4}$ alkoxy), $OR^{25a}$, $NR^{25g}R^{25h}$, aryl and Het[7]), $C_{4-6}$ cycloalkyl (which latter group is unsubstituted or substituted by one or more substituents selected from Cl, F, OH, =O, $C_{1-4}$ alkyl and $C_{1-4}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 5- to 6-membered heterocyclic ring that may be aromatic, fully saturated or partially unsaturated and which may additionally contain one or more heteroatoms selected from O, S and N, which heterocyclic ring is unsubstituted or substituted by one or more substituents selected from halo, nitro, CN, $C_{1-3}$ alkyl (which latter group is unsubstituted or substituted by one or more substituents selected from OH, =O, Cl, F, $C_{1-4}$ alkyl and $C_{1-4}$ alkoxy);

(e) $Het^1$ to $Het^8$ (e.g. $Het^1$ to $Het^7$) and $Het^a$ to $Het^c$ independently represent a 5- to 8-membered heterocyclic group containing one or more heteroatoms selected from O, S and N, which heterocyclic groups may comprise one, two or three rings and may be substituted by one or more substituents selected from =O, or more particularly, Cl, Br, F, $C_{1-3}$ alkyl, which latter group is optionally substituted by one or more substituents selected from halo, $-OR^{26a}$, $-NR^{26b}R^{26c}$, $-C(O)OR^{26d}$ and $-C(O)NR^{26e}R^{26f}$).

Further embodiments of the invention that may be mentioned include those that relate to compounds of formula I (or Ia, Ib, Ic, Id or Ie) in which:

(a) $R^2$ represents Br, Cl or, more particularly, H;

(b) $R^3$, $R^4$, $R^8$ and $R^{10}$, at each occurrence, each represent H;

(c) $R^{11a}$ represents, (i) $C_{1-5}$ alkyl which group is unsubstituted or substituted by one or more substituents selected from Cl, F, =O, CN, $C_{1-3}$ alkyl (which latter group is unsubstituted or substituted by one or more substituents selected from OH, =O, Cl, F, $C_{1-4}$ alkyl and $C_{1-4}$ alkoxy), $OR^{21a}$, $NR^{21g}R^{21h}$;

(ii) $C_{3-6}$ cycloalkyl which latter group is unsubstituted or substituted by one or more substituents selected from Cl, F, OH, =O, $C_{1-4}$ alkyl and $C_{1-4}$ alkoxy;

(iii) $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, or more particularly, OH, =O, Cl, F, $C_{1-4}$ alkyl and $C_{1-4}$ alkoxy), $OR^{23a}$, $NR^{23g}R^{23h}$) (e.g. $Het^b$ (which $Het^b$ group is unsubstituted or substituted by one or more substituents selected from Cl, Br, F, $C(O)OC_{1-4}$ alkyl, $C_{1-4}$ alkyl, (which latter group is unsubstituted or substituted by one or more substituents selected from OH, =O, Cl, F, $C_{1-4}$ alkyl and $C_{1-4}$ alkoxy), $OR^{23a}$, $NR^{23g}R^{23h}$));

(iv) $OR^{24a}$; or (v) $NR^{24d}R^{24e}$, (d) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23b}$ and $R^{24a}$ to $R^{24e}$ independently represent, at each occurrence, H, $C_{1-3}$ alkyl (which latter group is unsubstituted or substituted by one or more substituents selected from F, =O, $C(O)OC_{1-4}$ alkyl, $C_{1-3}$ alkyl (which latter group is unsubstituted or substituted by one or more substituents selected from OH, =O, Cl, F, $C_{1-4}$ alkyl and $C_{1-4}$ alkoxy), $OR^{25a}$, $NR^{25g}R^{25h}$).

In certain embodiments of the invention, L represents $-C(CN)=C(H)-$, $X_1$ represents N, $X_2$ to $X_5$ each represent $CR^8$, $X_6$ and $X_7$ each represent $CR^9$, Z represents $CR^4$, Y represents $CR^{19}$ and $R^5$ represents H, and the compound of formula I may be represented as a compound of formula If, If

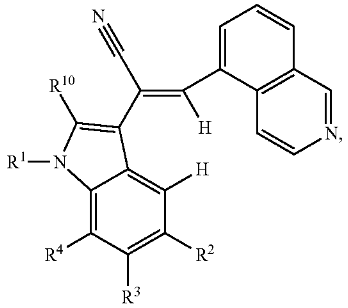

provided that $R^4$ is not Br or methylenepyrrolidine; and/or provided that $R^2$ is not Cl, F, or $OR^{15a}$ (where $R^{15a}$ comprises more than one carbon atom) or $NR^{15g}R^{15h}$.

Further embodiments of the invention that may be mentioned include those that relate to compounds of formula I (or If) in which:

$R^3$ represents H; and/or $R^{10}$ represents H or $CH_3$; and/or $R^2$ represents H, Br or $OCH_3$; and/or $R^4$ represents H or $OCH_3$.

Further embodiments of the invention that may be mentioned include those that relate to compounds of formula I (or If) in which $R^1$ represents $C(O)R^{11a}$ and $R^{11a}$ represents:

(a) H;

(b) $C_{1-6}$ alkyl (which group is unsubstituted or substituted by one or more substituents selected from =O, $C_{1-6}$ alkyl (which latter group is unsubstituted or substituted by one or more substituents selected from OH, =O, $C_{1-4}$ alkyl and $C_{1-4}$ alkoxy), $OR^{21a}$, $NR^{21g}R^{21n}$, aryl, $Cy^3$, and $Het^5$);

(c) $C_{3-10}$ cycloalkyl (which group is optionally substituted by one or more substituents selected from halo, OH, =O, $C_{1-6}$ alkyl and $C_{1-6}$ alkoxy);

(d) $Het^b$ (which $Het^b$ group is unsubstituted or substituted by one or more substituents selected from halo, nitro, CN, $C(O)OC_{1-4}$ alkyl, $C_{1-6}$ alkyl (which latter group is optionally substituted by one or more substituents selected from $Het^8$, or more particularly, OH, =O, halo, $C_{1-4}$ alkyl and $C_{1-4}$ alkoxy), $OR^{23a}$, $NR^{23g}R^{23h}$, aryl and $Het^6$), (e) $OR^{24a}$;

(f) $NR^{24d}R^{24e}$ (e.g. $R^{11a}$ represents:

(a) H;

(b) $C_{1-6}$ alkyl (which group is unsubstituted or substituted by one or more substituents selected from =O, $OR^{21a}$, and $NR^{21g}R^{21h}$);

(c) piperidinyl or piperazinyl (which $Het^b$ group is unsubstituted or substituted by one or more substituents selected from $C(O)OC_{1-4}$ alkyl, $C_{1-6}$ alkyl (which group is optionally substituted by one or more substituents selected from $Het^8$, or more particularly, =O, $C_{1-4}$ alkyl and $C_{1-4}$ alkoxy), $OR^{23a}$, and $NR^{23g}R^{23h}$)).

In certain embodiments of the invention, L represents $-C(R^{6a})=C(H)-$, $X_1$ represents N, $X_2$, $X_4$ and $X_5$ each represent $CR^8$, $X_3$ represents N or $CR^8$, $X_6$ and $X_7$ each represent $CR^9$, and $R^5$ represents H, and the compound of formula I may be represented as a compound of formula Ig, Ig

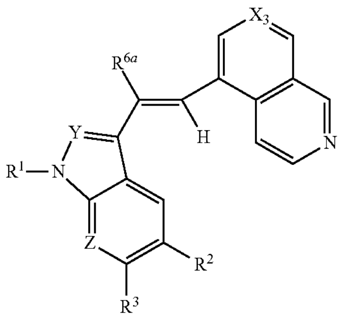

provided that when $R^{6a}$ represents CN:

$R^2$ is not F, Br or $OCH_3$; and/or when Z is $OR^4$, $OR^4$ is not $OCH_3$.

Further embodiments of the invention that may be mentioned include those that relate to compounds of formula I (or Ig) in which:

$R^3$ represents H or methylenepyrrolidinyl;

$R^2$ and $R^3$ independently represent H, $OR^{16a}$, Cl or $C_{1-6}$ alkyl (which latter group is unsubstituted or substituted by one or more substituents selected from $OR^{12a}$, $NR^{12g}R^{12h}$, aryl and $Het^1$); and/or $R^4$, when present, represents H or Br.

Embodiments of the invention that may be mentioned include those in which the compound of formula I is a compound selected from the list:

(i) (Z)-2-(1H-indol-3-yl)-3-(5-isoquinolyl)prop-2-enenitrile, also described herein as (Z)-2-(1H-indol-3-yl)-3-(isoquinolin-5-yl)acrylonitrile;

(ii) (Z)-3-(5-isoquinolyl)-2-(5-methoxy-1H-indol-3-yl) prop-2-enenitrile, also described herein as (Z)-3-(isoquinolin-5-yl)-2-(5-methoxy-1H-indol-3-yl)acrylonitrile;

(iii) 5-[(3aS,4S,6aR)-2-oxo-1,3,3a,4,6,6a-hexahydrothieno[3,4-d-]imidazol-4-yl]-N-[3-[(Z)-1-cyano-2-(5-isoquinolyl)vinyl]-1H-indol-5-yl]pentanamide, also described herein as N-(3-((Z)-1-cyano-2-(isoquinolin-5-yl)vinyl)-1H-indol-5-yl)-5-((3aS,4S,6aR)-2-oxo-hexahydro-1H-thieno[3,4-d]imidazol-4-yl)pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl] pentanamide, also described herein as N-(3-((Z)-1-cyano-2-(isoquinolin-5-yl)vinyl)-1H-indol-5-yl)-5-((3aR,4R,6aS)-2-oxohexahydro-1H-thieno[3,4-d] imidazol-4-yl)pentanamide;

(iv) (Z)-2-(5-chloro-1H-indol-3-yl)-3-(5-isoquinolyl) prop-2-enenitrile, also described herein as (Z)-2-(5-chloro-1H-indol-3-yl)-3-(isoquinolin-5-yl)acrylonitrile;

(v) (Z)-2-(5-bromo-1H-indol-3-yl)-3-(5-isoquinolyl) prop-2-enenitrile, also described herein as (Z)-2-(5-bromo-1H-indol-3-yl)-3-(isoquinolin-5-yl)acrylonitrile;

(vi) (Z)-3-(5-isoquinolyl)-2-[1-[2-(4-methylpiperazin-1-yl)acetyl]indol-3-yl]prop-2-enenitrile, also described herein as (Z)-3-(isoquinolin-5-yl)-2-(1-(2-(4-methylpiperazin-1-yl)acetyl)-1H-indol-3-yl)acrylonitrile;

(vii) N-[3-[3-[(Z)-1-cyano-2-(5-isoquinolyl)vinyl]indol-1-yl]-3-oxo-propyl]acetamide, also described herein as (Z)—N-(3-(3-(1-cyano-2-(isoquinolin-5-yl)vinyl)-1H-indol-1-yl)-3-oxopropyl)acetamide;

(viii) (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop-2-enenitrile, also described herein as (Z)-3-(isoquinolin-5-yl)-2-(1-(5-((3aS,4S,6aR)-2-oxohexahydro-1H-thieno[3,4-d]imidazol-4-yl) pentanoyl)-1H-indol-3-yl)acrylonitrile and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile, also described herein as (Z)-3-(isoquinolin-5-yl)-2-(1-(5-((3aR,4R,6aS)-2-oxohexahydro-1H-thieno[3,4-d]imidazol-4-yl) pentanoyl)-1H-indol-3-yl)acrylonitrile;

(ix) tert-butyl 4-[3-[(Z)-1-cyano-2-(5-isoquinolyl)vinyl] indole-1-carbonyl]piperidine-1-carboxylate, also described herein as (Z)-tert-butyl 4-(3-(1-cyano-2-(isoquinolin-5-yl)vinyl)-1H-indole-1-carbonyl)piperidine-1-carboxylate;

(x) (Z)-3-(5-isoquinolyl)-2-[1-(piperidine-4-carbonyl)indol-3-yl]prop-2-enenitrile, also described herein as (Z)-3-(isoquinolin-5-yl)-2-(1-(piperidine-4-carbonyl)-1H-indol-3-yl)acrylonitrile;

(xi) (Z)-3-(5-isoquinolyl)-2-[1-(1-methylpiperidine-4-carbonyl)indol-3-yl]prop-2-enenitrile;

(xii) (Z)-3-(5-isoquinolyl)-2-[1-(1-(3-fluorophenyl)-piperidine-4-carbonyl)indol-3-yl]prop-2-enenitrile;

(xiii) (Z)-3-(5-isoquinolyl)-2-[1-(1-oxazol-4-yl-piperidine-4-carbonyl)indol-3-yl]prop-2-enenitrile;

(xiv) (Z)-3-(5-isoquinolyl)-2-[1-(1-(2-methoxyacetyl)-piperidine-4-carbonyl)indol-3-yl]prop-2-enenitrile;

(xv) (Z)-2-(6-bromo-1H-indol-3-yl)-3-(5-isoquinolyl) prop-2-enenitrile, also described herein as (Z)-2-(6-bromo-1H-indol-3-yl)-3-(isoquinolin-5-yl)acrylonitrile;

(xvi) (Z)-2-(6-chloro-1H-indol-3-yl)-3-(5-isoquinolyl) prop-2-enenitrile;

(xvii) (Z)-3-(5-isoquinolyl)-2-(6-methoxy-1H-indol-3-yl) prop-2-enenitrile, also described herein as (Z)-3-(isoquinolin-5-yl)-2-(6-methoxy-1H-indol-3-yl)acrylonitrile;

(xviii) (Z)-2-(5,6-dimethoxy-1H-indol-3-yl)-3-(5-isoquinolyl)prop-2-enenitrile;

(xix) (Z)-3-(5-isoquinolyl)-2-(7-methyl-1H-indol-3-yl) prop-2-enenitrile;

(xx) 3-[(Z)-1-cyano-2-(5-isoquinolyl)vinyl]-N-methyl-1H-indole-7-carboxamide;

(xxi) 5-chloro-3-[(Z)-1-cyano-2-(5-isoquinolyl)vinyl]-N-methyl-1H-indole-7-carboxamide;

(xxii) (Z)-2-(5,7-dimethoxy-1H-indol-3-yl)-3-(5-isoquinolyl)prop-2-enenitrile;

(xxiii) (Z)-3-(5-isoquinolyl)-2-(7-methoxy-1H-indol-3-yl)prop-2-enenitrile, also described herein as (Z)-3-(isoquinolin-5-yl)-2-(7-methoxy-1H-indol-3-yl)acrylonitrile;

(xxiv) N-[3-[(Z)-1-cyano-2-(5-isoquinolyl)vinyl]-1H-indol-7-yl]acetamide, also described herein as N-(3-((Z)-1-cyano-2-(isoquinolin-5-yl)vinyl)-1H-indol-5-yl)acetamide;

(xxv) (Z)-2-(7-chloro-1H-indol-3-yl)-3-(5-isoquinolyl)prop-2-enenitrile;

(xxvi) (Z)-2-(7-fluoro-1H-indol-3-yl)-3-(5-isoquinolyl)prop-2-enenitrile;

(xxvii) (Z)-2-[7-(2-fluorophenyl)-1H-indol-3-yl]-3-(5-isoquinolyl)prop-2-enenitrile;

(xxviii) 2-(1H-indol-3-yl)-3-(5-isoquinolyl)propanenitrile;

(xxix) (Z)-2-(1H-indol-3-yl)-3-(5-isoquinolyl)but-2-enenitrile;

(xxx) (Z)-3-(1H-indol-3-yl)-2-(5-isoquinolyl)prop-2-enenitrile;

(xxxi) N-(1H-indol-3-yl)isoquinoline-5-carboxamide;

(xxxii) tert-butyl N-[3-[3-[(Z)-1-cyano-2-(5-isoquinolyl)vinyl]indol-1-yl]-3-oxopropyl]carbamate;

(xxxiii) (Z)-2-[1-(3-amino-1-oxo-propyl)indol-3-yl]-3-(5-isoquinolyl)prop-2-enenitrile;

(xxxiv) tert-butyl N-[5-[3-[(Z)-1-cyano-2-(5-isoquinolyl)vinyl]indol-1-yl]-5-oxo-pentyl]carbamate;

(xxxv) (Z)-2-[1-(5-amino-1-oxo-pentyl)indol-3-yl]-3-(5-isoquinolyl)prop-2-enenitrile;

(xxxvi) tert-butyl N-[6-[3-[(Z)-1-cyano-2-(5-isoquinolyl)vinyl]indol-1-yl]-6-oxo-hexyl]carbamate;

(xxxvii) (Z)-2-(1-(6-aminohexanoyl)-1H-indol-3-yl)-3-(isoquinolin-5-yl)acrylonitrile;

(xxxviii) (Z)-2-(1H-indazol-3-yl)-3-(5-isoquinolyl)prop-2-enenitrile;

(xxxix) (Z)-3-(5-isoquinolyl)-2-(4-methyl-1H-indol-3-yl)prop-2-enenitrile;

(xl) (Z)-3-(5-isoquinolyl)-2-(4-methoxy-1H-indol-3-yl)prop-2-enenitrile;

(xli) (Z)-2-(4,5-dimethoxy-1H-indol-3-yl)-3-(5-isoquinolyl)prop-2-enenitrile;

(xlii) (Z)-2-(4-chloro-1H-indol-3-yl)-3-(5-isoquinolyl)prop-2-enenitrile;

(xliii) 4-chloro-3-[(Z)-1-cyano-2-(5-isoquinolyl)vinyl]-1H-indole-5-carboxamide;

(xliv) (Z)-2-(1H-indol-3-yl)-3-(5-quinolyl)prop-2-enenitrile, also described herein as (Z)-2-(1H-indol-3-yl)-3-(quinolin-5-yl)acrylonitrile;

(xlv) 5-((E)-2-(1H-indol-3-yl)vinyl)isoquinoline;

(xlvi) 4-((E)-2-(1H-indol-3-yl)vinyl)-2,7-naphthyridine;

(xlvii) 5-((E)-2-(1H-pyrrolo[2,3-b]pyridin-3-yl)vinyl)isoquinoline;

(xlviii) 4-((E)-2-(1H-pyrrolo[2,3-b]pyridin-3-yl)vinyl)-2,7-naphthyridine;

(xlix) [3-[(E)-2-(5-isoquinolyl)vinyl]-1H-indol-5-yl]azinic acid;

(l) N-(5-isoquinolyl)-1H-indole-3-carboxamide, also described herein as N-(isoquinolin-5-yl)-1H-indole-3-carboxamide;

(li) (Z)-2-(1H-indol-3-yl)-3-(2,7-naphthyridin-4-yl)prop-2-enenitrile, also described herein as (Z)-2-(1H-indol-3-yl)-3-(2,7-naphthyridin-4-yl)acrylonitrile;

(lii) (Z)-3-(5-isoquinolyl)-2-[5-(3-pyrrolidin-1-ylpropoxy)-1H-indol-3-yl]prop-2-enenitrile, also described herein as (Z)-2-(5-(3-(pyrrolidin-1-yl)propoxy)-1H-indol-3-yl)-3-(isoquinolin-5-yl)acrylonitrile;

(liii) (Z)-3-(5-isoquinolyl)-2-[5-(2-methoxyethoxy)-1H-indol-3-yl]prop-2-enenitrile, also described herein as (Z)-2-(5-(2-methoxyethoxy)-1H-indol-3-yl)-3-(isoquinolin-5-yl)acrylonitrile;

(liv) (Z)-2-(6-chloro-1H-indol-3-yl)-3-(5-isoquinolyl)prop-2-enenitrile;

(lv) (Z)-2-(7-bromo-1H-indol-3-yl)-3-(5-isoquinolyl)prop-2-enenitrile, also described herein as (Z)-2-(7-bromo-1H-indol-3-yl)-3-(isoquinolin-5-yl)acrylonitrile;

(lvi) tert-butyl N-[3-[3-[(Z)-1-cyano-2-(5-isoquinolyl)vinyl]indol-1-yl]-3-oxo-propyl]carbamate, also described herein as (Z)-tert-butyl (3-(3-(1-cyano-2-(isoquinolin-5-yl)vinyl)-1H-indol-1-yl)-3-oxopropyl)carbamate;

(lvii) (Z)-2-[1-(3-aminopropanoyl)indol-3-yl]-3-(5-isoquinolyl)prop-2-enenitrile, also described herein as (Z)-2-(1-(3-aminopropanoyl)-1H-indol-3-yl)-3-(isoquinolin-5-yl)acrylonitrile;

(lviii) 5-[(3aS,4S,6aR)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide, also described herein as N-(3-(3-((Z)-1-cyano-2-(isoquinolin-5-yl)vinyl)-1H-indol-1-yl)-3-oxopropyl)-5-((3aS,4S,6aR)-2-oxohexahydro-1H-thieno[3,4-d]imidazol-4-yl)pentanamide and/or 5-[(3aR,4R,6aS)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide;

(lix) (Z)-2-(5-(2-(1,3-dioxolan-2-yl)ethoxy)-1H-indol-3-yl)-3-(isoquinolin-5-yl)acrylonitrile; and (lx) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile.

Embodiments of the invention that may be mentioned include those in which the compound of formula I is a compound selected from the list:

(lxi) (Z)-2-(1-(2-(2-methoxyethoxy)acetyl)-1H-indol-3-yl)-3-(isoquinolin-5-yl)acrylonitrile;

(lxii) (Z)-3-(isoquinolin-5-yl)-2-(6-((pyrrolidin-1-yl)methyl)-1H-indol-3-yl)acrylonitrile;

(lxiii) (Z)-3-(isoquinolin-5-yl)-2-(5-((pyrrolidin-1-yl)methyl)-1H-indol-3-yl)acrylonitrile;

(lxiv) (Z)-3-(isoquinolin-5-yl)-2-(7-((pyrrolidin-1-yl)methyl)-1H-indol-3-yl)acrylonitrile; and (lxv) (Z)-2-(1H-indazol-3-yl)-3-(isoquinolin-5-yl)acrylonitrile.

In certain embodiments of the invention, the compounds of formula I may be a chemoprotective agent for normal cells and inhibit mitosis in cancer cells and/or may be capable of inhibiting mitosis and autophagy. Compounds of formula I (or Ia, Ib, Ic, Id, Ie or If (e.g. or Ia, Ib, Ic, Id or Ie)) that may be mentioned include:

(i) (Z)-2-(1H-indol-3-yl)-3-(5-isoquinolyl)prop-2-enenitrile;

(ii) (Z)-3-(5-isoquinolyl)-2-(5-methoxy-1H-indol-3-yl)prop-2-enenitrile:

(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno

[3,4-d]imidazol-4-yl]-N-[3-[(Z)-1-cyano-2-(5-isoquinolyl)vinyl]-1H-indol-5-yl]pentanamide;

(iv) (Z)-2-(5-chloro-1H-indol-3-yl)-3-(5-isoquinolyl)prop-2-enenitrile;

(v) (Z)-2-(5-bromo-1H-indol-3-yl)-3-(5-isoquinolyl)prop-2-enenitrile;

(vi) (Z)-3-(5-isoquinolyl)-2-[1-[2-(4-methylpiperazin-1-yl)acetyl]indol-3-yl]prop-2-enenitrile;

(vii) N-[3-[3-[(Z)-1-cyano-2-(5-isoquinolyl)vinyl]indol-1-yl]-3-oxo-propyl]acetamide;

(viii) tert-butyl 4-[3-[(Z)-1-cyano-2-(5-isoquinolyl)vinyl]indole-1-carbonyl]piperidine-1-carboxylate;

(ix) (Z)-3-(5-isoquinolyl)-2-[1-(piperidine-4-carbonyl)indol-3-yl]prop-2-enenitrile;

(x) (Z)-3-(isoquinolin-5-yl)-2-(7-methoxy-1H-indol-3-yl)acrylonitrile;

(xi) (Z)-3-(isoquinolin-5-yl)-2-(6-methoxy-1H-indol-3-yl)acrylonitrile;

(xii) (Z)-tert-butyl (3-(3-(1-cyano-2-(isoquinolin-5-yl)vinyl)-1H-indol-1-yl)-3-oxopropyl)carbamate;

(xiii) N-(3-(3-((Z)-1-cyano-2-(isoquinolin-5-yl)vinyl)-1H-indol-1-yl)-3-oxopropyl)-5-((3aS,4S,6aR)-2-oxohexahydro-1H-thieno[3,4-d]imidazol-4-yl)pentanamide;

(xiv) N-(3-((Z)-1-cyano-2-(isoquinolin-5-yl)vinyl)-1H-indol-5-yl)acetamide;

(xv) (Z)-2-(6-bromo-1H-indol-3-yl)-3-(5-isoquinolyl)prop-2-enenitrile;

(xvi) (Z)-2-(7-bromo-1H-indol-3-yl)-3-(5-isoquinolyl)prop-2-enenitrile;

(xvii) (Z)-2-[1-(3-aminopropanoyl)indol-3-yl]-3-(5-isoquinolyl)prop-2-enenitrile; and (xviii) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile.

Additional compounds of formula I (or Ia, Ib, Ic, Id, Ie or If (e.g. or Ia, Ib, Ic, Id or Ie)) that may be mentioned having a dual chemoprotective/anti-mitotic and/or anti-mitotic/anti-autophagy effect include (Z)-2-(1-(2-(2-methoxyethoxy)acetyl)-1H-indol-3-yl)-3-(isoquinolin-5-yl)acrylonitrile.

In certain embodiments of the invention, the compounds of formula I may be capable of inhibiting mitosis selectively. Compounds of formula I that may be mentioned include (Z)-2-(1H-indol-3-yl)-3-(5-quinolyl)prop-2-enenitrile and (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop-2-enenitrile (and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile).

In certain embodiments of the invention, the compounds of formula I may be capable of inhibiting autophagy selectively and/or provide a chemoprotective effect for normal cells. Compounds of formula I that may be mentioned include:

(a) 5-((E)-2-(1H-indol-3-yl)vinyl)isoquinoline;

(b) 4-((E)-2-(1H-indol-3-yl)vinyl)-2,7-naphthyridine;

(c) 5-((E)-2-(1H-pyrrolo[2,3-b]pyridin-3-yl)vinyl)isoquinoline;

(d) 4-((E)-2-(1H-pyrrolo[2,3-b]pyridin-3-yl)vinyl)-2,7-naphthyridine;

(e) N-(5-isoquinolyl)-1H-indole-3-carboxamide;

(f) (Z)-2-(1H-indol-3-yl)-3-(2,7-naphthyridin-4-yl)prop-2-enenitrile;

(g) (Z)-3-(5-isoquinolyl)-2-[5-(3-pyrrolidin-1-ylpropoxy)-1H-indol-3-yl]prop-2-enenitrile;

(h) (Z)-3-(5-isoquinolyl)-2-[5-(2-methoxyethoxy)-1H-indol-3-yl]prop-2-enenitrile; and (i) (Z)-2-(5-(2-(1,3-dioxolan-2-yl)ethoxy)-1H-indol-3-yl)-3-(isoquinolin-5-yl)acrylonitrile.

Further compounds of formula I (or Ia, Ib, Ic, Id, Ie or If (e.g. or Ia, Ib, Ic, Id or Ie)) that may be mentioned that inhibit autophagy and/or provide a chemoprotective effect for normal cells include:

(i) (Z)-3-(isoquinolin-5-yl)-2-(6-((pyrrolidin-1-yl)methyl)-1H-indol-3-yl)acrylonitrile;

(ii) (Z)-3-(isoquinolin-5-yl)-2-(5-((pyrrolidin-1-yl)methyl)-1H-indol-3-yl)acrylonitrile;

(iii) (Z)-3-(isoquinolin-5-yl)-2-(7-((pyrrolidin-1-yl)methyl)-1H-indol-3-yl)acrylonitrile; and (iv) (Z)-2-(1H-indazol-3-yl)-3-(isoquinolin-5-yl)acrylonitrile.

In embodiments of the invention, the compound of formula I is not (Z)-3-(isoquinolin-5-yl)-2-(1H-pyrrolo[2,3-b]pyridin-3-yl)acrylonitrile.

When used herein "chemoprotective effect", "chemoprotective effect for normal cells", "chemoprotectant", "chemoprotective agent" and synonyms thereof refers to a property of a compound of formula I to protect normal cells (i.e. non-transformed cells) from the cytotoxic effects of one or more cytotoxic compositions. In certain embodiments, said protection may result from the reversible, selective arrest of normal cells at the $G_1$/S boundary, while allowing cancer cells to proceed through the cell cycle. Without wishing to be bound by theory, the arrest of normal cells at the $G_1$/S boundary may enable an anti-cancer agent (e.g. an antimitotic agent) to be provided at a higher dose than would normally be possible, thereby increasing its potential effectiveness. In some embodiments, it will be noted that the compound of formula I may also have additional biological effects, such as an anti-mitotic effect.

For the avoidance of doubt, references herein to compounds of formula I include, where the context permits, references to any of compounds of formula I, Ia, Ib, Ic, Id, Ie, If or Ig, (e.g. I, Ia, Ib, Ic, Id or Ie, such as I, Ia, Ib, Ic or Id). Further, references to any of the compounds of formula I, Ia, Ib, Ic, Id, Ie, If or Ig, (e.g. I, Ia, Ib, Ic, Id or Ie, such as I, Ia, Ib, Ic or Id) includes references to such compounds per se, to tautomers of such compounds, as well as to pharmaceutically acceptable salts or solvates, or pharmaceutically functional derivatives of such compounds.

Further embodiments of the invention that may be mentioned include those in which the compound of formula I is isotopically labelled. However, other, particular embodiments of the invention that may be mentioned include those in which the compound of formula I is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I. Thus, the term "isotopically labelled" includes references to compounds of formula I that are isotopically enriched at one or more positions in the compound.

The isotopic labelling or enrichment of the compound of formula I may be with a radioactive or non-radioactive isotope of any of hydrogen, carbon, nitrogen, oxygen, sulfur, fluorine, chlorine, bromine and/or iodine. Particular isotopes that may be mentioned in this respect include $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$).

When the compound of formula I is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

In accordance with the invention, compounds of formula I may be administered alone (i.e. as a monotherapy, such as a monotherapy of a hyperproliferative disease or disorder). In alternative embodiments of the invention, however, compounds of formula I may be administered in combination with another therapeutic agent (e.g. another therapeutic agent for the treatment of a hyperproliferative disease or disorder). In yet another embodiment of the invention, compounds of formula I may be administered as an adjuvant therapy after surgical treatment or as a neoadjuvant therapy before the main treatment (e.g. surgery) of the proliferative disorder or disease, either as a stand-alone compound or in combination with another therapeutic agent (e.g. another therapeutic agent for the treatment of a hyperproliferative disease or disorder).

Thus further aspects of the invention relate to the following.

(a) A compound of formula I having only antimitotic activity, as defined hereinbefore, and an anti-autophagy and/or chemoprotective agent for use in the treatment of a proliferative disease or disorder.
  In this aspect of the invention, the compound of formula I, as hereinbefore defined, may be administered sequentially, simultaneously or concomitantly with the other therapeutic agent.
(b) A compound of formula I having only antimitotic activity, as defined hereinbefore, for use in the treatment of a proliferative disease or disorder, wherein the compound of formula I is administered sequentially, simultaneously or concomitantly with an anti-autophagy and/or chemoprotective agent.
(c) Use of a compound of formula I having only antimitotic activity, as defined hereinbefore, and an anti-autophagy and/or chemoprotective agent for the preparation of a medicament for the treatment of a proliferative disease or disorder, wherein the compound of formula I is administered sequentially, simultaneously or concomitantly with the other therapeutic agent.
(d) Use of a compound of formula I having only antimitotic activity, as defined hereinbefore, for the preparation of a medicament for the treatment of a proliferative disease or disorder, wherein the medicament is administered in combination with an anti-autophagy and/or chemoprotective agent.
(e) A method of treatment of a proliferative disease or disorder, which method comprises the administration of an effective amount of a compound of formula I having only antimitotic activity, as defined hereinbefore, and an anti-autophagy and/or chemoprotective agent to a patient in need of such treatment.
(f) A combination product comprising
  (A) a compound of formula I having only antimitotic activity, as defined hereinbefore, and
  (B) an anti-autophagy and/or chemoprotective agent, wherein each of components (A) and (B) is formulated in admixture with a pharmaceutically-acceptable adjuvant, diluent or carrier.
(g) A combination product as defined at (f) above for use in the treatment of a hyperproliferative disease or disorder.
(h) The use of a combination product as defined at (f) above for the manufacture of a medicament for the treatment of a hyperproliferative disease or disorder.
(i) A method of treatment of a hyperproliferative disease or disorder, which method comprises the administration of an effective amount of a combination product as defined at (f) above.
(j) The uses and methods of the compound of formula I as defined in (a) to (e) or the uses and methods of its combination products as defined in (g) to (i), where the therapy is as an adjuvant therapy after surgical treatment or as a neoadjuvant therapy before main treatment of the proliferative disorder or disease.

As mentioned hereinbefore, compounds of formula I with antimitotic activity only (or are selective for antimitotic activity over anti-autophagy and/or chemoprotective activity) that may be mentioned herein include (Z)-2-(1H-indol-3-yl)-3-(5-quinolyl)prop-2-enenitrile and (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop-2-enenitrile (and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile).

When used herein, the term "antimitotic activity only" refers to a compound that has little to no anti-autophagy and/or chemoprotective activity. For example, the ratio between the compound's antimitotic activity and anti-autophagy activity (antimitotic:anti-autophagy and/or chemoprotective effect) may be greater than 50:1, such as greater than or equal to 100:1, for example greater than or equal to 1,000:1.

When used herein, the term "anti-autophagy agent" includes references to one or more (e.g. one) therapeutic agents that are known to be useful as anti-autophagy agents, as well as compounds of formula I that are anti-autophagy and/or chemoprotective agents; the compounds of formula I that are anti-autophagy and/or chemoprotective agents may be anti-autophagy and/or chemoprotective agents only or may also have anti-mitotic activity themselves. Anti-autophagy agents that may be mentioned herein include PI3K inhibitors (e.g. 3-methyladenine, wortmannin, LY294002 (2-(4-Morpholinyl)-8-phenyl-1(4H) benzopyran-4-one)), bafilomycin A1, thapsigargin, lysophosphatidic acid sodium salt, spautin-1, forskolin, nocodazole, L-asparagine, vinblastine, dibutyryl cAMP, hydroxychloroquine, tolazamide, quinine, SP600125 (1,9-pyrazoloanthrone), AICAR (5-aminoimidazole-4-carboxamide 1-β-D-ribofuranoside), anisomycin, SB-216763 (3-(2,4-dichlorophenyl)-4-(1-methyl-1H-indol-3-yl)-1H-pyrrole-2,5-dione), chloroquine, hydroxychloroquine, Lys05, E64d ((2S,3S)-trans-epoxysuccinyl-L-leucylamido-3-methylbutane ethyl ester), leupeptin, pepstatin A, desmethylclomipramine hydrochloride, rolipram, PMSF (phenylmethylsulfonyl fluoride), EHNA (erythro-9-(2-hydroxy-3-nonyl)adenine hydrochloride), pifithrin-μ, clomipramine, cycloheximide, N-acetyl-L-cysteine, GMX1778, p97 inhibitors (e.g. DBeQ (N2,N4-dibenzylquinazoline-2,4-diamine), MDBN (3,4-Methylenedioxy-β-nitrostyrene)) and pharmaceutically acceptable salts or solvates thereof. Anti-autophagy and/or chemoprotective only compounds of formula I that may be mentioned herein include:

(a) 5-((E)-2-(1H-indol-3-yl)vinyl)isoquinoline;
(b) 4-((E)-2-(1H-indol-3-yl)vinyl)-2,7-naphthyridine;
(c) 5-((E)-2-(1H-pyrrolo[2,3-b]pyridin-3-yl)vinyl)isoquinoline;
(d) 4-((E)-2-(1H-pyrrolo[2,3-b]pyridin-3-yl)vinyl)-2,7-naphthyridine
(e) N-(5-isoquinolyl)-1H-indole-3-carboxamide;
(f) (Z)-2-(1H-indol-3-yl)-3-(2,7-naphthyridin-4-yl)prop-2-enenitrile;
(g) (Z)-3-(5-isoquinolyl)-2-[5-(3-pyrrolidin-1-ylpropoxy)-1H-indol-3-yl]prop-2-enenitrile;
(h) (Z)-3-(5-isoquinolyl)-2-[5-(2-methoxyethoxy)-1H-indol-3-yl]prop-2-enenitrile; and
(i) (Z)-2-(5-(2-(1,3-dioxolan-2-yl)ethoxy)-1H-indol-3-yl)-3-(isoquinolin-5-yl)acrylonitrile.

Further anti-autophagy only compounds of formula I that may be mentioned herein include:

(i) (Z)-3-(isoquinolin-5-yl)-2-(6-((pyrrolidin-1-yl)methyl)-1H-indol-3-yl)acrylonitrile;
(ii) (Z)-3-(isoquinolin-5-yl)-2-(5-((pyrrolidin-1-yl)methyl)-1H-indol-3-yl)acrylonitrile;
(iii) (Z)-3-(isoquinolin-5-yl)-2-(7-((pyrrolidin-1-yl)methyl)-1H-indol-3-yl)acrylonitrile; and
(iv) (Z)-2-(1H-indazol-3-yl)-3-(isoquinolin-5-yl)acrylonitrile.

In certain embodiments of the invention, compounds of formula I may be chemoprotective agents and antimitotic agents. Chemoprotective and antimitotic compounds of formula I include:

(i) (Z)-2-(1H-indol-3-yl)-3-(5-isoquinolyl)prop-2-enenitrile;
(ii) (Z)-3-(5-isoquinolyl)-2-(5-methoxy-1H-indol-3-yl)prop-2-enenitrile:
(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide;
(iv) (Z)-2-(5-chloro-1H-indol-3-yl)-3-(5-isoquinolyl)prop-2-enenitrile;
(v) (Z)-2-(5-bromo-1H-indol-3-yl)-3-(5-isoquinolyl)prop-2-enenitrile;
(vi) (Z)-3-(5-isoquinolyl)-2-[1-[2-(4-methylpiperazin-1-yl)acetyl]indol-3-yl]prop-2-enenitrile;
(vii) N-[3-[3-[(Z)-1-cyano-2-(5-isoquinolyl)vinyl]indol-1-yl]-3-oxo-propyl]acetamide;
(viii) tert-butyl 4-[3-[(Z)-1-cyano-2-(5-isoquinolyl)vinyl]indole-1-carbonyl]piperidine-1-carboxylate;
(ix) (Z)-3-(5-isoquinolyl)-2-[1-(piperidine-4-carbonyl)indol-3-yl]prop-2-enenitrile;
(x) (Z)-3-(isoquinolin-5-yl)-2-(7-methoxy-1H-indol-3-yl)acrylonitrile;
(xi) (Z)-3-(isoquinolin-5-yl)-2-(6-methoxy-1H-indol-3-yl)acrylonitrile;
(xii) (Z)-tert-butyl (3-(3-(1-cyano-2-(isoquinolin-5-yl)vinyl)-1H-indol-1-yl)-3-oxopropyl)carbamate;
(xiii) N-(3-(3-((Z)-1-cyano-2-(isoquinolin-5-yl)vinyl)-1H-indol-1-yl)-3-oxopropyl)-5-((3aS,4S,6aR)-2-oxohexahydro-1H-thieno[3,4-d]imidazol-4-yl)pentanamide;
(xiv) N-(3-((Z)-1-cyano-2-(isoquinolin-5-yl)vinyl)-1H-indol-5-yl)acetamide;
(xv) (Z)-2-(6-bromo-1H-indol-3-yl)-3-(5-isoquinolyl)prop-2-enenitrile;
(xvi) (Z)-2-(7-bromo-1H-indol-3-yl)-3-(5-isoquinolyl)prop-2-enenitrile;
(xvii) (Z)-2-[1-(3-aminopropanoyl)indol-3-yl]-3-(5-isoquinolyl)prop-2-enenitrile;
(xviii) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile; and
(xix) (Z)-2-(1-(2-(2-methoxyethoxy)acetyl)-1H-indol-3-yl)-3-(isoquinolin-5-yl)acrylonitrile.

Chemoprotective only compounds of formula I include:

(a) 5-((E)-2-(1H-indol-3-yl)vinyl)isoquinoline;
(b) 4-((E)-2-(1H-indol-3-yl)vinyl)-2,7-naphthyridine;
(c) 5-((E)-2-(1H-pyrrolo[2,3-b]pyridin-3-yl)vinyl)isoquinoline;
(d) 4-((E)-2-(1H-pyrrolo[2,3-b]pyridin-3-yl)vinyl)-2,7-naphthyridine
(e) N-(5-isoquinolyl)-1H-indole-3-carboxamide;
(f) (Z)-2-(1H-indol-3-yl)-3-(2,7-naphthyridin-4-yl)prop-2-enenitrile;
(g) (Z)-3-(5-isoquinolyl)-2-[5-(3-pyrrolidin-1-ylpropoxy)-1H-indol-3-yl]prop-2-enenitrile;
(h) (Z)-3-(5-isoquinolyl)-2-[5-(2-methoxyethoxy)-1H-indol-3-yl]prop-2-enenitrile; and
(i) (Z)-2-(5-(2-(1,3-dioxolan-2-yl)ethoxy)-1H-indol-3-yl)-3-(isoquinolin-5-yl)acrylonitrile;
(j) (Z)-3-(isoquinolin-5-yl)-2-(6-((pyrrolidin-1-yl)methyl)-1H-indol-3-yl)acrylonitrile;
(k) (Z)-3-(isoquinolin-5-yl)-2-(5-((pyrrolidin-1-yl)methyl)-1H-indol-3-yl)acrylonitrile;
(l) (Z)-3-(isoquinolin-5-yl)-2-(7-((pyrrolidin-1-yl)methyl)-1H-indol-3-yl)acrylonitrile; and
(m) (Z)-2-(1H-indazol-3-yl)-3-(isoquinolin-5-yl)acrylonitrile.

When used herein "anti-autophagy compounds of formula I" and "chemoprotective compounds of formula I" may be used interchangeably and may also relate to compounds that have dual anti-mitotic and chemoprotective (or anti-autophagy) activity. When used herein "anti-autophagy only compounds of formula I" and "chemoprotective only compounds of formula I" may be used interchangeably.

When used herein, the term "administered sequentially, simultaneously or concomitantly" includes references to:

administration of separate pharmaceutical formulations (one containing the compound of formula I and one or more others containing the one or more other therapeutic agents); and administration of a single pharmaceutical formulation containing the compound of formula I and the other therapeutic agent(s).

The combination product described above provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)).

Thus, there is further provided:

(I) a pharmaceutical formulation including a compound of formula I with antimitotic activity only, as hereinbefore defined and an anti-autophagy and/or chemoprotective agent, in admixture with a pharmaceutically-acceptable adjuvant, diluent or carrier (which formulation is hereinafter referred to as a "combined preparation"); and (II) a kit of parts comprising components:

(i) a pharmaceutical formulation including a compound of formula I with antimitotic activity only, as hereinbefore defined, in admixture with a pharmaceutically-acceptable adjuvant, diluent or carrier; and (ii) a pharmaceutical formulation including an anti-autophagy and/or chemoprotective agent, in admixture with a pharmaceutically-acceptable adjuvant, diluent or carrier, which components (i) and (ii) are each provided in a form that is suitable for administration in conjunction with the other.

Component (i) of the kit of parts is thus component (A) in admixture with a pharmaceutically-acceptable adjuvant, diluent or carrier. Similarly, component (ii) is component (B) in admixture with a pharmaceutically-acceptable adjuvant, diluent or carrier.

Further aspects of the invention relate to the following.

(a) A compound of formula I having only anti-autophagy and/or chemoprotective activity, as defined hereinbefore, and an antimitotic agent for use in the treatment of a hyperproliferative disease or disorder.

In this aspect of the invention, the compound of formula I, as hereinbefore defined, may be administered sequentially, simultaneously or concomitantly with the other therapeutic agent.

(b) A compound of formula I having only anti-autophagy and/or chemoprotective activity, as defined hereinbefore, for use in the treatment of a hyperproliferative disease or disorder, wherein the compound of formula I is administered sequentially, simultaneously or concomitantly with an antimitotic agent.

(c) Use of a compound of formula I having only anti-autophagy and/or chemoprotective activity, as defined hereinbefore, and an antimitotic agent for the preparation of a medicament for the treatment of a hyperproliferative disease or disorder, wherein the compound of formula I is administered sequentially, simultaneously or concomitantly with the other therapeutic agent.

(d) Use of a compound of formula I having only anti-autophagy and/or chemoprotective activity, as defined hereinbefore, for the preparation of a medicament for the treatment of a hyperproliferative disease or disorder, wherein the medicament is administered in combination with an antimitotic agent.

(e) A method of treatment of a hyperproliferative disease or disorder, which method comprises the administration of an effective amount of a compound of formula I having only anti-autophagy and/or chemoprotective activity, as defined hereinbefore, and an antimitotic agent to a patient in need of such treatment.

(f) A combination product comprising (C) a compound of formula I having only anti-autophagy and/or chemoprotective activity, as defined hereinbefore, and (D) an antimitotic agent, wherein each of components (C) and (D) is formulated in admixture with a pharmaceutically-acceptable adjuvant, diluent or carrier.

(g) A combination product as defined at (f) above for use in the treatment of a hyperproliferative disease or disorder.

(h) The use of a combination product as defined at (f) above for the manufacture of a medicament for the treatment of a hyperproliferative disease or disorder.

(i) A method of treatment of a hyperproliferative disease or disorder, which method comprises the administration of an effective amount of a combination product as defined at (f) above.

(j) The uses and methods of the compound of formula I as defined in (a) to (e) or the uses and methods of its combination products as defined in (g) to (i), where the therapy is as an adjuvant therapy after surgical treatment or as a neoadjuvant therapy before main treatment of the proliferative disorder or disease.

As mentioned hereinbefore, compounds of formula I with anti-autophagy and/or chemoprotective activity only (or are selective for anti-autophagy and/or chemoprotective activity over antimitotic activity) that may be mentioned herein include:

(a) 5-((E)-2-(1H-indol-3-yl)vinyl)isoquinoline;

(b) 4-((E)-2-(1H-indol-3-yl)vinyl)-2,7-naphthyridine;

(c) 5-((E)-2-(1H-pyrrolo[2,3-b]pyridin-3-yl)vinyl)isoquinoline;

(d) 4-((E)-2-(1H-pyrrolo[2,3-b]pyridin-3-yl)vinyl)-2,7-naphthyridine;

(e) N-(5-isoquinolyl)-1H-indole-3-carboxamide;

(f) (Z)-2-(1H-indol-3-yl)-3-(2,7-naphthyridin-4-yl)prop-2-enenitrile;

(g) (Z)-3-(5-isoquinolyl)-2-[5-(3-pyrrolidin-1-yl-propoxy)-1H-indol-3-yl]prop-2-enenitrile;

(h) (Z)-3-(5-isoquinolyl)-2-[5-(2-methoxyethoxy)-1H-indol-3-yl]prop-2-enenitrile; and (i) (Z)-2-(5-(2-(1,3-dioxolan-2-yl)ethoxy)-1H-indol-3-yl)-3-(isoquinolin-5-yl)acrylonitrile.

Further compounds of formula I with anti-autophagy and/or chemoprotective activity only (or are selective for anti-autophagy and/or chemoprotective activity over antimitotic activity) that may be mentioned herein include:

(i) (Z)-3-(isoquinolin-5-yl)-2-(6-((pyrrolidin-1-yl)methyl)-1H-indol-3-yl)acrylonitrile;

(ii) (Z)-3-(isoquinolin-5-yl)-2-(5-((pyrrolidin-1-yl)methyl)-1H-indol-3-yl)acrylonitrile;

(iii) (Z)-3-(isoquinolin-5-yl)-2-(7-((pyrrolidin-1-yl)methyl)-1H-indol-3-yl)acrylonitrile; and (iv) (Z)-2-(1H-indazol-3-yl)-3-(isoquinolin-5-yl)acrylonitrile.

When used herein, the terms "anti-autophagy activity only", "chemoprotective activity only" and "anti-autophagy and/or chemoprotective activity only" refer to a compound that has little to no antimitotic activity. For example, the ratio between the compound's antimitotic activity and anti-autophagy and/or chemoprotective activity (anti-autophagy: antimitotic and/or chemoprotective) may be greater than 50:1, such as greater than or equal to 100:1, for example greater than or equal to 1,000:1.

When used herein, the term "antimitotic agent" includes references to one or more (e.g. one) therapeutic agents that are known to be useful as antimitotic agents, as well as compounds of formula I that are antimitotic agents only. Antimitotic agents that may be mentioned herein include taxanes (e.g. paclitaxel, docetaxel, cabazitaxel), vinca alkaloids (e.g. vinblastine, vincristine, vindesine, vinorelbine), colchicine, podophyllotoxin, podophyllin, teniposide, griseofulvin, halichondrin B, eribulin, estramustine, epothilones (e.g. epothilones A-F, ixabepilone, patupilone, sagopilone, BMS-310705, BMS-247550) and pharmaceutically acceptable salts or solvates thereof. Antimitotic only compounds of formula I that may be mentioned herein includes (Z)-2-(1H-indol-3-yl)-3-(5-quinolyl)prop-2-enenitrile and (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop- 2-enenitrile (and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile).

The combination product described above provides for the administration of component (C) in conjunction with component (D), and may thus be presented either as separate formulations, wherein at least one of those formulations comprises component (C) and at least one comprises component (D), or may be presented (i.e. formulated) as a combined preparation (i.e. presented as a single formulation including component (C) and component (D)).

Thus, there is further provided:

(I) a pharmaceutical formulation including a compound of formula I with anti-autophagy and/or chemoprotective activity only, as hereinbefore defined and an antimitotic agent, in admixture with a pharmaceutically-acceptable adjuvant, diluent or carrier (which formulation is hereinafter referred to as a "combined preparation"); and (II) a kit of parts comprising components:

(i) a pharmaceutical formulation including a compound of formula I with anti-autophagy and/or chemoprotective activity only, as hereinbefore defined, in admixture with a pharmaceutically-acceptable adjuvant, diluent or carrier; and (ii) a pharmaceutical formulation including an antimitotic agent, in admixture with a pharmaceutically-acceptable adjuvant, diluent or carrier, which components (i) and (ii) are each provided in a form that is suitable for administration in conjunction with the other.

Component (i) of the kit of parts is thus component (C) in admixture with a pharmaceutically-acceptable adjuvant, diluent or carrier. Similarly, component (ii) is component (D) in admixture with a pharmaceutically-acceptable adjuvant, diluent or carrier.

Further aspects of the invention relate to the following.

(a) A compound having only antimitotic activity, as defined hereinbefore, and an anti-autophagy and/or chemoprotective agent for use in the treatment of a proliferative disease or disorder.

In this aspect of the invention, the compound having antimitotic activity only and the anti-autophagy and/or chemoprotective agent are as hereinbefore defined and they may be administered sequentially, simultaneously or concomitantly with one another.

(b) A compound having only antimitotic activity, as defined hereinbefore, for use in the treatment of a proliferative disease or disorder, wherein the compound having only antimitotic activity is administered sequentially, simultaneously or concomitantly with an anti-autophagy and/or chemoprotective agent.

(c) Use of a compound having only antimitotic activity, as defined hereinbefore, and an anti-autophagy and/or chemoprotective agent for the preparation of a medicament for the treatment of a proliferative disease or disorder, wherein the compound having only antimitotic activity is administered sequentially, simultaneously or concomitantly with the other therapeutic agent.

(d) Use of a compound having only antimitotic activity, as defined hereinbefore, for the preparation of a medicament for the treatment of a proliferative disease or disorder, wherein the medicament is administered in combination with an anti-autophagy and/or chemoprotective agent.

(e) A method of treatment of a proliferative disease or disorder, which method comprises the administration of an effective amount of a compound having only antimitotic activity, as defined hereinbefore, and an anti-autophagy and/or chemoprotective agent to a patient in need of such treatment.

(f) A combination product comprising (E) a compound having only antimitotic activity, as defined hereinbefore, and (F) an anti-autophagy and/or chemoprotective agent, wherein each of components (E) and (F) is formulated in admixture with a pharmaceutically-acceptable adjuvant, diluent or carrier.

(g) A combination product as defined at (f) above for use in the treatment of a hyperproliferative disease or disorder.

(h) The use of a combination product as defined at (f) above for the manufacture of a medicament for the treatment of a hyperproliferative disease or disorder.

(i) A method of treatment of a hyperproliferative disease or disorder, which method comprises the administration of an effective amount of a combination product as defined at (f) above.

(j) The uses and methods of the compound of formula I as defined in (a) to (e) or the uses and methods of its combination products as defined in (g) to (i), where the therapy is as an adjuvant therapy after surgical treatment or as a neoadjuvant therapy before main treatment of the proliferative disorder or disease.

When used herein, the term "antimitotic agent" includes references to one or more (e.g. one) therapeutic agents that are known to be useful as antimitotic agents, as well as compounds of formula I that are antimitotic agents only. Antimitotic agents that may be mentioned herein include taxanes (e.g. paclitaxel, docetaxel, cabazitaxel), vinca alkaloids (e.g. vinblastine, vincristine, vindesine, vinorelbine), colchicine, podophyllotoxin, podophyllin, teniposide, griseofulvin, halichondrin B, eribulin, estramustine, epothilones (e.g. epothilones A-F, ixabepilone, patupilone, sagopilone, BMS-310705, BMS-247550) and pharmaceutically acceptable salts or solvates thereof. Antimitotic only compounds of formula I that may be mentioned herein includes (Z)-2-(1H-indol-3-yl)-3-(5-quinolyl)prop-2-enenitrile and (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop-2-enenitrile (and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile).

When used herein, the term "anti-autophagy agent" includes references to one or more (e.g. one) therapeutic agents that are known to be useful as anti-autophagy agents, as well as compounds of formula I that are anti-autophagy and/or chemoprotective agents only. Anti-autophagy agents that may be mentioned herein include PI3K inhibitors (e.g. 3-methyladenine, wortmannin, LY294002 (2-(4-Morpholinyl)-8-phenyl-1(4H) benzopyran-4-one)), bafilomycin A1, thapsigargin, lysophosphatidic acid sodium salt, spautin-1, forskolin, nocodazole, L-asparagine, vinblastine, dibutyryl cAMP, hydroxychloroquine, tolazamide, quinine, SP600125 (1,9-pyrazoloanthrone), AICAR (5-aminoimidazole-4-carboxamide 1-β-D-ribofuranoside), anisomycin, SB-216763 (3-(2,4-dichlorophenyl)-4-(1-methyl-1H-indol-3-yl)-1H-pyrrole-2,5-dione), chloroquine, hydroxychloroquine, Lys05, E64d ((2S,3S)-trans-epoxysuccinyl-L-leucylamido-3-methylbutane ethyl ester), leupeptin, pepstatin A, desmethylclomipramine hydrochloride, rolipram, PMSF (phenylmethylsulfonyl fluoride), EHNA (erythro-9-(2-hydroxy-3-nonyl)adenine hydrochloride), pifithrin-p, clomipramine, cycloheximide, N-acetyl-L-cysteine, GMX1778, p97 inhibitors (e.g. DBeQ (N2,N4-dibenzylquinazoline-2,4-diamine), MDBN (3,4-Methylenedioxy-8-nitrostyrene)) and pharmaceutically acceptable salts or solvates thereof. Anti-autophagy and/or chemoprotective only compounds of formula I that may be mentioned herein include:

(a) 5-((E)-2-(1H-indol-3-yl)vinyl)isoquinoline;
(b) 4-((E)-2-(1H-indol-3-yl)vinyl)-2,7-naphthyridine;
(c) 5-((E)-2-(1H-pyrrolo[2,3-b]pyridin-3-yl)vinyl)isoquinoline;
(d) 4-((E)-2-(1H-pyrrolo[2,3-b]pyridin-3-yl)vinyl)-2,7-naphthyridine
(e) N-(5-isoquinolyl)-1H-indole-3-carboxamide;
(f) (Z)-2-(1H-indol-3-yl)-3-(2,7-naphthyridin-4-yl)prop-2-enenitrile;
(g) (Z)-3-(5-isoquinolyl)-2-[5-(3-pyrrolidin-1-yl-propoxy)-1H-indol-3-yl]prop-2-enenitrile;
(h) (Z)-3-(5-isoquinolyl)-2-[5-(2-methoxyethoxy)-1H-indol-3-yl]prop-2-enenitrile; and
(i) (Z)-2-(5-(2-(1,3-dioxolan-2-yl)ethoxy)-1H-indol-3-yl)-3-(isoquinolin-5-yl)acrylonitrile.

Further anti-autophagy and/or chemoprotective only compounds of formula I that may be mentioned herein include:

(i) (Z)-3-(isoquinolin-5-yl)-2-(6-((pyrrolidin-1-yl)methyl)-1H-indol-3-yl)acrylonitrile;
(ii) (Z)-3-(isoquinolin-5-yl)-2-(5-((pyrrolidin-1-yl)methyl)-1H-indol-3-yl)acrylonitrile;
(iii) (Z)-3-(isoquinolin-5-yl)-2-(7-((pyrrolidin-1-yl)methyl)-1H-indol-3-yl)acrylonitrile; and
(iv) (Z)-2-(1H-indazol-3-yl)-3-(isoquinolin-5-yl)acrylonitrile.

In certain embodiments of the invention, compounds of formula I may be chemoprotective agents and antimitotic agents as hereinbefore defined.

When used herein "anti-autophagy only compounds of formula I" and "chemoprotective only compounds of formula I" may be used interchangeably.

When used herein, the term "antimitotic activity only", "chemoprotective activity only" and "anti-autophagy only" are as defined hereinbefore.

The combination product described above provides for the administration of component (E) in conjunction with component (F), and may thus be presented either as separate formulations, wherein at least one of those formulations comprises component (E) and at least one comprises component (F), or may be presented (i.e. formulated) as a combined preparation (i.e. presented as a single formulation including component (E) and component (F)).

Thus, there is further provided:

(I) a pharmaceutical formulation including a compound with antimitotic activity only and an anti-autophagy and/or chemoprotective agent, both as hereinbefore defined, in admixture with a pharmaceutically-acceptable adjuvant, diluent or carrier (which formulation is hereinafter referred to as a "combined preparation"); and (II) a kit of parts comprising components:

(i) a pharmaceutical formulation including a compound with antimitotic activity only, as hereinbefore defined, in admixture with a pharmaceutically-acceptable adjuvant, diluent or carrier; and
(ii) a pharmaceutical formulation including an anti-autophagy and/or chemoprotective agent, in admixture with a pharmaceutically-acceptable adjuvant, diluent or carrier, which components (i) and (ii) are each provided in a form that is suitable for administration in conjunction with the other.

Component (i) of the kit of parts is thus component (E) in admixture with a pharmaceutically-acceptable adjuvant, diluent or carrier. Similarly, component (ii) is component (F) in admixture with a pharmaceutically-acceptable adjuvant, diluent or carrier.

Compounds of formula I may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy,* 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula I in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

Other compounds of formula I may be prepared in accordance with techniques that are well known to those skilled in the art, for example as described hereinafter in the examples section.

Substituents, such as $R^2$ in final compounds of formula I (or precursors thereto and other relevant intermediates) may be modified one or more times, after or during the processes described hereinafter by way of methods that are well known to those skilled in the art. Examples of such methods include substitutions, reductions (e.g. carbonyl bond reductions in the presence of suitable and, if necessary, chemoselective, reducing agents such as $LiBH_4$ or $NaBH_4$), oxidations, alkylations, acylations, hydrolyses, esterifications, and etherifications. The precursor groups can be changed to a different such group, or to the groups defined in formula I, at any time during the reaction sequence.

Compounds of the invention may be isolated from their reaction mixtures using conventional techniques (e.g. recrystallisation, column chromatography, preparative HPLC, etc.).

In the processes described hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described hereinafter may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis",* 3rd edition, T. W. Greene & P. G. M. Wutz, Wiley-Interscience (1999).

As used herein, the term "functional groups" means, in the case of unprotected functional groups, hydroxy-, thiolo-, amino function, carboxylic acid and, in the case of protected functional groups, lower alkoxy, N-, O-, S-acetyl, carboxylic acid ester.

Non-limiting examples which embody certain aspects of the invention will now be described.

EXAMPLES

Chemical Examples

General Methods:

Reagents for organic synthesis were purchased from commercial sources. Reactions were routinely monitored by thin-layer chromatography (TLC) on silica gel coated aluminium plates (Merck 60, F254) with visualization under UV light, and potassium permanganate, anisaldehyde or cerium ammonium molybdate solutions as developing stains. Flash column chromatography was performed on silica gel (Merck 60, 70-230 mesh). Microwave reactions were performed using a Biotage Microwave Reactor. The preliminary purity and identity of compounds were assessed post-purification by tandem HPLC/mass spectral (LC-MS) analyses on an Agilent 6130 quadrupole mass spectrometer in electrospray ionization (ESI) positive mode following separation on an Agilent 1200 Infinity Series module. The HPLC separations were performed on a Thermo Scientific Hypersil GOLD column (5 μm, 150×2.1 mm) at a UV detection wavelength of 254 nm. The following HPLC method was applied: at a flow rate of 0.5 mL/min, separation using a gradient of 10-95% acetonitrile in water+0.1% formic acid over 2 min, holding for 4.5 min, then reversing to 10% acetonitrile within 0.1 min and holding for an additional 1.4 min. $^1H$ and $^{13}C$ nuclear magnetic resonance (NMR) spectra were recorded using a Bruker Avance 400 Ultrashield spectrometer. Peak locations were referenced using the residual solvent peak. High resolution MS (HRMS) was determined using a Bruker microTOF-Q II. Single crystal X-ray crystallography structure determination was performed at the Chemical, Molecular and Materials Analysis Centre, X-ray Diffraction Laboratory, Department of Chemistry, National University of Singapore.

Scheme A

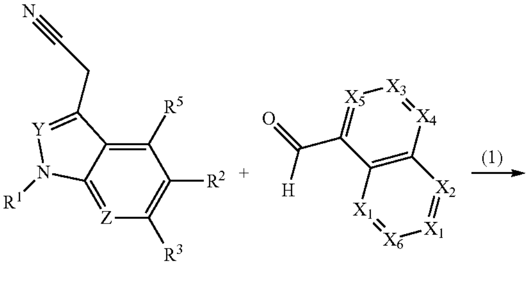

-continued

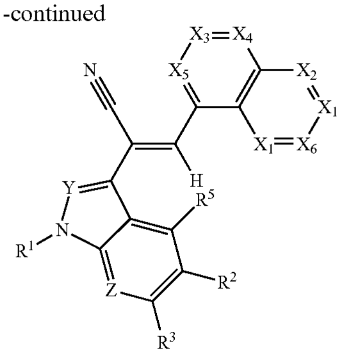

General Procedure (1):

Microwave method: To an indole-3-acetonitrile derivative (1.0 equiv) dissolved in anhydrous methanol (4 mL for 2.31 mmol of starting material) in a dried microwave vial, sodium methoxide (1.7 equiv) was added and stirred at room temperature for 15 min protected from light. Quinoline/isoquinoline-carboxaldehyde derivative (1.2 equiv) was added and the mixture was subjected to microwave irradiation at 95° C. for 8.5 min. The reaction was cooled to room temperature and then chilled in an ice/salt bath. The resulting precipitate was filtered, washed with methanol, and dried under vacuum to afford a solid as the product.

Sealed tube method: To an indole-3-acetonitrile derivative (1.0 equiv), quinoline/isoquinoline-carboxaldehyde derivative (1.0 equiv), sodium methoxide (3.0 equiv) in a dried glass reaction tube, anhydrous methanol (15 mL for 7.72 mmol of indole-3-acetonitrile derivative) was added. The reaction tube was sealed and heated at 75° C. in an oil bath for 16 h protected from light. The reaction was allowed to cool to room temperature and then chilled in an ice/salt bath. The resulting precipitate was filtered, washed with methanol, and dried under vacuum to afford a solid as the product.

Chemical Example 1 (Compound 1) [a131]

(Z)-2-(1H-indol-3-yl)-3-(isoquinolin-5-yl)acrylonitrile

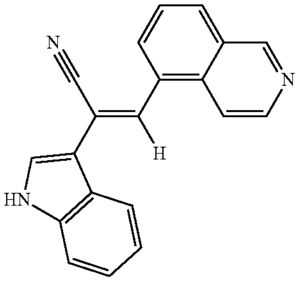 [SMILES: N#C/C(=C\c1cccc2cnccc12)c1c[nH]c2ccccc12]

Compound 1 [a131] (114 mg, 0.386 mmol) was prepared as a yellow solid from indole-3-acetonitrile (120 mg, 0.769 mmol), isoquinoline-5-carboxaldehyde (147 mg, 0.938 mmol) and sodium methoxide (71 mg, 1.307 mmol) according to general procedure (1) microwave method. Yield: 47%. Yellow crystals were obtained by recrystallization using acetone and methanol. $^1$H NMR (400 MHz, DMSO) δ: 9.41 (s, 1H), 8.60 (d, J=6.0 Hz, 1H), 8.34 (s, 1H), 8.26 (d, J=7.3 Hz, 1H), 8.22 (d, J=8.1 Hz, 1H), 8.12 (d, J=7.6 Hz, 1H), 8.05 (d, J=6.0 Hz, 1H), 7.95 (s, 1H), 7.82 (t, J=7.8 Hz, 1H), 7.54 (d, J=7.9 Hz, 1H), 7.28-7.19 (m, 2H). $^{13}$C NMR (100 MHz, DMSO) δ: 152.93, 143.69, 137.26, 133.54, 132.54, 131.29, 130.25, 128.91, 128.23, 127.44, 127.11, 123.83, 122.56, 120.69, 119.50, 117.96, 117.12, 112.56, 110.43, 110.41. LC-MS (ESI): m/z 296.1 $[M+H]^+$. HRMS (ESI): m/z calculated $[M+H]^+$ $C_{20}H_{14}N_3^+$ 296.1182, found 296.1190.

Chemical Example 2 (Compound 2) [a156]

(Z)-3-(isoquinolin-5-yl)-2-(5-methoxy-1H-indol-3-yl)acrylonitrile

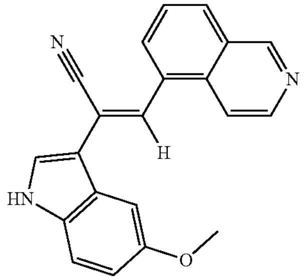 [SMILES: COc1ccc2[nH]cc(/C(C#N)=C/c3cccc4cnccc34)c2c1]

Compound 2 [a156] (602 mg, 1.849 mmol) was prepared as a yellow solid from 5-methoxy-indole-3-acetonitrile (525 mg, 2.819 mmol) and isoquinoline-5-carboxaldehyde (545 mg, 3.468 mmol) according to general procedure (1) microwave method. Yield: 66%. $^1$H NMR (400 MHz, DMSO) δ: 9.40 (s, 1H), 8.60 (d, J=6.0 Hz, 1H), 8.30 (s, 1H), 8.26-8.21 (m, 2H), 8.04 (d, J=6.0 Hz, 1H), 7.89 (s, 1H), 7.86-7.76 (m, 1H), 7.53 (d, J=2.3 Hz, 1H), 7.43 (d, J=8.9 Hz, 1H), 6.91 (dd, J=8.9, 2.3 Hz, 1H), 3.82 (s, 3H). $^{13}$C NMR (100 MHz, DMSO) δ: 154.55, 152.91, 143.64, 133.57, 132.44, 132.19, 131.47, 130.27, 128.81, 128.23, 127.67, 127.11, 124.26, 117.98, 117.18, 113.20, 112.41, 110.47, 110.15, 101.66, 55.51. LC-MS (ESI): m/z 326.1 $[M+H]^+$. HRMS (ESI): m/z calculated $[M+H]^+$ $C_{21}H_{16}N_3O^+$ 326.1288, found 326.1294.

Chemical Example 3 (Compound 3) [a159]

(Z)-2-(1H-indol-3-yl)-3-(quinolin-5-yl)acrylonitrile

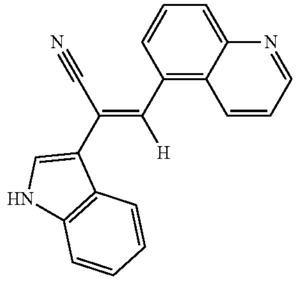 [SMILES: N#C/C(=C\c1cccc2ncccc12)c1c[nH]c2ccccc12]

Compound 3 [a159] (137 mg, 0.464 mmol) was prepared as a yellow solid from indole-3-acetonitrile (118 mg, 0.758 mmol) and quinoline-5-carboxaldehyde (147 mg, 0.932 mmol) according to general procedure (1) microwave method. Yield: 54%. $^1$H NMR (400 MHz, DMSO) δ: 8.99 (dd, J=4.1, 1.5 Hz, 1H), 8.62 (d, J=8.1 Hz, 1H), 8.38 (s, 1H), 8.14-8.10 (m, 2H), 8.07 (d, J=7.2 Hz, 1H), 7.94 (s, 1H), 7.92-7.87 (m, 1H), 7.63 (dd, J=8.6, 4.1 Hz, 1H), 7.54 (d, J=8.0 Hz, 1H), 7.33-7.14 (m, 2H). $^{13}C$ NMR (100 MHz, DMSO) δ: 150.87, 147.73, 137.24, 133.12, 132.90, 132.81, 130.24, 129.08, 127.36, 126.65, 126.28, 123.83, 122.54, 121.84, 120.65, 119.55, 117.99, 112.52, 110.46.

Chemical Example 4 (Compound 4) [a181]

(Z)-2-(1H-indol-3-yl)-3-(2,7-naphthyridin-4-yl)acrylonitrile

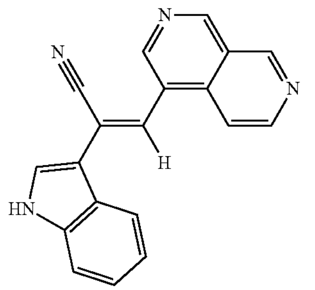 [SMILES: N#C/C(=C\c1cncc2cnccc12)c1c[nH]c2ccccc12]

Compound 4 [a181] (42 mg, 0.142 mmol) was prepared as an orange solid from indole-3-acetonitrile (93 mg, 0.595 mmol) and 2,7-napthyridine-4-carboxaldehyde (86 mg, 0.541 mmol) according to general procedure (1) microwave method. Yield: 24%. $^1H$ NMR (400 MHz, DMSO) δ: 9.63 (d, J=0.9 Hz, 1H), 9.59 (s, 1H), 9.16 (d, J=0.9 Hz, 1H), 8.84 (d, J=6.0 Hz, 1H), 8.25 (s, 1H), 8.17-8.13 (m, 1H), 8.11 (d, J=6.0 Hz, 1H), 7.97 (s, 1H), 7.55 (d, J=7.9 Hz, 1H), 7.24 (m, 2H). $^{13}C$ NMR (100 MHz, DMSO) δ: 153.40, 147.51, 145.50, 137.39, 136.17, 128.89, 128.06, 125.48, 123.79, 122.64, 120.78, 119.60, 117.72, 116.46, 112.64, 111.68, 110.32.

Scheme B

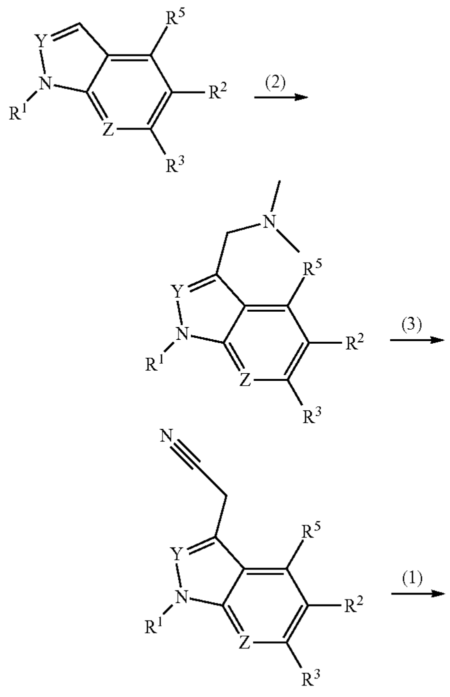

-continued

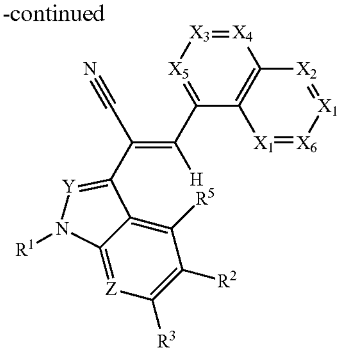

General Procedure (2):

An indole derivative (1.0 equiv) was dissolved in acetic acid (1.7 mL for 3.23 mmol of starting material) and water (1.7 mL for 3.23 mmol of starting material) and chilled to 0° C. in an ice bath. Formaldehyde 37% w/w in $H_2O$ (1.25 equiv) and dimethylamine 40% w/w in $H_2O$ (1.75 equiv) was then added. The reaction was allowed to warm to room temperature and stirred for 16 h. The reaction was quenched by adding ice and basified to pH 12-14 with 5N NaOH. The resulting mixture was extracted with dichloromethane 3 times. The combined organic layer was washed with brine, dried over anhydrous sodium sulphate and evaporated under vacuum to obtain the gramine product which was used in the next step without further purification.

General Procedure (3):

A gramine derivative (1.0 equiv) was dissolved in ethanol (5.5 mL for 1.34 mmol of starting material) and water (0.55 mL for 1.34 mmol of starting material). The gramine solution was added to potassium cyanide (2.0 equiv) weighed out in a separate flask. Iodomethane (2.6 equiv) was added and the reaction was stirred vigorously at room temperature for 16 h. Saturated sodium bicarbonate was added to quench the reaction, followed by extraction with ethyl acetate 3 times. The combined organic layer was washed with brine, dried over anhydrous sodium sulphate and concentrated in vacuo. Purification by flash silica gel column chromatography afforded the indole-3-acetonitrile derivative product.

Chemical Example 5 (Compound 5) [b44]

(Z)-2-(7-bromo-1H-indol-3-yl)-3-(isoquinolin-5-yl)acrylonitrile

Intermediate 1
(7-bromo-1H-indol-3-yl)-N,N-dimethylmethanamine

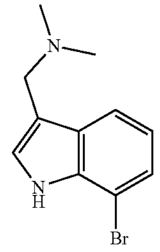

Intermediate 1 (610 mg, 2.410 mmol) was prepared as a brown solid from 7-bromoindole (546 mg, 2.785 mmol) according to general procedure (2). Yield: 86%. $^1H$ NMR (400 MHz, $CDCl_3$) δ: 7.55 (dd, J=8.0, 0.8 Hz, 1H), 7.30 (d, J=7.6 Hz, 1H), 7.25 (s, 1H), 6.97 (t, J=7.8 Hz, 1H), 3.67 (s, 2H), 2.29 (s, 6H).

Intermediate 2
2-(7-bromo-1H-indol-3-yl)acetonitrile

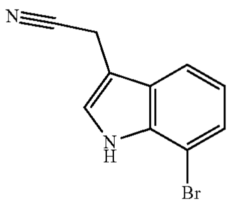 [SMILES: N#CCc1c[nH]c2c(Br)cccc12]

Intermediate 2 (224 mg, 0.951 mmol) was prepared as an off-white solid from Intermediate 1 (592 mg, 2.339 mmol) according to general procedure (3) using 4:1 hexane/ethyl acetate as the eluent for flash silica gel column chromatography. Yield: 41%. $^1$H NMR (400 MHz, $CDCl_3$) δ: 8.37 (bs, 1H), 7.55 (d, J=8.0 Hz, 1H), 7.45-7.38 (m, 1H), 7.32-7.28 (m, 1H), 7.08 (t, J=7.8 Hz, 1H), 3.83 (d, J=1.0 Hz, 2H).

Chemical Example 5 (Z)-2-(7-bromo-1H-indol-3-yl)-3-(isoquinolin-5-yl)acrylonitrile

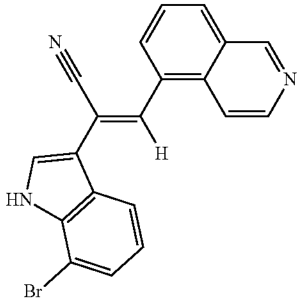 [SMILES: N#C/C(=C\c1cccc2cnccc12)c1c[nH]c2c(Br)cccc12]

Compound 5 [b44] (66 mg, 0.176 mmol) was prepared as a shiny yellow solid from Intermediate 2 (46 mg, 0.197 mmol) and isoquinoline-5-carboxaldehyde (31 mg, 0.197 mmol) according to general procedure (1) sealed tube method. Yield: 90%. $^1$H NMR (400 MHz, DMSO) δ: 9.40 (d, J=0.8 Hz, 1H), 8.60 (d, J=6.0 Hz, 1H), 8.38 (s, 1H), 8.28 (d, J=7.3 Hz, 1H), 8.23 (d, J=8.2 Hz, 1H), 8.12 (dd, J=8.1, 0.7 Hz, 1H), 8.07 (d, J=6.0 Hz, 1H), 7.99 (s, 1H), 7.86-7.79 (m, 1H), 7.48 (d, J=7.1 Hz, 1H), 7.15 (t, J=7.8 Hz, 1H). $^{13}$C NMR (100 MHz, DMSO) δ: 152.94, 143.71, 135.86, 134.00, 133.55, 131.11, 130.33, 129.12, 128.63, 128.22, 127.12, 125.69, 124.99, 121.85, 118.89, 117.88, 117.19, 111.42, 109.70, 105.32. LC-MS (ESI): m/z 374.0, 376.0 $[M+H]^+$.

Chemical Example 6 (Compound 6) [b46]

(Z)-3-(isoquinolin-5-yl)-2-(7-methoxy-1H-indol-3-yl)acrylonitrile

Intermediate 3
(7-methoxy-1H-indol-3-yl)-N,N-dimethylmethanamine

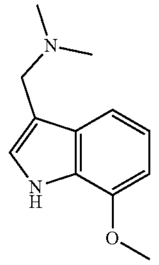

Intermediate 3 (574 mg, 2.810 mmol) was prepared as a dark yellow oil from 7-methoxyindole (427 mg, 2.897 mmol) according to general procedure (2). Yield: 97%. $^1$H NMR (400 MHz, $CDCl_3$) δ: 8.40 (bs, 1H), 7.29 (d, J=8.0 Hz, 1H), 7.14 (d, J=2.3 Hz, 1H), 7.05 (t, J=7.9 Hz, 1H), 6.65 (d, J=7.6 Hz, 1H), 3.96 (s, 3H), 3.66 (s, 2H), 2.30 (s, 6H).

Intermediate 4
2-(7-methoxy-1H-indol-3-yl)acetonitrile

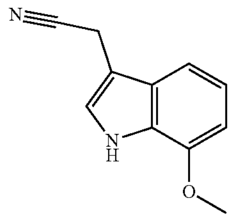

Intermediate 4 (138 mg, 0.739 mmol) was prepared as a white solid from Intermediate 3 (392 mg, 1.919 mmol) according to general procedure (3) using 3:1 hexane/ethyl acetate as the eluent for flash silica gel column chromatography. Yield: 39%. $^1$H NMR (400 MHz, $CDCl_3$) δ: 8.38 (bs, 1H), 7.20-7.18 (m, 2H), 7.10 (t, J=7.8 Hz, 1H), 6.70 (d, J=7.7 Hz, 1H), 3.97 (s, 3H), 3.82 (s, 2H).

Chemical Example 6 (Z)-3-(isoquinolin-5-yl)-2-(7-methoxy-1H-indol-3-yl)acrylonitrile

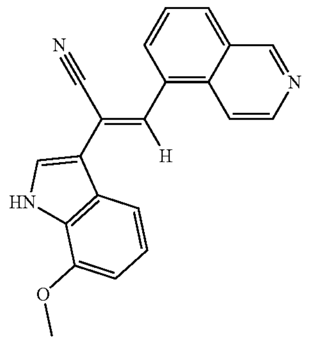 [SMILES: COc1cccc2c(/C(C#N)=C/c3cccc4cnccc34)c[nH]c12]

Compound 6 [b46] (105 mg, 0.323 mmol) was prepared as a yellow solid from Intermediate 4 (73 mg, 0.393 mmol) and isoquinoline-5-carboxaldehyde (62 mg, 0.393 mmol) according to general procedure (1) sealed tube method.

Yield: 82%. $^1$H NMR (400 MHz, DMSO) δ: 9.40 (d, J=0.5 Hz, 1H), 8.60 (d, J=6.0 Hz, 1H), 8.31 (s, 1H), 8.26 (d, J=7.3 Hz, 1H), 8.22 (d, J=8.2 Hz, 1H), 8.04 (d, J=6.0 Hz, 1H), 7.86-7.78 (m, 2H), 7.69 (d, J=8.0 Hz, 1H), 7.14 (t, J=8.0 Hz, 1H), 6.83 (d, J=7.7 Hz, 1H), 3.97 (s, 3H). $^{13}$C NMR (100 MHz, DMSO) δ: 152.92, 146.53, 143.69, 133.54, 132.59, 131.24, 130.21, 128.90, 128.22, 127.45, 127.10, 126.71, 125.33, 121.41, 117.97, 117.09, 112.00, 110.91, 110.35, 103.07, 55.32. LC-MS (ESI): m/z 326.1 [M+H]$^+$.

Scheme C

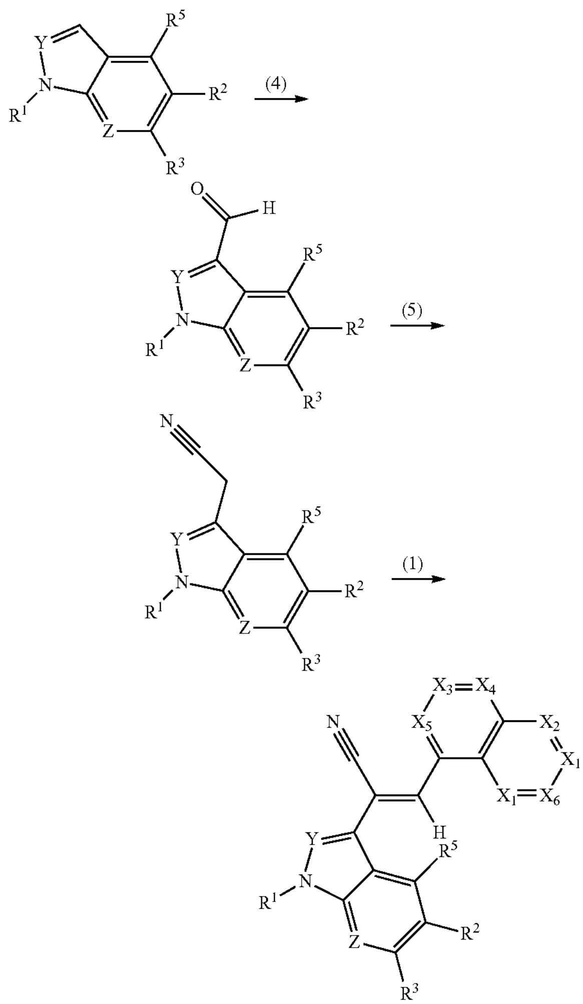

General Procedure (4):

To a dried two-neck round-bottom flask containing DMF (0.7 mL for 1.10 mmol of starting material) chilled in an ice bath, $POCl_3$ (1.95 equiv) was added slowly. After stirring for 20 min, a solution of the indole derivative (1.0 equiv) in DMF (3 mL for 1.10 mmol of starting material) was added drop-wise. The reaction was allowed to warm to room temperature and allowed to stir for 1.5 h. The reaction was quenched by adding ice followed by 1N NaOH (40 mL) drop-wise in an ice bath. The crude mixture was allowed to stand at room temperature and the precipitate formed was filtered to afford the 3-formyl-indole derivative product.

General Procedure (5):

To a 3-formyl-indole derivative (1.0 equiv) and sodium borohydride (3.0 equiv), methanol (9 mL for 1.0 mmol of starting material) and formamide (9 mL for 1.0 mmol of starting material) was added and stirred at room temperature for 15 min. The mixture was added to potassium cyanide (10.0 equiv) weighed out in a separate flask and stirred at 54° C. for 16 h. The reaction was quenched by adding brine and a few drops of 5N NaOH, followed by extraction with dichloromethane 3 times. The combined organic layer was washed with brine, dried over anhydrous sodium sulphate and concentrated in vacuo. Purification by flash silica gel column chromatography afforded the indole-3-acetonitrile derivative product.

Chemical Example 7 (Compound 7) [b2]

(Z)-2-(5-chloro-1H-indol-3-yl)-3-(isoquinolin-5-yl) acrylonitrile

Intermediate 5
2-(5-chloro-1H-indol-3-yl)acetonitrile

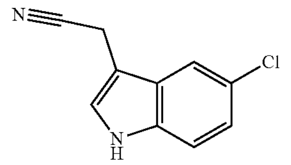 [SMILES: N#CCc1c[nH]c2ccc(Cl)cc12]

Intermediate 5 (687 mg, 3.604 mmol) was prepared as a beige solid from 5-chloro-1H-indole-3-carboxaldehyde (959 mg, 5.338 mmol) according to general procedure (5) using 7:3 hexane/ethyl acetate as the eluent for flash silica gel column chromatography. Yield: 68%. $^1$H NMR (400 MHz, $CDCl_3$) δ: 8.28 (bs, 1H), 7.55 (d, J=1.9 Hz, 1H), 7.34-7.29 (m, 1H), 7.25-7.23 (m, 1H), 7.20 (dd, J=8.7, 1.9 Hz, 1H), 3.79 (d, J=1.0 Hz, 2H).

Chemical Example 7 (Z)-2-(5-chloro-1H-indol-3-yl)-3-(isoquinolin-5-yl)acrylonitrile

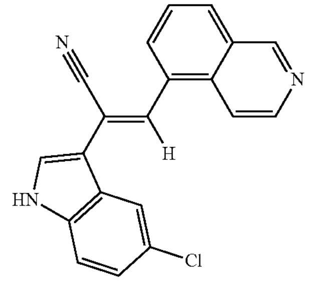 [SMILES: N#C/C(=C\c1cccc2cnccc12)c1c[nH]c2ccc(Cl)cc12]

Compound 7 [b2] (55 mg, 0.165 mmol) was prepared as a shiny yellow solid from Intermediate 5 (82 mg, 0.431 mmol) and isoquinoline-5-carboxaldehyde (75 mg, 0.474 mmol) according to general procedure (1) microwave method. Yield: 38%. $^1$H NMR (400 MHz, DMSO) δ: 9.40 (d, J=0.6 Hz, 1H), 8.60 (d, J=6.0 Hz, 1H), 8.35 (s, 1H), 8.23 (t, J=7.8 Hz, 2H), 8.11 (d, J=1.9 Hz, 1H), 8.08-8.01 (m, 2H), 7.86-7.77 (m, 1H), 7.55 (d, J=8.7 Hz, 1H), 7.25 (dd, J=8.7, 2.0 Hz, 1H). $^{13}$C NMR (100 MHz, DMSO) δ: 152.89, 143.62, 136.04, 133.66, 133.56, 131.36, 130.39, 129.22, 128.98, 128.20, 127.11, 125.20, 125.02, 122.39, 118.58, 117.92, 117.33, 114.22, 109.97, 109.78. LC-MS (ESI): m/z 330.0 $[M+H]^+$.

Chemical Example 8 (Compound 8) [b3]

(Z)-2-(5-bromo-1H-indol-3-yl)-3-(isoquinolin-5-yl) acrylonitrile

Intermediate 6
2-(5-bromo-1H-indol-3-yl)acetonitrile

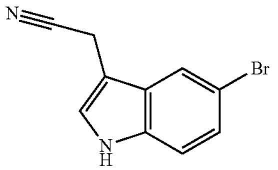 [SMILES: N#CCc1c[nH]c2ccc(Br)cc12]

Intermediate 6 (295 mg, 1.255 mmol) was prepared as a white solid from 5-bromo-1H-indole-3-carboxaldehyde (366 mg, 1.631 mmol) according to general procedure (5) using 65:35 hexane/ethyl acetate as the eluent for flash silica gel column chromatography. Yield: 76%. $^1$H NMR (400 MHz, $CDCl_3$) δ 8.25 (bs, 1H), 7.76-7.69 (m, 1H), 7.34 (dd, J=8.7, 1.8 Hz, 1H), 7.29-7.26 (m, 1H), 7.25-7.23 (m, 1H), 3.80 (d, J=1.0 Hz, 2H).

Chemical Example 8 (Z)-2-(5-bromo-1H-indol-3-yl)-3-(isoquinolin-5-yl)acrylonitrile

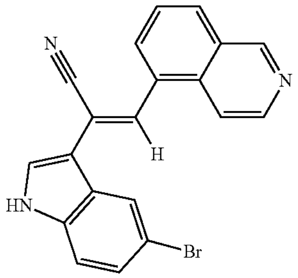 [SMILES: N#C/C(=C\c1cccc2cnccc12)c1c[nH]c2ccc(Br)cc12]

Compound 8 [b3] (31 mg, 0.083 mmol) was prepared as a yellow solid from Intermediate 6 (61 mg, 0.261 mmol) and isoquinoline-5-carboxaldehyde (45 mg, 0.287 mmol) according to general procedure (1) microwave method. Yield: 32%. $^1$H NMR (400 MHz, DMSO) δ: 9.40 (d, J=0.8 Hz, 1H), 8.60 (d, J=6.0 Hz, 1H), 8.35 (s, 1H), 8.28-8.17 (m, 3H), 8.06 (d, J=6.0 Hz, 1H), 8.03 (s, 1H), 7.87-7.73 (m, 1H), 7.51 (d, J=8.7 Hz, 1H), 7.36 (dd, J=8.7, 1.8 Hz, 1H). $^{13}$C NMR (100 MHz, DMSO) δ: 152.88, 143.60, 136.41, 133.61, 133.54, 131.37, 130.36, 129.20, 128.94, 128.19, 127.09, 125.75, 124.87, 121.47, 117.93, 117.32, 114.71, 113.14, 109.80, 109.74. LC-MS (ESI): m/z 374.0, 376.0 $[M+H]^+$.

Chemical Example 9 (Compound 9) [b38]

(Z)-3-(isoquinolin-5-yl)-2-(6-methoxy-1H-indol-3-yl)acrylonitrile

Intermediate 7
6-methoxy-1H-indole-3-carbaldehyde

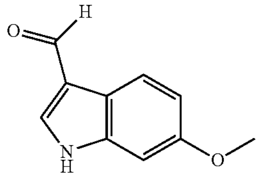

Intermediate 7 (1.579 g, 9.011 mmol) was prepared as a black solid from 6-methoxyindole (2.244 g, 15.25 mmol) according to general procedure (4). Yield: 59%. $^1$H NMR (400 MHz, Acetone) δ: 10.95 (bs, 1H), 9.97 (s, 1H), 8.08-8.05 (m, 2H), 7.06 (d, J=2.3 Hz, 1H), 6.90 (dd, J=8.7, 2.3 Hz, 1H), 3.82 (s, 3H).

Intermediate 8
2-(6-methoxy-1H-indol-3-yl)acetonitrile

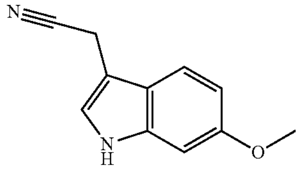

Intermediate 8 (268 mg, 1.438 mmol) was prepared as a beige solid from Intermediate 7 (561 mg, 3.201 mmol) according to general procedure (5) using 65:35 hexane/ethyl acetate as the eluent for flash silica gel column chromatography. Yield: 45%. $^1$H NMR (400 MHz, $CDCl_3$) δ: 8.08 (bs, 1H), 7.45 (d, J=8.4 Hz, 1H), 7.10-7.08 (m, 1H), 6.87-6.84 (m, 2H), 3.85 (s, 3H), 3.79 (d, J=1.1 Hz, 2H).

Chemical Example 9 (Z)-3-(isoquinolin-5-yl)-2-(6-methoxy-1H-indol-3-yl)acrylonitrile

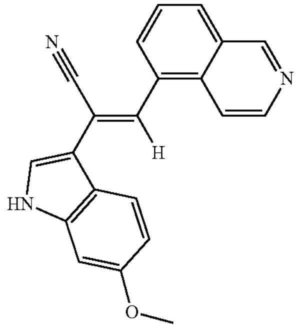 [SMILES: COc1ccc2c(/C(C#N)=C/c3cccc4cnccc34)c[nH]c2c1]

Compound 9 [b38] (89 mg, 0.274 mmol) was prepared as a yellow solid from Intermediate 8 (58 mg, 0.313 mmol) and isoquinoline-5-carboxaldehyde (49 mg, 0.313 mmol) according to general procedure (1) sealed tube method. Yield: 88%. $^1$H NMR (400 MHz, DMSO) δ: 9.40 (d, J=0.7 Hz, 1H), 8.60 (d, J=6.0 Hz, 1H), 8.28 (s, 1H), 8.26-8.19 (m, 2H), 8.03 (d, J=6.0 Hz, 1H), 8.00 (d, J=8.8 Hz, 1H), 7.84-7.79 (m, 1H), 7.79 (s, 1H), 7.02 (s, 1H), 6.86 (dd, J=8.8, 2.4 Hz, 1H), 3.82 (s, 3H). $^{13}$C NMR (100 MHz, DMSO) δ: 156.30, 152.94, 143.69, 138.28, 133.56, 131.90, 131.37, 130.28, 128.88, 128.25, 127.14, 126.34, 120.33, 117.99, 117.94, 117.16, 110.78, 110.67, 110.56, 95.38, 55.26. LC-MS (ESI): m/z 326.1 [M+H]$^+$.

Chemical Example 10 (Compound 10) [b39]

(Z)-2-(6-bromo-1H-indol-3-yl)-3-(isoquinolin-5-yl) acrylonitrile

Intermediate 9 6-bromo-1H-indole-3-carbaldehyde

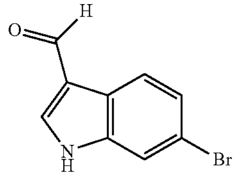 [SMILES: O=Cc1c[nH]c2cc(Br)ccc12]

Intermediate 9 (7.800 g, 34.81 mmol) was prepared as a brown solid from 6-bromoindole (7.533 g, 38.42 mmol) according to general procedure (4). Yield: 90%. $^1$H NMR (400 MHz, $CDCl_3$) δ: 9.85 (s, 1H), 8.03 (d, J=8.4 Hz, 1H), 7.77 (s, 1H), 7.54-7.53 (m, 1H), 7.30 (dd, J=8.4, 1.7 Hz, 1H).

Intermediate 10
2-(6-bromo-1H-indol-3-yl)acetonitrile

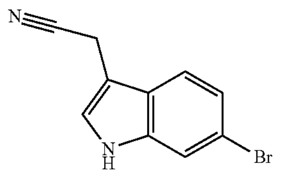 [SMILES: N#CCc1c[nH]c2cc(Br)ccc12]

Intermediate 10 (347 mg, 1.476 mmol) was prepared as a beige solid from Intermediate 9 (843 mg, 3.764 mmol) according to general procedure (5) using 7:3 hexane/ethyl acetate as the eluent for flash silica gel column chromatography. Yield: 39%. $^1$H NMR (400 MHz, $CDCl_3$) δ: 8.34 (bs, 1H), 7.55 (d, J=1.6 Hz, 1H), 7.44 (d, J=8.5 Hz, 1H), 7.28 (dd, J=8.5, 1.7 Hz, 1H), 7.20-7.17 (m, 1H), 3.81 (d, J=1.0 Hz, 2H).

Chemical Example 10 (Z)-2-(6-bromo-1H-indol-3-yl)-3-(isoquinolin-5-yl)acrylonitrile

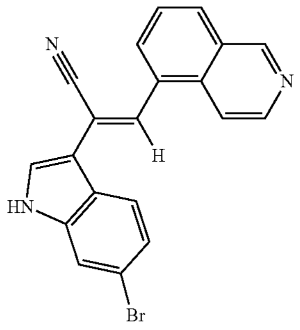 [SMILES: N#C/C(=C\c1cccc2cnccc12)c1c[nH]c2cc(Br)ccc12]

Compound 10 [b39] (99 mg, 0.265 mmol) was prepared as a yellow solid from Intermediate 10 (71 mg, 0.301 mmol) and isoquinoline-5-carboxaldehyde (47 mg, 0.301 mmol) according to general procedure (1) sealed tube method. Yield: 87%. $^1$H NMR (400 MHz, DMSO) δ: 9.40 (d, J=0.5 Hz, 1H), 8.60 (d, J=6.0 Hz, 1H), 8.33 (s, 1H), 8.26 (d, J=7.3 Hz, 1H), 8.22 (d, J=8.2 Hz, 1H), 8.07-8.04 (m, 2H), 7.99 (s, 1H), 7.85-7.79 (m, 1H), 7.73 (d, J=1.7 Hz, 1H), 7.32 (dd, J=8.6, 1.8 Hz, 1H). $^{13}$C NMR (100 MHz, DMSO) δ: 152.92, 143.67, 138.53, 133.52, 133.15, 131.18, 130.29, 129.00, 128.82, 128.21, 127.10, 123.28, 123.01, 121.17, 117.87, 117.16, 115.27, 115.02, 110.48, 109.87. LC-MS (ESI): m/z 374.0, 376.0 [M+H]$^+$.

Scheme D

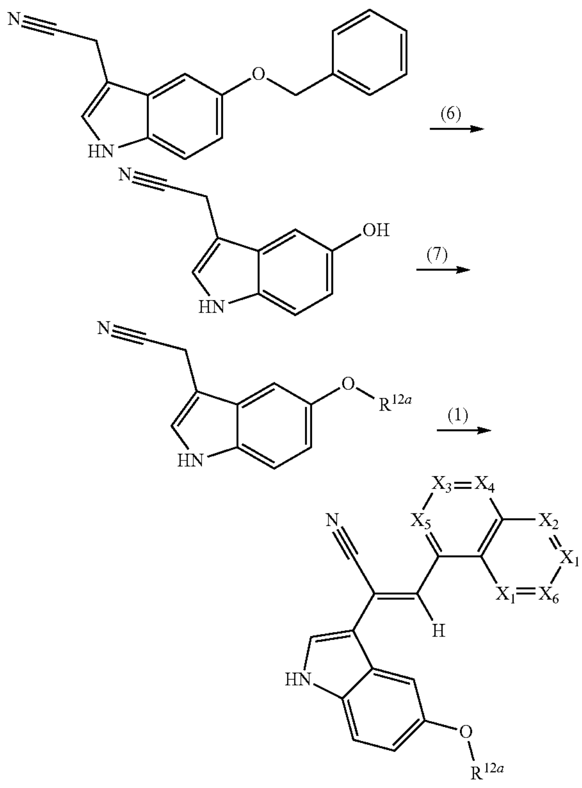

General Procedure (6):

To a solution of benzyloxyindole derivative (1.0 equiv) in THF (18 mL for 11.28 mmol of starting material) was added 10% palladium on carbon (10 mmol %). The reaction mixture was shaken under hydrogen at 30 psi using the Parr Shaker Hydrogenation Apparatus for 7 h. The mixture was filtered over celite and washed with ethyl acetate. The filtrate was concentrated in vacuo and purified by silica gel flash column chromatography to afford the hydroxyindole derivative product.

General Procedure (7):

To a solution of the hydroxyindole derivative (1.0 equiv) in DMF (5 mL for 0.99 mmol starting material), alkyl halide (3.0 equiv) and potassium carbonate (3.5 equiv) was added. The reaction was stirred at 47° C. for 16 h. The mixture was poured into water and extracted with ethyl acetate 3 times. The combined organic layer was washed with brine, dried over anhydrous sodium sulphate and concentrated in vacuo. Purification by flash silica gel column chromatography afforded the alkoxyindole product.

Chemical Example 11 (Compound 11) [b15]

(Z)-2-(5-(2-(1,3-dioxolan-2-yl)ethoxy)-1H-indol-3-yl)-3-(isoquinolin-5-yl)acrylonitrile Intermediate 11 2-(5-hydroxy-1H-indol-3-yl)acetonitrile

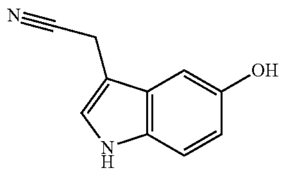 [SMILES: N#CCc1c[nH]c2ccc(O)cc12]

Intermediate 11 (1.65 g, 9.57 mmol) was prepared as an off-white solid from 5-benzyloxyindole-3-acetonitrile (2.96 g, 11.28 mmol, 1.0 equiv) in THF (18 mL) according to general procedure (6) using 1:1 hexane/ethyl acetate as the eluent for flash silica gel column chromatography. Yield: 84%. $^{1}H$ NMR (400 MHz, Acetone) δ: 10.04 (bs, 1H), 7.76 (s, 1H), 7.30-7.28 (m, 1H), 7.26 (dd, J=8.7, 0.4 Hz, 1H), 7.01 (d, J=2.3 Hz, 1H), 6.77 (dd, J=8.7, 2.3 Hz, 1H), 3.90 (d, J=0.9 Hz, 2H).

Intermediate 12 2-(5-(2-(1,3-dioxolan-2-yl)ethoxy)-1H-indol-3-yl)acetonitrile

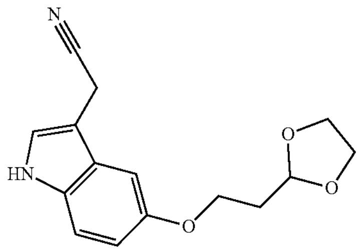 [SMILES: N#CCc1c[nH]c2ccc(OCCC3OCCO3)cc12]

Intermediate 12 (121 mg, 0.444 mmol) was prepared as a light-yellow oil from Intermediate 11 (170 mg, 0.989 mmol) and 2-(2-bromoethyl)-1,3-dioxolane (348 μL, 537 mg, 2.966 mmol) according to general procedure (7) using 3:2 hexane/ethyl acetate as the eluent for flash silica gel column chromatography. Yield: 45%. $^{1}H$ NMR (400 MHz, $CDCl_3$) δ: 8.22 (bs, 1H), 7.27 (d, J=8.7 Hz, 1H), 7.18-7.14 (m, 1H), 7.01 (d, J=2.3 Hz, 1H), 6.90 (dd, J=8.8, 2.4 Hz, 1H), 5.14 (t, J=4.9 Hz, 1H), 4.18 (t, J=6.5 Hz, 2H), 4.04-3.97 (m, 2H), 3.94-3.85 (m, 2H), 3.77 (d, J=0.9 Hz, 2H), 2.22-2.18 (m, 2H).

Chemical Example 11 (Z)-2-(5-(2-(1,3-dioxolan-2-yl)ethoxy)-1H-indol-3-yl)-3-(isoquinolin-5-yl)acrylonitrile

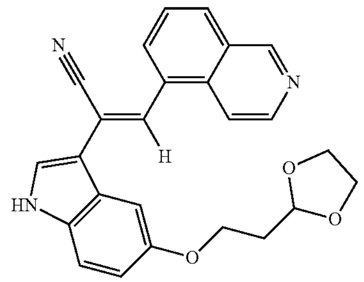 [SMILES: N#C/C(=C\c1cccc2cnccc12)c1c[nH]c2ccc(OCCC3OCCO3)cc12]

Compound 11 [b15] (42 mg, 0.101 mmol) was prepared as a yellow solid from Intermediate 12 (116 mg, 0.426 mmol) and isoquinoline-5-carboxaldehyde (107 mg, 0.682 mmol) according to general procedure (1) microwave method. Yield: 24%. $^{1}H$ NMR (400 MHz, DMSO) δ: 9.40 (d, J=0.6 Hz, 1H), 8.59 (d, J=6.0 Hz, 1H), 8.28 (s, 1H), 8.25-8.21 (m, 2H), 8.03 (d, J=6.0 Hz, 1H), 7.89 (s, 1H), 7.84-7.80 (m, 1H), 7.53 (d, J=2.3 Hz, 1H), 7.44 (d, J=8.7 Hz, 1H), 6.90 (dd, J=8.9, 2.3 Hz, 1H), 5.01 (t, J=5.0 Hz, 1H), 4.14 (t, J=6.6 Hz, 2H), 3.90-3.82 (m, 2H), 3.81-3.71 (m, 2H), 2.07-2.03 (m, 2H). $^{13}C$ NMR (100 MHz, DMSO) δ: 153.59, 152.92, 143.60, 133.57, 132.46, 132.40, 131.52, 130.29, 128.79, 128.24, 127.87, 127.13, 124.33, 117.99, 117.22, 113.32, 112.84, 110.47, 110.13, 102.64, 101.31, 64.22, 64.10, 33.52. LC-MS (ESI): m/z 412.2 $[M+H]^{+}$.

Chemical Example 12 (Compound 12) [b16]

(Z)-2-(5-(2-methoxyethoxy)-1H-indol-3-yl)-3-(isoquinolin-5-yl)acrylonitrile

Intermediate 13 2-(5-(2-methoxyethoxy)-1H-indol-3-yl)acetonitrile

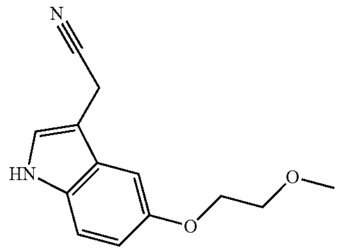 [SMILES: COCCOc1ccc2[nH]cc(CC#N)c2c1]

Intermediate 13 (76 mg, 0.330 mmol) was prepared as light-yellow oil from Intermediate 11 (91 mg, 0.530 mmol) and 2-bromoethyl-methyl-ether (150 μL, 221 mg, 1.591 mmol) according to general procedure (7) using 3:2 hexane/ethyl acetate as the eluent for flash silica gel column chromatography. Yield: 62%. $^{1}H$ NMR (400 MHz, $CDCl_3$) δ: 8.22 (bs, 1H), 7.27 (d, J=8.7 Hz, 1H), 7.18-7.15 (m, 1H), 7.02 (d, J=2.4 Hz, 1H), 6.94 (dd, J=8.8, 2.4 Hz, 1H), 4.21-4.16 (m, 2H), 3.81-3.78 (m, 2H), 3.78 (d, J=1.0 Hz, 2H), 3.48 (s, 3H).

Chemical Example 12 (Z)-2-(5-(2-methoxyethoxy)-1H-indol-3-yl)-3-(isoquinolin-5-yl)acrylonitrile

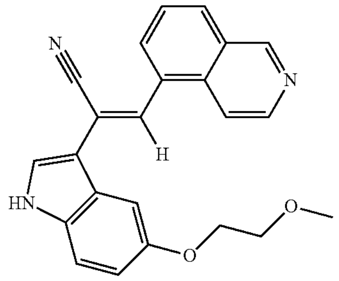 [SMILES: COCCOc1ccc2[nH]cc(/C(C#N)=C/c3cccc4cnccc34)c2c1]

Compound 12 [b16] (34 mg, 0.092 mmol) was prepared as a yellow solid from Intermediate 13 (75 mg, 0.326 mmol) and isoquinoline-5-carboxaldehyde (67 mg, 0.423 mmol) according to general procedure (1) microwave method. Yield: 28%. $^{1}H$ NMR (400 MHz, DMSO) δ: 9.40 (d, J=0.7 Hz, 1H), 8.59 (d, J=6.0 Hz, 1H), 8.29 (s, 1H), 8.23 (t, J=7.5 Hz, 2H), 8.03 (d, J=6.0 Hz, 1H), 7.88 (s, 1H), 7.85-7.76 (m, 1H), 7.55 (d, J=2.3 Hz, 1H), 7.43 (d, J=8.8 Hz, 1H), 6.92 (dd, J=8.9, 2.3 Hz, 1H), 4.21-4.09 (m, 2H), 3.83-3.58 (m, 2H), 3.31 (s, 3H). $^{13}C$ NMR (100 MHz, DMSO) δ: 153.71, 152.91, 143.61, 133.57, 132.54, 132.29, 131.53, 130.30, 128.80, 128.23, 127.73, 127.12, 124.25, 117.97, 117.24, 113.21, 112.89, 110.50, 110.18, 102.70, 70.62, 67.54, 58.17. LC-MS (ESI): m/z 370.1 $[M+H]^+$.

Scheme E

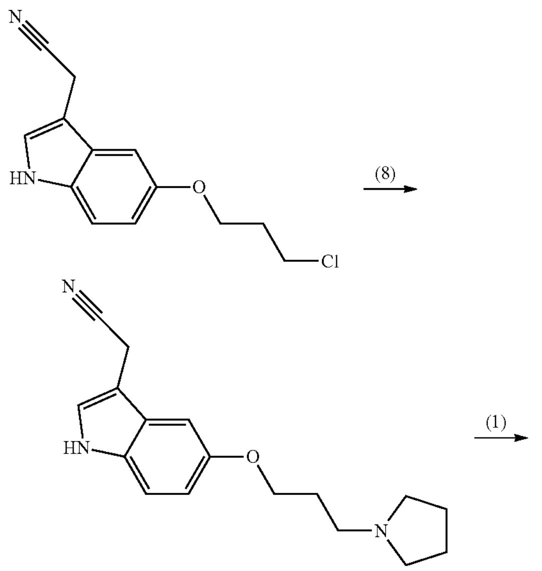

-continued

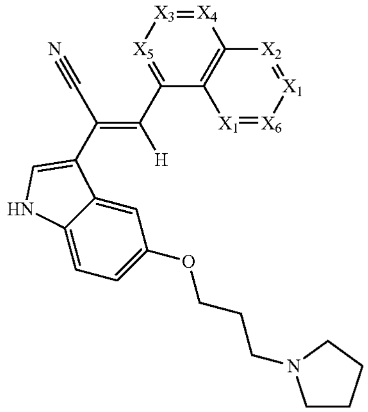

General Procedure (8):

To a solution of alkyl halide (1.0 equiv) in acetonitrile (5 mL for 1.20 mmol of starting material), potassium carbonate (3.7 equiv), sodium iodide (1.5 equiv) and amine (3.0 equiv) was added. The mixture was heated to reflux for 40 h. After cooling to room temperature, the reaction was filtered and washed with small amounts of ethyl acetate. The filtrate and washings were concentrated in vacuo and purified by flash silica gel column chromatography to afford the alkylamine product.

Chemical Example 13 (Compound 13) [b12]

(Z)-2-(5-(3-(pyrrolidin-1-yl)propoxy)-1H-indol-3-yl)-3-(isoquinolin-5-yl)acrylonitrile Intermediate 14 2-(5-(3-chloropropoxy)-1H-indol-3-yl)acetonitrile

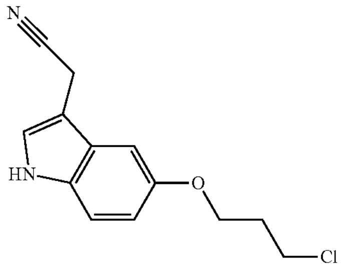 [SMILES: N#CCc1c[nH]c2ccc(OCCCCl)cc12]

Intermediate 14 (150 mg, 0.603 mmol) was prepared as dark-yellow oil from Intermediate 11 (207 mg, 1.200 mmol) and 1-chloro-3-iodopropane (258 μL, 490 mg, 2.70 mmol) according to general procedure (7) using 65:35 hexane/ethyl acetate as the eluent for flash silica gel column chromatography. Yield: 50%. $^{1}H$ NMR (400 MHz, $CDCl_3$) δ: 8.08 (bs, 1H), 7.29 (d, J=8.8 Hz, 1H), 7.21-7.19 (m, 1H), 7.03 (d, J=2.3 Hz, 1H), 6.91 (dd, J=8.8, 2.4 Hz, 1H), 4.18 (t, J=5.8 Hz, 2H), 3.77-3.80 (m, 4H), 2.32-2.21 (m, 2H).

Intermediate 15 2-(5-(3-(pyrrolidin-1-yl)propoxy)-1H-indol-3-yl)acetonitrile

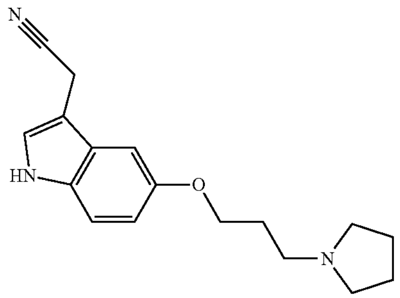 [SMILES: N#CCc1c[nH]c2ccc(OCCCN3CCCC3)cc12]

Intermediate 15 was prepared as a dark-yellow oil (132 mg, 0.466 mmol) from Intermediate 14 (149 mg, 0.599 mmol, 1.0 equiv), potassium carbonate (306 mg, 2.214 mmol, 3.7 equiv), sodium iodide (135 mg, 0.899 mmol, 1.5 equiv) and pyrrolidine (149 μL, 128 mg, 1.799 mmol, 3.0 equiv) according to general procedure (8) using 9:1:0.01 dichloromethane/methanol/ammonium hydroxide solution as the eluent for flash silica gel column chromatography. Yield: 78%. $^{1}H$ NMR (400 MHz, MeOD) δ: 7.37-7.31 (m, 1H), 7.26 (s, 1H), 7.17 (d, J=2.3 Hz, 1H), 6.90 (dd, J=8.8, 2.4 Hz, 1H), 4.17 (t, J=5.8 Hz, 2H), 3.96 (d, J=0.8 Hz, 2H), 3.44-3.29 (m, 6H), 2.27-2.20 (m, 2H), 2.13-2.05 (m, 4H).

Chemical Example 13 (Z)-2-(5-(3-(pyrrolidin-1-yl)propoxy)-1H-indol-3-yl)-3-(isoquinolin-5-yl)acrylonitrile

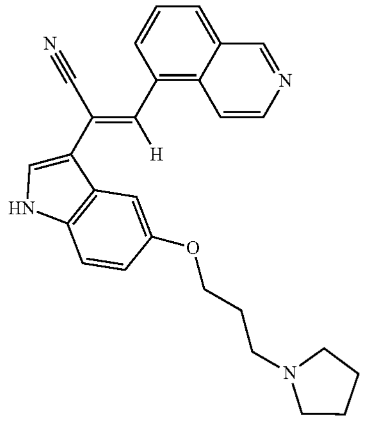 [SMILES: N#C/C(=C\c1cccc2cnccc12)c1c[nH]c2ccc(OCCCN3CCCC3)cc12]

Compound 13 [b12] (8 mg, 0.019 mmol) was prepared as a yellow solid from Intermediate 15 (84 mg, 0.295 mmol) and isoquinoline-5-carboxaldehyde (70 mg, 0.442 mmol) according to general procedure (1) microwave method. The reaction was evaporated under vacuum to remove the solvent and purified by silica gel flash column chromatography (85:15:0.015 dichloromethane/methanol/ammonium hydroxide solution). The material obtained was dried under vacuum and triturated with small amounts of methanol and acetone to obtain a yellow precipitate. Yield: 7%. $^{1}H$ NMR (400 MHz, MeOD) δ: 9.32 (s, 1H), 8.54 (d, J=6.0 Hz, 1H), 8.32 (d, J=7.3 Hz, 1H), 8.21-8.19 (m, 2H), 8.05 (d, J=6.1 Hz, 1H), 7.86-7.79 (m, 1H), 7.77 (s, 1H), 7.57 (d, J=2.2 Hz, 1H), 7.43 (d, J=8.9 Hz, 1H), 6.97 (dd, J=8.9, 2.3 Hz, 1H), 4.20 (t, J=5.7 Hz, 2H), 3.49-3.36 (m, 6H), 2.27-2.24 (m, 2H), 2.11-2.08 (m, 4H). $^{13}C$ NMR (100 MHz, MeOD) δ: 155.19, 153.95, 143.72, 135.85, 134.38, 133.25, 133.02, 132.25, 130.27, 128.61, 128.35, 126.02, 118.96, 118.76, 114.15, 114.09, 112.73, 112.21, 104.10, 66.79, 55.46, 54.13, 27.35, 23.97. LC-MS (ESI): m/z 423.2 $[M+H]^+$.

Scheme F

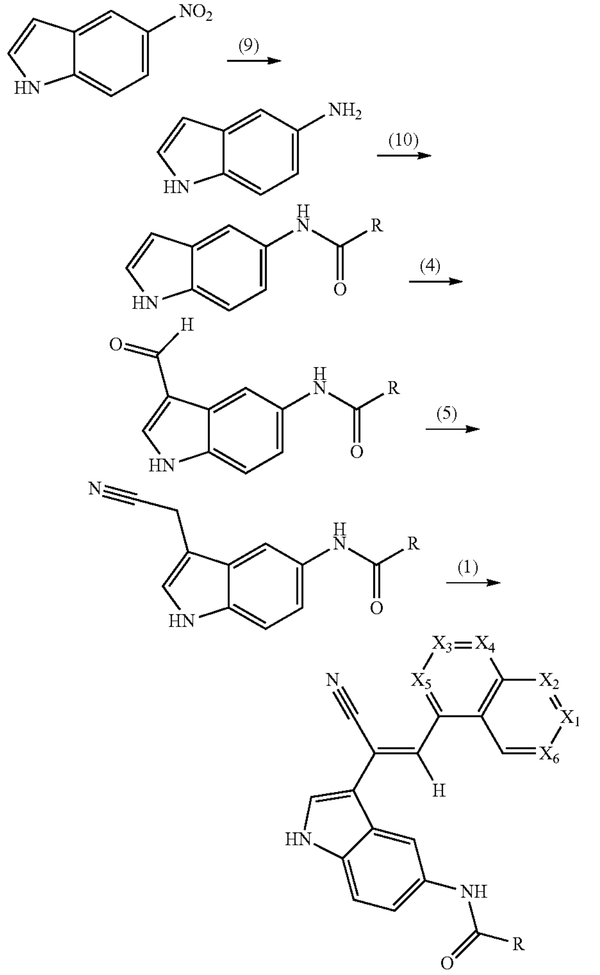

General Procedure (9):

Nitroindole derivative (1 equiv) was dissolved in ethanol (30 mL for 20.40 mmol of starting material) and 10% palladium on carbon (10 mmol %) was added. The reaction flask was shaken under hydrogen at 30 psi using the Parr Shaker Hydrogenation Apparatus for 2.5 h. The reaction was filtered over celite and washed with ethyl acetate. The filtrate was concentrated in vacuo and purified by silica gel flash column chromatography to afford the aminoindole product.

General Procedure (10):

To a solution of aminoindole (1.0 equiv) and triethylamine (3.6 equiv) in dichloromethane (10 mL for 1.182 mmol of starting material), acetyl chloride (1.2 equiv) was added. The reaction was stirred at room temperature for 3 h. The mixture was poured into water and extracted with dichloromethane 3 times. The combined organic layer was washed with brine, dried over anhydrous sodium sulphate and concentrated in vacuo. Purification by flash silica gel column chromatography afforded the indole-acetamide product.

Chemical Example 14 (Compound 14) [b213]

N-(3-((Z)-1-cyano-2-(isoquinolin-5-yl)vinyl)-1H-indol-5-yl)acetamide

Intermediate 16 1H-indol-5-amine

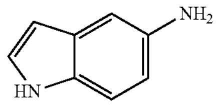

Intermediate 16 (2.7 g, 20.4 mmol) was prepared as a black solid from 5-nitro-1H-indole (6.3 g, 38.9 mmol, 1 equiv) according to general procedure (9) using 1:1 hexane/ethyl acetate as the eluent for flash silica gel column chromatography. Yield: 53%. $^1$H NMR (400 MHz, $CDCl_3$) δ: 7.96 (bs, 1H), 7.22-7.17 (m, 1H), 7.13 (t, J=2.8 Hz, 1H), 6.97-6.94 (m, 1H), 6.67 (dd, J=8.5, 2.2 Hz, 1H), 6.39-6.37 (m, 1H), 3.49 (s, 2H).

Intermediate 17 N-(1H-indol-5-yl)acetamide

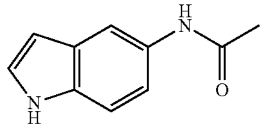

Intermediate 17 (177 mg, 1.016 mmol) was prepared as a clear oil from Intermediate 16 (156 mg, 1.182 mmol) according to general procedure (10) using 7:3 hexane/ethyl acetate as the eluent for flash silica gel column chromatography. Yield: 85%. $^1$H NMR (400 MHz, $CDCl_3$) δ 8.27 (bs, 1H), 7.80 (s, 1H), 7.30 (d, J=8.5 Hz, 2H), 7.20 (dd, J=8.8, 2.0 Hz, 2H), 6.50 (s, 1H), 2.18 (s, 3H).

Intermediate 18
N-(3-formyl-1H-indol-5-yl)acetamide

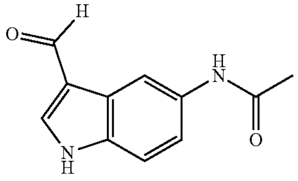

Intermediate 18 (115 mg, 0.569 mmol) was prepared as a light yellow solid from Intermediate 17 (192 mg, 1.102 mmol) according to general procedure (4). Following drop-wise addition of 1N NaOH (10× reaction volume), extraction with ethyl acetate was performed 3 times. The combined organic layer was washed with brine, dried over anhydrous sodium sulphate and concentrated in vacuo. Purification by flash silica gel column chromatography (100% ethyl acetate) afforded the product. Yield: 52%. $^1$H NMR (400 MHz, Acetone) δ: 11.08 (bs, 1H), 9.99 (s, 1H), 9.12 (bs, 1H), 8.38 (d, J=1.7 Hz, 1H), 8.14 (d, J=2.3 Hz, 1H), 7.71 (dd, J=8.8, 2.1 Hz, 1H), 7.44 (d, J=8.8 Hz, 1H), 2.11 (s, 3H).

Intermediate 19
N-(3-(cyanomethyl)-1H-indol-5-yl)acetamide

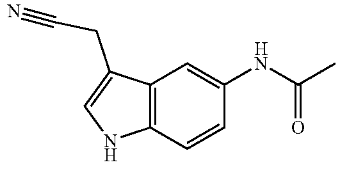 [SMILES: CC(=O)Nc1ccc2[nH]cc(CC#N)c2c1]

Intermediate 19 (42 mg, 0.197 mmol) was prepared as a pale yellow solid from Intermediate 18 (109 mg, 0.539 mmol) according to general procedure (5) using 15:85 hexane/ethyl acetate as the eluent for flash silica gel column chromatography. Yield: 36%. $^1$H NMR (400 MHz, Acetone) δ: 10.25 (bs, 1H), 9.10 (bs, 1H), 7.95 (d, J=1.7 Hz, 1H), 7.41-7.32 (m, 3H), 3.94 (d, J=0.8 Hz, 2H), 2.10 (s, 3H).

Chemical Example 14 N-(3-((Z)-1-cyano-2-(isoquinolin-5-yl)vinyl)-1H-indol-5-yl)acetamide

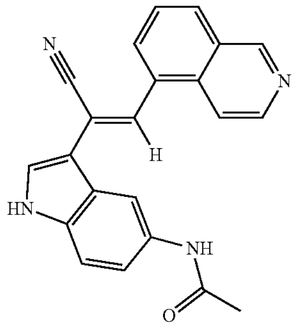 [SMILES: CC(=O)Nc1ccc2[nH]cc(/C(C#N)=C/c3cccc4cnccc34)c2c1]

Compound 14 [a213] (5 mg, 0.014 mmol) was prepared as a yellow solid from Intermediate 19 (42 mg, 0.197 mmol) and isoquinoline-5-carboxaldehyde (35 mg, 0.223 mmol) according to general procedure (1) sealed tube method. The reaction was concentrated in vacuo and purified by silica gel flash column chromatography (90:10 ethyl acetate/methanol). The crude material obtained was dried under vacuum and triturated with small amounts of methanol to obtain a yellow precipitate. Yield: 7%. $^1$H NMR (400 MHz, DMSO) δ: 11.74 (s, 1H), 9.92 (s, 1H), 9.41 (s, 1H), 8.61 (d, J=6.0 Hz, 1H), 8.42 (s, 1H), 8.30 (d, J=7.3 Hz, 1H), 8.23 (d, J=8.2 Hz, 1H), 8.21 (s, 1H), 8.09 (d, J=6.0 Hz, 1H), 7.88 (s, 1H), 7.86-7.77 (m, 1H), 7.45 (d, J=1.0 Hz, 2H), 2.05 (s, 3H). $^{13}$C NMR (100 MHz, DMSO) δ: 168.11, 153.13, 143.89, 133.73, 133.59, 133.34, 131.93, 130.98, 130.20, 129.13, 128.34, 127.86, 127.26, 123.74, 117.88, 116.87, 116.12, 112.48, 110.55, 110.29, 109.52, 24.03. LC-MS (ESI): m/z 353.1 $[M+H]^+$. HRMS (ESI): m/z calculated $[M+H]^+$ $C_{22}H_{17}N_4O^+$ 353.1402, found 353.1403.

Scheme G

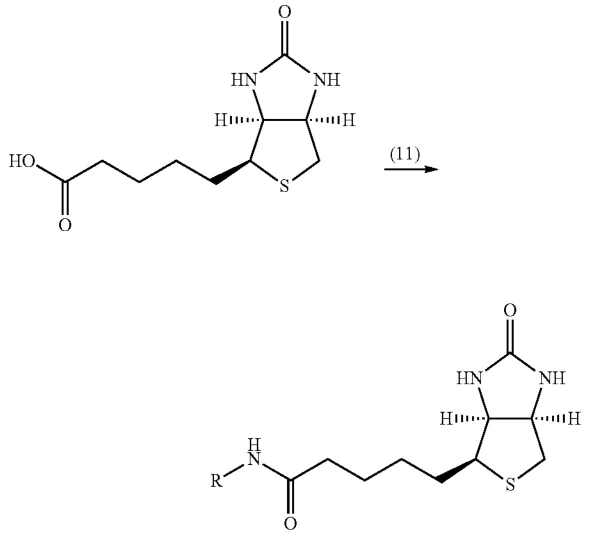

General Procedure (11):

To a carboxylic acid (1.0 equiv), HBTU (2.0 equiv) and an amine (2.0 equiv), DMF (2.5 mL for 1.72 mmol of carboxylic acid) was added followed by DIPEA (2.0 equiv). The reaction was stirred at room temp for 16 h. The mixture was poured into water and extracted with ethyl acetate 3 times. The combined organic layer was washed with brine, dried over anhydrous sodium sulphate and concentrated in vacuo. Purification by flash silica gel column chromatography afforded the amide product.

Chemical Example 15 (Compound 15) [b215]

N-(3-((Z)-1-cyano-2-(isoquinolin-5-yl)vinyl)-1H-indol-5-yl)-5-((3aS,4S,6aR)-2-oxohexahydro-1H-thieno[3,4-d]imidazol-4-yl)pentanamide Intermediate 20 N-(1H-indol-5-yl)-5-((3aS,4S,6aR)-2-oxohexahydro-1H-thieno[3,4-d]imidazol-4-yl) pentanamide

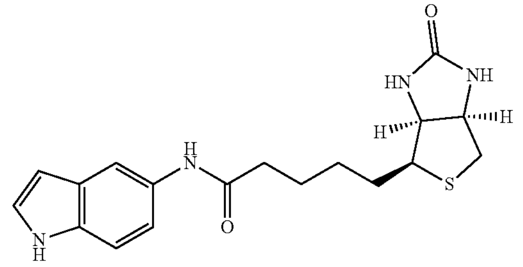 [SMILES: O=C(CCCC[C@@H]1SC[C@@H]2NC(=O)N[C@@H]21)Nc1ccc2[nH]ccc2c1]

Intermediate 20 (234 mg, 0.653 mmol) was prepared as a white solid from D-Biotin (743 mg, 3.041 mmol) and Intermediate 16 (442 mg, 3.345 mmol) according to general procedure (11) using 85:15 ethyl acetate/methanol as the eluent for flash silica gel column chromatography. Yield: 22%. $^{1}$H NMR (400 MHz, MeOD) δ: 7.74 (d, J=1.8 Hz, 1H), 7.32 (d, J=8.7 Hz, 1H), 7.22 (d, J=3.1 Hz, 1H), 7.17 (dd, J=8.7, 2.0 Hz, 1H), 6.40 (dd, J=3.1, 0.8 Hz, 1H), 4.50-4.47 (m, 1H), 4.32-4.29 (m, 1H), 3.25-3.20 (m, 1H), 2.93 (dd, J=12.7, 5.0 Hz, 1H), 2.71 (d, J=12.7 Hz, 1H), 2.40 (t, J=7.2 Hz, 2H), 1.82-1.49 (m, 6H).

Intermediate 21 N-(3-formyl-1H-indol-5-yl)-5-((3aS,4S,6aR)-2-oxohexahydro-1H-thieno[3,4-d] imidazol-4-yl)pentanamide

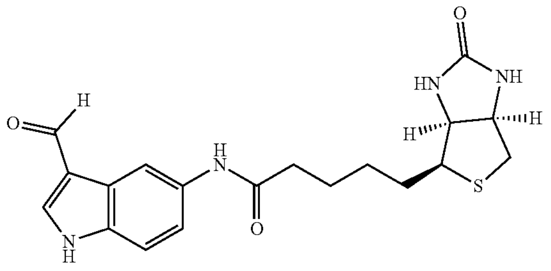 [SMILES: O=Cc1c[nH]c2ccc(NC(=O)CCCC[C@@H]3SC[C@@H]4NC(=O)N[C@@H]43)cc12]

Intermediate 21 (109 mg, 0.282 mmol) was prepared as a light grey solid from Intermediate 20 (224 mg, 0.625 mmol) according to general procedure (4). Yield: 45%. $^{1}$H NMR (400 MHz, DMSO) δ: 12.08 (bs, 1H), 9.89 (s, 1H), 9.86 (s, 1H), 8.36 (d, J=1.7 Hz, 1H), 8.23 (s, 1H), 7.52 (dd, J=8.8, 1.9 Hz, 1H), 7.41 (d, J=8.7 Hz, 1H), 6.44 (s, 1H), 6.36 (s, 1H), 4.37-4.28 (m, 1H), 4.17-4.14 (m, 1H), 3.16-3.12 (m, 1H), 2.84 (dd, J=12.4, 5.1 Hz, 1H), 2.59 (d, J=12.4 Hz, 1H), 2.32 (t, J=7.3 Hz, 2H), 1.73-1.34 (m, 6H).

Intermediate 22 N-(3-(cyanomethyl)-1H-indol-5-yl)-5-((3aS,4S,6aR)-2-oxohexahydro-1H-thieno[3,4-d] imidazol-4-yl)pentanamide

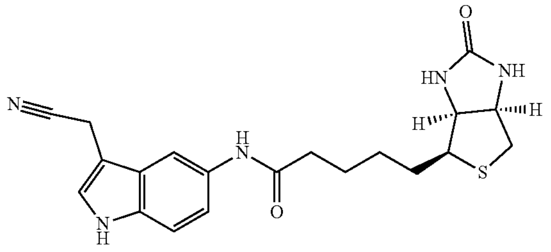 [SMILES: N#CCc1c[nH]c2ccc(NC(=O)CCCC[C@@H]3SC[C@@H]4NC(=O)N[C@@H]43)cc12]

A inseparable mixture (80 mg) of Intermediate 22 (LC-MS (ESI): m/z 398.2 [M+H]$^{+}$) and its 3-methyl side-product (LC-MS (ESI): m/z 373.2 [M+H]$^{+}$) was prepared as a white solid from Intermediate 21 (108 mg, 0.280 mmol) according to general procedure (5) using 85:15 ethyl acetate/methanol as the eluent for flash silica gel column chromatography. This mixture was used in the next synthetic step.

Chemical Example 15 N-(3-((Z)-1-cyano-2-(isoquinolin-5-yl)vinyl)-1H-indol-5-yl)-5-((3aS,4S,6aR)-2-oxohexahydro-1H-thieno[3,4-d]imidazol-4-yl)pentanamide

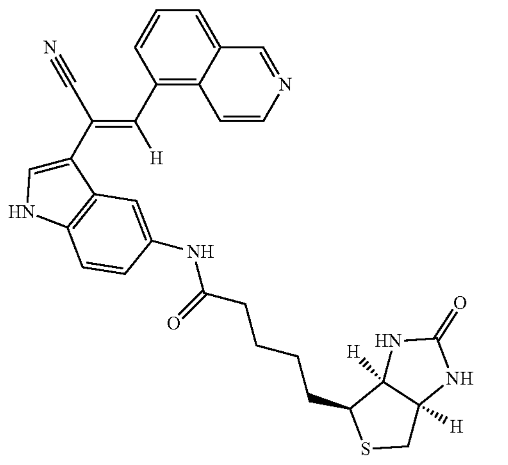 [SMILES: N#C/C(=C\c1cccc2cnccc12)c1c[nH]c2ccc(NC(=O)CCCC[C@@H]3SC[C@@H]4NC(=O)N[C@@H]43)cc12]

Compound 15 [a215] (33 mg, 0.061 mmol) was prepared as a dark yellow solid from Intermediate 22 mixture (80 mg, 0.202 mmol) and isoquinoline-5-carboxaldehyde (45 mg, 0.286 mmol) according to general procedure (1) microwave method. Yield: 22% over last two steps. $^1$H NMR (400 MHz, DMSO) δ: 9.87 (s, 1H), 9.42 (s, 1H), 8.61 (d, J=5.9 Hz, 1H), 8.46 (s, 1H), 8.30 (d, J=7.3 Hz, 1H), 8.24-8.22 (m, 1H), 8.21 (s, 1H), 8.11 (d, J=6.0 Hz, 1H), 7.89 (s, 1H), 7.84 (t, J=7.8 Hz, 1H), 7.46-7.44 (m, 2H), 6.42 (s, 1H), 6.33 (s, 1H), 4.30-4.27 (m, 1H), 4.14-4.11 (m, 1H), 3.13-3.09 (m, 2H), 2.80 (dd, J=12.3, 5.0 Hz, 1H), 2.56 (d, J=12.3 Hz, 1H), 2.33 (t, J=7.4 Hz, 2H), 1.70-1.31 (m, 6H). $^{13}$C NMR (100 MHz, DMSO) δ: 170.84, 162.67, 153.06, 143.83, 133.78, 133.51, 133.28, 131.66, 130.95, 130.04, 129.00, 128.28, 127.18, 123.79, 117.83, 116.83, 115.97, 110.41, 110.23, 109.40, 61.04, 59.17, 55.38, 39.81, 36.25, 28.28, 28.08, 25.17. LC-MS (ESI): m/z 537.2 $[M+H]^+$. HRMS (ESI): m/z calculated $[M+H]^+$ $C_{30}H_{29}N_6O_2S^+$ 537.2067, found 537.2067.

Scheme H

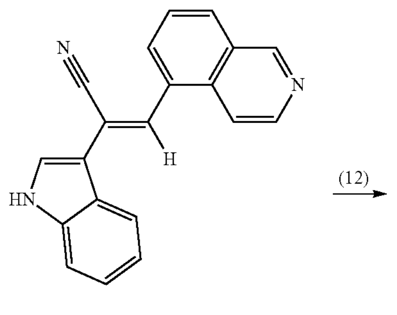

-continued

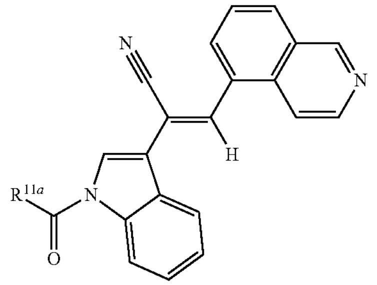

General Procedure (12):

Compound 1 (1.0 equiv), carboxylic acid (1.35 equiv), PyBOP (1.55 equiv) and triethylamine (2.1 equiv) was dissolved in DMF (3 mL for 0.264 mmol of starting material). The reaction was allowed to stir at room temperature for 16 h. The mixture was poured into water (10× reaction volume), shaken gently and allowed to stand. The precipitate formed was filtered, washed with water and dried under vacuum to afford the product.

Chemical Example 16 (Compound 16) [b5]

(Z)-3-(isoquinolin-5-yl)-2-(1-(2-(4-methylpiperazin-1-yl)acetyl)-1H-indol-3-yl)acrylonitrile

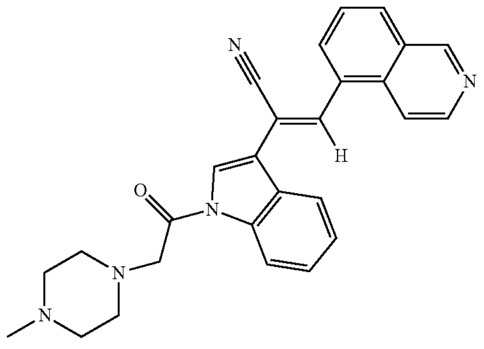 [SMILES: CN1CCN(CC(=O)n2cc(/C(C#N)=C/c3cccc4cnccc34)c3ccccc32)CC1]

Compound 16 [b5] (88 mg, 0.202 mmol) was prepared as a yellow solid from Compound 1 (99 mg, 0.333 mmol) and 4-methyl-1-piperazine acetic acid (66 mg, 0.417 mmol) according to general procedure (12). Yield: 70%. $^1$H NMR (400 MHz, DMSO) δ 9.44 (s, 1H), 8.64 (d, J=5.8 Hz, 1H), 8.61 (s, 1H), 8.48 (d, J=7.8 Hz, 1H), 8.41 (s, 1H), 8.35 (d, J=7.2 Hz, 1H), 8.31 (d, J=8.2 Hz, 1H), 8.17 (d, J=7.3 Hz, 1H), 8.08 (d, J=5.8 Hz, 1H), 7.87 (t, J=7.8 Hz, 1H), 7.53-7.44 (m, 2H), 4.19 (s, 2H), 3.23-3.15 (m, 4H), 2.99-2.90 (m, 4H), 2.76 (s, 3H). $^{13}$C NMR (100 MHz, DMSO) δ: 168.85, 153.09, 143.90, 139.57, 135.80, 133.46, 130.77, 130.38, 130.03, 128.18, 127.18, 126.35, 126.29, 126.00, 124.53, 119.97, 117.30, 117.08, 116.30, 116.05, 107.89, 59.01, 52.99, 49.21, 42.62. LC-MS (ESI): m/z 436.2 $[M+H]^+$.

Chemical Example 17 (Compound 17) [b9]

(Z)—N-(3-(3-(1-cyano-2-(isoquinolin-5-yl)vinyl)-1H-indol-1-yl)-3-oxopropyl)acetamide

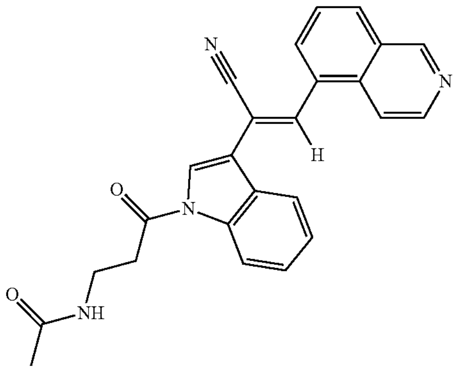 [SMILES: CC(=O)NCCC(=O)n1cc(/C(C#N)=C/c2cccc3cnccc23)c2ccccc21]

Compound 17 [b9] (76 mg, 0.186 mmol) was prepared as a yellow solid from Compound 1 (78 mg, 0.264 mmol) and N-acetyl-beta-alanine (47 mg, 0.357 mmol) according to general procedure (12). Yield: 72%. $^1$H NMR (400 MHz, DMSO) δ: 9.43 (s, 1H), 8.67-8.60 (m, 2H), 8.50 (d, J=7.6 Hz, 1H), 8.46 (s, 1H), 8.36 (d, J=7.3 Hz, 1H), 8.30 (d, J=8.2 Hz, 1H), 8.17-8.05 (m, 3H), 7.90-7.82 (m, 1H), 7.51-7.43 (m, 2 Hz), 3.52-3.47 (m, 2H), 3.38-3.32 (m, 2H), 1.82 (s, 3H). $^{13}$C NMR (100 MHz, DMSO) δ: 170.77, 169.45, 153.04, 143.87, 139.56, 135.65, 133.49, 130.70, 130.35, 129.96, 128.16, 127.14, 126.56, 126.41, 125.81, 124.29, 119.73, 117.37, 117.10, 116.36, 115.79, 107.70, 35.33, 34.32, 22.52. LC-MS (ESI): m/z 436.2 $[M+H]^+$.

Chemical Example 18 (Compound 18) [b19]

(Z)-3-(isoquinolin-5-yl)-2-(1-(5-((3aS,4S,6aR)-2-oxohexahydro-1H-thieno[3,4-d]imidazol-4-yl)pentanoyl)-1H-indol-3-yl)acrylonitrile

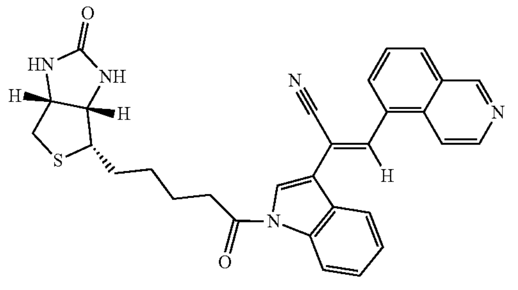 [SMILES: N#C/C(=C\c1cccc2cnccc12)c1cn(C(=O)CCCC[C@@H]2SC[C@@H]3NC(=O)N[C@@H]32)c2ccccc12]

Compound 18 [b19] (84 mg, 0.160 mmol) was prepared as a pale yellow solid from Compound 1 (79 mg, 0.267 mmol) and D-Biotin (88 mg, 0.360 mmol) according to general procedure (12). Yield: 60%. $^1$H NMR (400 MHz, DMSO): δ 9.44 (s, 1H), 8.66-8.60 (m, 2H), 8.50 (d, J=8.0 Hz, 1H), 8.47 (s, 1H), 8.35 (d, J=7.3 Hz, 1H), 8.30 (d, J=8.2 Hz, 1H), 8.14-8.10 (m, 2H), 7.87 (t, J=7.7 Hz, 1H), 7.50-7.42 (m, 2H), 6.45 (s, 1H), 6.36 (s, 1H), 4.35-4.29 (m, 1H), 4.20-4.14 (m, 1H), 3.27-3.10 (m, 3H), 2.84 (dd, J=12.4, 5.0 Hz, 1H), 2.59 (d, J=12.4 Hz, 1H), 1.86-1.49 (m, 6H). $^{13}$C NMR (100 MHz, DMSO) δ: 172.23, 162.69, 153.04, 143.88, 139.58, 135.67, 133.49, 130.74, 130.39, 129.95, 128.16, 127.15, 126.55, 126.50, 125.79, 124.20, 119.72, 117.39, 117.12, 116.38, 115.68, 107.82, 61.03, 59.19, 55.39, 39.64, 34.69, 28.09, 27.97, 23.93. LC-MS (ESI): m/z 522.2 $[M+H]^+$.

Chemical Example 19 (Compound 19) [b27]

(Z)-tert-butyl 4-(3-(1-cyano-2-(isoquinolin-5-yl)vinyl)-1H-indole-1-carbonyl)piperidine-1-carboxylate

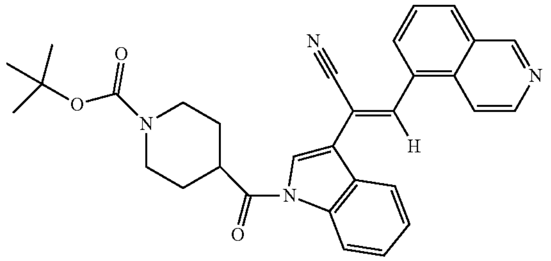 [SMILES: CC(C)(C)OC(=O)N1CCC(C(=O)n2cc(/C(C#N)=C/c3cccc4cnccc34)c3ccccc32)CC1]

Compound 19 [b27] (236 mg, 0.466 mmol) was prepared as a yellow solid from Compound 1 (151 mg, 0.511 mmol) and 1-Boc-piperidine-4-carboxylic acid (158 mg, 0.690 mmol) according to general procedure (12). The yellow precipitate obtained from the reaction work-up was further purified by flash silica gel column chromatography (96:4 dichloromethane/methanol) to afford the product. Yield: 91%. $^1$H NMR (400 MHz, Acetone) δ: 9.40 (d, J=0.9 Hz, 1H), 8.63-8.58 (m, 2H), 8.56 (s, 1H), 8.47 (s, 1H), 8.40 (dt, J=7.3, 1.0 Hz, 1H), 8.28 (d, J=8.2 Hz, 1H), 8.21-8.15 (m, 1H), 8.04 (dt, J=6.0, 0.9 Hz, 1H), 7.89-7.84 (m, 1H), 7.56-7.40 (m, 2H), 4.17 (d, J=13.2 Hz, 2H), 3.84-3.71 (m, 1H), 3.10-3.05 (m, 2H), 2.15-2.07 (m, 2H), 1.88-1.73 (m, 2H), 1.46 (s, 9H). $^{13}$C NMR (100 MHz, Acetone) δ: 174.93, 155.05, 154.10, 145.06, 140.06, 137.52, 134.93, 131.65, 131.63, 130.83, 129.64, 128.06, 127.92, 126.88, 126.67, 125.32, 120.75, 118.18, 117.97, 117.90, 117.60, 109.60, 79.61, 41.87, 29.5, 28.59. LC-MS (ESI): m/z 507.2 $[M+H]^+$.

Chemical Example 20 (Compound 20) [b31]

(Z)-tert-butyl (3-(3-(1-cyano-2-(isoquinolin-5-yl)vinyl)-1H-indol-1-yl)-3-oxopropyl)carbamate

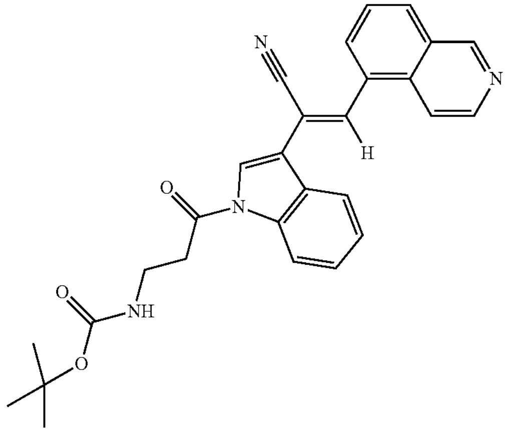 [SMILES: CC(C)(C)OC(=O)NCCC(=O)n1cc(/C(C#N)=C/c2cccc3cnccc23)c2ccccc21]

Compound 20 [b31] (107 mg, 0.230 mmol) was prepared as a beige solid from Compound 1 (73 mg, 0.248 mmol) and Boc-β-alanine (63 mg, 0.335 mmol) according to general procedure (12). Yield: 92%. $^1$H NMR (400 MHz, DMSO): δ 9.43 (s, 1H), 8.64-8.63 (m, 2H), 8.49 (d, J=7.8 Hz, 1H), 8.43 (s, 1H), 8.35 (d, J=7.2 Hz, 1H), 8.30 (d, J=8.2 Hz, 1H), 8.14 (d, J=7.3 Hz, 1H), 8.10 (d, J=6.0 Hz, 1H), 7.87 (t, J=7.8 Hz, 1H), 7.55-7.38 (m, 2H), 6.97 (s, 1H), 3.41-3.40 (m, 2H), 3.31-3.27 (m, 2H), 1.35 (s, 9H). $^{13}$C NMR (100 MHz, DMSO) δ: 170.76, 155.57, 153.06, 143.87, 139.54, 135.68, 133.49, 130.72, 130.37, 129.97, 128.17, 127.16, 126.59, 126.51, 125.79, 124.29, 119.71, 117.37, 117.08, 116.42, 115.76, 107.79, 77.77, 35.89, 35.65, 28.19. LC-MS (ESI): m/z 467.2 $[M+H]^+$.

Scheme I

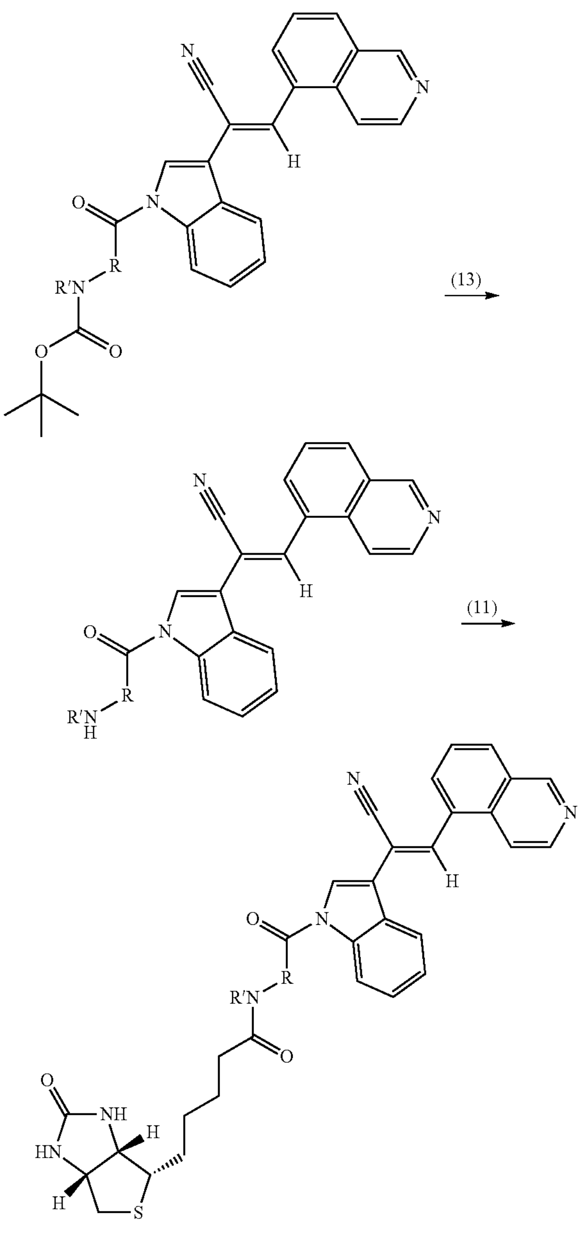

General Procedure (13):

To a suspension of N-Boc protected starting material (1.0 equiv) in ethanol (12 mL for 0.184 mmol starting material), acetyl chloride (50.0 equiv) was added. The reaction was stirred at room temperature for 40 h. Solvent was removed under vacuum and the resulting solid was washed with diethyl ether to afford the amine product as a hydrochloride salt.

Chemical Example 21 (Compound 21) [b35]

(Z)-3-(isoquinolin-5-yl)-2-(1-(piperidine-4-carbonyl)-1H-indol-3-yl)acrylonitrile

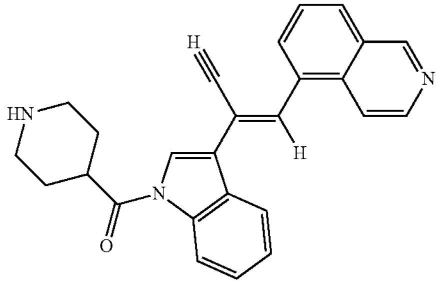

Compound 21 [b35] (76 mg, 0.159 mmol) was prepared as a yellow solid in the form of a hydrochloride salt (2HCl) from Compound 19 (82 mg, 0.162 mmol) according to general procedure (13). Yield: 98%. $^1$H NMR (400 MHz, $D_2O$) δ: 9.51 (s, 1H), 8.51 (d, J=7.2 Hz, 1H), 8.37-8.22 (m, 4H), 8.13 (d, J=8.1 Hz, 1H), 7.96-7.87 (m, 2H), 7.84 (d, J=7.7 Hz, 1H), 7.41-7.32 (m, 2H), 3.57 (d, J=13.1 Hz, 2H), 3.47-3.42 (m, 1H), 3.22 (t, J=11.6 Hz, 2H), 2.19 (d, J=12.5 Hz, 2H), 2.07-1.98 (m, 2H). $^{13}$C NMR (100 MHz, $D_2O$) δ: 173.65, 147.03, 137.23, 136.24, 136.13, 135.54, 132.07, 131.66, 130.74, 130.31, 126.99, 126.53, 125.91, 125.71, 125.08, 121.44, 119.61, 117.53, 116.72, 116.51, 109.57, 42.63, 38.18, 24.96. LC-MS (ESI): m/z 407.2 $[M+H]^+$.

Chemical Example 22 (Compound 22) [b42]

(Z)-2-(1-(3-aminopropanoyl)-1H-indol-3-yl)-3-(isoquinolin-5-yl)acrylonitrile

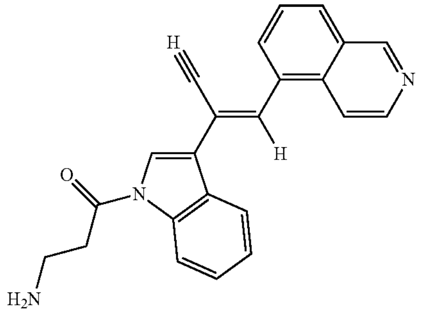

Compound 22 [b42] (69 mg, 0.159 mmol) was prepared as a yellow-orange solid in the form of a hydrochloride salt (2HCl) from Compound 20 (86 mg, 0.184 mmol) according to general procedure (13). Yield: 86%. $^1$H NMR (400 MHz, $D_2O$) δ: 9.49 (s, 1H), 8.52 (d, J=7.3 Hz, 1H), 8.36 (d, J=6.7 Hz, 1H), 8.32 (d, J=8.3 Hz, 1H), 8.26 (s, 1H), 8.24-8.19 (m, 2H), 7.93 (t, J=7.8 Hz, 1H), 7.88 (d, J=7.7 Hz, 1H), 7.79 (s, 1H), 7.48-7.38 (m, 2H), 3.54 (t, J=6.3 Hz, 2H), 3.37 (t, J=6.2

Hz, 2H). $^{13}C$ NMR (100 MHz, $D_2O$) δ: 170.09, 147.43, 137.03, 136.19, 135.98, 135.56, 132.42, 132.02, 130.74, 130.26, 127.15, 126.57, 125.99, 125.88, 125.15, 121.18, 119.84, 117.42, 116.74, 116.44, 109.69, 34.68, 32.59. LC-MS (ESI): m/z 367.1 $[M+H]^+$.

Chemical Example 23 (Compound 23) [b36]

(Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile

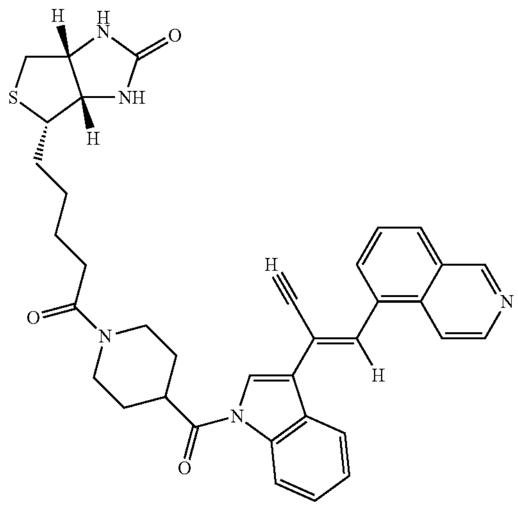

Compound 23 [b36] (64 mg, 0.017 mmol) was prepared as a yellow solid from Compound 21 (67 mg, 0.140 mmol) and D-Biotin (60 mg, 0.247 mmol) according to general procedure (11) with 5.0 equiv of DIPEA. Flash silica gel column chromatography was performed using 80:20 ethyl acetate/methanol as the eluent. Yield: 13%. $^{13}C$ NMR (100 MHz, DMSO) δ: 174.21, 170.49, 162.70, 150.01, 139.35, 137.02, 135.73, 135.27, 134.13, 131.47, 131.15, 129.15, 127.76, 126.75, 126.49, 126.01, 124.45, 120.34, 119.72, 117.13, 116.62, 116.12, 108.92, 61.06, 59.20, 55.47, 44.10, 39.95, 39.61, 32.16, 28.95, 28.32, 28.14, 24.93. LC-MS (ESI): m/z 633.3 $[M+H]^+$.

Chemical Example 24 (Compound 24) [b45]

N-(3-(3-((Z)-1-cyano-2-(isoquinolin-5-yl)vinyl)-1H-indol-1-yl)-3-oxopropyl)-5-((3aS,4S,6aR)-2-oxo-hexahydro-1H-thieno[3,4-d]imidazol-4-yl)pentanamide

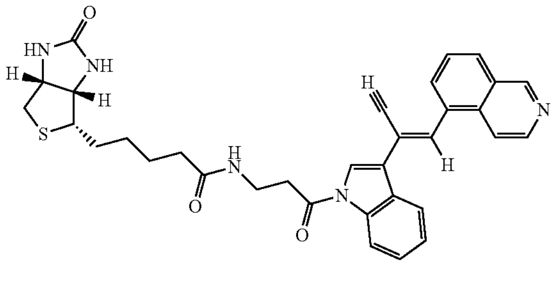

Compound 24 [b45] (31 mg, 0.052 mmol) was prepared as a light yellow solid from Compound 22 (51 mg, 0.116 mmol) and D-Biotin (51 mg, 0.201 mmol) according to general procedure (11) with 5.0 equiv of DIPEA. The reaction was poured into water (10× reaction volume) and left to stand. The precipitate formed was filtered, washed with water and methanol and dried under vacuum to afford Compound 24 as the product. Yield: 45%. $^1H$ NMR (400 MHz, DMSO) δ: 9.44 (s, 1H), 8.64 (s, 2H), 8.52-8.48 (m, 1H), 8.46 (s, 1H), 8.36 (d, J=7.3 Hz, 1H), 8.30 (d, J=8.2 Hz, 1H), 8.18-8.09 (m, 2H), 8.04 (t, J=5.5 Hz, 1H), 7.90-7.83 (m, 1H), 7.51-7.43 (m, 2H), f6.38 (s, 1H), 6.32 (s, 1H), 4.25-4.21 (m, 1H), 4.11-3.96 (m, 1H), 3.53-3.49 (m, 2H), 3.30-3.33 (m, 2H), 3.01-2.96 (m, 1H), 2.73 (dd, J=12.4, 5.1 Hz, 1H), 2.54-2.51 (m, 1H), 2.08 (t, J=7.3 Hz, 2H), 1.64-1.15 (m, 6H). $^{13}C$ NMR (100 MHz, DMSO) δ: 172.36, 170.79, 162.65, 153.05, 143.88, 139.58, 135.67, 133.50, 130.72, 130.36, 129.98, 128.21, 127.16, 126.58, 126.44, 125.82, 124.31, 119.73, 117.38, 117.11, 116.39, 115.79, 107.72, 60.95, 59.15, 55.36, 39.77, 35.35, 35.07, 34.35, 28.11, 27.98, 25.21. LC-MS (ESI): m/z 593.2 $[M+H]^+$.

Scheme J

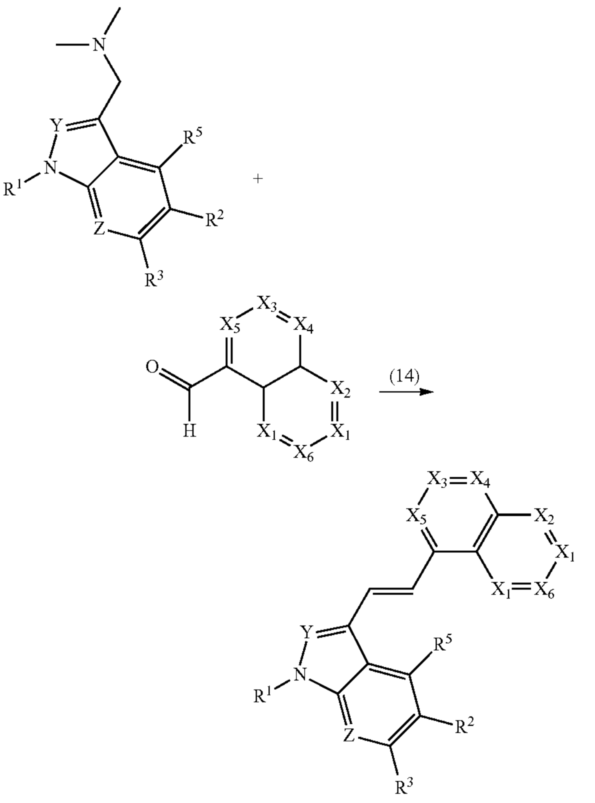

General Procedure (14):

In a dry sealed tube, a quinoline/isoquinoline-carboxaldehyde derivative (1.0 equiv) and a gramine derivative (1.0 equiv) were dissolved in anhydrous acetonitrile (3 mL for 0.530 mmol of gramine derivative). Tributyllphosphine (2.25 equiv) was added and the sealed reaction was heated at 90° C. in an oil bath for 22 h. After the reaction was allowed to cool to room temperature, the solvent was removed under vacuum. The crude material was washed with methanol and diethyl ether to afford the alkene product as a yellow precipitate which was filtered and dried under vacuum.

Chemical Example 25 (Compound 25) [a166]

5-((E)-2-(1H-indol-3-yl)vinyl)isoquinoline

Intermediate 23
(1H-indol-3-yl)-N,N-dimethylmethanamine

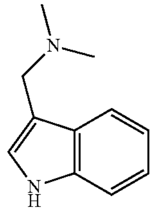

Intermediate 23 (374 mg, 2.146 mmol) was prepared as an off-white solid from indole (379 mg, 3.232 mmol) according to general procedure (2). Yield: 66%. $^1$H NMR (400 MHz, $CDCl_3$) δ: 8.21 (bs, 1H), 7.75-7.67 (m, 1H), 7.39-7.33 (m, 1H), 7.22-7.17 (m, 1H), 7.15-7.10 (m, 2H), 3.65 (s, 2H), 2.30 (s, 6H).

Chemical Example 25 5-((E)-2-(1H-indol-3-yl)vinyl)isoquinoline

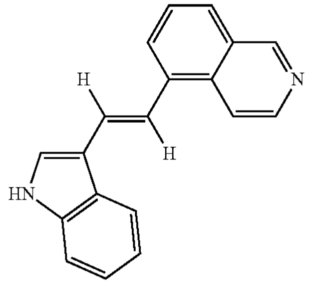 [SMILES: C(=C\c1c[nH]c2ccccc12)/c1cccc2cnccc12]

Compound 25 [a166] (40 mg, 0.148 mmol) was prepared as a yellow solid from Intermediate 23 (92 mg, 0.530 mmol) and isoquinoline-5-carboxaldehyde (83 mg, 0.530 mmol) according to general procedure (14). Yield: 28%. $^1$H NMR (400 MHz, Acetone) δ: 10.57 (s, 1H), 9.28 (d, J=0.8 Hz, 1H), 8.56 (d, J=6.0 Hz, 1H), 8.22 (d, J=6.0 Hz, 1H), 8.17-8.11 (m, 2H), 7.98 (d, J=8.2 Hz, 1H), 7.90 (d, J=16.2 Hz, 1H), 7.78 (d, J=2.5 Hz, 1H), 7.69 (t, J=7.7 Hz, 1H), 7.62 (d, J=16.2 Hz, 1H), 7.53-7.47 (m, 1H), 7.29-7.14 (m, 2H). $^{13}$C NMR (100 MHz, Acetone) δ: 154.07, 151.28, 147.70, 143.48, 138.48, 136.75, 129.59, 128.49, 127.67, 126.60, 124.40, 123.17, 121.19, 120.89, 116.74, 116.54, 115.67, 112.82. LC-MS (ESI): m/z 272.1 $[M+H]^+$.

Chemical Example 26 (Compound 26) [a183]

4-((E)-2-(1H-indol-3-yl)vinyl)-2,7-naphthyridine

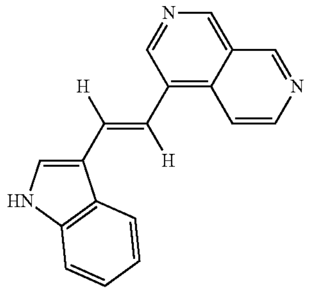 [SMILES: C(=C\c1c[nH]c2ccccc12)/c1cncc2cnccc12]

Compound 26 [a183] (47 mg, 0.172 mmol) was prepared as a yellow solid from Intermediate 23 (72 mg, 0.413 mmol) and 2,7-napthyridine-4-carbaldehyde (65 mg, 0.413 mmol) according to general procedure (14). Yield: 42%. $^1$H NMR (400 MHz, Acetone): δ 10.63 (s, 1H), 9.50 (d, J=1.0 Hz, 1H), 9.35 (d, J=0.6 Hz, 1H), 9.09 (s, 1H), 8.78 (d, J=6.0 Hz, 1H), 8.25 (dt, J=6.0, 0.9 Hz, 1H), 8.20-8.14 (m, 1H), 7.81 (d, J=2.6 Hz, 1H), 7.80-7.66 (m, 2H), 7.55-7.48 (m, 1H), 7.27-7.17 (m, 2H). $^{13}$C NMR (100 MHz, Acetone) δ: 154.07, 151.28, 147.70, 143.48, 138.48, 136.75, 129.59, 128.49, 127.67, 126.60, 124.40, 123.17, 121.19, 120.89, 116.74, 116.54, 115.67, 112.82. LC-MS (ESI): m/z 272.1 $[M+H]^+$.

Chemical Example 27 (Compound 27) [a191]

5-((E)-2-(1H-pyrrolo[2,3-b]pyridin-3-yl)vinyl)isoquinoline

Intermediate 24 N,N-dimethyl(1H-pyrrolo[2,3-b]pyridin-3-yl)methanamine

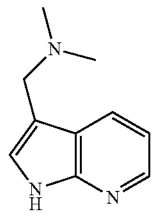

Intermediate 24 (443 mg, 2.528 mmol) was prepared as a white solid from 7-azaindole (346 mg, 2.925 mmol) according to general procedure (2). Yield: 86%. $^1$H NMR (400 MHz, $CDCl_3$) δ: 10.44 (bs, 1H), 8.31 (dd, J=4.7, 1.3 Hz, 1H), 8.05 (dd, J=7.8, 1.3 Hz, 1H), 7.27 (s, 1H), 7.08 (dd, J=7.8, 4.8 Hz, 1H), 3.61 (s, 2H), 2.27 (s, 6H).

Compound 27 5-((E)-2-(1H-pyrrolo[2,3-b]pyridin-3-yl)vinyl)isoquinoline

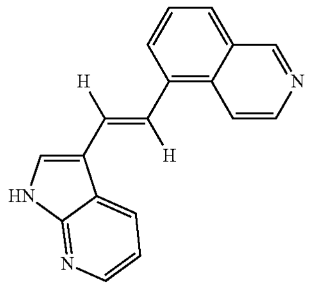 [SMILES: C(=C\c1c[nH]c2ncccc12)/c1cccc2cnccc12]

Compound 27 [a191] (61 mg, 0.225 mmol) was prepared as a pale yellow solid from Intermediate 24 (105 mg, 0.601 mmol) and isoquinoline-5-carboxaldehyde (94 mg, 0.601 mmol) according to general procedure (14). Yield: 37%. $^1$H NMR (400 MHz, DMSO) δ: 11.95 (s, 1H), 9.32 (s, 1H), 8.57-8.53 (m, 2H), 8.31-8.28 (m, 2H), 8.15 (d, J=7.3 Hz, 1H), 8.01 (d, J=8.1 Hz, 1H), 7.96 (s, 1H), 7.83 (d, J=16.3 Hz, 1H), 7.71 (t, J=7.7 Hz, 1H), 7.57 (d, J=16.2 Hz, 1H), 7.21 (dd, J=7.9, 4.7 Hz, 1H). $^{13}$C NMR (100 MHz, DMSO) δ: 152.85, 149.19, 143.24, 142.92, 134.42, 132.80, 128.70, 128.27, 127.35, 126.93, 126.16, 125.55, 125.56, 118.68, 117.49, 116.80, 116.21, 112.77. LC-MS (ESI): m/z 272.1 $[M+H]^+$.

Chemical Example 28 (Compound 28) [a194]

4-((E)-2-(1H-pyrrolo[2,3-b]pyridin-3-yl)vinyl)-2,7-naphthyridine

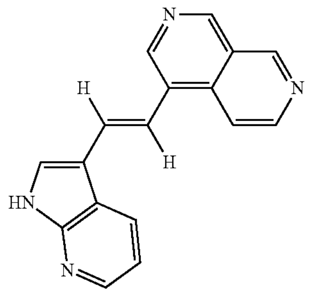 [SMILES: C(=C\c1c[nH]c2ncccc12)/c1cncc2cnccc12]

Compound 28 [a194] (40 mg, 0.146 mmol) was prepared as a yellow solid from Intermediate 24 (121 mg, 0.692 mmol) and 2,7-napthyridine-4-carbaldehyde (110 mg, 0.692 mmol) according to general procedure (14). Yield: 21%. $^1$H NMR (400 MHz, DMSO) δ: 11.99 (s, 1H), 9.53 (d, J=0.9 Hz, 1H), 9.38 (d, J=0.4 Hz, 1H), 9.12 (s, 1H), 8.80 (d, J=6.0 Hz, 1H), 8.57 (dd, J=7.9, 1.5 Hz, 1H), 8.33 (d, J=6.1 Hz, 1H), 8.31 (dd, J=4.7, 1.5 Hz, 1H), 7.98 (s, 1H), 7.69 (s, 2H), 7.21 (dd, J=7.9, 4.7 Hz, 1H). $^{13}$C NMR (100 MHz, DMSO) δ: 153.19, 150.52, 149.18, 146.69, 143.33, 142.28, 135.25, 128.36, 127.93, 127.40, 126.82, 122.93, 117.45, 116.28, 116.07, 115.86, 112.64. LC-MS (ESI): m/z 273.1 $[M+H]^+$.

Scheme K

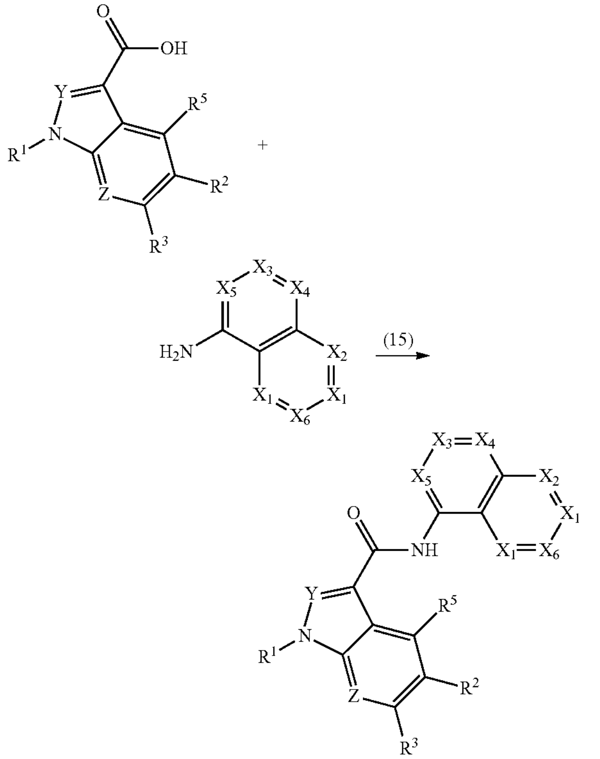

General Procedure (15):

To a suspension of the carboxylic acid (1.0 equiv) in dichloromethane (10 mL for 0.838 mmol of starting material), oxalyl chloride 2.0 M solution in dichloromethane (approximately 1.5 mL) was added, followed by one drop of DMF. The reaction was stirred at room temperature for 2 h. The solution was evaporated under vacuum to afford the crude acid chloride. Dichloromethane was added to the crude acid chloride and evaporated under vacuum again for 2 times. The acid chloride was then re-dissolved in THF and added slowly to a solution of the amine derivative (1.2 equiv) and triethylamine (2.5 equiv) in THF. The reaction was stirred at room temperature for 16 h. The mixture was poured into water and extracted with ethyl acetate 3 times. The combined organic layer was washed with brine, dried over anhydrous sodium sulphate, concentrated in vacuo and purified by flash silica gel column chromatography to afford the amide product.

Chemical Example 29 (Compound 29) [a219]

N-(isoquinolin-5-yl)-1H-indole-3-carboxamide

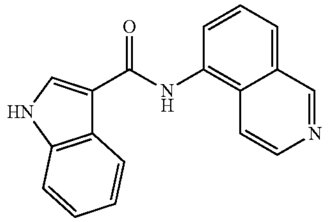 [SMILES: O=C(Nc1cccc2cnccc12)c1c[nH]c2ccccc12]

Compound 29 [a219] (101 mg, 0.352 mmol) was prepared as a brown solid from 1H-indole-3-carboxylic acid (135 mg, 0.838 mmol) and 5-aminoisoquinoline (145 mg, 1.006 mmol) according to general procedure (15) using 9:1 ethyl acetate/methanol as eluent for flash silica gel column chromatography and subsequent recrystallization from methanol. Yield: 42%. $^{1}H$ NMR (400 MHz, DMSO) δ: 11.80 (s, 1H), 9.98 (s, 1H), 9.35 (d, J=0.7 Hz, 1H), 8.53 (d, J=6.0 Hz, 1H), 8.44 (s, 1H), 8.20-8.14 (m, 1H), 7.99 (t, J=7.0 Hz, 2H), 7.94 (d, J=6.0 Hz, 1H), 7.72 (t, J=7.8 Hz, 1H), 7.53-7.47 (m, 1H), 7.22-7.13 (m, 2H). $^{13}C$ NMR (100 MHz, DMSO) δ: 163.86, 152.45, 142.51, 136.24, 133.55, 131.11, 129.15, 128.87, 127.17, 126.48, 126.43, 124.59, 122.16, 121.02, 120.71, 116.41, 111.96, 109.97. LC-MS (ESI): m/z 288.1 $[M+H]^{+}$.

Chemical Example 30 (Compound 30) [b67]

(Z)-2-(1-(2-(2-methoxyethoxy)acetyl)-1H-indol-3-yl)-3-(isoquinolin-5-yl)acrylonitrile

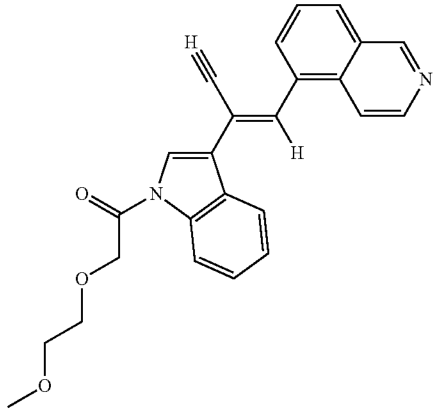

Compound 30 [B67] (65 mg, 0.157 mmol) was prepared as a light yellow solid from Compound 1 (81 mg, 0.276 mmol) and 2-(2-methoxyethoxy)acetic acid (45 μl, 54 mg, 0.400 mmol) according to general procedure (12). Yield: 56%. $^{1}H$ NMR (400 MHz, DMSO) δ: 9.44 (d, J=0.7 Hz, 1H), 8.63 (d, J=6.0 Hz, 1H), 8.61 (s, 1H), 8.48 (dd, J=7.4, 0.9 Hz, 1H), 8.36-8.34 (m, 2H), 8.30 (d, J=8.2 Hz, 1H), 8.15 (dd, J=7.0, 1.0 Hz, 1H), 8.09 (d, J=6.0 Hz, 1H), 7.91-7.82 (m, 1H), 7.53-7.44 (m, 2H), 4.96 (s, 2H), 3.79-3.73 (m, 2H), 3.57-3.52 (m, 2H), 3.26 (s, 3H). $^{13}C$ NMR (100 MHz, DMSO) δ: 169.07, 153.03, 143.87, 139.60, 135.69, 133.44, 130.73, 130.34, 129.97, 128.14, 127.12, 126.21, 125.96, 125.73, 124.47, 119.86, 117.24, 117.04, 116.18, 107.78, 71.09, 70.18, 69.91, 58.04. LC-MS (ESI): m/z 412.1 $[M+H]^{+}$.

Scheme L

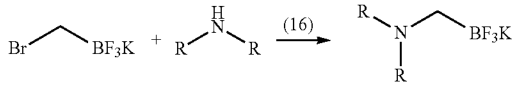

General Procedure (16):

To an amine (1.05 equiv) in dry THF (6.5 ml for 6.014 mmol amine), potassium (bromomethyl) trifluoroborate (1.0 equiv) was added. The mixture was allowed to stir at room temperature for 40 h. The solvent was evaporated under vacuum and the resulting crude material was dissolved in acetone. Potassium carbonate (1.0 equiv) was added and stirred at room temperature for 1 h. The mixture was filtered through a pad of Celite to remove the insoluble salts, and the filtrate was evaporated under vacuum afforded the product.

Scheme M

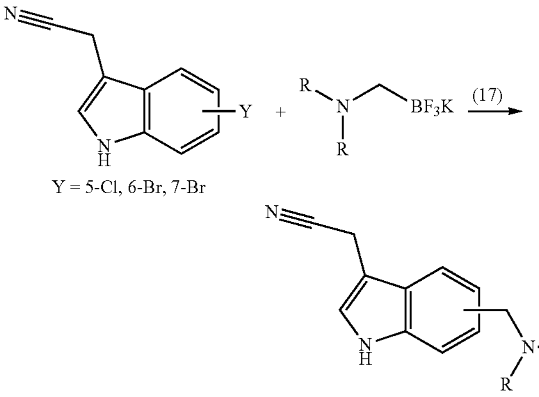

General Procedure (17):

Bromo/chloro-indole-3-acetonitrile (1.0 equiv), intermediate 29 [b43] (1.2 equiv), XPhos (0.06 equiv), $Pd(OAc)_2$ (0.03 equiv) and $Cs_2CO_3$ (3.0 equiv) were added to a reaction flask. The flask, with an attached condenser, was sealed with a septum and purged with nitrogen. A degassed mixture of 10:1 THF/$H_2O$ (2.5 ml for 0.262 mmol of bromo/chloro-indole-3-acetonitrile starting material) was added and the mixture was heated at 85° C. for 24 h. After the reaction was allowed to cool to room temperature, the mixture was poured into water and extracted with ethyl acetate 3 times. The combined organic layer was washed with brine, dried over anhydrous sodium sulphate and concentrated in vacuo. Purification by flash silica gel column chromatography (85:15:0.015 dichloromethane/methanol/ammonium hydroxide solution) afforded the product.

Chemical Example 31 (Compound 31) [b52]

(Z)-3-(isoquinolin-5-yl)-2-(6-((pyrrolidin-1-yl)methyl)-1H-indol-3-yl)acrylonitrile Intermediate 25 [b43] Potassium ((pyrrolidin-1-yl)methyl)trifluoroborate

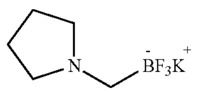

Intermediate 25 [b43] was prepared as an orange needle-like solid (171 mg, 0.895 mmol) from pyrrolidine (494 μL, 428 mg, 6.014 mmol) and potassium (bromomethyl) trifluoroborate (1150 mg, 5.728 mmol, 1.0 equiv) according to general procedure (16). Recrystallization with acetone afforded gave the desired product. Yield: 16%. $^{13}C$ NMR (100 MHz, Acetone) δ: 57.09, 23.66. $^{19}F$ NMR (376 MHz, Acetone) δ: −144.14.

Intermediate 26 [b51] 2-(6-((pyrrolidin-1-yl) methyl)-1H-indol-3-yl)acetonitrile

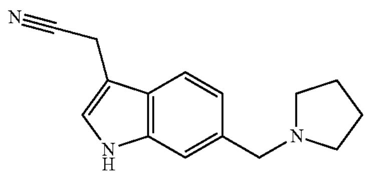 [SMILES: N#CCc1c[nH]c2cc(CN3CCCC3)ccc12]

Intermediate 26 [B51] (30 mg, 0.125 mmol) was prepared as a light-yellow oil from Intermediate 10 [b37] (55 mg, 0.236 mmol) according to general procedure (17). Yield: 53%. $^1$H NMR (400 MHz, MeOD) δ: 7.56 (dd, J=8.2, 0.5 Hz, 1H), 7.39 (d, J=0.7 Hz, 1H), 7.25 (s, 1H), 7.11 (dd, J=8.2, 1.4 Hz, 1H), 3.93 (d, J=0.9 Hz, 2H), 3.77 (s, 2H), 2.64-2.60 (m, 4H), 1.87-1.78 (m, 4H).

Chemical Example 31 [b52] (Z)-3-(isoquinolin-5-yl)-2-(6-((pyrrolidin-1-yl)methyl)-1H-indol-3-yl) acrylonitrile

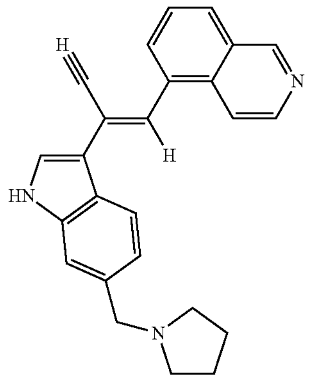

Compound 31 [B52] (47 mg, 0.095 mmol) was prepared as a yellow solid from Intermediate 26 [b51] (30 mg, 0.125 mmol) and isoquinoline-5-carboxaldehyde (22 mg, 0.137 mmol) according to general procedure (1) sealed tube method. The reaction was evaporated under vacuum to remove the solvent and purified by silica gel flash column chromatography (85:15:0.015 dichloromethane/methanol/ammonium hydroxide solution). The material obtained was dried under vacuum and triturated with small amount of methanol to obtain a yellow precipitate. Yield: 76%. $^1$H NMR (400 MHz, MeOD) δ: 9.32 (s, 1H), 8.54 (d, J=6.1 Hz, 1H), 8.33 (d, J=7.3 Hz, 1H), 8.27 (s, 1H), 8.19 (d, J=8.3 Hz, 1H), 8.07-8.04 (m, 2H), 7.84-7.78 (m, 1H), 7.77 (s, 1H), 7.52 (s, 1H), 7.27 (dd, J=8.3, 1.4 Hz, 1H), 3.84 (s, 2H), 2.69-2.66 (m, 4H), 1.90-1.85 (m, 4H). $^{13}$C NMR (100 MHz, MeOD) δ: 153.90, 143.75, 139.24, 135.84, 133.78, 133.08, 133.06, 132.21, 130.24, 130.23, 128.59, 128.49, 124.89, 123.89, 120.46, 118.86, 118.76, 114.25, 112.84, 112.65, 61.65, 54.90, 24.10. LC-MS (ESI): m/z 379.2 [M+H]$^+$.

Chemical Example 32 (Compound 32) [b59]

(Z)-3-(isoquinolin-5-yl)-2-(5-((pyrrolidin-1-yl) methyl)-1H-indol-3-yl)acrylonitrile Intermediate 27 [b55] 2-(5-((pyrrolidin-1-yl) methyl)-1H-indol-3-yl)acetonitrile

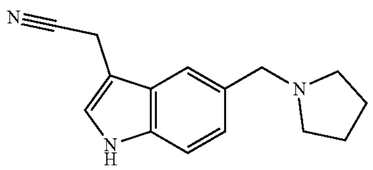 [SMILES: N#CCc1c[nH]c2ccc(CN3CCCC3)cc12]

Intermediate 27 [B55] (37 mg, 0.154 mmol) was prepared as a light-yellow oil from Intermediate 5 [a220] (55 mg, 0.262 mmol) and according to general procedure (17). Yield: 59%. $^1$H NMR (400 MHz, MeOD) δ: 7.58 (d, J=0.9 Hz, 1H), 7.38 (dd, J=8.4, 0.5 Hz, 1H), 7.26 (s, 1H), 7.20 (dd, J=8.4, 1.6 Hz, 1H), 3.95 (d, J=0.9 Hz, 2H), 3.84 (s, 2H), 2.78-2.58 (m, 4H), 1.88-1.75 (m, 4H).

Chemical Example 32 [b59] (Z)-3-(isoquinolin-5-yl)-2-(5-((pyrrolidin-1-yl)methyl)-1H-indol-3-yl) acrylonitrile

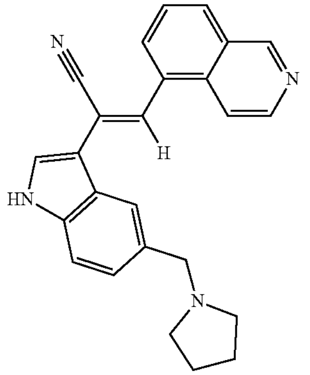 [SMILES: N#C/C(=C\c1cccc2cnccc12)c1c[nH]c2ccc(CN3CCCC3)cc12]

Compound 32 [B59] (27 mg, 0.071 mmol) was prepared as a yellow solid from Intermediate 27 [b55] (38 mg, 0.157 mmol) and isoquinoline-5-carboxaldehyde (27 mg, 0.173 mmol) according to general procedure (1) sealed tube method. The reaction was evaporated under vacuum to remove the solvent and purified by silica gel flash column chromatography (85:15:0.015 dichloromethane/methanol/ammonium hydroxide solution) to yield a dark yellow oil. Recrystallization with dichloromethane/methanol afforded Compound 32 [b59] as a yellow precipitate. Yield: 45%. $^1$H NMR (400 MHz, MeOD) δ: 9.31 (s, 1H), 8.53 (d, J=6.1 Hz, 1H), 8.34-8.26 (m, 2H), 8.18 (d, J=8.3 Hz, 1H), 8.09-8.05 (m, 2H), 7.85-7.76 (m, 1H), 7.75 (s, 1H), 7.47 (d, J=8.3 Hz, 1H), 7.27 (dd, J=8.4, 1.5 Hz, 1H), 3.81 (s, 2H), 2.67-2.57 (m, 4H), 1.84-1.81 (m, 4H). $^{13}$C NMR (100 MHz, MeOD) δ: 153.89, 143.72, 138.59, 135.85, 133.28, 133.22, 132.28, 131.90, 130.25, 130.21, 128.63, 128.59, 125.89, 125.57, 121.47, 118.89, 113.08, 112.97, 112.70, 61.98, 54.88, 24.10. LC-MS (ESI): m/z 379.1 [M+H]$^+$.

Chemical Example 33 (Compound 33) [b68]

B68 (Z)-3-(isoquinolin-5-yl)-2-(7-((pyrrolidin-1-yl) methyl)-1H-indol-3-yl)acrylonitrile Intermediate 28 [b66] 2-(7-((pyrrolidin-1-yl) methyl)-1H-indol-3-yl)acetonitrile

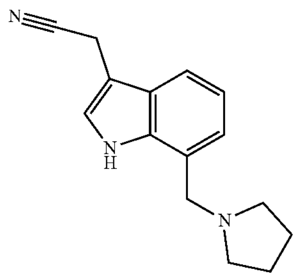 [SMILES: N#CCc1c[nH]c2c(CN3CCCC3)cccc12]

Intermediate 28 [B66] (32 mg, 0.134 mmol) was prepared as a light-yellow oil from Intermediate 2 [b41cn] (70 mg, 0.302 mmol) according to general procedure (17). Yield: 53%. $^1H$ NMR (400 MHz, MeOD) δ: 7.55 (dd, J=7.8, 1.1 Hz, 1H), 7.29 (s, 1H), 7.14 (d, J=6.6 Hz, 1H), 7.11-7.05 (m, 1H), 4.01 (s, 2H), 3.95 (d, J=0.9 Hz, 2H), 2.76-2.65 (m, 4H), 1.90-1.77 (m, 4H).

Chemical Example 33 [b68] (Z)-3-(isoquinolin-5-yl)-2-(7-((pyrrolidin-1-yl)methyl)-1H-indol-3-yl) acrylonitrile

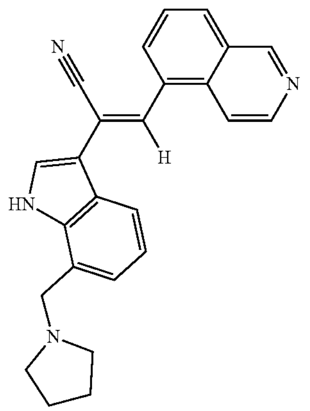 [SMILES: N#C/C(=C\c1cccc2cnccc12)c1c[nH]c2c(CN3CCCC3)cccc12]

Compound 33 [B68] (18 mg, 0.048 mmol) was prepared as a yellow solid from Intermediate 28 [b66] (32 mg, 0.134 mmol) and isoquinoline-5-carboxaldehyde (24 mg, 0.154 mmol) according to general procedure (1) sealed tube method. The reaction was evaporated under vacuum to remove the solvent and purified by silica gel flash column chromatography (87:13:0.008 dichloromethane/methanol/ammonium hydroxide solution) to yield a yellow sticky solid. Recrystallization with dichloromethane/methanol afforded Compound 33 [b68] as a yellow precipitate. Yield: 35%. $^1H$ NMR (400 MHz, $CDCl_3$) δ: 10.55 (bs, 1H), 9.32 (s, 1H), 8.62 (d, J=5.5 Hz, 1H), 8.34 (d, J=7.3 Hz, 1H), 8.18 (s, 1H), 8.03 (d, J=8.2 Hz, 1H), 7.95 (d, J=8.0 Hz, 1H), 7.86 (d, J=5.9 Hz, 1H), 7.75-7.71 (m, 1H), 7.70 (s, 1H), 7.25-7.20 (m, 1H), 7.12 (d, J=7.1 Hz, 1H), 4.04 (s, 2H), 2.64-2.59 (m, 4H), 1.90-1.86 (m, 4H). $^{13}C$ NMR (100 MHz, $CDCl_3$) δ: 153.41, 144.03, 137.04, 134.49, 132.32, 131.46, 130.57, 129.07, 128.91, 127.29, 126.39, 124.36, 122.34, 121.41, 118.82, 118.13, 116.75, 112.56, 111.41, 59.22, 54.42, 23.89. LC-MS (ESI): m/z 379.1 $[M+H]^+$.

Scheme N

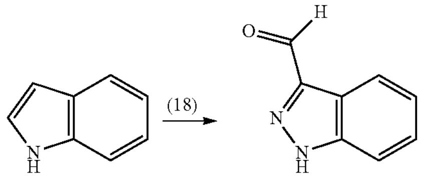

General Procedure (18):

An aqueous solution of 0.25 M $NaNO_2$ (1.05 equiv) was acidified with dilute HCl to pH 2.5. To this solution, dioxane (15% v/v) was added. The flask was protected from light by wrapping with aluminium foil. Indole (1.0 equiv) was added slowly in small portions. The mixture was stirred vigorously for 2 h. The liquid in the reaction flask was decanted out and extracted with ethyl acetate 3 times. The combined organic layer was washed with brine, dried over anhydrous sodium sulphate, concentrated in vacuo and purified by flash silica gel column chromatography to afford the product.

Chemical Example 34 (Compound 34) [b81]

(Z)-2-(1H-indazol-3-yl)-3-(isoquinolin-5-yl)acrylonitrile

Intermediate 29 [b79] 1H-indazole-3-carbaldehyde

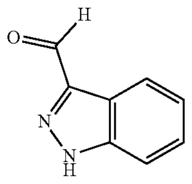 [SMILES: O=Cc1n[nH]c2ccccc12]

Intermediate 29 [B79] was prepared as a brown solid (514 mg, 3.517 mmol) from indole (5.578 g, 47.62 mmol) according to general procedure (18) using 7:3 hexane/ethyl acetate as the eluent for flash silica gel column chromatography. Yield: 7%. $^1H$ NMR (400 MHz, Acetone) δ: 10.23 (s, 1H), 8.23 (dt, J=8.1, 1.0 Hz, 1H), 7.74 (dt, J=8.5, 0.9 Hz, 1H), 7.55-7.48 (m, 1H), 7.41-7.36 (m, 1H).

Intermediate 30 [b80] 2-(1H-indazol-3-yl)acetonitrile

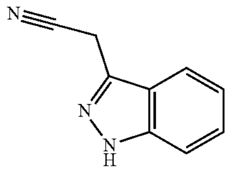 [SMILES: N#CCc1n[nH]c2ccccc12]

Intermediate 30 [B80] (330 mg, 2.100 mmol) was prepared as a brown oil from Intermediate 29 [b79] (513 mg, 3.513 mmol) according to general procedure (5) using 63:27 hexane/ethyl acetate as the eluent for flash silica gel column chromatography. Yield: 60%. $^1$H NMR (400 MHz, Acetone) δ: 12.25 (s, 1H), 7.86 (dt, J=8.2, 0.9 Hz, 1H), 7.60 (dt, J=8.5, 0.8 Hz, 1H), 7.45-7.39 (m, 1H), 7.23-7.17 (m, 1H), 4.28 (s, 2H).

Chemical Example 34 [b81] (Z)-2-(1H-indazol-3-yl)-3-(isoquinolin-5-yl)acrylonitrile

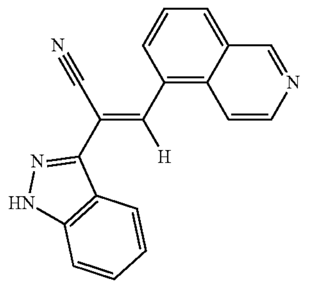 [SMILES: N#C/C(=C\c1cccc2cnccc12)c1n[nH]c2ccccc12]

Compound 34 [B81] (30 mg, 0.101 mmol) was prepared as a light yellow-orange solid from Intermediate 30 [b80] (104 mg, 0.663 mmol) and isoquinoline-5-carboxaldehyde (130 mg, 0.829 mmol) according to general procedure (1) sealed tube method. After the reaction was cooled to room temperature, the mixture was filtered and the evaporated under vacuum and the resulting material was recrystallized with methanol to afford Compound 34 [b81] as a light yellow-orange solid. Yield: 15%. $^1$H NMR (400 MHz, DMSO) δ: 9.43 (d, J=0.7 Hz, 1H), 8.70 (s, 1H), 8.62 (d, J=6.0 Hz, 1H), 8.36 (d, J=7.3 Hz, 1H), 8.28 (d, J=8.2 Hz, 1H), 8.24 (d, J=8.3 Hz, 1H), 8.04 (d, J=6.0 Hz, 1H), 7.89-7.82 (m, 1H), 7.68 (d, J=8.4 Hz, 1H), 7.45-7.39 (m, 1H), 7.26 (t, J=7.5 Hz, 1H). $^{13}$C NMR (100 MHz, DMSO) δ: 152.98, 143.85, 142.72, 138.12, 137.53, 133.49, 130.63, 130.51, 129.68, 128.17, 127.09, 126.18, 121.65, 120.20, 119.80, 117.04, 116.96, 111.59, 110.00. LC-MS (ESI): m/z 297.1 $[M+H]^+$.

Biology Examples

Biology Example 1

Compound 1 (a131) Inhibits Both Lysosome Function and Mitosis

Immunoblot Analysis of Compound 1

The ability of Compound 1 to inhibit lysosome function was examined using immunoblotting. HeLa cervical cancer cells were cultured in Dulbecco's modified Eagle's medium (DMEM) supplemented with 10% Fetal Bovine Serum (FBS, Thermo Scientific). The HeLa cells were treated with different concentrations of Compound 1 (0.625, 1.25, 2.5, 5 and 10 μM, dimethyl sulfoxide (DMSO, Kanto Kagaku)), chloroquine (CQ) (1.25, 2.5, 10, 50 and 100 μM, DMSO) or DMSO for 6 h. Then, the treated cells were harvested and lysed in 1% triton lysis buffer [25 mM Tris HCl (pH8.0), 150 mM NaCl, 1% triton-X100, 1 mM dithiothreitol (DTT), protease inhibitor mix (Complete Mini, Roche) and phosphatase inhibitor (PhosphoStop, Roche)]. The proteins in total lysates were boiled with sample buffer (60 mM Tris-HCl (pH 6.8), 25% glycerol, 2% SDS, 14.4 mM 2-mercaptoethanol, 0.1% bromophenol blue) and resolved by 14% tris-glycine sodium dodecyl sulfate polyacrylamide gel electrophoresis (SDS-PAGE) and subjected to immunoblot analysis.

Defects in lysosome function and inhibition of autophagy can be measured by accumulation of LC3-phosphatidylethanolamine conjugated non-soluble form (LC3-II), which are converted from soluble LC3-I. Thus, antibodies raised against LC3 (Cell Signaling, Cat#4108) were used to determine lysosomal function and integrity. Antibodies raised against phosphorylated histone H3 at serine 10 residue (pH3) (Cell signaling, Cat#3377) were used as the marker for mitotic dysfunction and arrest. Antibodies raised against β-actin (Millipore, Cat#MAB1501) were used as an internal loading control. The inhibitory ability of Compound 1 was also quantitatively compared to CQ. These results are depicted in FIG. 1.

As can be seen, Compound 1 markedly increased the levels of LC3-II in HeLa cells, indicating that Compound 1 inhibits the lysosome-mediated autophagy process. The band relative intensity ratio of LC3-II to LC3-I as compared to DMSO treated control indicated that Compound 1 is between 4 and 10 times more potent as an inhibitor of the lysosome function than CQ. Moreover, unlike CQ, treatment with Compound 1 also potently inhibits mitotic progression of HeLa cells as indicated by the increase in the levels of phospho-histone H3 (pH3).

Immunofluorescence Analysis of Compound 1

To confirm the results of the immunoblot analysis and the lysosome-mediated autophagy activity, HeLa cervical cancer cells as cultured above were treated with Compound 1 (2.5 μM, DMSO) or DMSO as a control for 6 h. The treated cells were fixed in ice-cold methanol and subjected to immunofluorescence analysis using antibodies against LC3 and counterstained with diamidino-2-phenylindole (DAPI) to visualize the nucleus.

The results shown in FIG. 2 are consistent with the immunoblot analysis: the cells treated with Compound 1, but not DMSO, increased LC3 puncta formation, indicating increase in lipidated LC3-II.

Immunofluorescence Analysis to Visualize Proper Formation of Mitotic Spindles

To confirm the inhibitory mitotic progression ability, HeLa cervical cancer cells as cultured above were treated with Compound 1 (2.5 μM, DMSO), CQ (15 or 25 μM, DMSO) or DMSO for 6 h. The treated cells were fixed in methanol and subjected to immunofluorescence analysis using antibodies against β-tubulin (Abcam, Cat#ab52623) to visualize proper formation of mitotic spindles. The condensed mitotic chromosomes were visualized by counterstaining with DAPI.

FIG. 3 confirms that Compound 1, but not CQ, has the ability to induce mitotic arrest. HeLa cells treated with Compound 1 were arrested in mitosis with massively misaligned chromosomes and disorganized mitotic spindles (FIG. 3*b*), but no such effects were seen in cells treated with DMSO or CQ (FIG. 3*a, c-d*). These data suggest that Compound 1 belongs to a unique class of inhibitors that can prevent lysosome function and mitotic progression simultaneously.

Biology Example 2

Classification of Derivatives of Compound 1

Derivatives of Compound 1 were tested to see if they had similar dual activity, or presented only one of the activities of Compound 1. The protocol for immunoblot analysis described in Biology Example 1 was applied to the additional indicated compounds. Results for a representative sample of 33 of these compounds are shown in FIG. 4.

Table 1 summarizes the results into three groups based on their activities: Group 1 possessing dual properties of inhibiting both lysosome function and mitosis, Group 2 inhibiting lysosome function only, Group 3 inhibiting mitosis only.

Activities of compounds were determined by two independent experiments. First, Compounds were classified according to the intensity of increase in each of the mitotic marker phospho-histone H3 at serine 10 (pH3 (Ser 10)) and the autophagosome marker LC3, respectively, at 1.25 μM, when compared with 1.25 μM Compound 1 (a131).

Compounds classified "+++" on either "mitosis" or "inhibits lysosome" show similar increase in each of the mitotic marker phospho-histone H3 at serine 10 (pH3 (Ser10)) and the autophagosome marker LC3, respectively, at 1.25 μM, when compared with 1.25 μM Compound 1 (a131), indicating that they arrest mitosis and/or inhibit autophagy to a similar extent.

Compounds classified "++" on either "mitosis" or "inhibits lysosome" show similar increase in each of the mitotic marker phospho-histone H3 at serine 10 (pH3 (Ser10)) and the autophagosome marker LC3, respectively, at 2.5 μM, when compared with 1.25 μM Compound 1 (a131); and compounds classified "+" on either "mitosis" or "inhibits lysosome" show similar increase in each of the mitotic marker phospho-histone H3 at serine 10 (pH3 (Ser10)) and the autophagosome marker LC3, respectively, at a concentration range of 5-10 μM, when compared with 1.25 μM Compound 1 (a131).

Compounds classified "+/−" on either "mitosis" or "inhibits lysosome" show less increase in each of the mitotic marker phospho-histone H3 at serine 10 (pH3 (Ser10)) and the autophagosome marker LC3, respectively, at a concentration range of 5-10 μM, when compared with 1.25 μM Compound 1 (a131).

Next, the ability of Compound 1 and its derivatives to induce mitotic arrest in transformed BJ cells was quantified as the fold induction of band intensities [pH3(Ser10)/β-actin] in comparison with DMSO control. Finally, the band intensities [LC3 II/LC3 I] in comparison with DMSO control were quantified to show the extent of inhibition of lysosome function. Compounds classified in each group show more than 2-fold increase in each of the mitotic marker phospho-histone H3 at serine 10 (pH3 (Ser10)) and the autophagosome marker LC3, respectively, relative to the levels of β-actin (loading control).

TABLE 1

| Group | Compound | Mitosis | Inhibits Lysosome | Fold induction (pH3 Ser10) | Fold induction (LC3 II/LC3 I) |
|---|---|---|---|---|---|
| 1 | Compound 1 (a131) | +++ | +++ | 7.3 | 5.0 |
| | Compound 2 (a156) | + | + | 3.0 | 3.2 |
| | Compound 14 (a213) | +/− | +/− | 1.2 | 0.5 |
| | Compound 15 (a215) | +/− | +/− | 1.7 | 1.1 |
| | Compound 7 (b2) | + | + | 1.4 | 2.0 |
| | Compound 8 (b3) | +++ | +++ | 2.1 | 4.0 |
| | Compound 9 (b38) | ++ | ++ | 4.3 | 2.6 |
| | Compound 10 (b39) | +/− | + | 1.6 | 0.7 |
| | Compound 5 (b44) | +/− | + | 1.4 | 2.2 |
| | Compound 6 (b46) | + | +++ | 3.9 | 2.7 |
| | Compound 16 (b5) | +++ | +++ | 11.8 | 5.0 |
| | Compound 17 (b9) | +++ | +++ | 2.8 | 2.3 |
| | Compound 19 (b27) | ++ | ++ | 16.2 | 5.2 |
| | Compound 21 (b35) | + | ++ | 10.1 | 7.3 |
| | Compound 23 (b36) | +++ | +++ | 18.6 | 5.7 |
| | Compound 20 (b31) | ++ | ++ | 4.8 | 3.9 |
| | Compound 22 (b42) | ++ | +++ | 2.1 | 4.1 |
| | Compound 24 (b45) | ++ | ++ | 3.2 | 3.3 |
| | Compound 30 (b67) | +++ | +++ | 12.8 | 4.1 |
| 2 | Compound 13 (b12) | >10 μM | ++ | 0.9 | 6.0 |
| | Compound 11 (b15) | >10 μM | +/− | 1.0 | 0.7 |
| | Compound 12 (b16) | >10 μM | ++ | 1.6 | 3.2 |
| | Compound 4 (a181) | >10 μM | + | 1.4 | 1.0 |
| | Compound 25 (a166) | >10 μM | +++ | 1.3 | 5.4 |
| | Compound 26 (a183) | >10 μM | + | 1.2 | 2.7 |
| | Compound 27 (a191) | >10 μM | +/− | 1.2 | 2.0 |
| | Compound 28 (a194) | >10 μM | +/− | N/A | N/A |
| | Compound 29 (a219) | >10 μM | +++ | 1.4 | 0.4 |
| | Compound 31 (b52) | >10 μM | +++ | 1.1 | 5.7 |
| | Compound 32 (b59) | >10 μM | +++ | 1.0 | 3.3 |
| | Compound 33 (b68) | >10 μM | +++ | 0.8 | 3.7 |
| | Compound 34 (b81) | >10 μM | +/− | 1.4 | 2.0 |
| 3 | Compound 3 (a159) | +++ | >10 μM | 10.5 | 0.7 |
| | Compound 18 (b19) | +/− | >10 μM | 2.2 | 1.7 |

As FIG. 4 shows, Compounds 1, 2, 6, 8, 9, 16, 17, 19, 20, 21, 22, 23, 24 and 30 all exhibit the dual properties of inhibiting both lysosome function and mitosis, while Compounds 7, 12, 13, 25, 26, 27, 31, 32, 33 and 34 inhibit lysosome function only, and Compounds 3 and 18 inhibit mitosis only.

Biology Example 3

Identification of Compound 1 and its Derivatives that Induce Cell Death Only in Oncogene-Transformed, but not in Isogenic Non-Transformed Normal Human BJ Cells Isogenic non-transformed and oncogene-transformed human fibroblast BJ cell lines were cultured in DMEM supplemented with 10% FBS. The cells were treated with Compound 1 (2.5 μM, DMSO). 48 h after treatment, the cells were fixed with ethanol at −30° C. overnight and stained with 20 μg/mL propidium iodide (PI) and 10 μg/mL RNase A for 30 min. These cells were then subjected to flow cytometry (FACS) analysis using MACSQuant (Miltenyi Biotec) to count the percentage of apoptotic cells in sub-G1 peak.

The above procedure was repeated for Group 1 Compounds 2, 16 and 17, Group 2 Compounds 29, 13, 11, 12 and 25 at a concentration of 10 μM, and Group 3 Compound 3 at a concentration of 5 μM.

As shown in FIG. 5A, FACS analysis revealed that treatment with the compounds in Group 1, which inhibit both lysosome function and mitosis, markedly induced the population of cells in sub-G1 only in oncogene-transformed BJ cells. By comparison, the abilities of compounds in Group 2 to induce cell death were compromised. Group 3 Compound 3 (a159) significantly induced cell death in both normal and transformed cells; however, cancer selectivity was compromised.

Collectively, these data demonstrate that compounds having the dual properties of inhibiting both lysosome function and mitosis selectively induce cell death in oncogene-transformed cells, while sparing isogenic non-transformed normal cells.

Whether Compound 1 (a131)-induced cancer cell-lethality was mediated by apoptosis or non-apoptotic programmed cell death was determined. For this purpose, isogenic non-transformed and oncogene-transformed human fibroblast BJ cell lines were cultured in DMEM supplemented with 10% FBS. The cells were treated with Compound 1 (2.5 μM and 5 μM, DMSO). 48 h after treatment, total cell lysates were prepared for immunoblot analysis using antibodies against cleaved PARP and cleaved caspase-3, well-known markers for apoptosis. In addition, a fraction of total cell lysates was also subjected to Caspase-3/7 Glo (Promega) assay to measure the combined activity of caspase 3/7. This was determined using caspase-Glo 3/7 Assay Kit (Promega) and its activity was normalized to a number of viable cells as determined by MTT assay.

As shown in FIG. 5B, Compound 1 treatment markedly increased the levels of both cleaved PARP and caspase-3 in oncogene-transformed human fibroblast BJ cells, but not in isogenic non-transformed BJ cells. Likewise, Caspase-3/7 Glo assay revealed that Compound 1 treatment caused a significant induction of caspase-3/7 activity only in oncogene-transformed human fibroblast BJ cells, but not in isogenic non-transformed BJ cells (FIG. 5C). Taken together, these results suggest that the observed Compound 1-induced cell death in oncogene-transformed human fibroblast BJ cells was mediated by apoptosis.

Biology Example 4

Synergistic Effect of Combined Treatment with Compounds in Compound 1 Derivative Groups 2 and 3

Having identified derivatives of Compound 1 that only possess the ability to inhibit one of lysosome function (Group 2) or mitosis (Group 3), compounds from these groups were used in combination to see if the combination would synergistically induce cancer cell death in the manner accomplished by Compound 1.

Isogenic non-transformed normal and oncogene-transformed BJ cells were cultured as in Biology Example 3. The cells were treated with a combination of Compound 3 (Group 3, at a concentration of 0.3 μM or 0.6 μM), and Compound 25 (Group 2, at a concentration of 1.25 μM) for 48 hours. Controls using DMSO, Compound 3 and Compound 25 alone (at the concentrations mentioned above) were also performed.

FIG. 6B shows that treatment of non-transformed BJ cells with Compounds 3 and 25, whether alone or in combination, did not lead to a significant increase in cell death. This is also the case for the use of Compound 25 alone on oncogene-transformed BJ cells. As shown in FIG. 6B, treatment of oncogene-transformed BJ cells with Compound 3 alone at 0.6 μM induced measurable cell death (−15%), but the lower concentration of 0.3 μM produced a negligible effect.

However, FIG. 6B also clearly shows that the combination of Compound 3 and Compound 25 results in the synergistically-enhanced cell death of oncogene-transformed BJ cells in comparison to either compound alone. The combination of Compound 3 at 0.3 μM with Compound 25 at 1.25 μM resulted in a measureable cell death of −12%, while the combination of Compound 3 at 0.6 μM with Compound 25 at 1.25 μM resulted in around 32% cell death on oncogene-transformed BJ cells. This demonstrates that combining compounds that selectively inhibit lysosome function (e.g. compounds of Group 2) with compounds that selectively inhibit mitosis (e.g. compounds of Group 3) results in a synergistic combination that induces cell death in cancer cells, but not in normal cells.

Biology Example 5

Compound 1 Induces Selective Cell Death in a Broad Spectrum of Human Cancer Cells Having shown that Compound 1 and its derivatives are effective against HeLa cervical cancer cells and human fibroblast BJ cell lines, Compound 1 was then tested against a panel of thirty different human cancer cells lines derived from gastric, colon, liver, breast, lung and cervical tumours and five different human normal cell lines, which were normal fibroblast cell lines (BJ normal, IMR90, WI38) and retinal pigmented epithelium cell lines (ARPE-19, hTert-immortalized RPE-1).

The cell lines detailed in Table 2, below, were cultured in the media shown and treated with Compound 1 at a range of different concentrations (from 0.1 μM to 10 μM) for 72 h in triplicate and a mean concentration value for Compound 1 to achieve 50% growth inhibition ($GI_{50}$) in each cell line was determined by use of the MTT assay.

The MTT assay was performed by adding thiazolyl blue tetrazolium bromide (MTT reagent, Invitrogen) at a concentration of 0.5 mg/mL to each cell culture and the resulting mixture incubated for 4 h at 37° C. The medium was then removed, and the blue dye remaining in each well was dissolved in DMSO by mixing with a microplate mixer. The absorbance of each well at 540 nm and 660 nm was measured using a microplate reader (Benchmark plus, BIO-RAD). The optical density (OD) values were calculated by subtracting the absorbance at 660 nm from the absorbance at 540 nm. Mean OD values from control cells containing only DMSO treated wells were set as 100%. The resulting $GI_{50}$ values (in μM) are set out in Table 2 below.

TABLE 2

| Normal | | | Cancer | | | |
|---|---|---|---|---|---|---|
| Cell Line | $GI_{50}$ | Culture medium | Cell Type | Cell Line | $GI_{50}$ | Culture medium |
| BJ Normal | 8.1 | DMEM | Gastric | NCC24 | 1.2 | RPMI[1] |
| IMR90 | 5.8 | DMEM | | IST1 | 2.2 | RPMI |
| ARPE-19 | >10 | DMEM/F12[2] | | HGC27 | 1.2 | RPMI |
| RPE-1/h-Tert | 5.2 | DMEM/F12 | | NCC59 | 0.9 | RPMI |
| WI38 | 3.4 | DMEM | | SNU620 | 1.0 | RPMI |
| | | | | SNU1 | 0.9 | RPMI |
| | | | | AZ521 | 2.4 | RPMI |
| | | | | SGCC-GC38 | 1.9 | RPMI |
| | | | | SNU216 | 1.9 | RPMI |
| | | | | SNU1750 | 0.7 | RPMI |
| | | | | SNU-16 | 1.0 | RPMI |
| | | | | SCH | 1.7 | RPMI |
| | | | | MKN45 | 1.0 | DMEM |
| | | | | AGS | 1.1 | RPMI |
| | | | | IM95 | 1.0 | DMEM |
| | | | | NUGC3 | 1.0 | RPMI |
| | | | | NUGC4 | >10 | RPMI |
| | | | | NCC19 | 4.6 | RPMI |
| | | | Colon | HCT15 | 0.5 | RPMI |
| | | | | DLD1 | 1.2 | RPMI |
| | | | Colon | HT29 | 0.9 | RPMI |
| | | | | HCT116 | 1.8 | DMEM |
| | | | Liver | Hep3 | 3.7 | DMEM |
| | | | | Huh7 | 1.2 | DMEM |
| | | | | SNU449 | 2.3 | RPMI |
| | | | Breast | MDA-MB-231 | 1.1 | DMEM |
| | | | | MCF7 | 1.2 | DMEM |
| | | | Others | A549 | 2.0 | DMEM |
| | | | | HeLa | 1.4 | DMEM |
| | | | | U2OS | 1.5 | DMEM |

[1]RMPI is Roswell Park Memorial Institute medium. All media were supplemented with 10% FBS.
[2]DMEM/F12 is DMEM Nutrient Mixture F-12.

FIG. 7 show that treatment with Compound 1 caused a strong anti-proliferative effect in most of the cancer cell lines treated, with a mean $GI_{50}$ value of 1.7 μM. In contrast, normal cell lines were resistant to Compound 1 treatment, having a mean $GI_{50}$ value of 6.5 μM, which was a statistically significant difference (Student's t-test, $*p<0.05$). Collectively, these data indicate that Compound 1 is an anti-proliferative agent with a clear potential therapeutic window between cancer and normal cells.

Biology Example 6

Compound 1 Potently Suppresses Anchorage-Independent Growth of Cancer Cells

Soft agar colony formation assays are known to better mimic the features of in vivo tumours growing in three dimensions than cancer cell lines growing in an in vitro tissue culture. Therefore, the anti-proliferative effects of Compound 1 on cancer cells growing anchorage-independently in soft agar were studied too.

HeLa cells as cultured in Biology Example 1 ($1\times10^4$ cells/well) were suspended in 2 mL of soft agar at a final concentration of 0.4%. The suspension was placed on top of a 2 mL layer of 1% agar in 6-well plates and Compound 1, at final concentrations of 0.15, 0.3, 0.6, 1.25, 2.5 or 5 μM, was added to different wells. The plates were run in triplicate and DMSO was used as a control. Seven days after the addition of Compound 1, the number of colonies per plate was counted in an unbiased manner using MATLAB software.

FIG. 8 shows the average number of colonies from the triplicated results (with standard deviations). FIG. 8 shows that treatment with Compound 1 causes a significant reduction in the number of colonies grown in soft agar in a dose-dependent manner. In particular, treatment with sub-micromolar concentrations of Compound 1 was sufficient to cause a greater than 50% reduction of HeLa cell colonies grown in soft agar. This suggests that Compound 1 possesses strong anti-proliferative ability against cancer cells growing anchorage-independently.

Biology Example 7

Compound 1 Induces Cell Cycle Arrest Only in Non-Transformed Cells in a p53-Dependent Manner The underlying mechanism of cancer cell selectivity of Compound 1 was investigated.

Isogenic non-transformed and oncogene-transformed BJ cells (cultured as in Biology Example 3) were treated with Compound 1 at final concentrations of 2.5 and 5 μM for 24 h. The treated cells were then treated with 30 μM final concentration of 5-bromo-2'-deoxyuridine (BrdU, SIGMA) for 1 h to detect DNA synthesis as a marker for cell proliferation. Subsequently, the cells were fixed in EtOH at 4° C. overnight and permeabilized with 2N HCl/0.5% Triton X-100 for 30 min. The cells were then treated with 0.1M sodium tetraborate for 2 min and stained with anti-BrdU antibody (Invitrogen, Cat#B35129) for 60 min, followed by a 30 min treatment with 20 μg/mL of propidium iodide (PI) and 10 μg/mL RNaseA.

Figure 9:
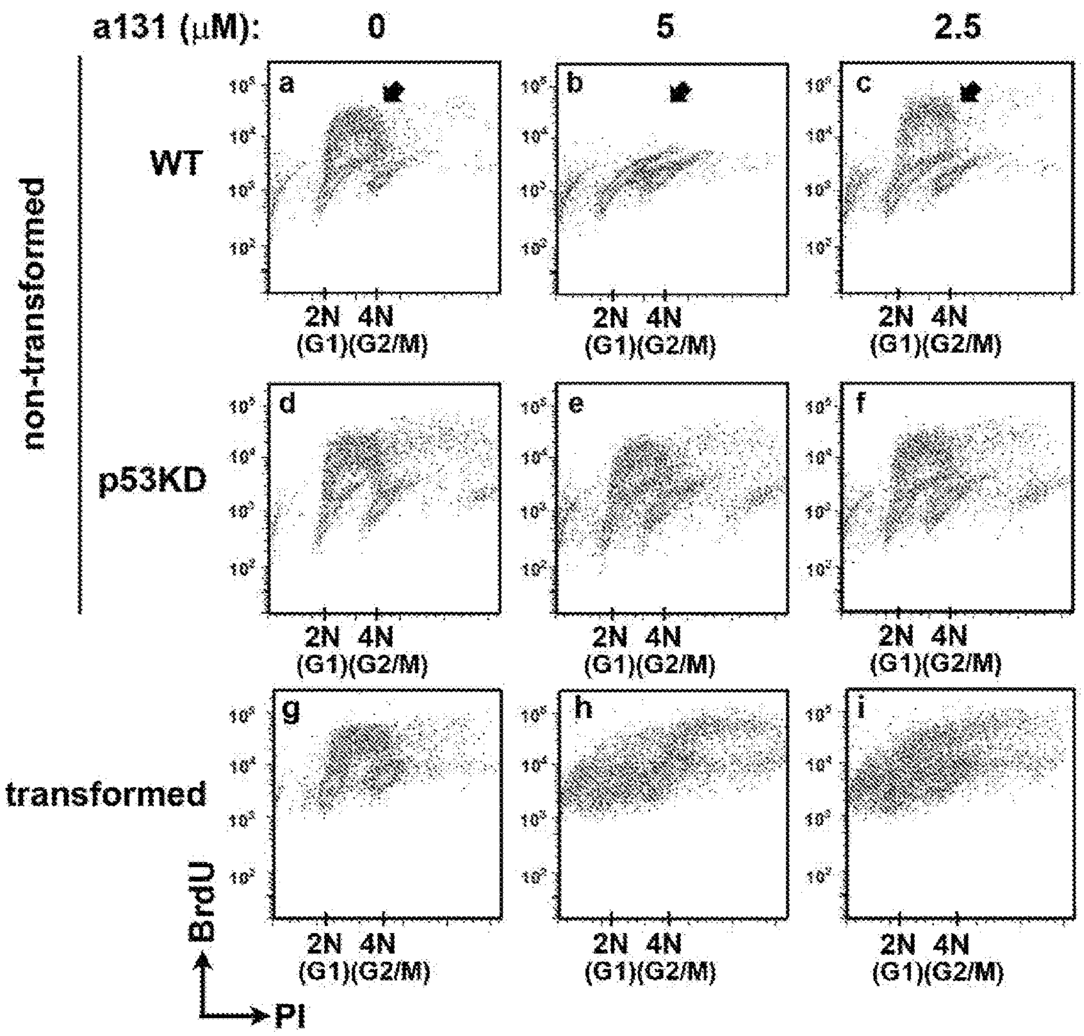
Figure 9:
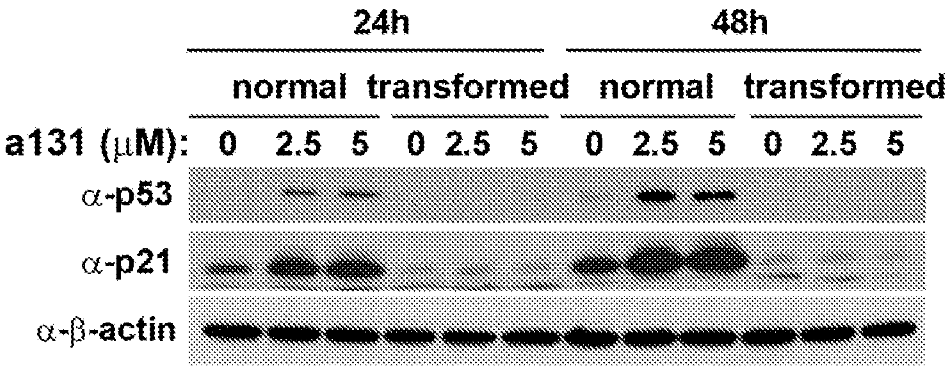
Figure 9:
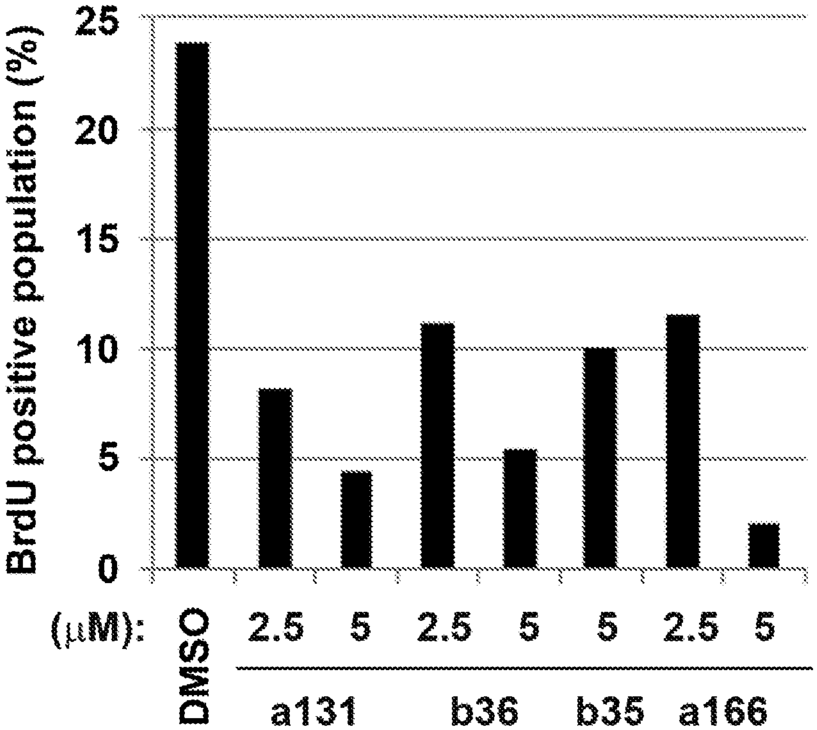
Figure 9:
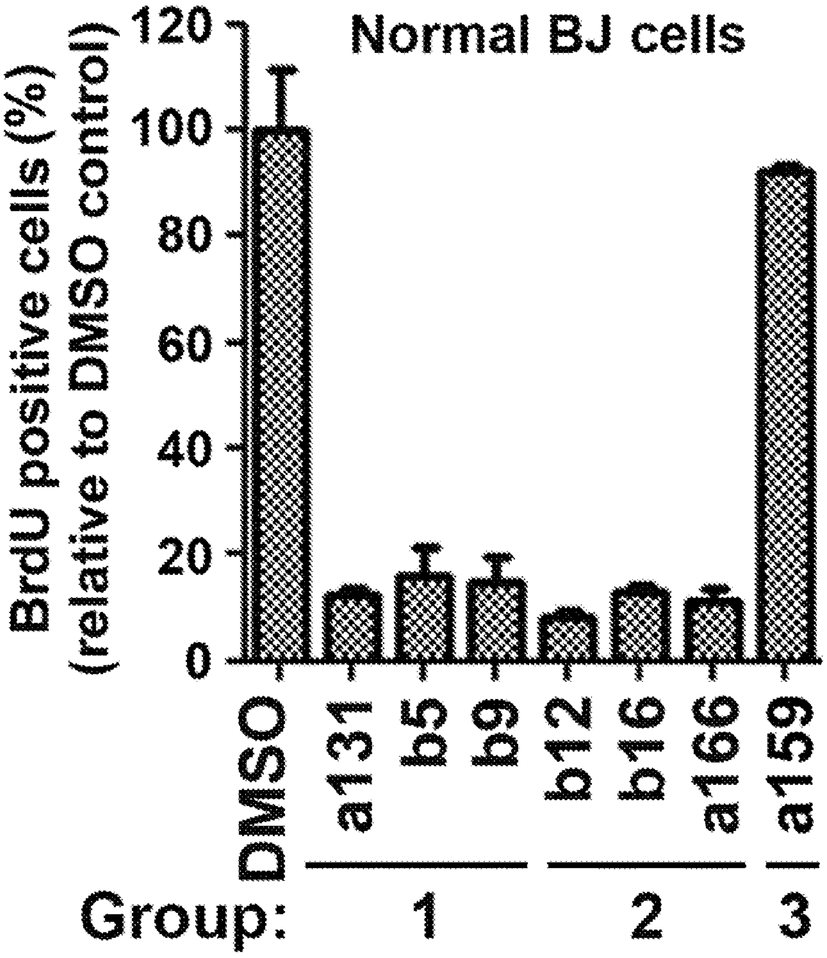

The cell cycle profile and cell proliferation were then determined by FACS analysis. FIG. 9A (panels a-c) show that Compound 1 markedly decreased the number of BrdU-positive non-transformed normal BJ cells in a dose-dependent manner, without a substantial increase in sub-G1 population, as was also observed in FIG. 5A. This suggests that Compound 1 causes cell cycle arrest, but not cell death in non-transformed normal BJ cells.

Cell cycle arrest is usually the result of p53 accumulation under a stress condition(s). Therefore, isogenic non-transformed BJ cells depleted of p53 by shRNA-mediated knockdown (KD) were substituted for non-transformed normal BJ cells in the protocol described above to confirm that the cell cycle arrest in non-transformed normal BJ cells treated with Compound 1 was indeed due to p53. As shown in FIG. 9A (panels d-f), FACS analysis confirmed that the ability of Compound 1 to induce cell cycle arrest was compromised in non-transformed normal BJ cells depleted of p53, indicating that the growth arrest displayed in non-transformed normal BJ cells treated with Compound 1 occurs in a p53-dependent manner. This was confirmed by immunoblot analysis of non-transformed BJ cells performed in a same manner to Biology Example 1, which showed that treatment of the non-transformed BJ cells with Compound 1 at concentrations of 2.5 and 5 μM (DMSO being used as control) resulted in increased protein levels of p53 (Santa Cruz, Cat#se-126, (DO-1)) and its key downstream target p21 (Santa Cruz, Cat#se-397, (C-19)) (FIG. 9B, lanes 1-3 & 7-9).

In contrast to non-transformed BJ cells, Compound 1 caused a massive increase in population of oncogene-transformed BJ cells in sub-G1, as shown in FIG. 9A (panels g-i), which is consistent with the data obtained in FIG. 5A and Biology Example 3. Furthermore, a substantial population of BrdU-positive cells, with 4N and >4N DNA contents, was observed, indicating that Compound 1 causes mitotic catastrophe or DNA reduplication only in oncogene-transformed BJ cells, but not in isogenic non-transformed normal BJ cells. As oncogene-transformed BJ cells do not express p53, Compound 1 did not alter the protein expression levels of p53 and p21 (FIG. 9B, lanes 4-6 & 10-12).

To further evaluate the effects of derivatives of Compound 1 on cell cycle arrest in non-transformed BJ cells, said cells were treated with Compound 21 and Compound 23 (Group 1 compounds that inhibit both lysosome function and mitosis) and Compound 25 (Group 2 compound that only inhibits lysosome function). As shown in FIG. 9C, all three compounds substantially decreased the population of BrdU-positive cells, showing that Group 1 and Group 2 derivatives of Compound 1 can also induce cell cycle arrest in non-transformed BJ cells in a p53-dependent manner.

Furthermore, the abilities of additional five (5) Compounds to arrest cells at the stage of G1/S phase of the cell cycle were evaluated. Non-transformed human fibroblast BJ cells cultured in DMEM supplemented with 10% FBS were treated with these Compounds for 48 h. The abilities of these Compounds to arrest cells at the stage of G1/S phase of the cell cycle were then measured by using BrdU incorporation assay and FACS analysis. The percentage of cells with BrdU positive population in comparison with DMSO control vehicle was determined and plotted with mean values±S.D. (n=3). As shown in FIG. 9D, Compounds 16 (b5), 17 (b9), 13 (b12), 12 (b16), and 25 (a166) were able to arrest non-transformed human fibroblast BJ cells at the stage of G1/S phase of the cell cycle to a similar extent as Compound 1, whereas Compound 3 (a159) failed to do so. Given that only Compounds in Group 1, including Compound 1, Compound 16 and Compound 17, selectively induced cell death in oncogene-transformed BJ cells while sparing normal counterparts as shown in FIG. 5A, these results demonstrate that both dual-inhibitory properties of the Compounds in Group 1 are essential to achieve the observed cancer-selective lethality.

Biology Example 8

Cell Cycle Arrest in Non-Transformed Normal BJ Cells by Compound 1 is Transient and Reversible As shown in Biology Examples 5 and 7, Compound 1 and its derivatives, which inhibit both lysosome function and mitosis, induce cell death only in transformed BJ cells, while inducing cell cycle arrest in isogenic non-transformed BJ cells. However, it was not fully clear if the cell cycle arrest was permanent or reversible. Therefore, to evaluate whether the effect was permanent or reversible, non-transformed normal BJ cells were synchronized in the G1 phase of the cell cycle by culturing them in DMEM media with 0.1% FBS for 2 days. Subsequently, the cells were synchronously released in fresh media with 10% FBS and then treated with 5 μM Compound 1 for 2, 3, 6 or 11 days. After treatment for the required amount of time, Compound 1 was removed by washing the cells with fresh media twice, and culturing of the washed cells was continued in fresh media for up to 11 days (see FIG. 10). At various time-points, the adherent cells were harvested with trypsin (Invitrogen) and the total number of cells was counted using automated Sceptor cell counter (Millipore).

While non-transformed normal BJ cells continuously treated with Compound 1 completely stop proliferating, FIG. 10 shows that removal of Compound 1 from the media is sufficient to enable these cells to recover from cell cycle arrest and to resume normal cell proliferation. This experiment suggests that Compound 1 and its derivatives, which inhibit both lysosome function and mitosis, induce growth arrest in non-transformed normal BJ cells in a transient and reversible manner.

Biology Example 9

Compound 1 and its Derivatives Induce Mitotic Catastrophe and Cell Death in Oncogene-Transformed BJ Cells Compound 1 can induce mitotic arrest in HeLa cells (e.g. see FIGS. 1 and 3), as well as selectively increasing the number of oncogene transformed BJ cells with 4N and >4N DNA content (see FIG. 9A, panels g-i), but not in non-transformed BJ cells (FIG. 9A, panels a-c). These data suggest that Compound 1 induces mitotic arrest and aberrant chromosome segregation, which causes mitotic catastrophe selectively in oncogene-transformed BJ cells. To determine if this is indeed the mechanism by which Compound 1 (and its derivatives in Group 1) acts, the effect of Compound 1 on mitotic progression using time-lapsed live cell analysis was evaluated.

Isogenic non-transformed and oncogene-transformed BJ cells stably expressing GFP-tagged Histone H2B as a marker for chromosome segregation were treated with Compound 1 at 2.5 μM final concentration. Mitotic progression of these cells was monitored every 10 min and images were acquired using a Super Resolution Microscope (Nikon) equipped with an iXon EM+ 885 EMCCD camera (Andor) mounted on a Nikon Eclipse Ti-E inverted microscope with a CFI Apo objective and a Stage Top Incubation with Digital CO2 mixer (Tokai). The images were processed with the NIS-Elements AR software. More than 100 cells per condition were quantified and classified into 3 groups:

no mitotic defects with prolonged mitotic arrest, chromosome mis-segregation and failure in cytokinesis;

mild mitotic defects with prolonged mitotic arrest, chromosome mis-segregation and failure in cytokinesis; and severe mitotic defects with prolonged mitotic arrest, chromosome mis-segregation and failure in cytokinesis.

As shown in FIG. 11, a majority of the transformed cells treated with Compound 1 showed severe mitotic defects with prolonged mitotic arrest, chromosome mis-segregations and failure in cytokinesis. The majority of these cells underwent subsequent cell death, supporting the results obtained by FACS analysis (FIG. 9A, panel g-i). In contrast, Compound 1 only induced a short period of mitotic arrest with mild mitotic defects in non-transformed normal BJ cells (FIG. 11A).

To investigate why massive chromosome mis-segregation occurs in oncogene-transformed BJ cells when treated with Compound 1, but not in non-transformed BJ cells, the effects of Compound 1 were studied on isogenic BJ cell lines (transformed and non-transformed) that stably express GFP-Histone H2B. Cells cultured in accordance with Biology Example 3 were treated with Compound 1 at 2.5 μM final concentration for 4 h followed by MG132 for another 1.5 h to allow chromosome alignment. The cells were then fixed in ice-cold methanol and subjected to immunofluorescence analysis to determine the formation of bipolar mitotic spindle using antibodies against β-tubulin and the formation of proper spindle poles using antibodies against the centrosome maker γ-tubulin (SIGMA, Cat#T5326). Images were acquired at RT with 3D-SIM using a Super Resolution Microscope (Nikon) equipped with an iXon EM+ 885 EMCCD camera (Andor) mounted on a Nikon Eclipse Ti-E inverted microscope with a CFI Apo TIRF (100×/1.40 oil) objective and processed with the NIS-Elements AR software.

Figure 11A:
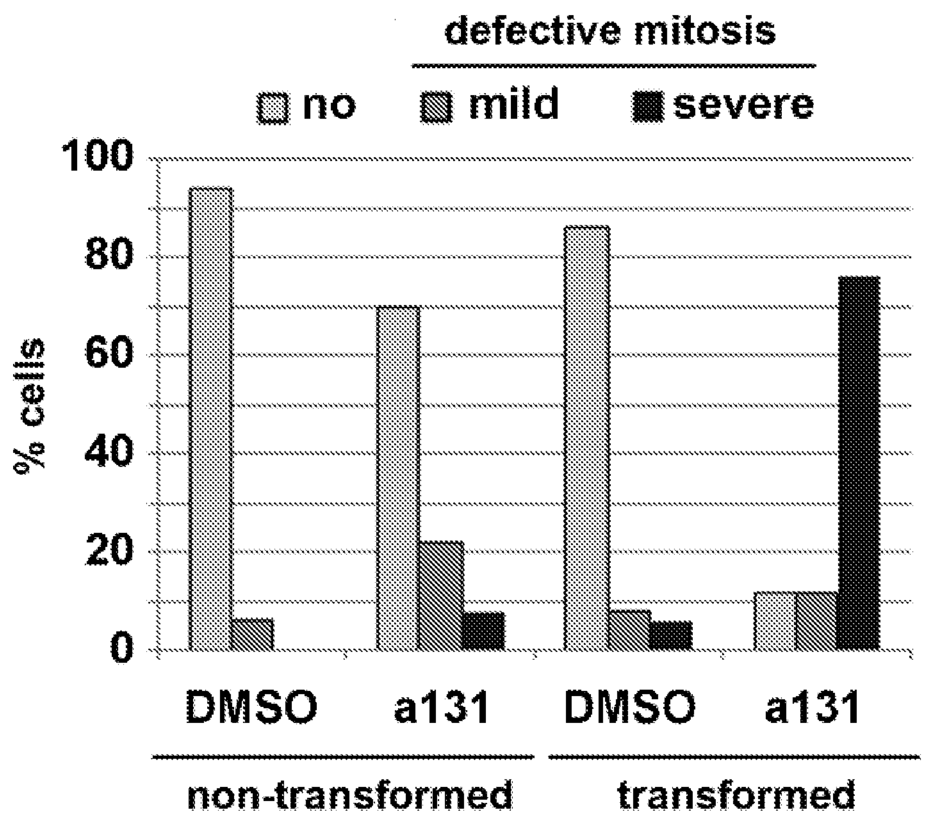
Figure 11B:
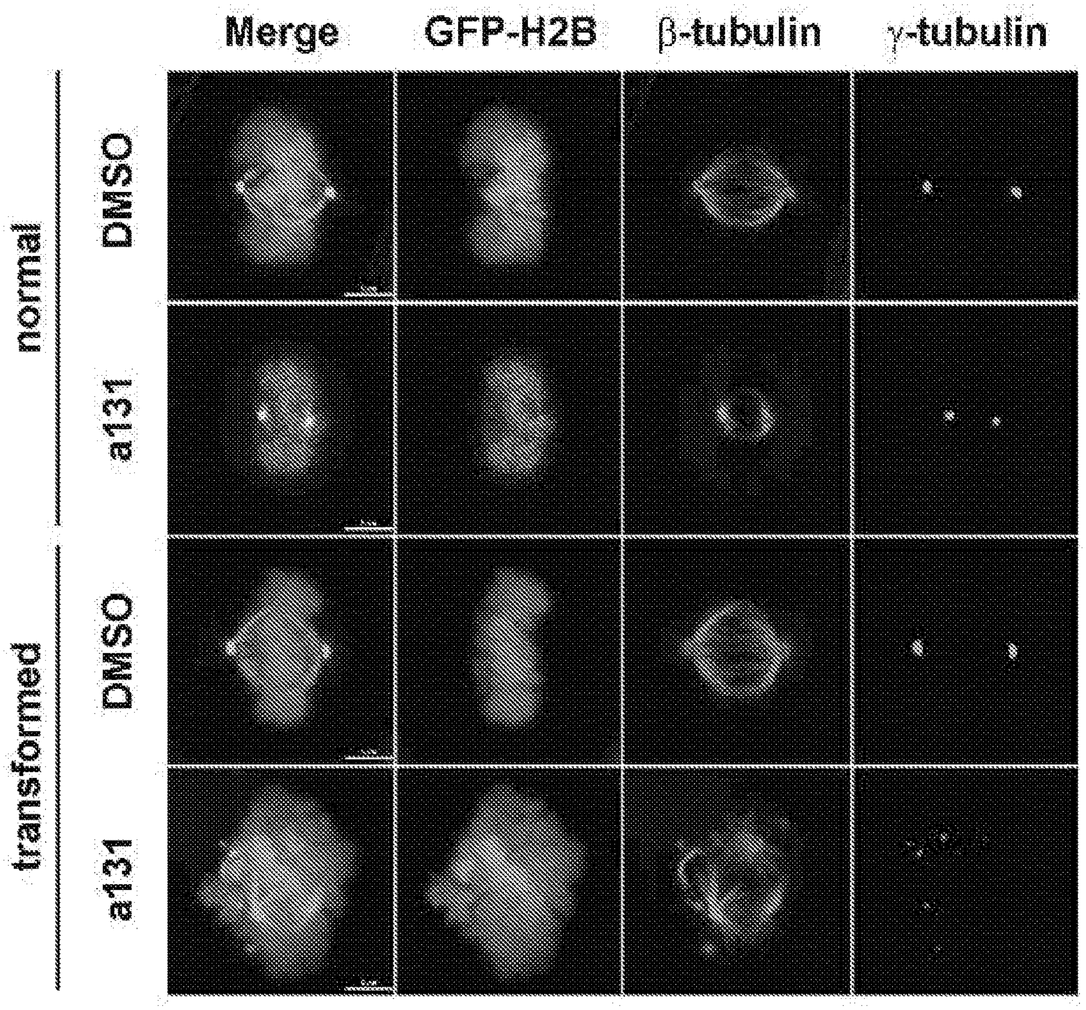
Figure 11C:
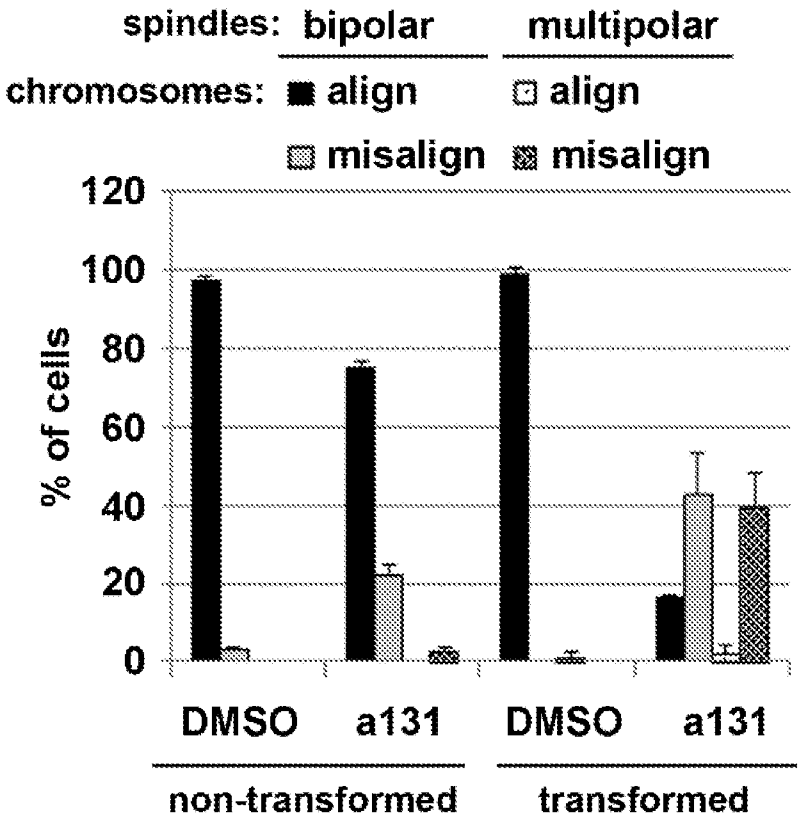

As shown in FIG. 11B, non-transformed normal BJ cells did not show marked defects in chromosome alignment or the formation of bipolar spindle and spindle poles in comparison to the DMSO treated control. In contrast, FIG. 11B shows that oncogene-transformed BJ cells treated with Compound 1 showed massively misaligned chromosomes with the formation of multipolar spindles in comparison to the control, suggesting that Compound 1 can inhibit centrosome clustering and subsequently cause cell death in a transformed cancer cell-specific manner. These defects were further quantified (n>100 cells per condition) and the results summarized in FIG. 11C.

Figure 11D:
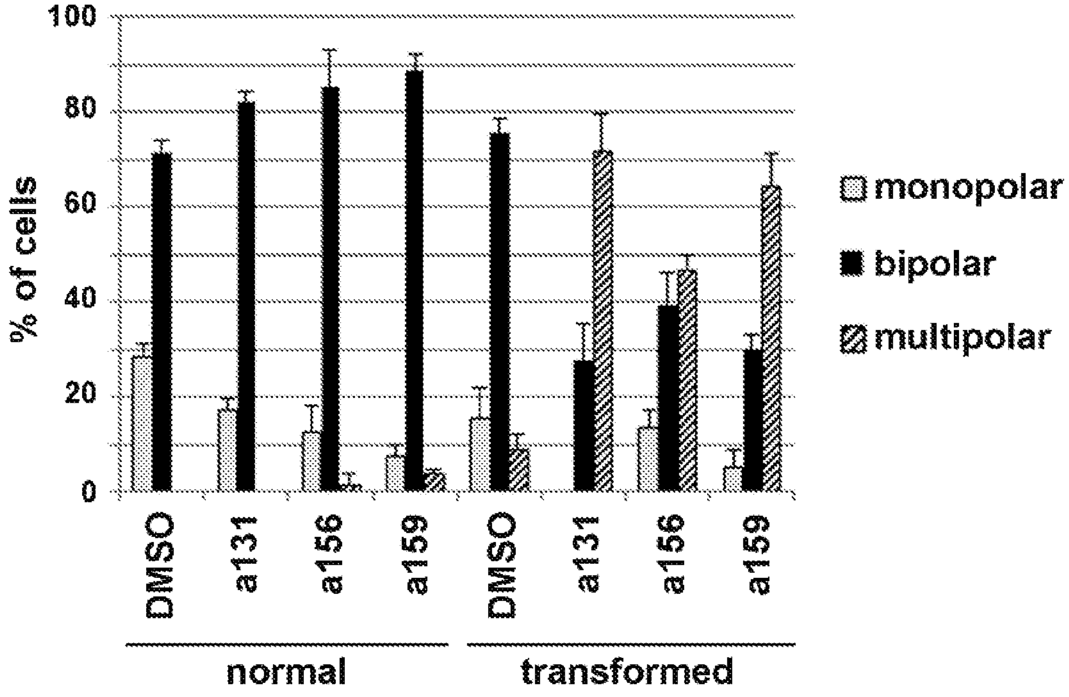

Of note, similar results were obtained with Compound 2 (inhibiting both lysosome function and mitosis, classified in Group 1) and Compound 3 (inhibiting only mitosis, classified in Group 3) (FIG. 11D). Collectively, these data suggest that compounds in Groups 1 and 3 possess a potent and selective antimitotic property in transformed cancer cells, but not non-transformed normal cells.

Biology Example 10

Compounds 1 and 16 Show Significant In Vivo Efficacy

To determine the in vivo antitumor efficacies of Compound 1 and a derivative with improved aqueous solubility (b5—Compound 16), tumor xenografts were established using (i) HCT-15 human colon adenocarcinoma harbouring mutant K-RasG13D and resistant to paclitaxel and (ii) MDA-MB-231 human breast tumor also harbouring mutant K-RasG13D.

Mice bearing established tumor xenografts using HCT15 or MDA-MB-231 cells were treated orally (PO) or intraperitoneally (IP) twice a day with the indicated doses of Compound 1 or its derivative Compound 16 (b5) for 12 or 15 days, respectively. Tumour volumes were estimated periodically as indicated in the FIG. 12A. For comparison, paclitaxel (PTX) was given intravenously to mice bearing established tumour xenografts using HCT15 at dose of 40 mg/kg, 3 times every 4 days.

As shown in FIG. 12A, intravenous paclitaxel (PTX) injections in tumour-bearing mice did not show significant anti-tumour effects when compared to vehicle-treated control. In contrast, both intravenous and intraperitoneal injections of Compound 1 and Compound 16 showed marked anti-tumour effects. Similar anti-tumour effects were also observed by intraperitoneal Compound 1 treatment of tumour xenografts using MDA-MB-231 human breast tumour (FIG. 12B). Taken together, these results demonstrate strong in vivo anti-tumour efficacies of Compound 1 and its derivative Compound 16.

Figure 12C:
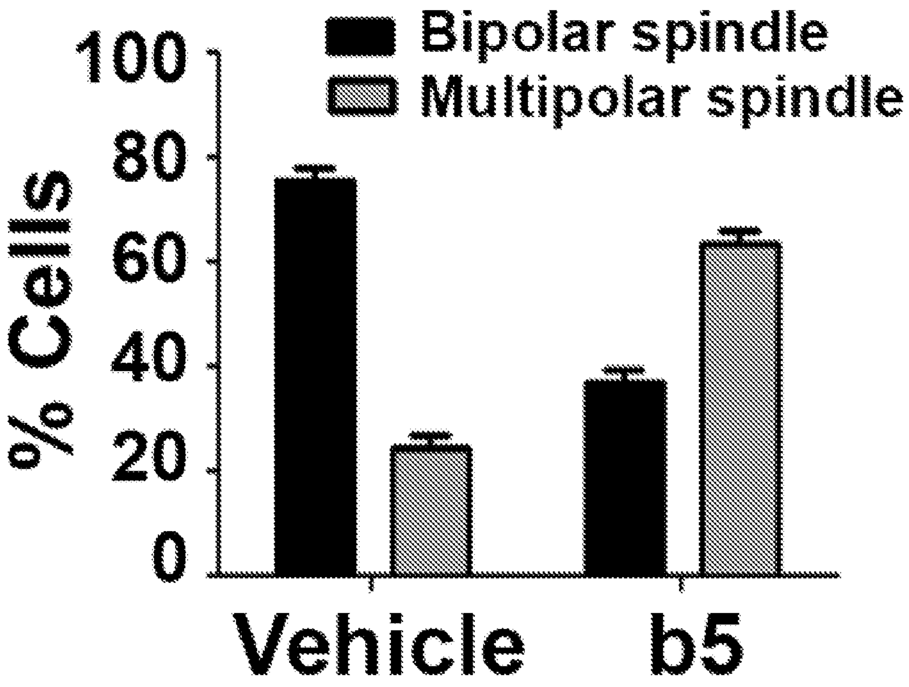

To confirm the antimitotic efficacy of Compound 16 (b5) in vivo, immunofluorescence analysis of HCT-15 tumor sections treated with Compound 16 (80 mg/kg) or control vehicle for 12 days were stained with anti-β-tubulin antibodies and DAPI. Images were obtained using 3D-SIM super-resolution microscopy and cancer cells (n>500 per condition) with misaligned chromosomes possessing multipolar mitotic-spindles were quantified in triplicated experiments. As shown in FIG. 12C, immunofluorescence analysis of HCT-15 tumour sections showed that Compound 16 significantly increased the number of cancer cells harbouring massively misaligned chromosomes with multipolar mitotic-spindles, which is consistent with the results from in vitro tissue culture (see FIG. 11C).

Taken together, these results demonstrate the ability of Compound 1 and its derivatives in Group 1 to cause mitotic defects and catastrophe in cancer cells in vivo as well as in vitro.

Biology Example 11

Compounds in Group 2 are Chemoprotective

The results suggest that the dual-inhibitory properties of the Compounds in Group 1 (e.g.: Compound 1—a131) are essential for cancer-selective lethality. Conversely, the Compounds in Group 2 (e.g.: Compound 25—a166) with single growth inhibitory effect in normal cells at the G1/S phase of the cell cycle, and those in Group 3 (e.g.: Compound 3—a159) with single antimitotic effect can be classified as chemoprotective and anti-proliferative chemotherapeutic agents, respectively.

The chemoprotective efficacies of the Compounds in Group 2 were further evaluated by measuring their ability to protect non-transformed normal cells, but not cancer and oncogene-transformed counterparts, from the most well-known as well as clinically-relevant chemotherapeutic agents, paclitaxel and etoposide. To determine this, isogenic non-transformed normal and oncogene-transformed human fibroblast BJ cell lines, cultured in DMEM supplemented with 10% FBS, were pre-treated with Compound 25 (a166—Group 2) at 5 μM. 48 h after treatment, cells were further treated with paclitaxel (PTX; FIG. 13A) or etoposide (FIG. 13B) for an additional 72 h. For PTX treatment, cells were collected, stained with Annexin V together with PI and subjected to FACS analysis to determine cell death. The percentage of cells doubly-positive for Annexin V and PI was plotted with mean values±S.D. (n=3). For etoposide, cell viability was determined using MTT assay and plotted in comparison with DMSO control vehicle with mean values±S.D. (n=4).

As shown in FIG. 13, while inducing mitotic disruption with paclitaxel treatment alone also showed a minimal selectivity for oncogene-transformed BJ cells, combined treatment with Group 2 Compound 25 (a166) markedly enhanced cancer-selective lethality, while largely protecting non-transformed normal counterparts (FIG. 13A). Similar protective effects from DNA damage-induced cell death were also observed in non-transformed normal BJ cells treated with Compound 25 and the TOPII inhibitor etoposide, but not in oncogene-transformed cells (FIG. 13B). Together, these results demonstrate that Compounds in Group 2 (e.g.: Compound 25—a166), with single growth inhibitory effect in normal cells, possess a remarkable chemoprotective ability. Furthermore, the results suggest that these Group 2 Compounds can be used to protect normal cells from the adverse effects caused by chemotherapeutic agents, while exposing cancer and transformed cells to the cytotoxic and anti-proliferative effects of chemotherapeutic agents.

Mechanistic Model

Without wishing to be bound by theory, FIG. 14 depicts a suggested molecular mechanism of action that may explain the manner in which compounds of Group 1, having the dual properties of inhibiting lysosome function and causing cancer cell specific mitotic disruption, selectively kill cancer cells. Compound 1 and its derivatives induce p53-dependent cell cycle arrest at the G1 phase without affecting normal cell viability, because the cell cycle arrest caused by Compound 1 in normal cells is only transient: removing Compound 1 from growth media is sufficient to permit normal cells to resume their proliferation. However, Compound 1 and its derivatives in Group 1 do not induce a transient cell cycle arrest in cancer cells. Instead, they cause dramatic mitotic catastrophe and also possible metabolic alteration by disputing lysosome function. Consequently, Compound 1 and its Group 1 derivatives manifest selective killing of cancer cells, while sparing normal cells. In addition, when Group 2 (inhibiting lysosome function) and Group 3 (antimitotic) compounds are combined together, they are able to induce the same effect, but do not provide activity similar to the compounds of Group 1 alone. Alternatively or additionally, the compounds of Group 1 and Group 2 may act as chemoprotective agents because they arrest the cell cycle in normal cells, while leaving cancer cells unaffected. As the compounds of Group 2 have a chemoprotective effect, they may be particularly suitable for use in combination treatments with agents that target rapidly dividing cells, such as anti-mitotic agents. While the same is true for the compounds of Group 1, as these compounds also have antimitotic efficacy they may be used effectively as a stand-alone agent as well.

ABBREVIATIONS

CQ=chloroquine
DAPI=diamino-2-phenylindole
DCM=dichloromethane
DMEM=Dulbecco's modified Eagle's medium
DMF=dimethylformamide
DMSO=dimethylsulfoxide
DNA=deoxyribonucleic acid
DTT=dithiothreitol
ESI=electro spray ionization
FACS=fluorescence-activated cell sorting
FBS=fetal bovine serum
FT=fourier transform
HPLC=high performance liquid chromatography
IR=infra-red
KD=knockdown
LC=liquid chromatography
MS=mass spectrometry
MTT=(3-(4,5-dimethylthiazol-2-yl)-2,5-diphenyltetrazolium bromide)
NMR=nuclear magnetic resonance
OD=optical density
PAGE=polyacrylamide gel electrophoresis
PI=propidium iodide
rt=room temperature
RPMI=Roswell Park Memorial Institute
SDS=sodium dodecyl sulfate
THF=tetrahydrofuran
TLC=thin layer chromatography Prefixes n-, s-, i-, t- and tert- have their usual meanings: normal, secondary, iso, and tertiary.

The invention claimed is:

1. A compound of formula I,

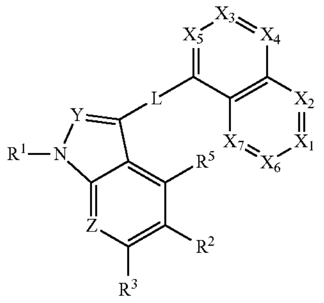

I wherein,

Z represents N or $CR^4$;

L represents $C(R^{6a})=C(R^{6b})$;

$X_1$ to $X_5$ are independently N or $CR^8$, provided that at least one of $X_1$ and $X_2$ is N;

$X_6$ and $X_7$ are independently N or $CR^9$;

Y represents N or $CR^{10}$;

$R^1$ represents H, $-C(O)R^{11a}$ or $-C(S)R^{11b}$;

$R^2$ to $R^4$, $R^8$ and $R^{10}$, at each occurrence, independently represents:

(a) H;

(b) halo;

(c) CN;

(d) $C_{1-6}$ alkyl, $C_{2-6}$ alkenyl, $C_{2-6}$ alkynyl (which latter three groups are unsubstituted or substituted by one or more substituents selected from halo, nitro, CN, $C_{1-6}$ alkyl, $C_{2-6}$ alkenyl, $C_{2-6}$ alkynyl (which latter three groups are unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{12}a$, $S(O)_qR^{12b}$, $S(O)_2NR^{12c}R^{12d}$, $NR^{12e}S(O)_2R^{12f}$, $NR^{12g}R^{12h}$, aryl and $Het^1$);

(e) $Cy^2$ (which $Cy^2$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{13}a$, $S(O)_qR^{13b}$, $S(O)_2NR^{13c}R^{13d}$, $NR^{13e}S(O)_2R^{13f}$, $NR^{13g}R^{13h}$, aryl and $Het^2$), (f) $Het^a$ (which $Het^a$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{14}a$, $S(O)_qR^{14b}$, $S(O)_2NR^{14c}R^{14d}$, $NR^{14e}S(O)_2R^{14f}$, $NR^{14g}R^{14h}$, aryl and $Het^3$);

(g) $OR^{15}a$;

(h) $S(O)_qR^{15b}$;

(i) $S(O)_2NR^{15c}R^{15d}$;

(j) $NR^{15e}S(O)_2R^{15f}$;

(k) $NR^{15g}R^{15h}$, where $R^3$, $R^4$ and each $R^8$, when present, may also, in addition, independently represent nitro;

$R^5$ and $R^9$, at each occurrence, independently represent H, halo, CN, nitro, $C_{1-4}$ alkyl (which latter group is unsubstituted or substituted by one or more substituents selected from halo, nitro, CN, $OR^{16}$a and $NR^{16g}R^{16h}$), $OR^{17s}$, $S(O)_q(O)R^{17b}$, $S(O)_2NR^{17c}R^{17d}$, $NR^{17e}S(O)_2R^{17f}$ or $NR^{17g}R^{17h}$;

$R^{6a}$ represents H, CN or —$C(O)NR^{18a}R^{18b}$;

$R^{6b}$, independently at each occurrence, represents H, CN or $C_{1-4}$ alkyl, which latter group is unsubstituted or substituted with halo or $OR^{19}$;

$R^{7a}$ and $R^{7b}$ represent H or $C_{1-4}$ alkyl, which latter group is unsubstituted or substituted with halo or $OR^{20}$;

$R^{11a}$ and $R^{11b}$, when present, represent, (a) H;

(b) $C_{1-6}$ alkyl, $C_{2-6}$ alkenyl, $C_{2-6}$ alkynyl (which latter three groups are unsubstituted or substituted by one or more substituents selected from halo, nitro, =O, CN, $C_{1-6}$ alkyl, $C_{2-6}$ alkenyl, $C_{2-6}$ alkynyl (which latter three groups are unsubstituted or substituted by one or more substituents selected from OH, =O, halo, $C_{1-4}$ alkyl and $C_{1-4}$ alkoxy), $OR^{21}$a, $S(O)_qR^{21b}$, $S(O)_2NR^{21c}R^{21d}$, $NR^{21e}S(O)_2R^{21f}$, $NR^{21g}R^{21h}$, aryl, $Cy^3$ (which $Cy^3$ group is unsubstituted or is substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{22a}$, $S(O)_qR^{22b}$, $S(O)_2NR^{22c}R^{22d}$, $NR^{22e}S(O)_2R^{22f}$, $NR^{22g}R^{22h}$, aryl and $Het^4$) and $Het^5$);

(c) $C_{3-10}$ cycloalkyl, $C_{4-10}$ cycloalkenyl (which latter two groups are optionally substituted by one or more substituents selected from halo, OH, =O, $C_{1-6}$ alkyl and $C_{1-6}$ alkoxy);

(d) $Het^b$ (which $Het^b$ group is unsubstituted or substituted by one or more substituents selected from halo, nitro, CN, $C(O)OC_{1-4}$ alkyl, $C_{1-6}$ alkyl, $C_{2-6}$ alkenyl, $C_{2-6}$ alkynyl (which latter three groups are optionally substituted by one or more substituents selected from $Het^8$, OH, =O, halo, $C_{1-4}$ alkyl and $C_{1-4}$ alkoxy), $OR^{23}$a, $S(O)_qR^{23b}$, $S(O)_2NR^{23c}R^{23d}$, $NR^{23e}S(O)_2R^{23f}$, $NR^{23g}R^{23h}$, aryl and $Het^6$), (e) $OR^{24a}$;

(f) $NR^{24b}S(O)_2R^{24c}$;

(g) $NR^{24d}R^{24e}$;

$R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-6}$ alkyl, $C_{2-6}$ alkenyl, $C_{2-6}$ alkynyl (which latter three groups are optionally substituted by one or more substituents selected from halo, nitro, =O, $C(O)OC_{1-4}$ alkyl, CN, $C_{1-6}$ alkyl, $C_{2-6}$ alkenyl, $C_{2-6}$ alkynyl, $C_{3-6}$ cycloalkyl (which latter three groups are optionally substituted by one or more substituents selected from OH, =O, halo, $C_{1-4}$ alkyl and $C_{1-4}$ alkoxy), $OR^{25a}$, $S(O)_qR^{25b}$, $S(O)_2NR^{25c}R^{25d}$, $NR^{25e}S(O)_2R^{25f}$, $NR^{25g}R^{25h}$, aryl and $Het^7$), $C_{3-10}$ cycloalkyl, or $C_{4-10}$ cycloalkenyl (which latter two groups are optionally substituted by one or more substituents selected from halo, OH, =O, $C_{1-6}$ alkyl and $C_{1-6}$ alkoxy) or $Het^c$, or $R^{12-17c}$ and $R^{12-17d}$, $R^{12-17g}$ and $R^{12-17h}$, $R^{21-23c}$ and $R^{21-23d}$, $R^{21-23g}$ and $R^{21-23h}$, $R^{24b}$ and $R^{24c}$, and $R^{24d}$ and $R^{24e}$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy);

$Het^1$ to $Het^8$ and $Het^a$ to $Het^c$ independently represent a 4- to 14-membered heterocyclic groups containing one or more heteroatoms selected from O, S and N, which heterocyclic groups may comprise one, two or three rings and may be substituted by one or more substituents selected from =O, halo, $C_{1-6}$ alkyl, which latter group is optionally substituted by one or more substituents selected from halo, —$OR^{26a}$, —$NR^{26b}R^{26c}$, —$C(O)OR^{26d}$ and —$C(O)NR^{26e}R^{26f}$;

$Cy^1$ to $Cy^3$, at each occurrence, independently represents a 3- to 10-membered aromatic, fully saturated or partially unsaturated carbocyclic ring;

$R^{25a}$ to $R^{25h}$ and $R^{26a}$ to $R^{26f}$ independently represent at each occurrence, H, $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, =O, halo, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from halo, OH, =O, $C_{1-4}$ alkyl and $C_{1-4}$ alkoxy), q represents 0, 1 or 2, or a pharmaceutically acceptable salt or solvate thereof.

2. The compound according to claim 1, wherein:

(a) $X_1$ to $X_3$ are independently N or $CR^8$, $X_4$ and $X_5$ are independently $CR^8$, and $X_6$ and $X_7$ are independently $CR^9$; and/or (b) Y represents $CR^{10}$ and/or Z represents $CR^4$; and/or (c) $R^1$ represents H, or —$C(O)R^{11a}$.

3. The compound according to claim 1, wherein:

(a) $R^2$ represents:

(i) H;

(ii) Br, Cl, F;

(iii) $C_{1-4}$ alkyl which is unsubstituted or substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{12a}$, $NR^{12g}R^{12h}$ aryl and $Het^1$);

(iv) $Cy^2$ (which $Cy^2$ group is unsubstituted or is substituted by one or more substituents selected from halo, CN, $C_{1-3}$ alkyl (which latter group is optionally substituted by one or more substituents selected from OH, =O, halo, $C_{1-4}$ alkyl and $C_{1-4}$ alkoxy), $NR^{13g}R^{13h}$ aryl and $Het^2$);

(v) $Het^a$ (which $Het^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and $C_{1-4}$ alkoxy), $OR^{14a}$, $NR^{14g}R^{14h}$, aryl and $Het^3$);

(vi) $OR^{15a}$; or (vii) $NR^{15g}R^{15h}$; and/or (b) $R^3$, $R^4$, $R^8$ and $R^{10}$, at each occurrence, independently represents:
(i) H;
(ii) Br, Cl, F;
(iii) CN;
(iv) $C_{1-4}$ alkyl, $C_{2-4}$ alkenyl, $C_{2-4}$ alkynyl (which latter three groups are unsubstituted or substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $Cy^1$ (which $Cy^1$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy)), $OR^{12a}$, $NR^{12g}R^{12h}$, aryl and $Het^1$),
(v) $Cy^2$ (which $Cy^2$ group is unsubstituted or is substituted by one or more substituents selected from halo, CN, $C_{1-3}$ alkyl (which latter group is unsubstituted or substituted by one or more substituents selected from OH, =O, halo, $C_{1-4}$ alkyl and $C_{1-4}$ alkoxy), $OR^{13}$a, $NR^{13g}R^{13h}$, aryl and $Het^2$);
(vi) $Het^a$ (which $Het^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and $C_{1-4}$ alkoxy), $OR^{14a}$, $NR^{14g}R^{14h}$, aryl and $Het^3$);
(vii) $OR^{15}$a;
(viii) $NR^{15g}R^{15h}$; or
(ix) nitro; and/or
(c) $R^5$ and $R^9$, at each occurrence, independently represent H, Br, Cl, F, CN, nitro, $C_{1-4}$ alkyl (which latter group is unsubstituted or substituted by one or more substituents selected from Br, Cl, F, $OR^{16a}$ and $NR^{16g}R^{16h}$), $OR^{17a}$ or $NR^{17g}R^{17h}$; and/or
(d) $R^{6a}$ represents H or CN; and
$R^{6b}$, independently at each occurrence, represents H or $C_{1-4}$ alkyl, which latter group is unsubstituted or substituted with F or $OR^{19}$; and/or
(e) $R^{11a}$ represents,
(i) $C_{1-5}$ alkyl which group is unsubstituted or substituted by one or more substituents selected from halo, =O, CN, $C_{1-3}$ alkyl (which latter group is unsubstituted or substituted by one or more substituents selected from OH, =O, halo, $C_{1-4}$ alkyl and $C_{1-4}$ alkoxy), $OR^{21}$a, $NR^{21g}R^{21h}$, aryl, $Cy^3$ (which $Cy^3$ group is unsubstituted or is substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy), $OR^{22}$a, $NR^{22g}R^{22h}$, aryl and $Het^4$) and $Het^5$;
(ii) $C_{3-6}$ cycloalkyl which latter group is unsubstituted or substituted by one or more substituents selected from halo, OH, =O, $C_{1-4}$ alkyl and $C_{1-4}$ alkoxy;
(iii) $Het^b$ (which $Het^b$ group is unsubstituted or substituted by one or more substituents selected from halo, nitro, CN, $C(O)OC_{1-4}$ alkyl, $C_{1-5}$ alkyl, (which latter group is unsubstituted or substituted by one or more substituents selected from $Het^8$, OH, =O, halo, $C_{1-4}$ alkyl and $C_{1-4}$ alkoxy), $OR^{23a}$, $NR^{23g}R^{23h}$ aryl and $Het^6$);
(iv) $OR^{24}$a; or
(v) $NR^{24d}R^{24e}$.

4. The compound according to claim 1, wherein:
(a) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl, $C_{2-4}$ alkenyl (which latter two groups are optionally substituted by one or more substituents selected from halo, nitro, =O, $C(O)OC_{1-4}$ alkyl, CN, $C_{1-3}$ alkyl, $C_{5-6}$ cycloalkyl (which latter two groups are optionally substituted by one or more substituents selected from OH, =O, halo, $C_{1-4}$ alkyl and $C_{1-4}$ alkoxy), $OR^{25a}$, $NR^{25g}R^{25h}$, aryl and $Het^7$), $C_{4-6}$ cycloalkyl, or $C_{5-6}$ cycloalkenyl (which latter two groups are optionally substituted by one or more substituents selected from halo, OH, =O, $C_{1-4}$ alkyl and $C_{1-4}$ alkoxy) or $Het^1$, or
$R^{12-17c}$ and $R^{12-17d}$, $R^{12-17g}$ and $R^{12-17h}$, $R^{21-23c}$ and $R^{21-23d}$, $R^{21-23g}$, and $R^{21-23h}$, $R^{24b}$ and $R^{24c}$, and $R^{24d}$ and $R^{24e}$ may represent, together with the nitrogen atom to which they are attached, a 3- to 6-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-3}$ alkyl (which latter group is unsubstituted or substituted by one or more substituents selected from OH, =O, halo, $C_{1-4}$ alkyl and $C_{1-4}$ alkoxy); and/or
(b) $Het^1$ to $Het^8$ and $Het^a$ to $Het^c$ independently represent a 4- to 10-membered heterocyclic group containing one or more heteroatoms selected from O, S and N, which heterocyclic groups may comprise one, two or three rings and may be substituted by one or more substituents selected from =O, halo, $C_{1-3}$ alkyl, which latter group is optionally substituted by one or more substituents selected from halo, $-OR^{26a}$, $-NR^{26b}R^{26c}$, $-C(O)OR^{26d}$ and $-C(O)NR^{26e}R^{26f}$; and/or
(c) $Cy^1$ to $Cy^3$, at each occurrence, independently represent a 4- to 6-membered aromatic, fully saturated or partially unsaturated carbocyclic ring; and/or
(d) $R^{25a}$ to $R^{25h}$ and $R^{26a}$ to $R^{26f}$ independently represent at each occurrence, H, $C_{1-4}$ alkyl, which latter group is optionally substituted by one or more substituents selected from halo, nitro, CN, $C_{1-4}$ alkyl, (which latter group is unsubstituted or substituted by one or more substituents selected from OH, =O, halo, $C_{1-4}$ alkyl and $C_{1-4}$ alkoxy), $C_{3-6}$ cycloalkyl (which latter group is unsubstituted or substituted by one or more substituents selected from halo, OH, =O, $C_{1-4}$ alkyl and $C_{1-4}$ alkoxy).

5. The compound according to claim 1, wherein:
(a) L represents —C(CN)=C(H)—, Z represents $CR^4$, and the compound of formula I is represented as a compound of formula Ia, Ia

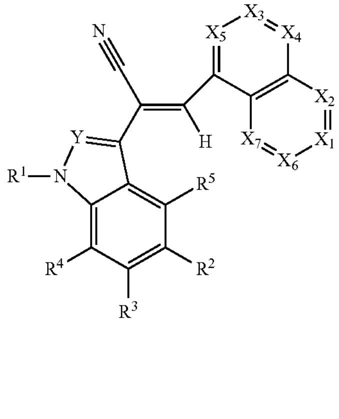

provided that no more than three of $X_1$ to $X_7$ represent N; and/or (b) L represents —C(CN)═C(H)—, Z represents $CR^4$, $X_1$ represents N, and the compound of formula I may be represented as a compound of formula Ib, Ib

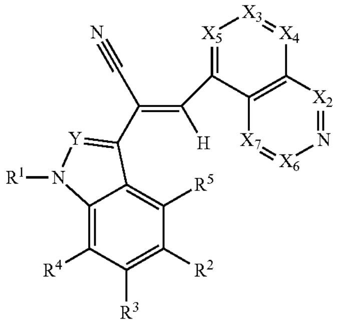

provided that no more than three of $X_2$ to $X_7$ represent N; and/or (c) L represents —C(CN)═C(H)—, $X_1$ represents N, Z represents $CR^4$, and $X_2$ to $X_5$ each represent $CR^8$, and the compound of formula I may be represented as a compound of formula Ic, Ic

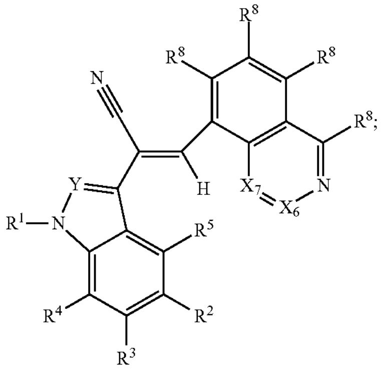

and/or (d) L represents —C(CN)═C(H)—, $X_1$ represents N, $X_2$ to $X_5$ each represent $CR^8$, Z represents $CR^4$, and Y represents $CR^{10}$, and the compound of formula I may be represented as a compound of formula Id, Id

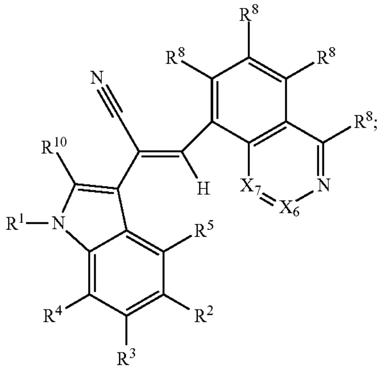

and/or (e) L represents —C(CN)═C(H)—, $X_1$ represents N, $X_2$ to $X_5$ each represent $CR^8$, Z represents $CR^4$, Y represents $CR^{10}$ and $R^5$ represents H, and the compound of formula I may be represented as a compound of formula Ie, Ie

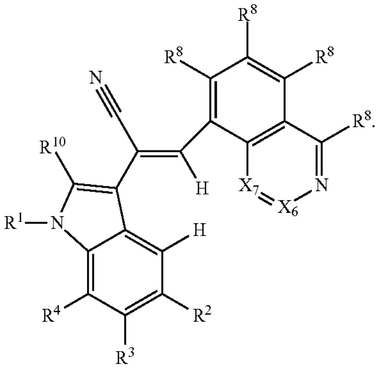

6. The compound according to claim 1, wherein when L represents —C($R^{6a}$)═C($R^{6b}$)—, the C═C double bond is in the E- or Z-configuration.

7. The compound according to claim 1, wherein:

(a) $R^2$ represents:

(i) H;

(ii) Br, Cl, F;

(iii) $C_{1-4}$ alkyl which is unsubstituted or substituted by one or more substituents selected from F, $C_{1-3}$ alkyl (which latter group is unsubstituted or substituted by one or more substituents selected from OH, ═O, F, $C_{1-4}$ alkyl and $C_{1-4}$ alkoxy), $OR^{12a}$ and $NR^{12g}R^{12h}$);

(iv) $OR^{15a}$; or (v) $NR^{15g}R^{15h}$); and/or (b) $R^3$, $R^4$, $R^8$ and $R^{10}$, at each occurrence, independently represents H, Br, Cl, F, CN, $C_{1-4}$ alkyl (which latter groups is unsubstituted or substituted by one or more substituents selected from F, $C_{1-3}$ alkyl (which latter group is unsubstituted or substituted by one or more substituents selected from OH, ═O, halo, $C_{1-4}$ alkyl and $C_{1-4}$ alkoxy), $OR^{12a}$ and $NR^{12g}R^{12h}$), $OR^{15a}$, $NR^{15g}R^{15h}$ nitro); and/or (c) $R^{11a}$ represents, $C_{1-5}$ alkyl which group is unsubstituted or substituted by one or more substituents selected from F, ═O, $C_{1-3}$ alkyl (which latter group is unsubstituted or substituted by one or more substituents selected from OH, ═O, F, $C_{1-4}$ alkyl and $C_{1-4}$ alkoxy), $OR^{21a}$, $NR^{21g}R^{21h}$, $Het^b$ (which $Het^b$ group is unsubstituted or substituted by one or more substituents selected from Cl, Br, F, $C(O)OC_{1-4}$ alkyl, $C_{1-5}$ alkyl, (which latter group is unsubstituted or substituted by one or more substituents selected from $Het^8$, OH, ═O, Cl, F, $C_{1-4}$ alkyl and $C_{1-4}$ alkoxy), $OR^{23a}$, $NR^{23g}R^{23h}$), or $OR^{24a}$; and/or (d) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-4}$ alkyl (which latter group is unsubstituted or substituted by one or more substituents selected from Cl, F, ═O, $C(O)OC_{1-4}$ alkyl, $C_{1-3}$ alkyl, $C_{5-6}$ cycloalkyl (which latter two groups are optionally substituted by one or more substituents selected from OH, ═O, Cl, F, $C_{1-4}$ alkyl and $C_{1-4}$ alkoxy), $OR^{25a}$, $NR^{25g}R^{25h}$ aryl and $Het^7$), $C_{4-6}$ cycloalkyl (which latter group is unsubstituted or substituted by one or more substituents selected from Cl, F, OH, ═O, $C_{1-4}$ alkyl and $C_{1-4}$ alkoxy) or $Het^c$, or $R^{12\text{-}17c}$ and $R^{12\text{-}17d}$, $R^{12\text{-}17g}$ and $R^{12\text{-}17h}$, $R^{21\text{-}23c}$ and $R^{21\text{-}23d}$, $R^{21\text{-}23g}$ and $R^{21\text{-}23h}$, $R^{24b}$ and $R^{24c}$, and $R^{24d}$ and $R^{24e}$ may represent, together with the nitrogen atom to which they are attached, a 5- to 6-membered heterocyclic ring that may be aromatic, fully saturated or partially unsaturated and which may additionally contain one or more heteroatoms selected from O, S and N, which heterocyclic ring is unsubstituted or substituted by one or more substituents selected from halo, nitro, CN, $C_{1-3}$ alkyl (which latter group is unsubstituted or substituted by one or more substituents selected from OH, =O, Cl, F, $C_{1-4}$ alkyl and $C_{1-4}$ alkoxy); and/or (e) $Het^1$ to $Het^1$ and $Het^a$ to $Het^c$ independently represent a 5- to 8-membered heterocyclic group containing one or more heteroatoms selected from O, S and N, which heterocyclic groups may comprise one, two or three rings and may be substituted by one or more substituents selected from =O, Cl, Br, F, $C_{1-3}$ alkyl, which latter group is optionally substituted by one or more substituents selected from halo, —$OR^{26a}$, —$NR^{26b}R^{26c}$, —C(O)$OR^{26d}$ and —C(O)$NR^{26e}R^{26f}$).

8. The compound according to claim 1, wherein:

(a) $R^2$ represents Br, Cl or H;

(b) $R^3$, $R^4$, $R^8$ and $R^{10}$, at each occurrence, each represent H;

(c) $R^{11a}$ represents, (i) $C_{1-5}$ alkyl which group is unsubstituted or substituted by one or more substituents selected from Cl, F, =O, CN, $C_{1-3}$ alkyl (which latter group is unsubstituted or substituted by one or more substituents selected from OH, =O, Cl, F, $C_{1-4}$ alkyl and $C_{1-4}$ alkoxy), $OR^{21a}$, $NR^{21g}R^{21h}$;

(ii) $C_{3-6}$ cycloalkyl which latter group is unsubstituted or substituted by one or more substituents selected from Cl, F, OH, =O, $C_{1-4}$ alkyl and $C_{1-4}$ alkoxy;

(iii) $Het^b$ (which $Het^b$ group is unsubstituted or substituted by one or more substituents selected from Cl, Br, F, C(O)$OC_{1-4}$ alkyl, $C_{1-5}$ alkyl, (which latter group is unsubstituted or substituted by one or more substituents selected from $Het^1$, OH, =O, Cl, F, $C_{1-4}$ alkyl and $C_{1-4}$ alkoxy), $OR^{23}$a, $NR^{23g}R^{23h}$);

(iv) $OR^{24a}$; or (v) $NR^{24d}R^{24e}$, (d) $R^{12a}$ to $R^{12h}$, $R^{13a}$ to $R^{13h}$, $R^{14a}$ to $R^{14h}$, $R^{15a}$ to $R^{15h}$, $R^{16a}$ to $R^{16h}$, $R^{17a}$ to $R^{17h}$, $R^{18a}$, $R^{18b}$, $R^{19}$, $R^{20}$, $R^{21a}$ to $R^{21h}$, $R^{22a}$ to $R^{22h}$, $R^{23a}$ to $R^{23h}$ and $R^{24a}$ to $R^{24e}$ independently represent, at each occurrence, H, $C_{1-3}$ alkyl (which latter group is unsubstituted or substituted by one or more substituents selected from F, =O, C(O)$OC_{1-4}$ alkyl, $C_{1-3}$ alkyl (which latter group is unsubstituted or substituted by one or more substituents selected from OH, =O, Cl, F, $C_{1-4}$ alkyl and $C_{1-4}$ alkoxy), $OR^{25a}$, $NR^{25g}R^{25h}$).

9. The compound according to claim 1, wherein:

(A) L represents —C(CN)=C(H)—, $X_1$ represents N, $X_2$ to $X_5$ each represent $CR^8$, $X_6$ and $X_7$ each represent $CR^9$, Z represents $CR^4$, Y represents $CR^{10}$ and $R^5$ represents H, and the compound of formula I may be represented as a compound of formula If, If

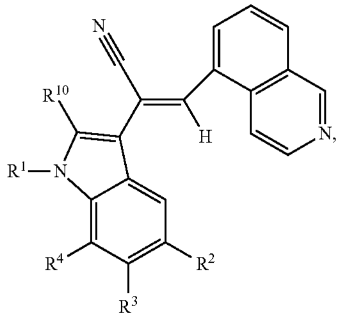

provided that $R^4$ is not Br or methylenepyrrolidine; and/or provided that $R^2$ is not Cl, F, or $OR^{15a}$ (where $R^{15a}$ comprises more than one carbon atom) or $NR^{15g}R^{15h}$ optionally wherein:

(i) $R^3$ represents H; and/or $R^{10}$ represents H or $CH_3$; and/or $R^2$ represents H, Br or $OCH_3$; and/or $R^4$ represents H or $OCH_3$; and/or (ii) $R^1$ represents C(O)$R^{11a}$ and $R^{11a}$ represents:

(a) H;

(b) $C_{1-6}$ alkyl (which group is unsubstituted or substituted by one or more substituents selected from =O, $C_{1-6}$ alkyl (which latter group is unsubstituted or substituted by one or more substituents selected from OH, =O, $C_{1-4}$ alkyl and $C_{1-4}$ alkoxy), $OR^{21a}$, $NR^{21g}R^{21h}$, aryl, $Cy^3$, and $Het^5$);

(c) $C_{3-10}$ cycloalkyl (which group is optionally substituted by one or more substituents selected from halo, OH, =O, $C_{1-6}$ alkyl and $C_{1-6}$ alkoxy);

(d) $Het^b$ (which $Het^b$ group is unsubstituted or substituted by one or more substituents selected from halo, nitro, CN, C(O)$OC_{1-4}$ alkyl, $C_{1-6}$ alkyl (which latter group is optionally substituted by one or more substituents selected from $Het^8$, or more particularly, OH, =O, halo, $C_{1-4}$ alkyl and $C_{1-4}$ alkoxy), $OR^{23a}$, $NR^{23g}R^{23h}$ aryl and $Het^6$), (e) $OR^{24a}$;

$NR^{24d}R^{24e}$; and/or (B) L represents —C($R^{6a}$)=C(H)—, $X_1$ represents N, $X_2$, $X_4$ and $X_5$ each represent $CR^8$, $X_3$ represents N or $CR^8$, $X_6$ and $X_7$ each represent $CR^9$, and $R^5$ represents H, and the compound of formula I may be represented as a compound of formula Ig, Ig

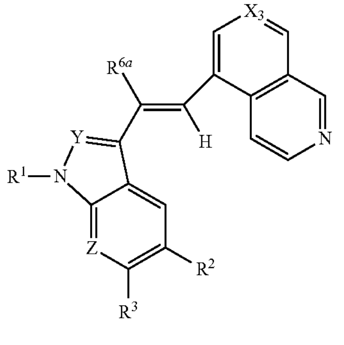

provided that when $R^h$a represents CN:

$R^2$ is not F, Br or $OCH_3$; and/or when Z is $CR^4$, $CR^4$ is not $CCH_3$, optionally wherein:

$R^3$ represents H or methylenepyrrolidinyl;

$R^2$ and $R^3$ independently represent H, $OR^{15a}$, Cl or $C_{1-6}$ alkyl (which latter group is unsubstituted or substituted by one or more substituents selected from $OR^{12a}$, $NR^{12g}R^{12h}$, aryl and $Het^1$); and/or $R^4$, when present, represents H or Br.

10. The compound according to claim 1, wherein the compound of formula I is selected from the list:

(i) (Z)-2-(1H-indol-3-yl)-3-(5-isoquinolyl)prop-2-enenitrile;

(ii) (Z)-3-(5-isoquinolyl)-2-(5-methoxy-1H-indol-3-yl) prop-2-enenitrile;

(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide;

(iv) (Z)-2-(5-chloro-1H-indol-3-yl)-3-(5-isoquinolyl) prop-2-enenitrile;

(v) (Z)-2-(5-bromo-1H-indol-3-yl)-3-(5-isoquinolyl) prop-2-enenitrile;

(vi) (Z)-3-(5-isoquinolyl)-2-[1-[2-(4-methylpiperazin-1-yl)acetyl]indol-3-yl]prop-2-enenitrile;

(vii) N-[3-[3-[(Z)-1-cyano-2-(5-isoquinolyl)vinyl]indol-1-yl]-3-oxo-propyl]acetamide;

(viii) (Z)-2-[1-[5-[(3aS,4S,6aR)-2-oxo-1,3,3a,4,6,6a-hexahydrothieno[3,4-d]imidazol-4-yl]pentanoyl]indol-3-yl]-3-(5-isoquinolyl)prop-2-enenitrile and/or (Z)-2-[1-[5-[(3aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile;

(ix) tert-butyl 4-[3-[(Z)-1-cyano-2-(5-isoquinolyl)vinyl] indole-1-carbonyl]piperidine-1-carboxylate;

(x) (Z)-3-(5-isoquinolyl)-2-[1-(piperidine-4-carbonyl)indol-3-yl]prop-2-enenitrile;

(xi) (Z)-3-(5-isoquinolyl)-2-[1-(1-methylpiperidine-4-carbonyl)indol-3-yl]prop-2-enenitrile;

(xii) (Z)-3-(5-isoquinolyl)-2-[1-(1-(3-fluorophenyl)-piperidine-4-carbonyl)indol-3-yl]prop-2-enenitrile;

(xiii) (Z)-3-(5-isoquinolyl)-2-[1-(1-oxazol-4-yl-piperidine-4-carbonyl)indol-3-yl]prop-2-enenitrile;

(xiv) (Z)-3-(5-isoquinolyl)-2-[1-(1-(2-methoxyacetyl)-piperidine-4-carbonyl)indol-3-yl]prop-2-enenitrile;

(xv) (Z)-2-(6-bromo-1H-indol-3-yl)-3-(5-isoquinolyl) prop-2-enenitrile;

(xvi) (Z)-2-(6-chloro-1H-indol-3-yl)-3-(5-isoquinolyl) prop-2-enenitrile;

(xvii) (Z)-3-(5-isoquinolyl)-2-(6-methoxy-1H-indol-3-yl) prop-2-enenitrile;

(xviii) (Z)-2-(5,6-dimethoxy-1H-indol-3-yl)-3-(5-isoquinolyl)prop-2-enenitrile;

(xix) (Z)-3-(5-isoquinolyl)-2-(7-methyl-1H-indol-3-yl) prop-2-enenitrile;

(xx) 3-[(Z)-1-cyano-2-(5-isoquinolyl)vinyl]-N-methyl-1H-indole-7-carboxamide;

(xxi) 5-chloro-3-[(Z)-1-cyano-2-(5-isoquinolyl)vinyl]-N-methyl-1H-indole-7-carboxamide;

(xiii) (Z)-2-(5,7-dimethoxy-1H-indol-3-yl)-3-(5-isoquinolyl)prop-2-enenitrile;

(xxiii) (Z)-3-(5-isoquinolyl)-2-(7-methoxy-1H-indol-3-yl)prop-2-enenitrile;

(xxiv)N-[3-[(Z)-1-cyano-2-(5-isoquinolyl)vinyl]-1H-indol-7-yl]acetamide;

(xxv) (Z)-2-(7-chloro-1H-indol-3-yl)-3-(5-isoquinolyl) prop-2-enenitrile;

(xxvi) (Z)-2-(7-fluoro-1H-indol-3-yl)-3-(5-isoquinolyl) prop-2-enenitrile;

(xxvii) (Z)-2-[7-(2-fluorophenyl)-1H-indol-3-yl]-3-(5-isoquinolyl)prop-2-enenitrile;

(xxviii)(Z)-2-(1H-indol-3-yl)-3-(5-isoquinolyl)but-2-enenitrile;

(xxix) (Z)-3-(1H-indol-3-yl)-2-(5-isoquinolyl)prop-2-enenitrile;

(xxx) tert-butyl N-[3-[3-[(Z)-1-cyano-2-(5-isoquinolyl) vinyl]indol-1-yl]-3-oxopropyl-]carbamate;

(xxxi) (Z)-2-[1-(3-amino-1-oxo-propyl)indol-3-yl]-3-(5-isoquinolyl)prop-2-enenitrile;

(xxxii) tert-butyl N-[5-[3-[(Z)-1-cyano-2-(5-isoquinolyl) vinyl]indol-1-yl]-5-oxo-pentyl]carbamate;

(xxxiii) (Z)-2-[1-(5-amino-1-oxo-pentyl)indol-3-yl]-3-(5-isoquinolyl)prop-2-enenitrile;

(xxxiv) tert-butyl N-[6-[3-[(Z)-1-cyano-2-(5-isoquinolyl) vinyl]indol-1-yl]-6-oxo-hexyl]carbamate;

(xxxv) (Z)-2-(1-(6-aminohexanoyl)-1H-indol-3-yl)-3-(isoquinolin-5-yl)acrylonitrile;

(xxxvi) (Z)-2-(1H-indazol-3-yl)-3-(5-isoquinolyl)prop-2-enenitrile;

(xxxvii) (Z)-3-(5-isoquinolyl)-2-(4-methyl-1H-indol-3-yl)prop-2-enenitrile;

(xxxviii) (Z)-3-(5-isoquinolyl)-2-(4-methoxy-1H-indol-3-yl)prop-2-enenitrile;

(xxxlx) (Z)-2-(4,5-dimethoxy-1H-indol-3-yl)-3-(5-isoquinolyl)prop-2-enenitrile;

(xl) (Z)-2-(4-chloro-1H-indol-3-yl)-3-(5-isoquinolyl) prop-2-enenitrile;

(xli) 4-chloro-3-[(Z)-1-cyano-2-(5-isoquinolyl)vinyl]-1H-indole-5-carboxamide;

(xlii) (Z)-2-(1H-indol-3-yl)-3-(5-quinolyl)prop-2-enenitrile;

(xliii) 5-((E)-2-(1H-indol-3-yl)vinyl)isoquinoline;

(xliv) 4-((E)-2-(1H-indol-3-yl)vinyl)-2,7-naphthyridine;

(xlv) 5-((E)-2-(1H-pyrrolo[2,3-b]pyridin-3-yl)vinyl)isoquinoline;

(xlvi) 4-((E)-2-(1H-pyrrolo[2,3-b]pyridin-3-yl)vinyl)-2,7-naphthyridine;

(xlvii) [3-[(E)-2-(5-isoquinolyl)vinyl]-1H-indol-5-yl] azinic acid;

(xlviii) (Z)-2-(1H-indol-3-yl)-3-(2,7-naphthyridin-4-yl) prop-2-enenitrile;

(xlix) (Z)-3-(5-isoquinolyl)-2-[5-(3-pyrrolidin-1-yl-propoxy)-1H-indol-3-yl]prop-2-enenitrile;

(l) (Z)-3-(5-isoquinolyl)-2-[5-(2-methoxyethoxy)-1H-indol-3-yl]prop-2-enenitrile;

(li) (Z)-2-(6-chloro-1H-indol-3-yl)-3-(5-isoquinolyl) prop-2-enenitrile;

(lii) (Z)-2-(7-bromo-1H-indol-3-yl)-3-(5-isoquinolyl) prop-2-enenitrile;

(liii) tert-butyl N-[3-[3-[(Z)-1-cyano-2-(5-isoquinolyl)vinyl]indol-1-yl]-3-oxo-propyl]carbamate;

(liv) (Z)-2-[1-(3-aminopropanoyl)indol-3-yl]-3-(5-isoquinolyl)prop-2-enenitrile;

(lv) 5-[(3aS,4S,6aR)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide and/or 5-[(3aR,4R,6aS)-2-oxo-1,3,3a,4,6,6a-hexahydrothieno[3,4-d]imidazol-4-yl]-N-[3-[3-[(Z)-1-cyano-2-(5-isoquinolyl)vinyl]indol-1-yl]-3-oxo-propyl]pentanamide;

(lvi) (Z)-2-(5-(2-(1,3-dioxolan-2-yl)ethoxy)-1H-indol-3-yl)-3-(isoquinolin-5-yl)acrylonitrile;

(lvii) (Z)-3-(isoquinolin-5-yl)-2-(1-(1-(5-((3aS,4S,6aR)-2-oxohexahydro-1H-thieno[3,4-d]imidazol-4-yl)pentanoyl)piperidine-4-carbonyl)-1H-indol-3-yl)acrylonitrile;

(lviii) (Z)-2-(1-(2-(2-methoxyethoxy)acetyl)-1H-indol-3-yl)-3-(isoquinolin-5-yl)acrylonitrile;

(lix) (Z)-3-(isoquinolin-5-yl)-2-(6-((pyrrolidin-1-yl)methyl)-1H-indol-3-yl)acrylonitrile;

(lx) (Z)-3-(isoquinolin-5-yl)-2-(5-((pyrrolidin-1-yl)methyl)-1H-indol-3-yl)acrylonitrile;

(lxi) (Z)-3-(isoquinolin-5-yl)-2-(7-((pyrrolidin-1-yl)methyl)-1H-indol-3-yl)acrylonitrile; and (lxii) (Z)-2-(1H-indazol-3-yl)-3-(isoquinolin-5-yl)acrylonitrile.

11. The compound according to claim 10, wherein the compound of formula I is selected from the list:

(i) (Z)-2-(1H-indol-3-yl)-3-(5-isoquinolyl)prop-2-enenitrile;

(ii) (Z)-3-(5-isoquinolyl)-2-(5-methoxy-1H-indol-3-yl)prop-2-enenitrile;

(iii) 5-[(3aS,4S,6aR)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide and/or 5-[(3aR,4R,6aS)-2-oxo-1,3,3a,4,6,6a-hexahydrothieno[3,4-d]imidazol-4-yl]-N-[3-[(Z)-1-cyano-2-(5-isoquinolyl)vinyl]-1H-indol-5-yl]pentanamide;

(iv) (Z)-2-(5-chloro-1H-indol-3-yl)-3-(5-isoquinolyl)prop-2-enenitrile;

(v) (Z)-2-(5-bromo-1H-indol-3-yl)-3-(5-isoquinolyl)prop-2-enenitrile;

(vi) (Z)-3-(5-isoquinolyl)-2-[1-[2-(4-methylpiperazin-1-yl)acetyl]indol-3-yl]prop-2-enenitrile;

(vii) N-[3-[3-[(Z)-1-cyano-2-(5-isoquinolyl)vinyl]indol-1-yl]-3-oxo-propyl]acetamide;

(viii) tert-butyl 4-[3-[(Z)-1-cyano-2-(5-isoquinolyl)vinyl]indole-1-carbonyl]piperidine-1-carboxylate;

(ix) (Z)-3-(5-isoquinolyl)-2-[1-(piperidine-4-carbonyl)indol-3-yl]prop-2-enenitrile;

(x) (Z)-3-(isoquinolin-5-yl)-2-(7-methoxy-1H-indol-3-yl)acrylonitrile;

(xi) (Z)-3-(isoquinolin-5-yl)-2-(6-methoxy-1H-indol-3-yl)acrylonitrile;

(xii) (Z)-tert-butyl (3-(3-(1-cyano-2-(isoquinolin-5-yl)vinyl)-1H-indol-1-yl)-3-oxopropyl)carbamate;

(xiii) N-(3-(3-((Z)-1-cyano-2-(isoquinolin-5-yl)vinyl)-1H-indol-1-yl)-3-oxopropyl)-5-((3aS,4S,6aR)-2-oxohexahydro-1H-thieno[3,4-d]imidazol-4-yl)pentanamide;

(xiv) N-(3-((Z)-1-cyano-2-(isoquinolin-5-yl)vinyl)-1H-indol-5-yl)acetamide (xv) (Z)-2-(6-bromo-1H-indol-3-yl)-3-(5-isoquinolyl)prop-2-enenitrile;

(xvi) (Z)-2-(7-bromo-1H-indol-3-yl)-3-(5-isoquinolyl)prop-2-enenitrile;

(xvii) (Z)-2-[1-(3-aminopropanoyl)indol-3-yl]-3-(5-isoquinolyl)prop-2-enenitrile;

(xviii) (Z)-3-(isoquinolin-5-yl)-2-(1-(1-(5-((3 aS,4S,6aR)-2-oxohexahydro-1H-thieno[3,4-d]imidazol-4-yl)pentanoyl)piperidine-4-carbonyl)-1H-indol-3-yl)acrylonitrile; and (xix) (Z)-2-(1-(2-(2-methoxyethoxy)acetyl)-1H-indol-3-yl)-3-(isoquinolin-5-yl)acrylonitrile.

12. The compound according to claim 10, wherein the compound of formula I is (Z)-2-(1H-indol-3-yl)-3-(5-quinolyl)prop-2-enenitrile, (Z)-tert-butyl 4-(3-(1-cyano-2-(isoquinolin-5-yl)vinyl)-1H-indole-1-carbonyl)piperidine-1-carboxylate and (Z)-2-[1-[5-[(3 aR,4R,6aS)-2-oxo-1,3,3a,4,6,6a-hexahydrothieno[3,4-d]imidazol-4-yl]pentanoyl]indol-3-yl]-3-(5-isoquinolyl)prop-2-enenitrile.

13. The compound according to claim 10, wherein the compound of formula I is selected from the list:

(a) 5-((E)-2-(1H-indol-3-yl)vinyl)isoquinoline;

(b) 4-((E)-2-(1H-indol-3-yl)vinyl)-2,7-naphthyridine;

(c) 5-((E)-2-(1H-pyrrolo[2,3-b]pyridin-3-yl)vinyl)isoquinoline;

(d) 4-((E)-2-(1H-pyrrolo[2,3-b]pyridin-3-yl)vinyl)-2,7-naphthyridine;

(e) (Z)-2-(1H-indol-3-yl)-3-(2,7-naphthyridin-4-yl)prop-2-enenitrile;

(f) (Z)-3-(5-isoquinolyl)-2-[5-(3-pyrrolidin-1-ylpropoxy)-1H-indol-3-yl]prop-2-enenitrile;

(g) (Z)-3-(5-isoquinolyl)-2-[5-(2-methoxyethoxy)-1H-indol-3-yl]prop-2-enenitrile;

(h) (Z)-2-(5-(2-(1,3-dioxolan-2-yl)ethoxy)-1H-indol-3-yl)-3-(isoquinolin-5-yl)acrylonitrile;

(i) (Z)-3-(isoquinolin-5-yl)-2-(6-((pyrrolidin-1-yl)methyl)-1H-indol-3-yl)acrylonitrile;

(j) (Z)-3-(isoquinolin-5-yl)-2-(5-((pyrrolidin-1-yl)methyl)-1H-indol-3-yl)acrylonitrile;

(k) (Z)-3-(isoquinolin-5-yl)-2-(7-((pyrrolidin-1-yl)methyl)-1H-indol-3-yl)acrylonitrile; and (l) (Z)-2-(1H-indazol-3-yl)-3-(isoquinolin-5-yl)acrylonitrile.

14. A pharmaceutical formulation including a compound of formula I, as defined in claim 1, in admixture with a pharmaceutically-acceptable adjuvant, diluent or carrier.

15. A compound of formula I, as defined in claim 1, for use in medicine.

16. A combination product comprising:

(a)

(A) a compound of formula I, as defined in claim 1, and (B) an anti-autophagy and/or chemoprotective agent, wherein each of components (A) and (B) is formulated in admixture with a pharmaceutically-acceptable adjuvant, diluent or carrier; or (b)

(I) a compound of formula I, as defined in claim 1, and (II) an antimitotic agent, wherein each of components (I) and (II) is formulated in admixture with a pharmaceutically-acceptable adjuvant, diluent or carrier.

17. A method of treatment of a cancer, which method comprises the administration of an effective amount of a compound of formula I, as defined in claim 1 to a patient having said cancer.

18. A method of treatment of a cancer, which method comprises the administration of an effective amount of a compound of formula I, as defined in claim 1, and an anti-autophagy and/or chemoprotective agent to a patient having said cancer.

19. A method of treatment of a cancer, which method comprises the administration of an effective amount of a combination product as defined in claim 16 (a) to a patient having said cancer.

20. A method of treatment of a cancer, which method comprises the administration of an effective amount of a combination product as defined in claim 16 (b) to a patient having said cancer.

* * * * *